(12) United States Patent
Gamsey et al.

(10) Patent No.: US 10,494,385 B2
(45) Date of Patent: Dec. 3, 2019

(54) NEAR-IR GLUCOSE SENSORS

(71) Applicant: Profusa, Inc., South San Francisco, CA (US)

(72) Inventors: Soya Gamsey, San Francisco, CA (US); Viachaslau Bernat, Burlingame, CA (US); Alex Kutyavin, Lake Stevens, WA (US); Jacob William Clary, Moss Beach, CA (US); Sulolit Pradhan, Foster City, CA (US)

(73) Assignee: Profusa, Inc., South San Francisco, CA (US)

( * ) Notice: Subject to any disclaimer, the term of this patent is extended or adjusted under 35 U.S.C. 154(b) by 0 days.

(21) Appl. No.: 16/038,657

(22) Filed: Jul. 18, 2018

(65) Prior Publication Data

US 2019/0010170 A1    Jan. 10, 2019

Related U.S. Application Data

(63) Continuation of application No. 15/855,555, filed on Dec. 27, 2017.

(60) Provisional application No. 62/439,363, filed on Dec. 27, 2016, provisional application No. 62/439,364, filed on Dec. 27, 2016.

(51) Int. Cl.

| | | |
|---|---|---|
| *C07F 5/02* | (2006.01) | |
| *A61B 5/1459* | (2006.01) | |
| *A61B 5/145* | (2006.01) | |
| *C09B 1/00* | (2006.01) | |
| *C09B 11/24* | (2006.01) | |
| *C09B 11/28* | (2006.01) | |
| *C09B 23/00* | (2006.01) | |
| *C09B 23/02* | (2006.01) | |
| *C09B 23/04* | (2006.01) | |
| *C09B 23/08* | (2006.01) | |
| *C09K 11/06* | (2006.01) | |
| *C09B 57/00* | (2006.01) | |
| *C09B 23/01* | (2006.01) | |
| *C09B 69/00* | (2006.01) | |
| *C09B 57/02* | (2006.01) | |

(52) U.S. Cl.
CPC ............ *C07F 5/025* (2013.01); *A61B 5/1459* (2013.01); *A61B 5/14532* (2013.01); *C09B 1/002* (2013.01); *C09B 11/24* (2013.01); *C09B 11/28* (2013.01); *C09B 23/0008* (2013.01); *C09B 23/0016* (2013.01); *C09B 23/0025* (2013.01); *C09B 23/0066* (2013.01); *C09B 23/04* (2013.01); *C09B 23/083* (2013.01); *C09B 23/086* (2013.01); *C09B 57/00* (2013.01); *C09B 57/02* (2013.01); *C09B 69/008* (2013.01); *C09K 11/06* (2013.01); *C09K 2211/104* (2013.01); *C09K 2211/1055* (2013.01); *C09K 2211/1096* (2013.01)

(58) Field of Classification Search
CPC ........ C09K 11/06; C07F 5/025; C09B 69/008
See application file for complete search history.

(56) References Cited

U.S. PATENT DOCUMENTS

| | | | |
|---|---|---|---|
| 6,013,122 A | 1/2000 | Klitzman et al. | |
| 7,388,110 B2* | 6/2008 | Ochiai | .................... C07F 5/025 |
| | | | 562/7 |
| 9,410,958 B2 | 8/2016 | Bertozzi et al. | |
| 2008/0075752 A1 | 3/2008 | Ratner et al. | |
| 2012/0265034 A1 | 10/2012 | Wisniewski et al. | |

FOREIGN PATENT DOCUMENTS

| | | |
|---|---|---|
| WO | WO 2008/014280 | 1/2008 |
| WO | WO 2008/066921 | 6/2008 |

OTHER PUBLICATIONS

Alexeev et al., "High ionic strength glucose-sensing photonic crystal," Anal. Chem., 75:2316-2323 (2003).
Badylak et al., "Immune response to biologic scaffold materials," Seminars in Immunology, 20(2):109-116 (2008).
Bridges et al., "Chronic inflammatory responses to microgel-based implant coatings," J Biomed. Mater. Res. A., 94(1):252-258 (2010).
Isenhath et al., "A mouse model to evaluate the interface between skin and a percutaneous device," J Biomed. Mater. Research, 83A:915-922 (2007).
Kaehr et al., "Multiphoton fabrication of chemically responsive protein hydrogels for microactuation," PNAS USA, 105(26):8850-8854 (2008).
Kasprzak, S. E., "Small-scale polymer structures enabled by thiol-ene copolymer systems," Doctoral Dissertation, Georgia Institute of Technology, May 2009.
Kloxin, A. M. et al., "Photodegradable hydrogels for dynamic tuning of physical and chemical properties," Science, 324:59-63 (2009).
Marshall et al., "Biomaterials with tightly controlled pore size that promote vascular in-growth," ACS Polymer Preprints, 45(2):100-101 (2004).
Ostendorf, A. et al., "Two-photon polymerization: a new approach to micromachining," Photonics Spectra, 40(10):72-79 (2006).
Ozdemir et al., "Axial pattern composite prefabrication of high-density porous polyethylene: experimental and clinical research," Plast. Reconstr. Surg., 115(1):183-196 (2005).
Phelps et al., "Bioartificial matrices for therapeutic vascularization," PNAS USA, 107(8):3323-3328 (2010).
Sanders et al., "Tissue response to single-polymer fibers of varying diameters: evaluation of fibrous encapsulation and macrophage density," J Biomed. Mater. Research, 52:231-237 (2000).

(Continued)

*Primary Examiner* — Paul A Zucker
(74) *Attorney, Agent, or Firm* — Cooley LLP

(57) ABSTRACT

The present disclosure provides polymerizable luminescent dyes useful for incorporation into polymers. The dyes and the polymers can be used in sensing and imaging applications, for example, to provide accurate and optionally long term measurements of glucose in vivo. The present disclosure also provides sensors including the polymers described herein. The sensors can be implanted into a tissue of a subject and used for long-term or short-term continuous and semi-continuous collection of data of various biochemical analytes, optionally without the use of implantable hardware of any type and/or enzymatic and electrochemical detection methods.

30 Claims, 2 Drawing Sheets

(56) References Cited

OTHER PUBLICATIONS

Sanders et al., "Tissue response to microfibers of different polymers: polyester, polyethylene, polylactic acid, and polyurethane," J Biomed. Mater. Research, 62(2):222-227 (2002).
Sanders et al., "Fibrous encapsulation of single polymer microfibers depends on their vertical dimension in subcutaneous tissue," J Biomed. Mater. Research, 67A:1181-1187 (2003).
Sanders et al., "Relative influence of polymer fiber diameter and surface charge on fibrous capsule thickness and vessel density for single-fiber implants," J Biomed. Mater. Research, 65A:462-467 (2003).
Sanders et al., "Polymer microfiber mechanical properties: a system for assessment and investigation of the link with fibrous capsule formation," J Biomed. Mater. Research, 67A:1412-1416 (2003).
Sanders et al., "Small fiber diameter fibro-porous meshes: tissue response sensitivity to fiber spacing," J Biomed Mater Research, 72A:335-342 (2005).
Sanders et al., "Fibro-porous meshes made from polyurethane micro-fibers: effects of surface charge on tissue response," Biomaterials, 26(7):813-818 (2005).
Young et al., "A novel porous collagen scaffold around an implantable biosensor for improving biocompatibility. I. In vitro/in vivo stability of the scaffold and in vitro sensitivity of the glucose sensor with scaffold," Journal of Biomedical Materials Research Part A., 2008, vol. 87, pp. 136-146.
Cherevatskaya, M. et al. "Visible-Light-Promoted Stereoselective Alkylation by Combining Heterogeneous Photocatalysis with Organocatalysis," Angew. Chem. Int. Ed., 51(17), 4062-4066, 2012.
Cui, J. et al., "Design, Synthesis and Biological Evaluation of Rose Bengal Analogues as SecA Inhibitors," ChemMedChem 2013,8 (8), 1384-1393.
Grimm, J. B. et al., "General Synthetic Method for Si-Fluoresceins and Si-Rhodamines," ACS Cent. Sci. 2017,3 (9), 975-985.
Jokic, T. et al., "Highly Photostable Near-Infrared Fluorescent pH Indicators and Sensors Based on BF2-Chelated Tetraarylazadipyrromethene Dyes," Anal. Chem. 2012,84 (15), 6723-6730.
Koide, et al., "Development of NIR Fluorescent Dyes Based on Si-rhodamine for in Vivo Imaging," J. Am. Chem. Soc., 134(11), 5029-5031.
Kumar A. et al., "Smart polymers: Physical forms and bioengineering applications," Prog. Polym. Sci. 32 (2007) 1205-1237.
Myochin, T. et al., "Development of a Series of Near-Infrared Dark Quenchers Based on Si-rhodamines and Their Application to Fluorescent Probes," J. Am. Chem. Soc. 2015,137 (14), 4759-4765.
Umezawa, K. et al., "Rational design of reversible fluorescent probes for live-cell imaging and quantification of fast glutathione dynamics," Nat. Chem. 2016,9 (3), 279-286.

\* cited by examiner

NEAR-IR GLUCOSE SENSORS

CROSS-REFERENCE TO RELATED APPLICATIONS

This application is a continuation of U.S. application Ser. No. 15/855,555, which was filed Dec. 27, 2017, which claims the benefit of U.S. Provisional Application Nos. 62/439,363 filed Dec. 27, 5 2016 and 62/439,364 filed Dec. 27, 2016, the contents of each of which are incorporated herein, in their entirety, by reference.

STATEMENT CONCERNING GOVERNMENT SUPPORT

This invention was made with government support under grant nos. NIHR01EB016414 and NIHR44DK101000, both awarded by the National Institutes of Health. The government has certain rights in the invention.

FIELD OF THE INVENTION

The disclosure is in the field of luminescent dyes, polymers and biosensors.

TECHNICAL BACKGROUND

Diagnosis, treatment, and management of diabetes and certain metabolic disorders require monitoring of glucose concentration in the blood. Despite many advances in the minimally invasive blood glucose monitoring, the currently used methods are expensive, cumbersome, time consuming, and do not provide accurate, real-time blood glucose concentration information. Thus, a need exists for a better long-term, minimally invasive glucose-monitoring system. Doing so non-invasively with minimal user maintenance is essential, and sensor longevity of days to months is crucial in actual user environments.

Such real-time, continuous measurement of glucose concentration in the blood can be achieved by the use of sensors inserted or implanted into the tissue and measuring the signal generated by the sensor by a device located outside the body. Luminescence provides a useful tool for the design of such sensors. The sensors, which are monitored optically through the skin, require a highly stable dye with excitation and emission spectra in the near-infrared (NIR) optical window of the skin. These dye properties are crucial for the successful design of a luminescent sensor that can be implanted deep into tissue. Monitoring non-invasively through the skin requires the use of dyes with excitation and emission wavelengths in the optical window of the skin (approximately 550 to 1100 nm) to minimize light scattering and absorbance, and to achieve a high signal-to-noise ratio. Presently used dyes require excitation with light which is largely absorbed by the skin and the underlying tissue. Additionally, the currently available sensors are made of rigid materials that vastly differ from the mechanical properties of tissue in which they are implanted, are bulky and inconvenient, and induce a series of biological events upon implantation that ultimately culminate in the formation of a fibrous capsule that walls it off from the body.

A need exists for glucose-sensing compositions that are Near IR-detectable, particularly in vivo, and are suitable for long-term, minimally invasive implantation into tissues.

SUMMARY OF THE INVENTION

Disclosed herein are luminescent dyes, polymers including said dyes, and sensors including the polymers.

One aspect relates to a compound Formula I:

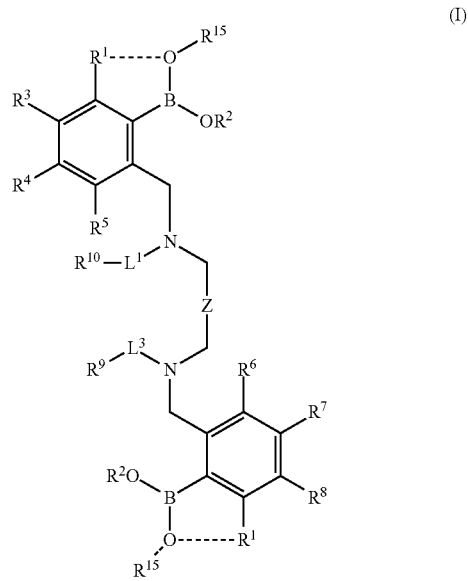

(I)

or an isomer, a tautomer, or a salt thereof, wherein the dotted lines denote a bond or absence of a bond;

when the dotted line connecting $R^1$ and O is a bond, $R^1$ is $CX^1X^2$ and $R^{15}$ is absent; and when the dotted line connecting $R^1$ and O is absence of a bond, $R^{15}$, at each occurrence, is independently H or $C_1$-$C_6$ alkyl, and $R^1$, at each occurrence, is H, optionally substituted $C_1$-$C_6$ alkyl, optionally substituted $C_2$-$C_6$ alkenyl, optionally substituted $C_2$-$C_6$ alkynyl, optionally substituted $C_2$-$C_{10}$ heteroalkyl, polymerizable moiety, NIR dye moiety, electron-withdrawing group, or electron-donating group;

$X^1$ and $X^2$ are independently H or $C_1$-$C_6$ alkyl;

$R^2$ is H or $C_1$-$C_6$ alkyl;

Z is a $C_6$-$C_{14}$ arylene optionally substituted with $R^{11}$, $R^{12}$, $R^{14}$, and $L^2R^{13}$;

$R^3$, $R^4$, $R^5$, $R^6$, $R^7$, $R^8$, $R^{11}$, $R^{12}$, $R^{13}$, and $R^{14}$ are independently H, optionally substituted $C_1$-$C_6$ alkyl, optionally substituted $C_2$-$C_6$ alkenyl, optionally substituted $C_2$-$C_6$ alkynyl, optionally substituted $C_2$-$C_{10}$ heteroalkyl, polymerizable moiety, NIR dye moiety, electron-withdrawing group, or electron-donating group;

$R^9$ and $R^{10}$ are independently H, $C_1$-$C_6$ alkyl, polymerizable moiety, or NIR dye moiety;

$L^1$, $L^2$, and $L^3$ are independently a bond or a linker group; and the compound includes one or more NIR dye moieties and one or more polymerizable moieties.

In some embodiments, the compounds have the structure of Formula IA, IB, or IC:

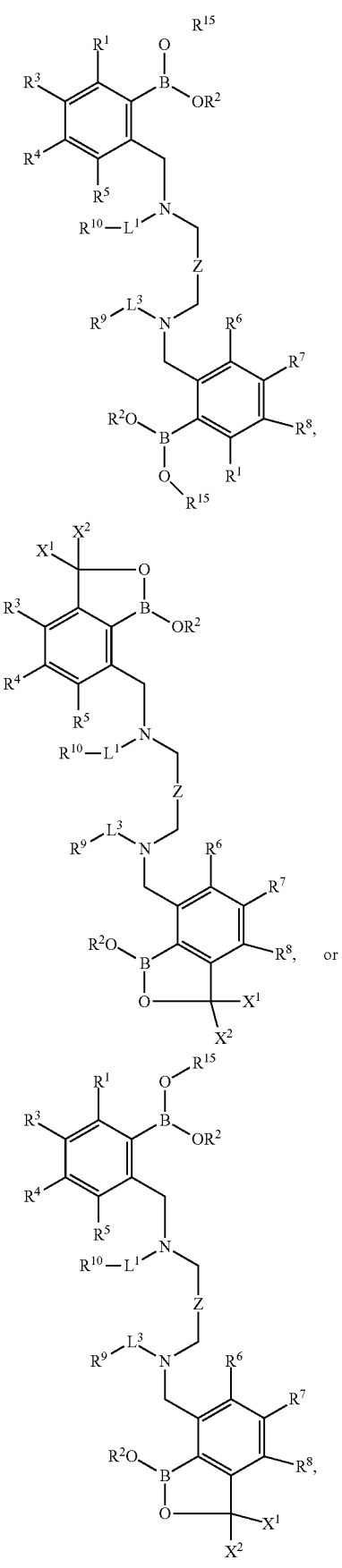

or an isomer, a tautomer, or a salt thereof.

In some embodiments of the compounds disclosed herein, the electron-withdrawing group is selected from the group consisting of halogen, C(O)R', COOR', C(O)NH$_2$, NHC(O)R', C(O)NR'R'', CF$_3$, CN, SO$_3$H, SO$_2$CF$_3$, SO$_2$R', SO$_2$NR'R'', ammonium, alkyl ammonium, and NO$_2$, wherein R' and R'' are independently H or C$_1$-C$_6$ alkyl.

In certain embodiments, electron-donating group is selected from the group consisting of NR$^{N1}$R$^{N2}$, OR', NHC(O)R', OC(O)R', phenyl, and vinyl, wherein R$^{N1}$, R$^{N2}$, and R' are independently H or C$_1$-C$_6$ alkyl.

In some embodiments, L$^1$ is a bond or a linker group selected from optionally substituted amino, optionally substituted amido, —O—, optionally substituted —CH$_2$C$_6$H$_4$O—, C$_2$-C$_{20}$ PEG linker, optionally substituted C$_6$-C$_{10}$ arylene, optionally substituted C$_5$-C$_{10}$ heteroarylene, optionally substituted —C$_1$-C$_6$ alkylene-Ar—, optionally substituted —C$_2$-C$_6$ alkenylene-Ar—, optionally substituted —C$_2$-C$_6$ alkynylene-Ar—, optionally substituted —C(O)NH—C$_1$-C$_6$ alkylene-Ar—, optionally substituted —C$_1$-C$_6$ alkylene-C(O)NH—C$_1$-C$_6$ alkylene-Ar—, —(CH$_2$CH$_2$O)$_n$—, optionally substituted C$_1$-C$_{10}$ alkyl, optionally substituted C$_2$-C$_{10}$ alkenyl, optionally substituted C$_2$-C$_{10}$ alkynyl, optionally substituted C$_2$-C$_{20}$ heteroalkyl, wherein n is an integer between 1 and 10 and Ar is C$_6$-C$_{10}$ arylene or C$_5$-C$_{10}$ heteroarylene.

In certain embodiments, L$^2$ is a bond or a linker group selected from optionally substituted amino, optionally substituted amido, —O—, optionally substituted —CH$_2$C$_6$H$_4$O—, C$_2$-C$_{20}$ PEG linker, optionally substituted C$_6$-C$_{10}$ arylene, optionally substituted C$_5$-C$_{10}$ heteroarylene, optionally substituted —C$_1$-C$_6$ alkylene-Ar—, optionally substituted C$_2$-C$_6$ alkenylene-Ar—, optionally substituted C$_2$-C$_6$ alkynylene-Ar—, optionally substituted —C(O)NH—C$_1$-C$_6$ alkylene-Ar—, optionally substituted —C$_1$-C$_6$ alkylene-C(O)NH—C$_1$-C$_6$ alkylene-Ar—, —(CH$_2$CH$_2$O)$_n$—, optionally substituted C$_1$-C$_{10}$ alkyl, optionally substituted C$_2$-C$_{10}$ alkenyl, optionally substituted C$_2$-C$_{10}$ alkynyl, optionally substituted C$_2$-C$_{20}$ heteroalkyl, wherein n is an integer between 1 and 10 and Ar is C$_6$-C$_{10}$ arylene or C$_5$-C$_{10}$ heteroarylene.

In some embodiments, L$^3$ is a bond or a linker group selected from optionally substituted amino, optionally substituted amido, —O—, optionally substituted —CH$_2$C$_6$H$_4$O—, C$_2$-C$_{20}$ PEG linker, optionally substituted C$_6$-C$_{10}$ arylene, optionally substituted C$_5$-C$_{10}$ heteroarylene, optionally substituted —C$_1$-C$_6$ alkylene-Ar—, optionally substituted C$_2$-C$_6$ alkenylene-Ar—, optionally substituted C$_2$-C$_6$ alkynylene-Ar—, optionally substituted —C(O)NH—C$_1$-C$_6$ alkylene-Ar—, optionally substituted —C$_1$-C$_6$ alkylene-C(O)NH—C$_1$-C$_6$ alkylene-Ar—, —(CH$_2$CH$_2$O)$_n$—, optionally substituted C$_1$-C$_{10}$ alkyl, optionally substituted C$_2$-C$_{10}$ alkenyl, optionally substituted C$_2$-C$_{10}$ alkynyl, optionally substituted C$_2$-C$_{20}$ heteroalkyl, wherein n is an integer between 1 and 10 and Ar is C$_6$-C$_{10}$ arylene or C$_5$-C$_{10}$ heteroarylene.

In certain embodiments, L$^1$ includes one or more substituents selected from carboxylic group, sulfonic acid group, ammonium, and amino group.

In some embodiments, L$^2$ includes one or more substituents selected from carboxylic group, sulfonic acid group, ammonium, and amino group.

In some embodiments, L$^3$ includes one or more substituents selected from carboxylic group, sulfonic acid group, ammonium, and amino group.

In certain embodiments of the compounds disclosed herein, the polymerizable moiety is selected from —NH(CO)C(R)CH$_2$, —O(CO)C(R)CH$_2$, and —CHCH$_2$, wherein R is H or C$_1$-C$_3$ alkyl.

In some embodiments of the compounds disclosed herein, R$^{13}$ is H, C$_1$-C$_6$ alkyl, polymerizable moiety, or NIR dye moiety.

In other embodiments of the compounds disclosed herein, R$^{13}$ is an NIR dye moiety.

Exemplary NIR dye moieties of the compounds disclosed herein are selected from cyanine, hemicyanine, fluorone, oxazine, phenanthridine, rhodamine, rosamine, indolium, quinolinium, benzophenoxazine, benzopyrillium, bisindoyl-maleimide, boron-dipyrromethene, boron-aza-dipyrromethene, carbopyronins, perylene, porphyrin, ruthenium complex, lanthanide complex, benzoxanthenium, xanthene, fluorescein, squaraine, coumarin, anthracene, tetracene, pentacene, and pyrene dyes.

In some instances, the NIR dye moiety has the structure selected from:

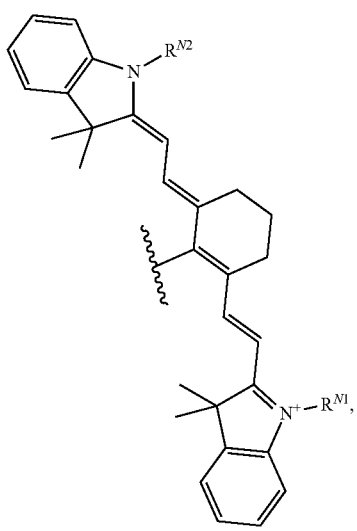

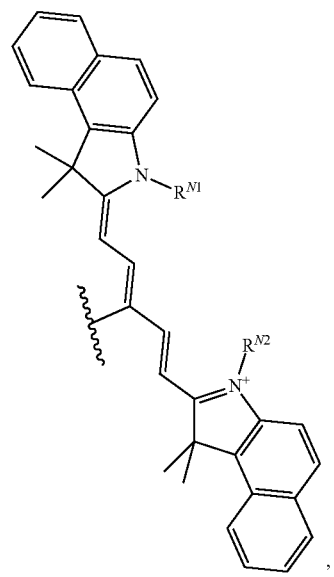

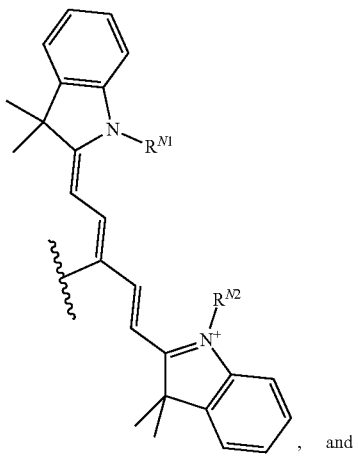

, and

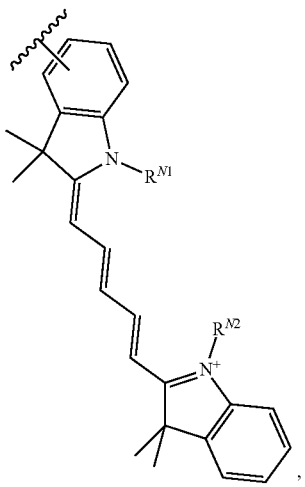

, wherein R$^{N1}$ and R$^{N2}$ are independently C$_1$-C$_{10}$ alkyl optionally substituted with one or more sulfo or carboxylic acid groups, and the wavy lines denote the point of attachment to L$^2$.

In other embodiments, the NIR dye moiety has the structure of:

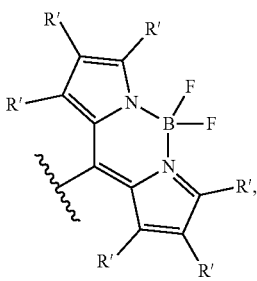

wherein R', at each occurrence, is independently H, optionally substituted C$_1$-C$_{10}$ alkyl, optionally substituted C$_2$-C$_{10}$ alkenyl, optionally substituted C$_2$-C$_{10}$ alkynyl, or optionally substituted C$_2$-C$_{20}$ heteroalkyl.

In yet other embodiments, the NIR dye moiety has the structure of:

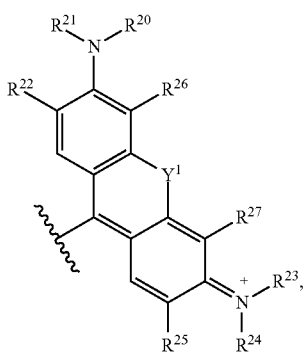

wherein $Y^1$ is selected from O, P(O)R', SiR'R", and NR', wherein R' and R" are independently H or $C_1$-$C_6$ alkyl;

$R^{20}$ and $R^{21}$ are independently H, $C_1$-$C_6$ alkyl, or $R^{21}$ and $R^{20}$, together with the nitrogen atom to which they are attached, form a form a 6- or 5-membered ring optionally substituted with a polymerizable moiety;

$R^{23}$ and $R^{24}$ are independently H, $C_1$-$C_6$ alkyl, or $R^{23}$ and $R^{24}$, together with the nitrogen atom to which they are attached, form a form a 6- or 5-membered ring optionally substituted with a polymerizable moiety;

$R^{22}$ and $R^{25}$ are independently H, $C_1$-$C_6$ alkyl, or $R^{21}$ and $R^{22}$, together with the atoms to which they are attached, form a 6- or 5-membered ring, or $R^{24}$ and $R^{25}$, together with the atoms to which they are attached, form a 6- or 5-membered ring; and $R^{26}$ and $R^{27}$ are independently H, $C_1$-$C_6$ alkyl, or $R^{26}$ and $R^{20}$, together with the atoms to which they are attached, form a 6- or 5-membered ring, or $R^{27}$ and $R^{23}$, together with the atoms to which they are attached, form a 6- or 5-membered ring.

In certain embodiments, $Y^1$ is $SiMe_2$.

In some embodiments of the compounds disclosed herein, Z is an optionally substituted phenylene or anthracenylene.

In some embodiments, the compounds have the structure of Formula II:

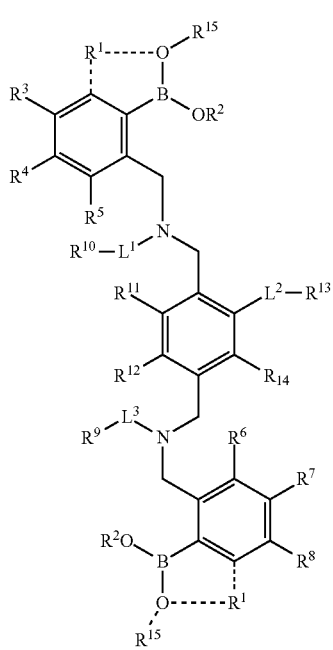

(II)

or an isomer, a tautomer, or a salt thereof, wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $L^1$, $L^2$ and $L^3$ are as defined for compound of Formula I, and wherein the compound includes one or more NIR dye moieties and one or more polymerizable moieties.

In some embodiments, the compounds have the structure of Formula III:

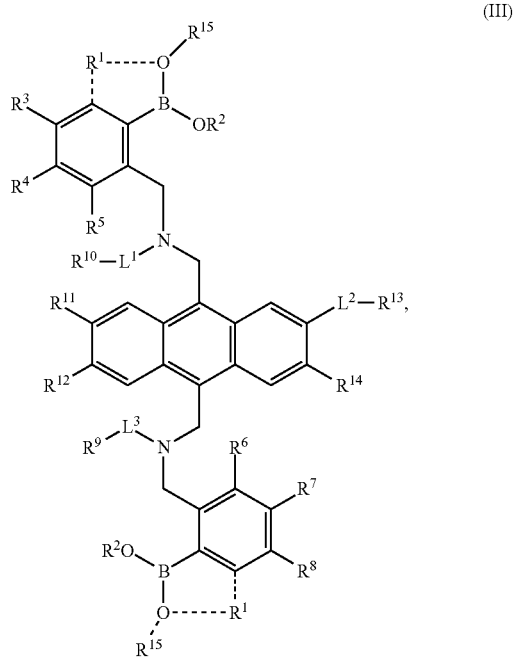

(III)

wherein the dotted lines denote a bond or absence of a bond;

when the dotted line connecting $R^1$ and O is a bond, $R^1$ is $CX^1X^2$ and $R^{15}$ is absent; and when the dotted line connecting $R^1$ and O is absence of a bond, $R^{15}$, at each occurrence, is independently H or $C_1$-$C_6$ alkyl, and $R^1$, at each occurrence, is H, optionally substituted $C_1$-$C_6$ alkyl, optionally substituted $C_2$-$C_6$ alkenyl, optionally substituted $C_2$-$C_6$ alkynyl, optionally substituted $C_2$-$C_{10}$ heteroalkyl, polymerizable moiety, NIR dye moiety, electron-withdrawing group, or electron-donating group;

$X^1$ and $X^2$ are independently H or $C_1$-$C_6$ alkyl;

$R^2$ is H or $C_1$-$C_6$ alkyl;

$R^3$, $R^4$, $R^5$, $R^6$, $R^7$, $R^8$, $R^{11}$, $R^{12}$, and $R^{14}$ are independently H, optionally substituted $C_1$-$C_6$ alkyl, optionally substituted $C_2$-$C_6$ alkenyl, optionally substituted $C_2$-$C_6$ alkynyl, optionally substituted $C_2$-$C_{10}$ heteroalkyl, polymerizable moiety, NIR dye moiety, electron withdrawing group, or electron donating group;

$R^9$, $R^{10}$, and $R^{13}$ are independently H, optionally substituted $C_1$-$C_6$ alkyl, optionally substituted $C_2$-$C_6$ alkenyl, optionally substituted $C_2$-$C_6$ alkynyl, optionally substituted $C_2$-$C_{10}$ heteroalkyl, polymerizable moiety, or NIR dye;

$L^1$, $L^2$, and $L^3$ are independently linker group or absent; and wherein the compound includes one or more NIR dye moieties and one or more polymerizable moieties.

In certain embodiments, the compounds have the structure of Formula IIIF:

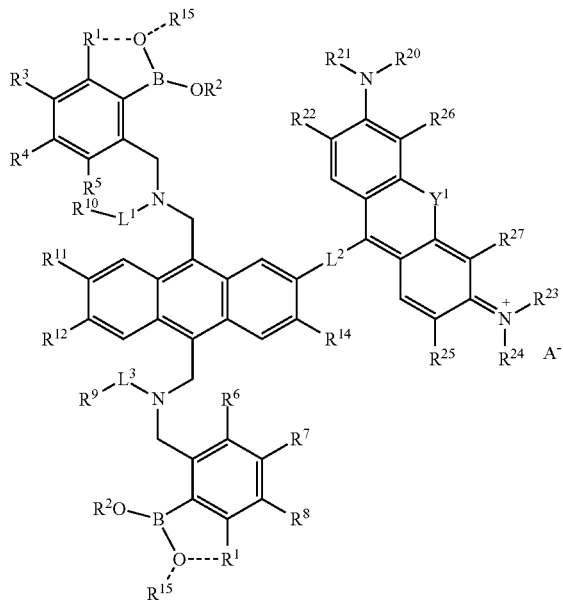

(IIIF)

or an isomer, a tautomer, or a salt thereof,
wherein the dotted lines at each occurrence independently denote a bond or absence of a bond; and when the dotted line connecting $R^1$ and 0 is a bond, $R^1$ is $CX^1X^2$ and $R^{15}$ is absent; and when the dotted line connecting $R^1$ and 0 is absence of a bond, $R^{15}$ is H or $C_1$-$C_6$ alkyl;
$X^1$ and $X^2$ are independently H or $C_1$-$C_6$ alkyl;
$R^2$ is H or $C_1$-$C_6$ alkyl;
$R^3$, $R^4$, $R^5$, $R^6$, $R^7$, $R^8$, $R^{11}$, $R^{12}$, and $R^{14}$ are independently H, $C_1$-$C_6$ alkyl, polymerizable moiety, electron-withdrawing group, or electron-donating group;
$R^9$ and $R^{10}$ are independently H, $C_1$-$C_6$ alkyl, polymerizable moiety, or NIR dye;
$L^1$ and $L^3$ are independently a bond or a linker group selected from optionally substituted $C_1$-$C_{10}$ alkyl, optionally substituted $C_2$-$C_{10}$ alkenyl, optionally substituted $C_2$-$C_{10}$ alkynyl, optionally substituted $C_2$-$C_{20}$ heteroalkyl;
$L^2$ is a bond, optionally substituted $C_1$-$C_{10}$ alkyl, optionally substituted $C_2$-$C_{10}$ alkenyl, optionally substituted $C_2$-$C_{10}$ alkynyl, optionally substituted $C_2$-$C_{20}$ heteroalkyl; —O—, optionally substituted —CH$_2$C$_6$H$_4$O—, amido, amino, optionally substituted $C_6$-$C_{10}$ arylene, or optionally substituted $C_5$-$C_{10}$ heteroarylene;
$Y^1$ is selected from O, P(O)R', SiR'R", and NR', wherein R' and R" are independently H or $C_1$-$C_6$ alkyl;
$R^{20}$ and $R^{21}$ are independently H, $C_1$-$C_6$ alkyl or $R^{21}$ and $R^{20}$, together with the nitrogen atom to which they are attached, form a form a 6- or 5-membered ring optionally substituted with a polymerizable moiety;
$R^{23}$ and $R^{24}$ are independently H, $C_1$-$C_6$ alkyl, or $R^{23}$ and $R^{24}$, together with the nitrogen atom to which they are attached, form a form a 6- or 5-membered ring optionally substituted with a polymerizable moiety;
$R^{22}$ and $R^{25}$ are independently H, $C_1$-$C_6$ alkyl, or $R^{21}$ and $R^{22}$, together with the atoms to which they are attached, form a 6- or 5-membered ring, or $R^{24}$ and $R^{25}$, together with the atoms to which they are attached, form a 6- or 5-membered ring;
$R^{26}$ and $R^{27}$ are independently H, $C_1$-$C_6$ alkyl, or $R^{26}$ and $R^{20}$, together with the atoms to which they are attached, form a 6- or 5-membered ring, or $R^{27}$ and $R^{23}$, together with the atoms to which they are attached, form a 6- or 5-membered ring; and
the compound includes one or more polymerizable moieties.

In some embodiments, $L^2$ is a bond, optionally substituted phenylene,

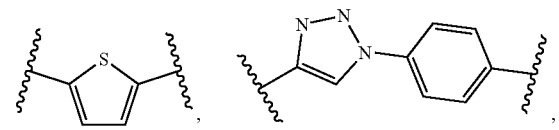 [SMILES: *c1ccc(*)s1 ; *C1=CN(c2ccc(*)cc2)NN1]

or —C$_6$H$_4$—O—.

In certain embodiments, $Y^1$ is SiMe$_2$.
In some embodiments, $R^{10}$ is NHC(O)C(CH$_3$)CH$_2$
In certain embodiments, $R^9$ is NHC(O)C(CH$_3$)CH$_2$.
In some embodiments of the compounds disclosed herein, the NIR dye moiety is a silicon rosamine dye moiety.

In certain embodiments, $L^1$ is optionally substituted $C_1$-$C_{10}$ alkyl or optionally substituted $C_2$-$C_{20}$ heteroalkyl. In certain embodiments, $L^3$ is optionally substituted $C_1$-$C_{10}$ alkyl or optionally substituted $C_2$-$C_{20}$ heteroalkyl.

In some embodiments, $R^{11}$, $R^{14}$, and $R^{12}$ are H. In other embodiments, $R^{22}$, $R^{25}$, $R^{26}$, and $R^{27}$ are H.

In some embodiments, wherein both $R^{15}$ are H, and $R^1$ at each occurrence is independently selected from the group consisting of H; an electron-withdrawing group selected from the group consisting of halogen, C(O)R', COOR', C(O)NH$_2$, NHC(O)R', C(O)NR'R", CF$_3$, CN, SO$_3$H, SO$_2$CF$_3$, SO$_2$R', SO$_2$NR'R", ammonium, alkyl ammonium, and NO$_2$, wherein R' and R" are independently H or $C_1$-$C_6$ alkyl; and electron-donating group selected from the group consisting of NR$^{N1}$R$^{N2}$, OR', NHC(O)R', OC(O)R', phenyl, and vinyl, wherein R$^{N1}$, R$^{N2}$, and R' are independently H or $C_1$-$C_6$ alkyl.

Another aspect relates to a polymer including, as a monomer repeat unit, the residue of a compound of Formulae I-IIIH The polymers provided herein can be luminescent biocompatible hydrogels.

A further aspect relates to various luminescent sensors including the polymers provided herein for detecting an analyte, e.g., glucose, in vivo or in vitro. The sensors can be in the form of a powder, fabric (e.g., bandage), needle, rod, disk, or any other suitable form.

In some embodiments, the luminescent sensors provided herein are tissue-integrating or include a tissue-integrating scaffold and produce a detectable signal in the presence of the analyte, for example, the sensors provide detection of the analyte when placed (e.g., implanted) into a tissue of a subject. The tissue-integrating sensors as described herein can provide long-term detection of the analyte(s).

DETAILED DESCRIPTION OF THE INVENTION

Figure 1:
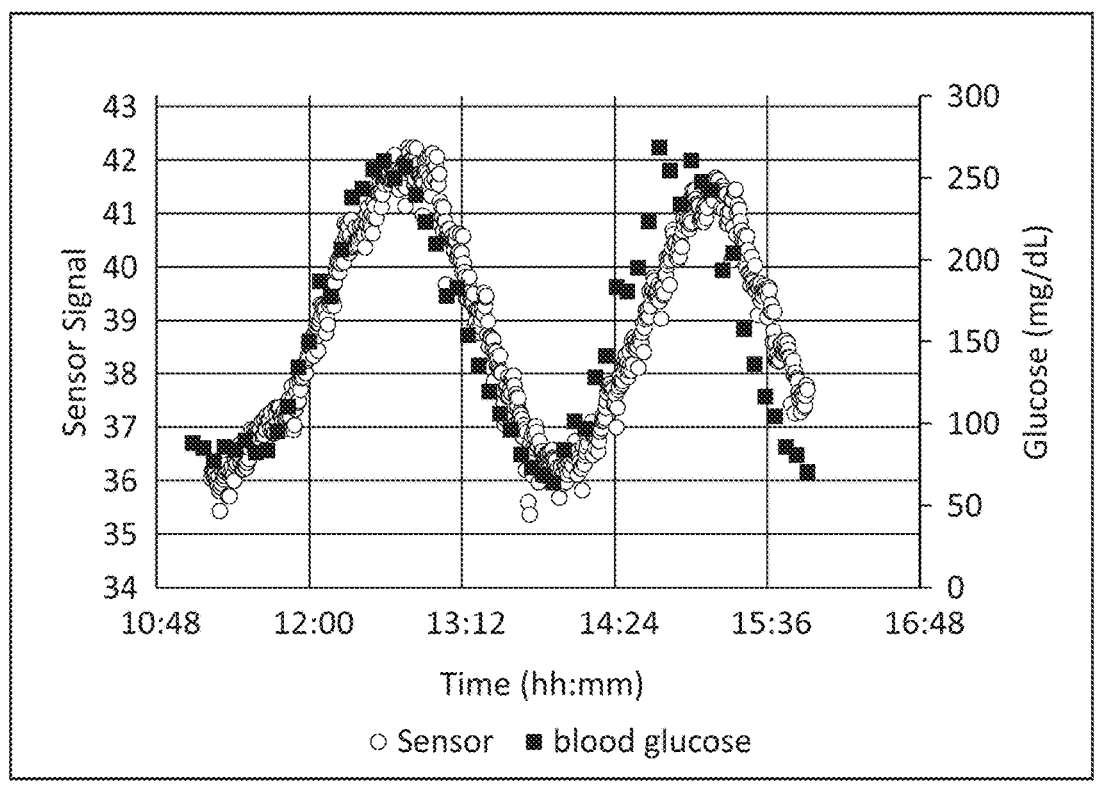
FIG. 1 depicts performance of a glucose sensor prepared by co-polymerization of an exemplary compound (compound 21) implanted in the subcutaneous tissue of a pig.

Described herein are polymerizable luminescent dyes useful for incorporation into polymers and polymers including covalently attached, e.g., as monomeric units, residues of the dyes. The dyes and the polymers are useful in sensing and imaging applications, for example, to provide accurate and optionally long term measurements of glucose in vivo.

Additionally, described herein are sensors including the polymers described herein. The sensors can be implanted into a tissue of a subject and used for long-term or short-term continuous and semi-continuous collection of data of various biochemical analytes, optionally without the use of implantable hardware of any type and/or enzymatic and electrochemical detection methods. In one aspect, the sensors are tissue integrating, e.g., allow capillaries to grow in close proximity to all regions of the sensor (e.g., on the surface and inside), which results in accurate analyte measurements, including over long term.

Advantages of the dyes and luminescent polymers provided herein include, but are not limited to: (1) excitation and emission wavelengths in the optical window of the skin (approximately 550 nm to 1100 nm) allowing detection of analytes deep within a tissue or an organ; (2) high signal-to-noise ratio; (3) large Stokes shifts and emission; (4) photostablity, e.g., the dyes and/or polymers do not undergo rapid photobleaching.

Advantages of the sensors described herein include, but are not limited to: (1) providing devices that generate stable signal over a long period of time (e.g., greater than a week, greater than 10 days, greater than 15 days, greater than 20 days, greater than a month, greater than 2 months, greater than 3 months, or greater than 6 months), (2) providing devices that are placed or implanted and integrate into the subject's tissue (e.g., through tissue and/or capillary in-growth); (3) providing devices which can be implanted through syringe injection or trocar injection, meaning that no surgery is required to put the sensing media in place in the body; (4) providing devices that do not include sensor electronics in the body; (5) providing devices that accurately assess analyte (e.g., glucose) concentration for long periods of time (e.g., greater than a week, weeks, months, or years) and/or (6) providing devices of small dimensions which will give result in increased patient comfort and better acceptance by the body.

It must be noted that, as used in this specification and the appended claims, the singular forms "a", "an", and "the" include plural referents unless the content clearly dictates otherwise. Thus, for example, reference to a sensor including "a sensing moiety" includes devices including two or more sensing moieties. Likewise, reference to "an analyte" refers to two or more analytes.

Definitions

The term "tissue integrating" refers to a material (e.g., scaffold) which, when integrated into living tissue remains in close proximity with the blood vessels of the tissue (e.g., capillaries).

By "long-term" it is meant that the implant senses the analyte for greater than about 7 days, greater than about four weeks, greater than about one or more weeks, greater than about six weeks, greater than about one or more months, greater than about 100 days, or greater than about one or more years.

By "biodegradable" or "bioabsorbable" it is meant that the material is capable of being broken down by the subject's body over a period of time, ranging from days to weeks to months or years.

By "hydrogel" it is meant a material that absorbs a solvent (e.g. water), undergoes rapid swelling without discernible dissolution, and maintains three-dimensional networks capable of reversible deformation.

The term "stimuli-responsive" refers to substances, e.g., polymers, that change their physical state, e.g., undergo a phase transition, when exposed to an external stimulus or according to the environment they are in. Non-limiting examples of such polymers are "smart polymers" (Kumar A. et al., Smart polymers: Physical forms and bioengineering applications. *Prog. Polym. Sci.* 32 (2007) 1205-1237).

As used herein, an electron-withdrawing group or EWG is a moiety, e.g., an atom or group, which draws electron density from the neighboring atoms towards itself, usually by resonance or inductive effects. An electron-donating group or EDG is a moiety, e.g., an atom or group, which releases electron density to the neighboring atoms from itself, usually by resonance or inductive effects. Non-limiting examples of EWG are halogen, C(O)R', COOR', C(O)NH$_2$, NHC(O)R', C(O)NR'R", CF$_3$, CN, SO$_3$H, SO$_2$CF$_3$, SO$_2$R', SO$_2$NR'R", alkyl ammonium, and NO$_2$, wherein R' and R" are independently H or C$_1$-C$_6$ alkyl. Non-limiting examples of EDG are NR$^{N1}$R$^{N2}$, OR', NHC(O)R', OC(O)R', phenyl, and vinyl, wherein R$^{N1}$, R$^{N2}$, and R' are independently H or C$_1$-C$_6$ alkyl.

As used herein, a "linker group" or a "linker" is an n-valent moiety that connects n other moieties within a molecule. Typically, a linker group is a divalent moiety connecting two other moieties within a molecule.

The term "acyl," as used herein, refers to a group of the form —C(O)R, wherein R is H or an optionally substituted group selected from alkyl, alkenyl, alkynyl, heteroalkyl, heteroalkenyl, heteroalkynyl, aryl, and heteroaryl.

As used herein, the terms "alkyl," "alkenyl," and "alkynyl" include straight-chain, branched-chain and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it can be represented as 1-10C, C$_1$-C$_{10}$, C1-C10, or C1-10. The term "heteroalkyl," "heteroalkenyl," and "heteroalkynyl," as used herein, mean the corresponding hydrocarbons wherein one or more chain carbon atoms have been replaced by a heteroatom. Exemplary heteroatoms include N, O, S, and P. When heteroatoms are allowed to replace carbon atoms, for example, in heteroalkyl groups, the numbers describing the group, though still written as e.g. C1-C10, represent the sum of the number of carbon atoms in the cycle or chain plus the number of such heteroatoms that are included as replacements for carbon atoms in the cycle or chain being described.

Alkyl, alkenyl, and alkynyl substituents may contain 1-10 carbon atoms (alkyl) or 2-10 carbon atoms (alkenyl or alkynyl). In an embodiment, they contain 1-8 carbon atoms (alkyl) or 2-8 carbon atoms (alkenyl or alkynyl). Sometimes they contain 1-6 carbon atoms (alkyl) or 2-6 carbon atoms (alkenyl or alkynyl). Sometimes they contain 1-4 carbon atoms (alkyl) or 2-4 carbon atoms (alkenyl or alkynyl). A single group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond.

Alkyl, alkenyl, and alkynyl groups can be optionally substituted to the extent that such substitution makes sense chemically. Substituents include, but are not limited to, halogens (F, Cl, Br, I), =O, =N—CN, =N—OR, =NR, OR, NR$_2$, SR, SO$_2$R, SO$_2$NR$_2$, NRSO$_2$R, NRCONR$_2$, NRC(O)OR, NRC(O)R, CN, C(O)OR, C(O)NR$_2$, OC(O)R, C(O)R, and NO$_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halogens (F, Cl, Br, I), =O, =N—CN, =N—OR', =NR', OR', NR'$_2$, SR', SO$_2$R', SO$_2$NR'$_2$, NR'SO$_2$R', NR'CONR'$_2$, NR'C(O)OR', NR'C(O)R', CN, C(O)OR', C(O)NR'$_2$, OC(O)R', C(O)R', and NO$_2$, wherein each R' is independently H, C1-C8 alkyl, C2-C8 heteroalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group.

While "alkyl" as used herein includes cycloalkyl and cycloalkylalkyl groups, the term "cycloalkyl" is used herein to describe a carbocyclic non-aromatic group that is connected via a ring carbon atom, and "cycloalkylalkyl" is used to describe a carbocyclic non-aromatic group that is connected to the molecule through an alkyl linker. Similarly, "heterocyclyl" is used to identify a non-aromatic cyclic group that contains at least one heteroatom as a ring member and that is connected to the molecule via a ring atom, which may be C or N; and "heterocyclylalkyl" may be used to describe such a group that is connected to another molecule through an alkylene linker. As used herein, these terms also include rings that contain a double bond or two, as long as the ring is not aromatic.

"Aromatic" or "aryl" substituent or moiety refers to a monocyclic, fused bicyclic, a fused tricyclic, or a fused tetracyclic moiety having the well-known characteristics of aromaticity; examples include phenyl, naphthyl, and anthracenyl. Similarly, "heteroaromatic" and "heteroaryl" refer to such aromatic ring systems which contain as ring members one or more heteroatoms. Suitable heteroatoms include N, O, and S, inclusion of which permits aromaticity in 5-membered rings as well as 6-membered rings. Heteroaromatic systems include monocyclic C5-C6 heterorayls such as pyridyl, pyrimidyl, pyrazinyl, thienyl, furanyl, pyrrolyl, pyrazolyl, thiazolyl, oxazolyl, and imidazolyl, and fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, monocyclic heteroaryls contain 5-6 ring members, and the bicyclic heteroaryls contain 8-10 ring members.

Aryl and heteroaryl moieties may be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halogens (F, Cl, Br, I), OR, NR$_2$, SR, SO$_2$R, SO$_2$NR$_2$, NRSO$_2$R, NRCONR$_2$, NRC(O)OR, NRC(O)R, CN, C(O)OR, C(O)NR$_2$, OC(O)R, C(O)R, and NO$_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C6-C10 aryl, C5-C10 heteroaryl, C7-C12 arylalkyl, or C6-C12 heteroarylalkyl, and each R is optionally substituted as described above for alkyl groups. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

"Optionally substituted," as used herein, indicates that the particular group being described may have one or more hydrogen substituents replaced by a non-hydrogen substituent. In some optionally substituted groups or moieties, all hydrogen substituents are replaced by a non-hydrogen substituent. If not otherwise specified, the total number of such substituents that may be present is equal to the number of H atoms present on the unsubstituted form of the group being described. Where an optional substituent is attached via a double bond, such as a carbonyl oxygen or oxo (=O), the group takes up two available valences, so the total number of substituents that may be included is reduced according to the number of available valences.

A. Luminescent Compounds Including a NIR Dye Moiety and One or More Polymerizable Groups One aspect relates to a compound of Formula I:

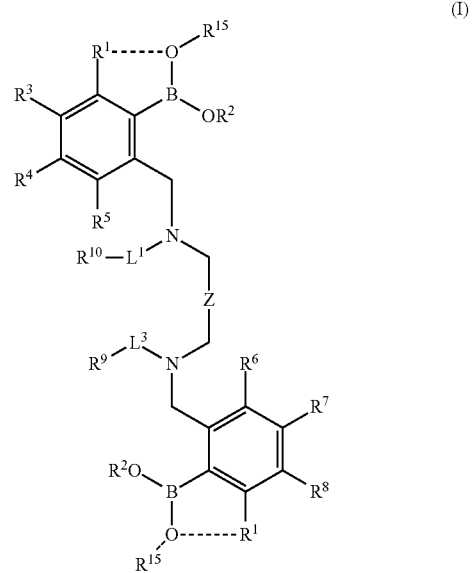

(I)

or an isomer, a tautomer, or a salt thereof, wherein the dotted lines denote a bond or absence of a bond, and when the dotted line connecting $R^1$ and O is a bond, $R^1$ is $CX^1X^2$ and $R^{15}$ is absent; and when the dotted line connecting $R^1$ and O is absence of a bond, $R^{15}$, at each occurrence, is independently H or $C_1$-$C_6$ alkyl, and $R^1$ at each occurrence, is selected from H, optionally substituted $C_1$-$C_6$ alkyl, optionally substituted $C_2$-$C_6$ alkenyl, optionally substituted $C_2$-$C_6$ alkynyl, optionally substituted $C_2$-$C_{10}$ heteroalkyl, polymerizable moiety, NIR dye moiety, electron-withdrawing group, and electron-donating group;

$R^2$ is H or $C_1$-$C_6$ alkyl;

Z is a $C_6$-$C_{14}$ arylene optionally substituted with $R^{11}$, $R^{12}$, $R^{14}$, and $L^2R^{13}$;

$R^3$, $R^4$, $R^5$, $R^6$, $R^7$, $R^8$, $R^{11}$, $R^{12}$, $R^{13}$, and $R^{14}$ are independently selected from H, $C_1$-$C_6$ alkyl, polymerizable moiety, NIR dye moiety, electron withdrawing group, and electron donating group;

$R^9$ and $R^{10}$ are independently selected from H, $C_1$-$C_6$ alkyl, polymerizable moiety, and NIR dye;

$X^1$ and $X^2$ are independently H, halogen, or $C_1$-$C_6$ alkyl;

$L^1$, $L^2$, and $L^3$ are independently linker group or absent;

the dotted line denotes a bond or absence of a bond, and wherein the compound includes one or more NIR dye moieties and one or more polymerizable moieties.

In certain embodiments of Formula I, the compound has a structure of Formula IA, IB, or IC:

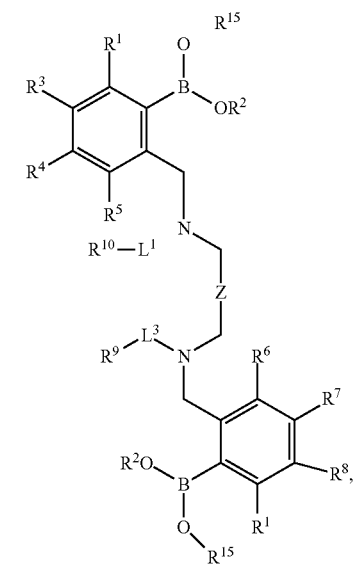

(IA)

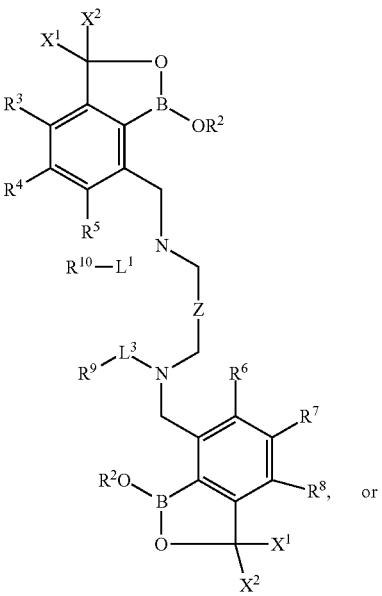

(IB)

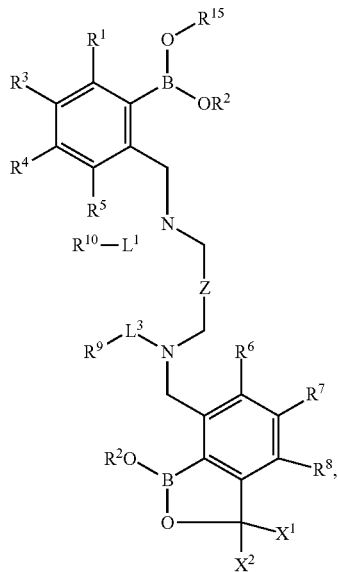

(IC)

or an isomer, a tautomer, or a salt thereof, wherein all substituents are as defined above for Formula I.

In other embodiments of Formula I, IA, IB, or IC, the compound includes 1 NIR dye moiety. In other embodiments of Formula I, IA, IB, or IC, the compound includes 1 polymerizable moiety. In still other embodiments of Formula I, IA, IB, or IC, the compound includes 2 polymerizable moieties. In certain embodiments of Formula I, IA, IB, or IC, the polymerizable moieties have the same structure. In other embodiments of Formula I, IA, IB, or IC, the polymerizable moieties have different structures.

In some embodiments of Formula I, IA, IB, or IC, the electron-withdrawing group is selected from the group consisting of halogen, C(O)R', COOR', C(O)NH$_2$, NHC(O)R', C(O)NR'R", CF$_3$, CN, SO$_3$H, SO$_2$CF$_3$, SO$_2$R', SO$_2$NR'R", ammonium, alkyl ammonium, and NO$_2$, and wherein R' and R" are independently H or $C_1$-$C_6$ alkyl.

In other embodiments of Formula I, IA, IB, or IC, the electron-donating group is selected from the group consisting of NR$^{N1}$R$^{N2}$, OR', NHC(O)R', OC(O)R', phenyl, and vinyl, wherein R$^{N1}$, R$^{N2}$, and R' are independently H or $C_1$-$C_6$ alkyl.

In other embodiments of Formula I, IA, IB, or IC, $L^1$ is a linker group selected from optionally substituted amino, optionally substituted amido, —O—, optionally substituted $C_1$-$C_6$ alkylene, optionally substituted $C_2$-$C_6$ alkenylene, optionally substituted $C_2$-$C_6$ alkynylene, optionally substituted $C_2$-$C_{20}$ heteroalkylene, optionally substituted C6-$C_{10}$ arylene, optionally substituted $C_2$-$C_{10}$ heteroarylene, and a combination thereof.

In other embodiments of Formula I, IA, IB, or IC, $L^2$ is a linker group selected from optionally substituted amino, optionally substituted amido, —O—, optionally substituted $C_1$-$C_6$ alkylene, optionally substituted $C_2$-$C_6$ alkenylene, optionally substituted $C_2$-$C_6$ alkynylene, optionally substituted $C_2$-$C_{20}$ heteroalkylene, optionally substituted $C_6$-$C_{10}$ arylene, optionally substituted $C_2$-$C_{10}$ heteroarylene, and a combination thereof.

In certain embodiments of Formula I, IA, IB, or IC, $L^3$ is a linker group selected from optionally substituted amino, optionally substituted amido, —O—, optionally substituted $C_1$-$C_6$ alkylene, optionally substituted $C_2$-$C_6$ alkenylene, optionally substituted $C_2$-$C_6$ alkynylene, optionally substituted $C_2$-$C_{20}$ heteroalkylene, optionally substituted $C6$-$C_{10}$ arylene, optionally substituted $C_2$-$C_{10}$ heteroarylene, and a combination thereof.

In other embodiments of Formula I, IA, IB, or IC, $L^1$, $L^2$, and $L^3$ are independently optionally substituted with one or more groups selected from carboxylic group, sulfonic acid group, ammonium, amino group, and a combination thereof.

In still other embodiments of Formula I, IA, IB, or IC, $L^1$, $L^2$, and $L^3$ independently include one or more substituents selected from carboxylic group, sulfonic acid group, ammonium, and amino group.

In some embodiments of Formula I, IA, IB, or IC, $L^1$, $L^2$, and $L^3$ are independently optionally substituted —$C_1$-$C_6$ alkylene-Ar—, optionally substituted $C_2$-$C_6$ alkenylene-Ar—, optionally substituted $C_2$-$C_6$ alkynylene-Ar—, optionally substituted —C(O)NH—$C_1$-$C_6$ alkylene-Ar—, optionally substituted —C1-C6 alkylene-C(O)NH—$C_1$-$C_6$ alkylene-Ar—, —$(CH_2CH_2O)_n$—, wherein n is an integer between 1 and 10 and Ar is an optionally substituted phenylene or an optionally substituted 5-membered heteroarylene. In some of the above embodiments, the one or more of the linker groups is optionally substituted with one or more groups selected from carboxylic group, sulfonic acid group, ammonium, amino group, and a combination thereof.

In particular embodiments of Formula I, IA, IB, or IC, the one or more polymerizable moiety includes a group selected from —NH(CO)C(R)CH$_2$, —O(CO)C(R)CH$_2$, and —CHCH$_2$, wherein R is H or $C_1$-$C_3$ alkyl. In certain embodiments of Formula I, IA, IB, or IC, the one or more polymerizable moiety is selected from —NH(CO)C(R)CH$_2$, —O(CO)C(R)CH$_2$, and —CHCH$_2$, wherein R is H or $C_1$-$C_3$ alkyl.

In some embodiments of Formula I, IA, IB, or IC, $R^{13}$ is H, $C_1$-$C_6$ alkyl, polymerizable moiety, or NIR dye moiety.

In other embodiments of Formula I, IA, IB, or IC, $R^{13}$ is an NIR dye moiety.

In some embodiments of Formula I, IA, IB, or IC, the one or more NIR dye moiety is cyanine, hemicyanine, fluorone, oxazine, phenanthridine, rhodamine, rosamine, indolium, quinolinium, benzophenoxazine, benzopyrillium, bisindoylmaleimide, boron-dipyrromethene, boron-aza-dipyrromethene, carbopyronins, perylene, porphyrin, ruthenium complex, lanthanide complex, benzoxanthenium, xanthene, fluorescein, squaraine, coumarin, anthracene, tetracene, pentacene, or pyrene dye residue.

In certain embodiments of Formula I, IA, IB, or IC, the NIR dye has excitation and emission wavelengths in the optical window of the skin. In other embodiments of Formula I, IA, IB, or IC, NIR dye has an absorbtion maximum between about 500 nm and about 900 nm, between about 600 nm and about 1000 nm, and between about 500 nm and about 1000 nm. In yet other embodiments of Formula I, IA, IB, or IC, the NIR dye has an emission maximum between about 550 nm and about 900 nm, between about 600 nm and about 1000 nm, and between about 550 nm and about 1100 nm. In certain embodiments of Formula I, IA, IB, or IC, the compound itself is a NIR dye and has an absorbtion maximum between about 550 nm and about 1000 nm and an emission maximum between about 600 nm and about 1100 nm. an absorption maximum greater than 500 nm, greater than 550 nm, greater than 600 nm, greater than 650 nm, greater than 700 nm. In certain embodiments of Formula I, IA, IB, or IC, the compound itself is a NIR dye and has an absorption maximum greater than 500 nm, greater than 550 nm, greater than 600 nm, greater than 650 nm, greater than 700 nm. In other embodiments of Formula I, IA, IB, or IC, the compound itself is a NIR dye and has an emission maximum greater than 550 nm, greater than 600 nm, greater than 650 nm, greater than 700 nm, greater than 800 nm, greater than 900 nm, greater than 1000 nm, greater than 1100 nm.

In particular embodiments of Formula I, IA, IB, or IC, Z is an optionally substituted phenylene.

In other embodiments of Formula I, IA, IB, or IC, compound has the structure of Formula II:

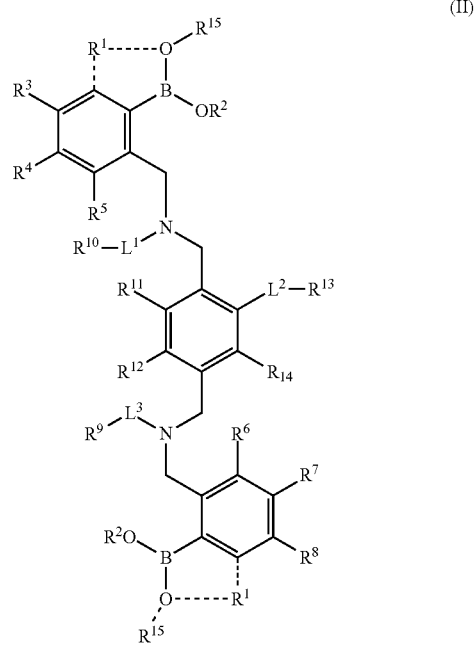

(II)

or an isomer, a tautomer, or a salt thereof,
wherein $R^1$, $R^2$, $R^3$, $R^4$, $R^5$, $R^6$, $R^7$, $R^8$, $R^9$, $R^{10}$, $R^{11}$, $R^2$, $R^{13}$, $R^{14}$, $R^{15}$, $L^1$, $L^2$ and $L^3$ are as defined for compound of Formula I, IA, IB, or IC, and wherein the compound includes one or more NIR dye moieties and one or more polymerizable moieties.

In other embodiments of Formula II, $R^3$, $R^5$, $R^6$, and $R^8$ are H.

In some embodiments of Formula II, the compound has a structure of Formula IIA:

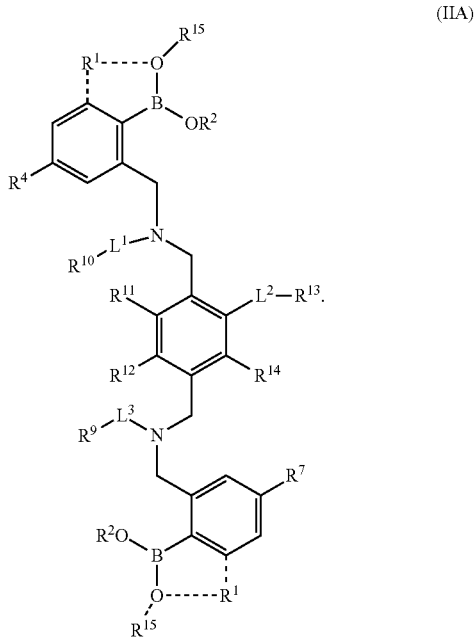

(IIA)

In certain embodiments of Formula II or IIA, $L^2$ is absent and $R^{13}$ is H. In other embodiments of Formula II or IIA, $R^4$, $R^7$, $R^{11}$, $R^{12}$, and $R^{14}$ are H. In yet other embodiments of Formula II or IIA, $L^3$ is optionally substituted $C_1$-$C_6$ alkylene. In particular embodiments of Formula II or IIA, $R^9$ is —NHC(O)CH$_3$CH$_2$.

In certain embodiments of Formula II or IIA, the dotted line between $R^1$ and O is absence of a bond, $R^{15}$ is absent, and $R^1$ and $R^2$ are H.

In some embodiments of Formula II or IIA, $R^{13}$ is H, $C_1$-$C_6$ alkyl, polymerizable moiety, or NIR dye moiety.

In other embodiments of Formula II or IIA, $R^{13}$ is an NIR dye moiety.

In certain embodiments of Formula II or IIA, the compound has a structure of Formula IIB:

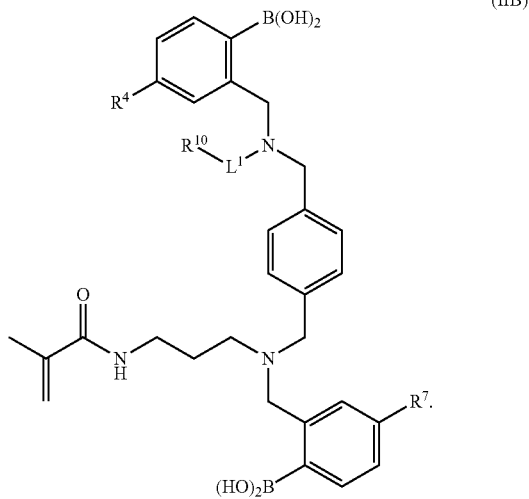

(IIB)

In some embodiments of Formula II, IIA, or IIB, the compound is selected from compounds 1, 2, 3, 4, 5, 6, or 7 of Table 1.

In certain embodiments of Formula I, IA, IB, or IC, the compound has a structure of Formula III:

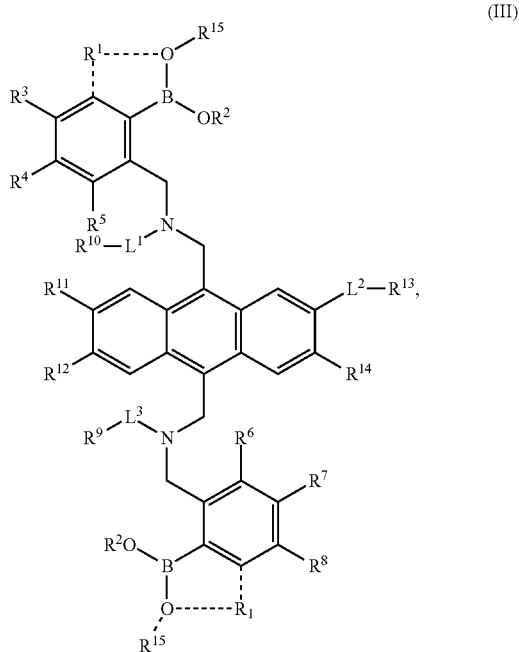

(III)

or an isomer, a tautomer, or a salt thereof, wherein the dotted lines denote a bond or absence of a bond;

when the dotted line connecting $R^1$ and O is a bond, $R^1$ is $CX^1X^2$ and $R^5$ is absent; and when the dotted line connecting $R^1$ and O is absence of a bond, $R^{15}$, at each occurrence, is independently H or $C_1$-$C_6$ alkyl, and $R^1$, at each occurrence, is selected from independently H, $C_1$-$C_6$ alkyl, polymerizable moiety, NIR dye moiety, electron withdrawing group, or electron donating group;

$X^1$ and $X^2$ are independently H or $C_1$-$C_6$ alkyl;

$R^2$ is H or $C_1$-$C_6$ alkyl;

Z is a $C_6$-$C_{14}$ arylene optionally substituted with $R^{11}$, $R^{12}$, $R^{14}$, and $L^2R^{13}$;

$R^3$, $R^4$, $R^5$, $R^6$, $R^7$, $R^8$, $R^{11}$, $R^{12}$, $R^{13}$, and $R^{14}$ are independently H, $C_1$-$C_6$ alkyl, polymerizable moiety, NIR dye moiety, electron-withdrawing group, or electron-donating group;

$R^9$ and $R^{10}$ are independently H, $C_1$-$C_6$ alkyl, polymerizable moiety, or NIR dye;

$L^1$, $L^2$, and $L^3$ are independently linker group or absent;

the dotted line denotes a bond or absence of a bond, and wherein the compound includes one or more NIR dye moieties and one or more polymerizable moieties.

In particular embodiments of Formula III, the electron-withdrawing group is selected from the group consisting of halogen, C(O)R', COOR', C(O)NH$_2$, NHC(O)R', C(O)NR'R", CF$_3$, CN, SO$_3$H, SO$_2$CF$_3$, SO$_2$R', ammonium, alkyl ammonium, and NO$_2$, and wherein R' and R" are independently H or $C_1$-$C_6$ alkyl. In other embodiments of Formula III, electron-donating group is selected from the group consisting of NR$^{N1}$R$^{N2}$ OR', NHC(O)R', OC(O)R', phenyl, and vinyl, wherein R$^{N1}$, R$^{N2}$, and R' are independently H or $C_1$-$C_6$ alkyl. In yet other embodiments of Formula III, $L^1$ is a linker group selected from optionally substituted amino, optionally substituted amido, —O—, optionally substituted C1-$C_6$ alkylene, optionally substituted $C_2$-$C_6$ alkenylene, optionally substituted $C_2$-$C_6$ alkynylene, optionally substituted $C_2$-$C_{20}$ heteroalkylene, $C_6$-$C_{10}$ arylene, optionally substituted $C_2$-$C_{10}$ heteroarylene, and a combination thereof. In certain embodiments of Formula III, wherein $L^2$ is a linker group selected from optionally substituted amino, optionally substituted amido, —O—, optionally substituted $C_1$-$C_6$ alkylene, optionally substituted $C_2$-$C_6$ alkenylene, optionally substituted $C_2$-$C_6$ alkynylene, optionally substituted $C_2$-$C_{20}$ heteroalkylene, $C_6$-$C_{10}$ arylene, optionally substituted $C_2$-$C_{10}$ heteroarylene, and a combination thereof. In some embodiments of Formula III, $L^3$ is a linker group selected from optionally substituted amino, optionally substituted amido, —O—, optionally substituted C1-$C_6$ alkylene, optionally substituted $C_2$-$C_6$ alkenylene, optionally substituted $C_2$-$C_6$ alkynylene, optionally substituted $C_2$-$C_{20}$ heteroalkylene, $C_6$-$C_{10}$ arylene, optionally substituted $C_2$-$C_{10}$ heteroarylene, and a combination thereof. In certain embodiments of Formula III, the linker group includes a substituent selected from carboxylic group, sulfonic acid group, ammonium, and amino group. In certain embodiments of Formula III, the polymerizable moiety is selected from —NH(CO)C(R)CH$_2$, —O(CO)C(R)CH$_2$, and —CHCH$_2$, wherein R is H or $C_1$-$C_3$ alkyl.

In some embodiments of Formula III, the NIR dye moiety is cyanine, hemicyanine, fluorone, oxazine, phenanthridine, rhodamine, rosamine, indolium, quinolinium, benzophenoxazine, benzopyrillium, bisindoylmaleimide, boron-dipyrromethene, boron-aza-dipyrromethene, carbopyronins, perylene, porphyrin, ruthenium complex, lanthanide complex, benzoxanthenium, xanthene, fluorescein, squaraine, coumarin, anthracene, tetracene, pentacene, or pyrene dye residues.

In some embodiments of Formula III, $R^{13}$ is H, $C_1$-$C_6$ alkyl, polymerizable moiety, or NIR dye moiety.

In other embodiments of Formula III, $R^{13}$ is an NIR dye moiety.

In other embodiments of Formula III, the NIR dye moiety has excitation and emission wavelengths in the optical window of the skin. In particular embodiments of Formula III, the NIR dye moiety has an absorbtion maximum between about 500 nm and about 900 nm, between about 600 nm and about 1000 nm, and between about 500 nm and about 1000 nm. In other embodiments of Formula III, the NIR dye has an emission maximum between about 550 nm and about 900 nm, between about 600 nm and about 1000 nm, and between about 550 nm and about 1100 nm. In certain embodiments of Formula III, compound itself is a NIR luminescent dye and has an absorbtion maximum between about 550 nm and about 1000 nm and an emission maximum between about 600 nm and about 1100 nm. an absorption maximum greater than 500 nm, greater than 550 nm, greater than 600 nm, greater than 650 nm, greater than 700 nm. In other embodiments of Formula III, the compound has an absorption maximum greater than 500 nm, greater than 550 nm, greater than 600 nm, greater than 650 nm, greater than 700 nm. In yet other embodiments of Formula III, the compound has an emission maximum greater than 550 nm, greater than 600 nm, greater than 650 nm, greater than 700 nm, greater than 800 nm, greater than 900 nm, greater than 1000 nm, greater than 1100 nm In certain embodiments of Formula III, $R^3$, $R^5$, $R^6$, and $R^8$ are H.

In certain embodiments of Formula III, the compound has a structure of Formula IIIA:

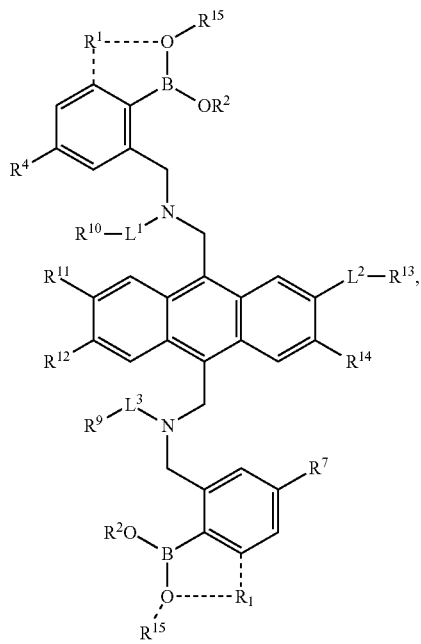

(IIIA)

or an isomer, a tautomer, or a salt thereof.

In certain embodiments of Formula III or IIIA, $L^2$ is absent and $R^{13}$ is H. In other embodiments of Formula III or IIIA, $R^4$, $R^7$, $R^{11}$, $R^{12}$, and $R^{14}$ are H. In some embodiments of Formula III or IIIA, $L^3$ is optionally substituted $C_1$-$C_6$ alkylene. In still other embodiments of Formula III or IIIA, $R^9$ is —NHC(O)C(CH$_3$)CH$_2$. In certain embodiments of Formula III or IIIA, the dotted line connecting $R^1$ and O denotes absence of a bond and $R^1$ and $R^2$ are H.

In some embodiments of Formula IIIA, $R^{13}$ is H, $C_1$-$C_6$ alkyl, polymerizable moiety, or NIR dye moiety.

In other embodiments of Formula IIIA, $R^{13}$ is an NIR dye moiety.

In certain embodiments of Formula III or IIIA, the compound has a structure of Formula IIIB:

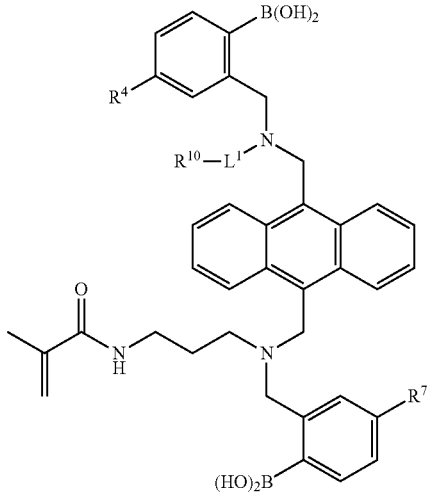

(IIIB)

or an isomer, a tautomer, or a salt thereof.

In certain embodiments of Formula IIIB, the compound is selected from compounds 8, 9, 10, 11, 12, or 13 of Table 1.

In certain embodiments of Formula III, the compound has a structure of Formula IIIC:

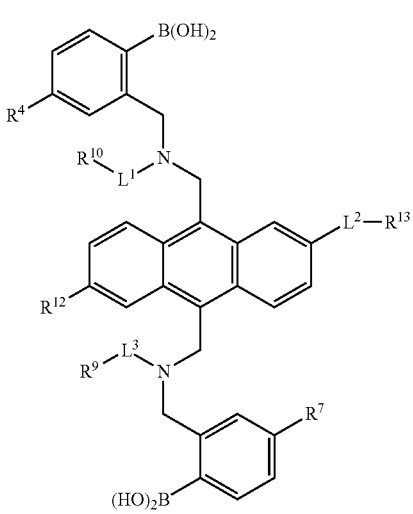

(IIIC)

or an isomer, a tautomer, or a salt thereof.

In some embodiments of Formula IIIC, $R^{13}$ is H, $C_1$-$C_6$ alkyl, polymerizable moiety, or NIR dye moiety.

In other embodiments of Formula IIIC, $R^{13}$ is an NIR dye moiety.

In some embodiments of Formula III or IIIC, $L^2$ is —CHCH— and $R^{13}$ is a NIR dye moiety. In other embodiments of Formula III or IIIC, $R^4$ and $R^7$ are H.

In some embodiments of Formula IIIC, the compound is compound 14, 15, 16, 17, or 18 of Table 1.

In certain embodiments of Formula III, the compound has a structure of Formula IIID:

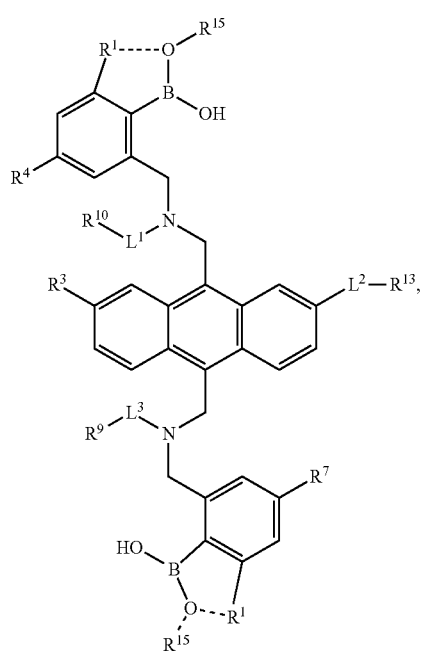

(IIID)

or an isomer, a tautomer, or a salt thereof, wherein the dotted line connecting $R^1$ and O is a bond or absence of a bond;

$R^1$ is H or $CX^1X^2$;

$R^{15}$ is H or absent;

$X^1$ and $X^2$ are independently H or $C_1$-$C_6$ alkyl;

$L^1$, $L^2$, and $L^3$ are linker moieties independently selected from a bond, optionally substituted $C_1$-$C_{10}$ alkyl, optionally substituted $C_2$-$C_{10}$ alkenyl, optionally substituted $C_2$-$C_{10}$ alkynyl, optionally substituted $C_2$-$C_{20}$ heteroalkyl; —$CH_2C_6H_4O$—, $C_2$-$C_{20}$ PEG linker, amido, amino, and phenylene;

$R^3$, $R^4$, and $R^7$ are independently H, $C_1$-$C_6$ alkyl, electron-withdrawing group, or electron-donating group;

$R^{13}$ is a NIR dye moiety; and $R^{10}$ and $R^9$ are H or polymerizable moiety.

In some embodiments of Formula III or IIID, $L^1$ and $L^2$ are independently $C_1$-$C_6$ alkylene. In other embodiments of Formula III or IIID, $R^{10}$ and $R^9$ are $NHC(O)C(CH_3)CH_2$. In yet other embodiments of Formula III or IIID, $R^3$, $R^4$, and $R^{14}$ are H. In certain embodiments of Formula III or IIID, the compound is compound 19, 20, 21, 22, 23, 24, 25, 26, 27, 28, 29, 30, 31, 32, 33, 34, or 35 of Table 1.

In certain embodiments of Formula III, the compound has a structure of Formula IIIE:

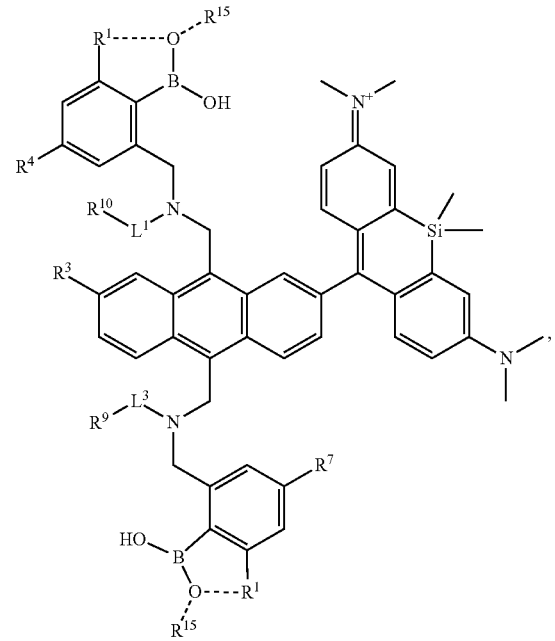

(IIIE)

or an isomer, a tautomer, or a salt thereof, wherein the dotted line connecting $R^1$ and O is a bond or absence of a bond;

$R^1$ is H or $CX^1X^2$;

$R^{15}$ is H or absent;

$X^1$ and $X^2$ are independently H or $C_1$-$C_6$ alkyl;

$L^1$ and $L^3$ are linker moieties independently selected from a bond, optionally substituted $C_1$-$C_6$ alkylene, optionally substituted $C_2$-$C_6$ alkenylene, optionally substituted $C_2$-$C_6$ alkynylene, —O—, optionally substituted $C_2$-$C_{20}$ PEG linker, optionally substituted amido, optionally substituted amino, and optionally substituted $C_6$-$C_{10}$ arylene;

$R^3$, $R^4$, and $R^7$ are independently selected from H, $C_1$-$C_6$ alkyl, electron-withdrawing group, and electron-donating group;

$R^{13}$ is a NIR dye moiety; and $R^{10}$ and $R^9$ are H or polymerizable moiety.

In particular embodiments of Formula IIIE, $R^{10}$ and $R^9$ are $NHC(O)C(CH_3)CH_2$.

In specific embodiments of Formula IIIE, the compound is compound 36, 37, 38, 39, 40, or 41 of Table 1.

In certain embodiments of Formula III, the compound has a structure of Formula IIIF:

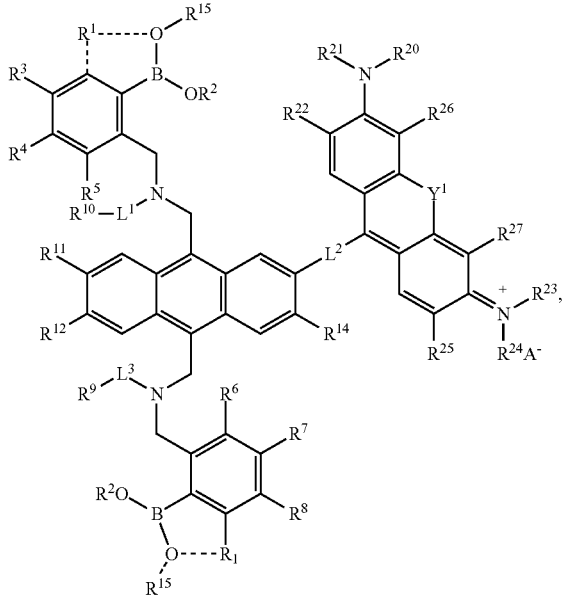

(IIIF)

or an isomer, a tautomer, or a salt thereof,
wherein the dotted lines independently denote a bond or absence of a bond; and when the dotted line connecting $R^1$ and O is a bond, $R^1$ is $CX^1X^2$ and $R^{15}$ is absent; and when the dotted line connecting $R^1$ and O is absence of a bond, $R^{15}$ is H or $C_1$-$C_6$ alkyl;

$X^1$ and $X^2$ are independently H or $C_1$-$C_6$ alkyl;

$R^2$ is H or $C_1$-$C_6$ alkyl;

$R^3$, $R^4$, $R^5$, $R^6$, $R^7$, $R^8$, $R^{11}$, $R^{12}$, and $R^{14}$ are independently H, $C_1$-$C_6$ alkyl, polymerizable moiety, electron-withdrawing group, or electron-donating group;

$R^9$ and $R^{10}$ are independently H, $C_1$-$C_6$ alkyl, polymerizable moiety, or NIR dye;

$L^1$ and $L^3$ are independently a bond or a linker group selected from optionally substituted $C_1$-$C_{10}$ alkyl, optionally substituted $C_2$-$C_{10}$ alkenyl, optionally substituted C2-$C_{10}$ alkynyl, optionally substituted $C_2$-$C_{20}$ heteroalkyl;

$L^2$ is a bond, optionally substituted $C_1$-$C_{10}$ alkyl, optionally substituted $C_2$-$C_{10}$ alkenyl, optionally substituted $C_2$-$C_{10}$ alkynyl, optionally substituted $C_2$-$C_{20}$ heteroalkyl; —O—, optionally substituted —$CH_2C_6H_4O$—, $C_2$-$C_{20}$ PEG linker, amido, amino, optionally substituted $C_6$-$C_{10}$ arylene, or optionally substituted $C_5$-$C_{10}$ heteroarylene;

A- is a counterion;

$Y^1$ is selected from O, P(O)R', SiR'R", and NR', wherein R' and R" are independently H or $C_1$-$C_6$ alkyl;

$R^{20}$ and $R^{21}$ are independently H, $C_1$-$C_6$ alkyl or $R^{21}$ and $R^{20}$, together with the nitrogen atom to which they are attached, form a form a 6- or 5-membered ring optionally substituted with a polymerizable moiety;

$R^{23}$ and $R^{24}$ are independently H, $C_1$-$C_6$ alkyl, or $R^{23}$ and $R^{24}$, together with the nitrogen atom to which they are attached, form a form a 6- or 5-membered ring optionally substituted with a polymerizable moiety;

$R^{22}$ and $R^{25}$ are independently H, $C_1$-$C_6$ alkyl, or $R^{21}$ and $R^{22}$, together with the atoms to which they are attached, form a 6- or 5-membered ring, or $R^{24}$ and $R^{25}$, together with the atoms to which they are attached, form a 6- or 5-membered ring;

$R^{26}$ and $R^{27}$ are independently H, $C_1$-$C_6$ alkyl, or $R^{26}$ and $R^{20}$, together with the atoms to which they are attached, form a 6- or 5-membered ring, or $R^{27}$ and $R^{23}$, together with the atoms to which they are attached, form a 6- or 5-membered ring; and the compound includes one or more polymerizable moieties.

In some embodiments of Formula IIIF, the compound is compound 42-77, 81, 82, 83, 84, 85, 86, 87, or 88 of Table 1.

In certain embodiments of Formula III, the compound has a structure of Formula IIIG:

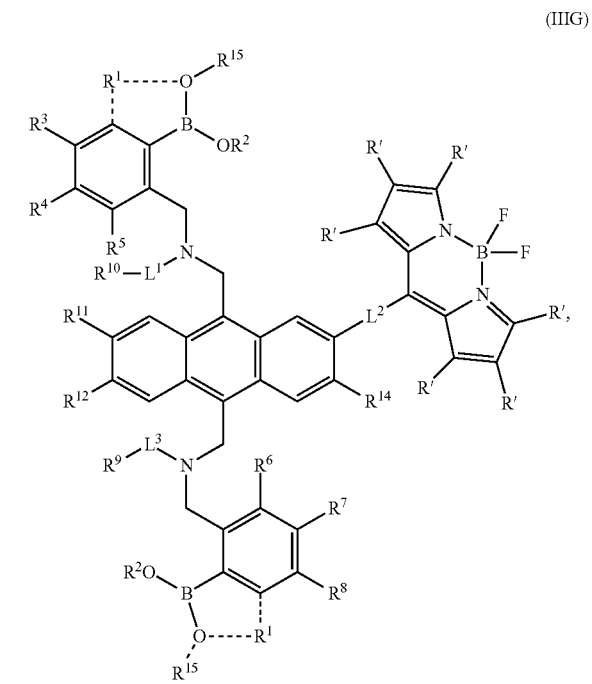

(IIIG)

or an isomer, a tautomer, or a salt thereof,
wherein the dotted lines independently denote a bond or absence of a bond; and when the dotted line connecting $R^1$ and O is a bond, $R^1$ is $CX^1X^2$ and $R^{15}$ is absent; and when the dotted line connecting $R^1$ and O is absence of a bond, $R^{15}$ is H or $C_1$-$C_6$ alkyl;

$X^1$ and $X^2$ are independently H or $C_1$-$C_6$ alkyl;

$R^2$ is H or $C_1$-$C_6$ alkyl;

$R^3$, $R^4$, $R^5$, $R^6$, $R^7$, $R^8$, $R^{11}$, $R^{12}$, and $R^{14}$ are independently H, $C_1$-$C_6$ alkyl, polymerizable moiety, electron-withdrawing group, or electron-donating group;

$R^9$ and $R^{10}$ are independently H, $C_1$-$C_6$ alkyl, polymerizable moiety, or NIR dye;

$L^1$ and $L^3$ are independently a bond or a linker group selected from optionally substituted $C_1$-$C_{10}$ alkyl, optionally substituted $C_2$-$C_{10}$ alkenyl, optionally substituted C2-$C_{10}$ alkynyl, optionally substituted $C_2$-$C_{20}$ heteroalkyl;

$L^2$ is a bond, optionally substituted $C_1$-$C_{10}$ alkyl, optionally substituted $C_2$-$C_{10}$ alkenyl, optionally substituted $C_2$-$C_{10}$ alkynyl, optionally substituted $C_2$-$C_{20}$ heteroalkyl; —O—, optionally substituted —CH$_2$C$_6$H$_4$O—, C$_2$-C$_{20}$ PEG linker, amido, amino, optionally substituted C$_6$-C$_{10}$ arylene, or optionally substituted C$_5$-C$_{10}$ heteroarylene;

R', at each occurrence, is independently H, optionally substituted C$_1$-C$_{10}$ alkyl, optionally substituted C$_2$-C$_{10}$ alkenyl, optionally substituted C$_2$-C$_{10}$ alkynyl, or optionally substituted C$_2$-C$_{20}$ heteroalkyl; and wherein the compound includes one or more polymerizable moieties.

In certain embodiments of Formula III, the compound has a structure of Formula IIIH:

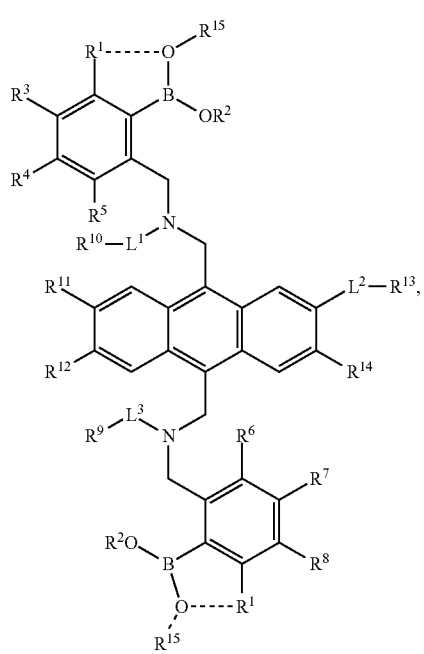

(IIIH)

or an isomer, a tautomer, or a salt thereof, wherein the dotted lines independently denote a bond or absence of a bond; and when the dotted line connecting R$^1$ and O is a bond, R$^1$ is CX$^1$X$^2$ and R$^{15}$ is absent; and when the dotted line connecting R$^1$ and O is absence of a bond, R$^{15}$ is H or C$_1$-C$_6$ alkyl;

X$^1$ and X$^2$ are independently H or C$_1$-C$_6$ alkyl;

R$^2$ is H or C$_1$-C$_6$ alkyl;

R$^3$, R$^4$, R$^5$, R$^6$, R$^7$, R$^8$, R$^{11}$, R$^{12}$, and R$^{14}$ are independently H, C$_1$-C$_6$ alkyl, polymerizable moiety, electron-withdrawing group, or electron-donating group;

R$^9$ and R$^{10}$ are independently H, C$_1$-C$_6$ alkyl, polymerizable moiety, or NIR dye;

L$^1$ and L$^3$ are independently a bond or a linker group selected from optionally substituted C$_1$-C$_{10}$ alkyl, optionally substituted C$_2$-C$_{10}$ alkenyl, optionally substituted C2-C$_{10}$ alkynyl, optionally substituted C$_2$-C$_{20}$ heteroalkyl;

L$^2$ is a bond, optionally substituted C$_1$-C$_{10}$ alkyl, optionally substituted C$_2$-C$_{10}$ alkenyl, optionally substituted C$_2$-C$_{10}$ alkynyl, optionally substituted C$_2$-C$_{20}$ heteroalkyl; —O—, optionally substituted —CH$_2$C$_6$H$_4$O—, C$_2$-C$_{20}$ PEG linker, amido, amino, optionally substituted C$_6$-C$_{10}$ arylene, or optionally substituted C$_6$-C$_{10}$ heteroarylene;

R$^{13}$ is an optionally substituted dye moiety selected from:

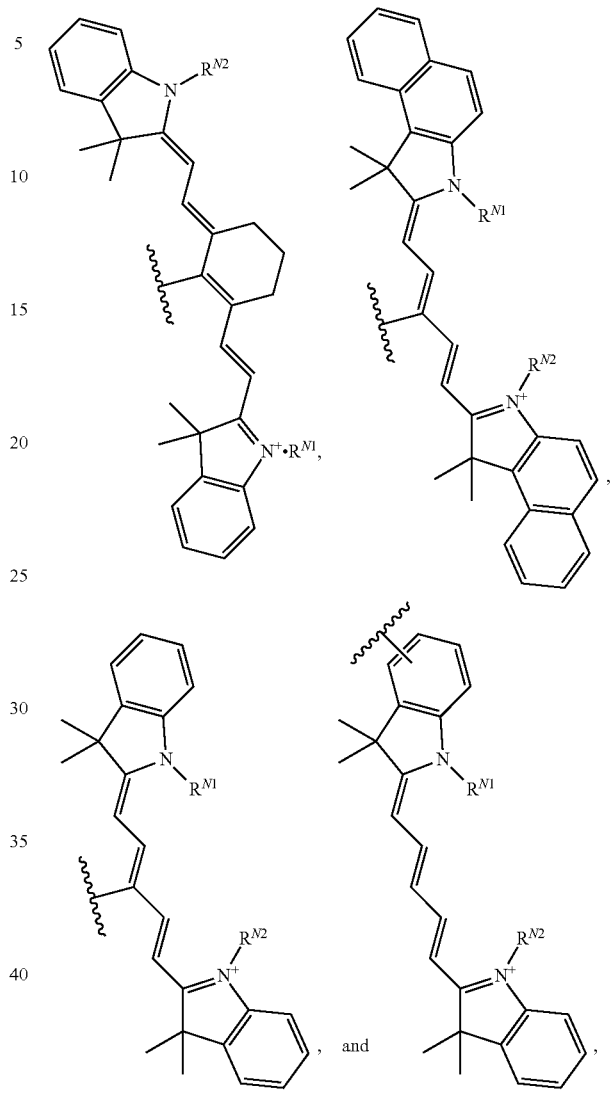

, and

, wherein R$^{N1}$ and R$^{N2}$ are independently H or C$_1$-C$_{10}$ alkyl optionally substituted with one or more sulfo or carboxylic acid groups, and the wavy line denotes the point of attachment to L$^2$.

In some embodiments of Formula IIIF-IIIH, L$^2$ is a bond, optionally substituted phenylene,

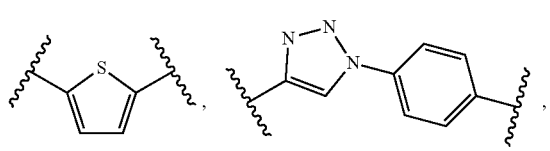 [SMILES: *c1ccc(*)s1 ; *C1=CN(c2ccc(*)cc2)NN1]

or —C$_6$H$_4$—O—.

In some embodiments of the compounds of Formula IIIF-IIIH, R$^{10}$ is NHC(O)C(CH$_3$)CH$_2$.

In certain embodiments of the compounds of Formula IIIF-IIIH, R$^9$ is NHC(O)C(CH$_3$)CH$_2$.

In some embodiments of the compounds of Formula IIIF-IIIH, the NIR dye moiety is a silicon rosamine dye moiety. In certain embodiments of the compounds of Formula IIIF-IIIH, $Y^1$ is $SiMe_2$.

In certain embodiments of the compounds of Formula IIIF-IIIH, $L^1$ is optionally substituted $C_1$-$C_{10}$ alkyl or optionally substituted $C_2$-$C_{20}$ heteroalkyl. In certain embodiments, $L^3$ is optionally substituted $C_1$-$C_{10}$ alkyl or optionally substituted $C_2$-$C_{20}$ heteroalkyl.

In some embodiments of the compounds of Formula IIIF-IIIH, $R^{11}$, $R^{14}$, and $R^{12}$ are H. In certain embodiments of the compounds of Formula IIIF, $R^{22}$, $R^{25}$, $R^{26}$, and $R^{27}$ are H.

In some embodiments, wherein both $R^{15}$ are H, and $R^1$ at each occurrence is independently selected from the group consisting of H; an electron-withdrawing group selected from the group consisting of halogen, C(O)R', COOR', C(O)NH$_2$, NHC(O)R', C(O)NR'R'', CF$_3$, CN, SO$_3$H, SO$_2$CF$_3$, SO$_2$R', SO$_2$NR'R'', ammonium, alkyl ammonium, and NO$_2$, wherein R' and R'' are independently H or $C_1$-$C_6$ alkyl; and electron-donating group selected from the group consisting of NR$^{N1}$R$^{N2}$, OR', NHC(O)R', OC(O)R', phenyl, and vinyl, wherein R$^{N1}$, R$^{N2}$, and R' are independently H or $C_1$-$C_6$ alkyl.

In one embodiment, the compounds of Formulae I-IIIH are near-IR luminescent dyes. In one embodiment, the compounds of Formulae I-IIIH have an absorption maximum between about 500 nm and about 1000 nm, between about 550 nm and about 700 nm, between about 550 nm and about 800 nm, between about 550 nm and about 900 nm, between about 600 nm and about 800 nm, between about 600 nm and about 900 nm, or between about 600 nm and about 1000 nm. In some embodiments, the compounds of Formulae I-IIIH have an emission maximum between 550 and 1100 nm, between about 600 nm and about 1100 nm, between about 700 nm and about 1100 nm, between about 600 nm and about 900 nm, between about 600 nm and about 800 nm, or between about 600 nm and about 1000 nm. In one embodiment, the compounds of Formulae I-IIIH are photostable and have excitation and emission spectra in the NIR optical window of the skin.

In certain embodiments, the compounds of Formulae I-IIIH have an absorption maximum greater than 500 nm, greater than 550 nm, greater than 600 nm, greater than 650 nm, greater than 700 nm. In other embodiments, the compounds of Formulae I-IIIH have an emission maximum greater than 550 nm, greater than 600 nm, greater than 650 nm, greater than 700 nm, greater than 800 nm, greater than 900 nm, greater than 1000 nm, greater than 1100 nm.

In some embodiments, the dyes are encapsulated into a solid, oxygen-impermeable nanosphere. The nanospheres can be used for luminescent, non-oxygen sensitive applications.

The compounds may be synthesized using techniques known in the art. Synthesis of non-limiting examples of the compounds is described in detail below.

B. Polymers

The fluorescent dyes include polymerizable moietys, e.g., residue of acrylic or methacrylic acid, and can be co-polymerized with other monomers to provide polymers including near-IR luminescent groups. When the compounds have 2 or more polymerizable moietys, the polymers obtained from their co-polymerization with other monomers can be crosslinked. Alternatively, another crosslinking monomer can be added into the polymerization mixture to achieve a higher degree of crosslinking of the resulting polymer.

Polymers described herein can be prepared in any suitable manner. Suitable synthetic methods used to produce the polymers provided herein include, by way of non-limiting examples, cationic, anionic, and free radical polymerization. In certain embodiments, polymer synthesis is performed neat or in any suitable solvent. Suitable solvents include, but are not limited to, pentane, hexane, dichloromethane, chloroform, water, ethylene glycol, propylene glycol, DMSO or dimethyl formamide (DMF). In certain embodiments, the polymer synthesis is performed at any suitable reaction temperature, including, e.g., from about −50° C. to about 100° C., or from about 0° C. to about 70° C.

In an embodiment, the polymers are prepared by the means of a free radical polymerization. When a free radical polymerization process is used, (i) the monomer, (ii) optionally, the co-monomer(s), and (iii) an optional source of free radicals are provided to trigger a free radical polymerization process. In some embodiments, the source of free radicals is optional because some monomers may self-initiate upon heating at high temperature. In certain instances, after forming the polymerization mixture, the mixture is subjected to polymerization conditions. Such conditions are optionally varied to any suitable level and include, by way of non-limiting example, temperature, pressure, light, atmosphere, ratios of starting components used in the polymerization mixture and reaction time. The polymerization is carried out in any suitable manner, including, e.g., in solution, dispersion, suspension, emulsion or bulk.

In some embodiments, initiators are present in the reaction mixture. Any suitable initiator is optionally utilized if useful in the polymerization processes described herein. Such initiators include, by way of non-limiting example, one or more of alkyl peroxides, substituted alkyl peroxides, aryl peroxides, substituted aryl peroxides, acyl peroxides, alkyl hydroperoxides, substituted alkyl hydroperoxides, aryl hydroperoxides, substituted aryl hydroperoxides, heteroalkyl peroxides, substituted heteroalkyl peroxides, heteroalkyl hydroperoxides, substituted heteroalkyl hydroperoxides, heteroaryl peroxides, substituted heteroaryl peroxides, heteroaryl hydroperoxides, substituted heteroaryl hydroperoxides, alkyl peresters, substituted alkyl peresters, aryl peresters, substituted aryl peresters, or azo compounds. In specific embodiments, benzoylperoxide (BPO) and/or AIBN are used as initiators.

In some embodiments, polymerization processes are carried out in a controlled (living) mode. Non-limiting examples of controlled (living) polymerization processes include reversible addition-fragmentation chain transfer (RAFT) polymerization processes and Atom Transfer Radical Polymerization (ATRP).

In certain embodiments, the polymer may be a hydrogel. For example, the hydrogel can be prepared by reacting hydroxyethyl methacrylate (HEMA), to form poly(hydroxyethyl methacrylate), pHEMA. Furthermore, various comonomers can be used in combination to alter the hydrophilicity, mechanical and swelling properties of the hydrogel (e.g. PEG, NVP, MAA). Non-limiting examples of polymers include 2-hydroxyethyl methacrylate, polyacrylamide, N-vinylpyrrolidone, N,N-dimethylacrylamide, poly(ethylene glycol) monomethacrylate (of varying molecular weights), diethylene glycol methacrylate, N-(2-hydroxypropyl)methacrylamide, glycerol monomethacrylate, 2,3-dihydroxypropyl methacrylate and combinations thereof. Non-limiting examples of cross-linkers include tetraethylene glycol dimethacrylate, poly(ethylene glycol)(n)diacrylate (of varying molecular weights), ethoxylated trimethylolpropane triacrylate, bisacrylamide, and combinations thereof. Non-limiting examples of initiators include Ingacure Series (UV), Azobisisobutyronitrile (AIBN) (thermal), Ammonium Persulfate (APS) (thermal).

In one embodiment, the polymer is a luminescent hydrogel prepared by co-polymerization of HEMA and compound of Formulae I-IIIH.

In an exemplary embodiment, the polymer is prepared by co-polymerization of DMA (N,N-dimethylacrylamide), AAm (acrylamide), PEGDAAm (poly-ethylene glycol diacrylamide), and a compound of Formulae I-IIIH in the presence of 2,2'-azobis[2-(2-imidazolin-2-yl)propane]dihydrochloride in a suitable solvent, e.g., a mixture of DMSO and water.

In another exemplary embodiment, the polymer is prepared by co-polymerization of AETACI ([2-(acryloyloxy)ethyl]trimethylammonium chloride), PEGDAAm (poly-ethylene glycol diacrylamide), a compound of Formulae I-IIIH in the presence of 2,2'-azobis[2-(2-imidazolin-2-yl)propane] dihydrochloride in a suitable solvent, e.g., a mixture of DMSO and water.

In yet other exemplary embodiment, the polymer is prepared by co-polymerization of HEMA (2-hydroxyethyl methacrylate) (44.1 uL), DMA (N,N-dimethylacrylamide) (29.4 uL), PEGDAAm (poly-ethylene glycol diacrylamide), a compound of Formulae I-IIIH in the presence of 2,2'-azobis[2-(2-imidazolin-2-yl)propane]dihydrochloride in a suitable solvent, e.g., a mixture of DMSO and water.

The polymer may be degradable, either by the body (biodegradable) or by the application of an external initiator to start or speed up the degradation process (e.g. UV, ultrasonics, radio frequency, temperature, or other exogenous sources to initiate degradation.). For example, the polymer may be biodegradable or bioresorbable or may include any biodegradable or bioresorbable segments, including but not limited to degradable forms of alginates, poly(lactic acid), poly(vinyl alcohol), polyanhydrides, poly (glycolic acid), microporous polyesters, microporous polyethers and cross-linked collagen. One specific example is UV-photopolymerization of poly(ethylene glycol)-diacrylate and acrylated protease-degradable peptides and VEGF as described by Phelps, et al (2010) *Proc. Nat'l. Acad. Sci. USA* 107(8):3323-3328

In one embodiment, polymers provided herein are biocompatible. In another aspect, the polymers are biodegradable. Degradable hydrogels can be synthesized using Atom Transfer Radical Polymerization (ATRP) through co-polymerization of the HEMA with polymerizable luminescent dyes described herein. Porous sensor scaffolds, based on non-degradable and degradable glucose-sensing hydrogels, can be generated by using a sphere-templating fabrication technique. Degradable and non-degradable HEMA reagents and polymerizable dye will be polymerized over templating microspheres, which are subsequently dissolved away with solvent to generate desirable non-degradable and degradable scaffolds. Briefly, using controlled ATRP, HEMA will be polymerized in the presence of bi-functional degradable PCL-based ATRP initiator and cross-linker. In this synthesis scheme, pHEMA chains grow at the same rate from both sides of degradable initiator, resulting in degradation products with a molecular weight (MW) that is half that of the parent polymer. By controlling the MW of the parent polymer and the PEG and PCL units in the initiator and/or crosslinker, the degradation rate of the polymers can be varied. Limiting the MW of the parent polymer to 10 kDa results in degradation products that can be cleared by the body and an increased degradation rate while still preserving the hydrogel's mechanical strength.

In certain embodiments, the polymers provided herein are stimuli-responsive, e.g., temperature or pH-sensitive polymers. One non-limiting example of such a stimuli-responsive polymer is a temperature-sensitive polymer derived from co-polymerization of NIPAM. Such polymers are useful for implantation of the sensor including said polymers in a desired location within tissue by first dissolving the polymer in a suitable for injection media at a lower than body temperature and then injecting the resulting solution into the tissue and/or at desired location of the body. As the polymer is subjected to a higher (e.g., body) temperature, it precipitates in or near the site of the injection where monitoring of the analyte is required.

C. Sensors

In some embodiments, the polymer may be incorporated into a sensor useful for detection of an analyte. The detection of the analyte can be in vitro or in vivo. The polymer may have the molecules of Formulae I-IIIH and optionally other polymerizable monomers covalently bound to the polymer backbone. The molecules of Formulae I-IIIE can be attached to, e.g. via a covalent bond or other means, or contained within nanoparticle carriers or microparticle carriers or other carriers that are attached to or contained within the polymer. Such carriers may be covalently bound to the polymer backbone. In some embodiments, the word "polymer" is used interchangeably with the word "sensor."

In an embodiment, the sensor may include catalase. As described in U.S. Pat. No. 6,858,403, which is hereby incorporated herein by reference in its entirety, catalase can be used to remove hydrogen peroxide in hydrogel-based sensors.

In one embodiment, the sensor may be a solid material that could be in form of a slab, disc, rod, cylinder, particle or powder. In a specific embodiment, the sensor is in the form of a rod. In another embodiment, the sensor is in the form of a cylinder. In yet other embodiment, the sensor is in the form of a disc.

In another embodiment, the polymer may be, or may be incorporated into, a tissue-integrating scaffold to provide a tissue-integrating sensor (as described in the US patent application 2012/0265034, which is incorporated herein by reference). In an embodiment, the tissue-integrating scaffold may be constructed with materials and/or micro-architecture such that the scaffold promotes tissue-integration and/or vascularization. For example, porous scaffolds provide tissue biomaterial anchoring and promote in-growth throughout the pores. The resulting "hallway" or "channel" pattern of tissue growth are healthy, space-filling masses that persist over time and promote host cell integration. Most or all of the pores of the biomaterials described herein may be interconnected (co-continuous). The co-continuous pore structure of the biomaterials promotes space-filling in-growth of cells in the implant, which in turn limits the foreign body response and leads to long-term (greater than one week and up to years) persistence of the implant's ability to act as a sensor. Alternative structures that provide tissue integrating scaffolds include fibers (e.g., 1 to 10 or more microns in diameter, such as 5, 6, 7, 8, 9, 10 or more microns), which may be arranged in non-random or random configuration. Tissue-integrating scaffolds (in any configuration) can also be formed by multiphoton polymerization techniques. Kaehr et al. (2008) *Proc. Nat'l. Acad. Sci. USA* 105(26):8850-8854; Nielson et al. (2009) *Small* 1:120-125; Kasprzak, Doctoral Dissertation, Georgia Institute of Technology, May 2009.

The polymers, which may be in the form of a tissue-integrating scaffold, may include any material in combination with the compound of Formulae I-IIIH, including but not limited to synthetic polymers, naturally-occurring substances, or mixtures thereof. Exemplary synthetic polymers include, but are not limited to polyethylene glycol (PEG), 2-hydroxyethyl methacrylate (HEMA), silicone rubber, poly ([epsilon]-caprolactone) dimethylacrylate, polysulfone, (poly)methy methacrylate (PMMA), soluble Teflon-AF, (poly) ethylenetetrapthalate (PET, Dacron), Nylon, polyvinyl alcohol, polyacrylamide, polyurethane, and mixtures thereof. Exemplary naturally-occurring materials include, but are not limited to, fibrous or globular proteins, complex carbohydrates, glycosaminoglycans, extracellular matrix, or mixtures thereof. Thus, the polymer scaffold may include collagens of all types, elastin, hyaluronic acid, alginic acid, desmin, versican, matricelluar proteins such as SPARC (osteonectin), osteopontin, thrombospondin 1 and 2, fibrin, fibronectin, vitronectin, albumin, chitosan etc. Natural polymers may be used as the scaffold or as an additive.

In certain embodiments, the polymer includes a hydrogel. For example, the polymer may include a hydrogel, for example by reacting hydroxyethyl methacrylate (HEMA) and a compound of Formulae I-IIE with one or more co-monomer to form poly (hydroxyethyl methacrylate), pHEMA-copolymer. Various co-monomers can be used in combination to alter the hydrophilicity, mechanical and swelling properties of the hydrogel (e.g. PEG, NVP, MAA). Non-limiting examples of polymers include 2-hydroxyethyl methacrylate, polyacrylamide, N-vinylpyrrolidone, N,N-dimethylacrylamide, poly(ethylene glycol) monomethacrylate (of varying molecular weights), diethylene glycol methacrylate, N-(2-hydroxypropyl)methacrylamide, glycerol monomethacrylate, 2,3-dihydroxypropyl methacrylate and combinations thereof. Non-limiting examples of cross-linkers include tetraethylene glycol dimethacrylate, poly(ethylene glycol) (n) diacrylate (of varying molecular weights), ethoxylated trimethylolpropane triacrylate, bisacrylamide and combinations thereof. Non-limiting examples of initiators include irgacure Series (UV), Azobisisobutyronitrile (AIBN) (thermal), Ammonium Persulfate (APS) (thermal).

The polymer may be a sphere-templated hydrogel, for instance an inverse colloid crystal, for example as described in U.S. Patent Publication No. 2008/0075752 to Ratner, et al., which is incorporated herein by reference, or other tissue integrating materials.

The polymer may be degradable, either by the body (biodegradable) or by the application of an external initiator to start or speed up the degradation process (e.g. UV, ultrasonics, radio frequency, or other exogenous sources to initiate degradation.). For example, the polymer may be include any biodegradable or bioresorbable polymers, including but not limited to degradable forms of alginates, poly(lactic acid), poly(vinyl alcohol), polyanhydrides, poly (glycolic acid), microporous polyesters, microporous polyethers and cross-linked collagen. One specific example is UV-photopolymerization of poly(ethylene glycol)-diacrylate and acrylated protease-degradable peptides and VEGF as described by Phelps, et al (2010) *Proc. Nat'l. Acad. Sci. USA* 107(8):3323-3328.

Other specific examples are polymers described by Kloxin et al (2009) *Science* 324:59-63 and U.S. Pat. No. 6,013,122 whose degradation is controlled through exposure to exogenous energy forms, as well as by Alexeev et al. (2003) *Anal. Chem.* 75:2316-2323; Badylak et al. (2008) *Seminars in Immunology* 20:109-116; Bridges et al. (2010) 94(1):252-258; Isenhath et al. (2007) *Research* 83A:915-922; Marshall et al. (2004) *Polymer Preprints, American Chemical Society, Division of Polymer Chemistry* 45:100-101; Phelps et al. (2010) *Proc Nat'l Acad Sci USA.* 107(8): 3323-8; Ostendorf and Chichkov (2006) *Two Photon Polymerization: A New Approach to MicroMachining, Photonics Spectra*; Ozdemir et al. (2005) *Experimental and Clinical Research, Plast. Reconstr. Surg.* 115:183; U.S. Patent Publication No. 20080075752; Sanders et al. (2003) *Journal of Biomedical Materials Research* Part A 67A(4): 1181-1187; Sanders et al. (2002) *Journal of Biomedical Materials Research* 62(2):222-227; Sanders et al. (2003) *Journal of Biomedical Materials Research* 65(4):462-467; Sanders et al. (2005) *Biomaterials* 26:813-818; Sanders et al. (2005) *Journal of Biomedical Materials Research Part A* 72(3): 335-342; Sanders (2003) *Journal of Biomedical Materials Research* 67(4):1412-1416; Sanders et al. (2000) *Journal of Biomedical Materials Research* 52(1):231-237; and Young Min Ju et al. (2008) *J Biomed Mater Res* 87A: 136-146.

In addition, the polymer may be constructed such that it has conduits, pores or pockets that are hollow or filled with degradable, angiogenic, or other substances (e.g. stem cells). As noted above, once in the body, the biodegradation of the material filling the conduits, pores or pockets, creates space for tissue, including capillaries to integrate with the material. The degradable material that initially fills the conduits, pores, or pockets, may enhance vessel growth or tissue growth within the scaffold. This architecture promotes new vessel formation and maintains healthy viable tissue within and around the implant.

The polymer may be constructed such that it is permeable to analytes of interest (e.g., glucose can diffuse into a hydrogel scaffold and reach the sensing moieties that are embedded within the hydrogel matrix).

The polymer can be of any suitable form, including, but not limited to block-like (or any thickness), cube-like, disk-shaped, cylindrical, oval, round, random or non-random configurations of fibers and the like. In certain embodiments, the sensor includes one or more fibers, which may be organized in a non-random fashion (e.g., grid, layered grid, etc.) or in a random fashion.

The polymer described herein may be combined with (or made up of) sensing moieties that detect one or more analytes. In one embodiment, the sensing moiety is the residue of compound of Formulae I-IIIH incorporated into the hydrogel scaffold.

In another embodiment, the polymer, which may be in the form of a tissue-integrating scaffold, includes, in addition to the residue of a first compound of Formulae I-IIIH, a second sensing moiety. In one embodiment, the second sensing moiety is a second compound of Formulae I-IIIH.

In another embodiment, the polymer, e.g., in the form of a tissue-integrating scaffold, may be a multi-analyte sensor where glucose is one of two or more analytes detected and reported. In this embodiment, the polymer includes a residue of compound of Formulae I-IIIH for detection of glucose, and a second sensing moiety for detection of another substance. Non-limiting examples of analytes that may be detected by the sensing moieties include oxygen, reactive oxygen species, glucose, lactate, pyruvate, cortisol, creatinine, urea, sodium, magnesium, calcium, potassium, vasopressin, hormones (e.g., Luteinizing hormone), pH, cytokines, chemokines, eicosanoids, insulin, leptins, small molecule drugs, ethanol, myoglobin, nucleic acids (RNAs, DNAs), fragments, polypeptides, single amino acids and the like.

In some embodiments, the sensing moieties, e.g., the polymers may include the residue of compound of Formulae I-IIIH that are reversible luminescent binding molecules. To measure an analyte such as glucose in the tissue, the polymer is illuminated from a patch reader on top of the skin above the implant with a light of a wavelength that can permeate the skin, e.g., with 650 nm light, at desired intervals over the long-term life of the implant (e.g., every 5-60 minutes over a period of 90 days or more). The amount of luminescent signal (e.g., from a luminescent molecule) detected is proportional to the concentration of analyte (e.g. glucose) in the tissue.

In another embodiment, internal reference control materials can be employed that facilitate correcting for tissue optical variation. The implanted biosensor may reside 1-6 mm, 2-6, mm, 3-6 mm, 3-4 mm, or 3-5 mm under the surface of the skin. It is well known that in skin excitation light and emitted fluorescent light in the near infrared range are highly scattered as the light traverses the tissue between the reader patch and the implant. The extent of absorption and scattering is affected by physical properties such as temperature or by tissue composition, including but not limited to variations in blood perfusion, hydration, and melanin concentration. Skin variations can occur between users or between different time points for a single patient, and these variations can affect the fluorescence excitation and emissions signals causing in accurate signals for the analyte-specific signal. Accordingly, a separate luminescent molecule with emission spectra distinguishable from the analyte-specific luminescence can be immobilized into the scaffold. The luminescence from the molecule can be measured separately from the analyte-specific luminescence to measure a signal that informs about variations in tissue composition. The second dye selected for this purpose may have a similar response to tissue variations as the analyte-specific dye.

In some embodiments, the sensors may be tissue-integrating sensors which include one or more cylindrical shaped elements (e.g., fibers) that eliminate or greatly reduce the foreign body response as compared to currently available implants. Moreover, the average diffusion distances from the capillary supply to all parts of the sensing media are comparable to native tissue, unlike other known sensors.

The overall dimensions of the sensing media (implantable sensor) vary according to the subject and/or the analyte(s) to be measured. The implant is between about 0.001 mm to about 2 mm in thickness (or any value therebetween) and between about 1 mm and about 1 cm in diameter (or an equivalent cross sectional area of a non-circular shape, for example length/width) and 15 mm in length or less, for example, a disk-shaped sensor that is 2 mm or less thick and 10 mm or less in diameter. In certain embodiments, the approximate sensor size is approximately 100-1000 microns in diameter and has the length of between 0.25 mm and 10 mm. The size of the tissue-integrating sensing media in disk form may be 2 mm or less thick and 10 mm or less in diameter.

Another aspect is a tissue-integrating biosensor system for semi-continuous, continuous, and/or long-term use within a mammalian body.

One advantageous property of the polymers and sensors described herein is their stability. In one aspect, the sensor is stable in a mammalian tissue for a long period of time, e.g., longer than a week, longer than a month, longer than 2 months, longer than 6 months.

EXAMPLES

NMR spectroscopic data were recorded on a 400 MHz instrument at room temperature. NMR spectra were calibrated to the solvent signals of deuterated DMSO-$d_6$, MeOH-$d_4$ or CDCl$_3$. The following abbreviations are used to indicate the signal multiplicity: s (singlet), d (doublet), t (triplet), q (quartet), quin (quintet), br (broad), m (multiplet). Analytical HPLC-MS data were recorded on a HPLC system with a C18 reversed-phase silica gel column coupled to an electrospray ionization (ESI) mass-spectrometer. Listed UV/Vis absorbance maxima were recorded by HPLC DAD in the eluent system (acetonitrile/water+0.1% HCOOH). Commercially available monomers and chemical building blocks were purchased from Polysciences, Sigma-Aldrich, VWR, Combi-Blocks, Acros Organics, Oakwood Chemical, AK Scientific, and Strem Chemicals. Some of the advanced intermediates were synthesized by BioDuro.

Synthesis of Exemplary Compounds of Formulae I-IIIH

Synthesis of Compound 1

Scheme 5. Synthesis of compound 1

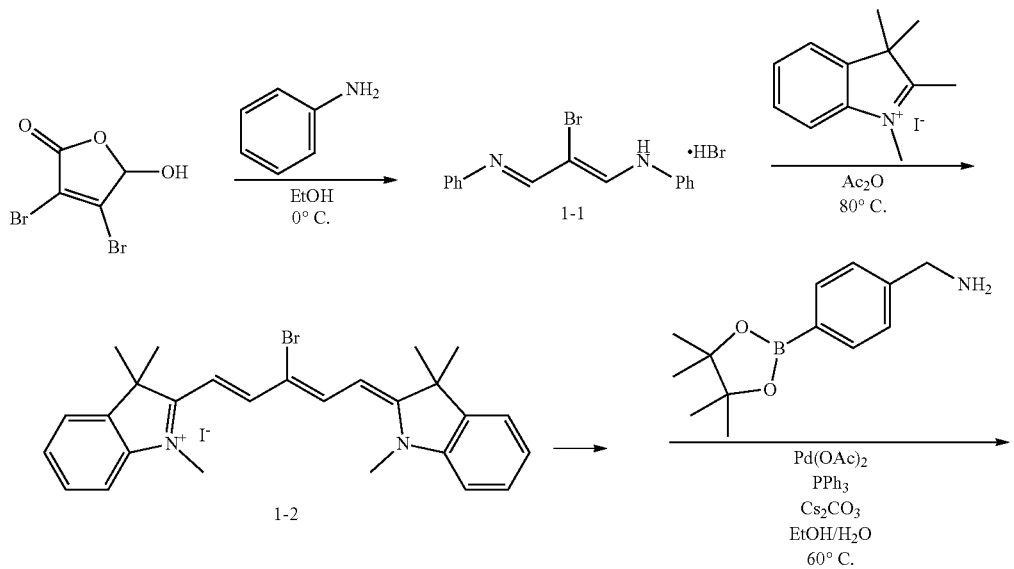

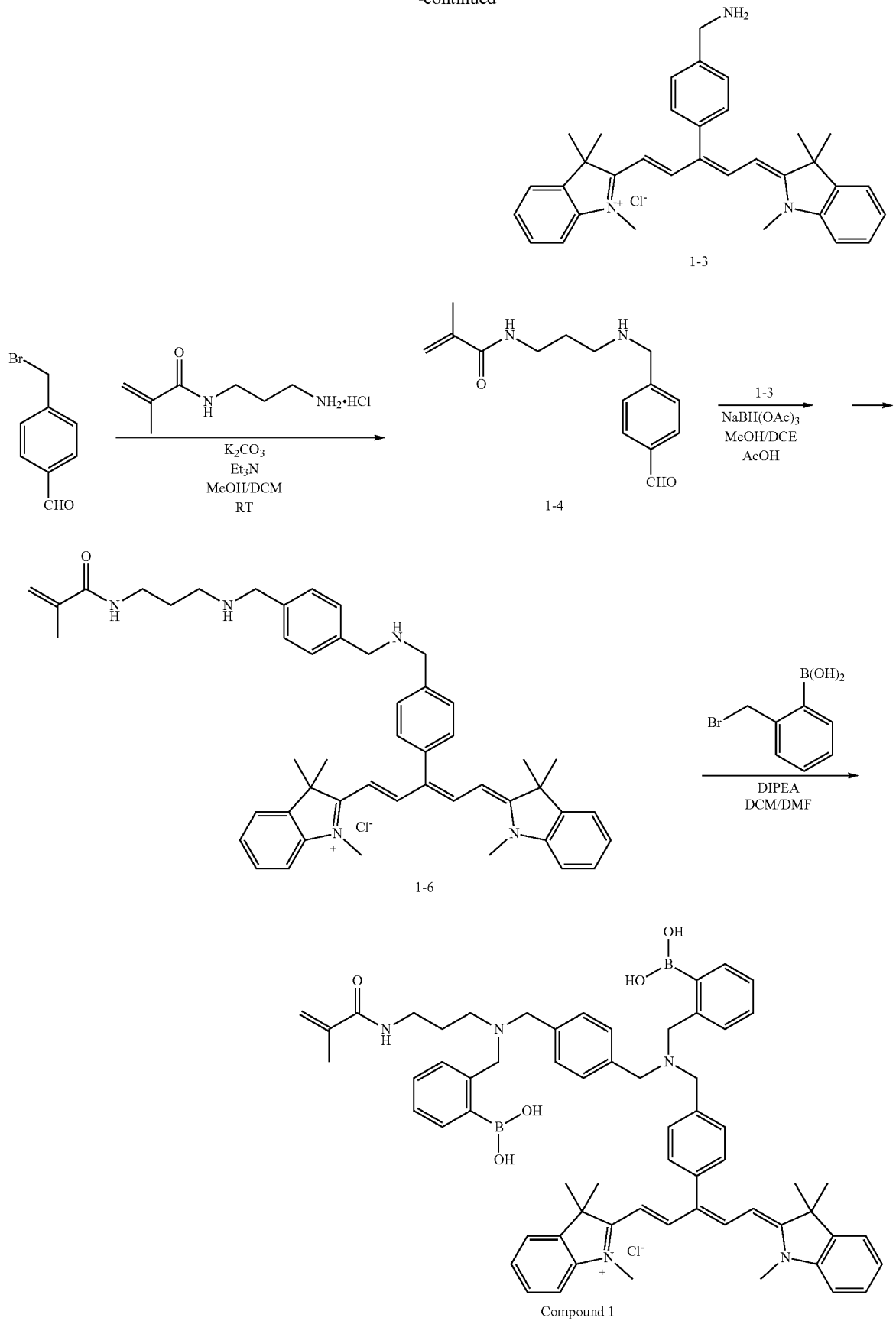

General Procedure I. Preparation of N-[2-bromo-3-(phenylamino)-2-propenylidene]-benzenammonium bromide 1-1

A solution of aniline (17.7 mL, 194 mmol) in anhydrous EtOH (25 mL) was added dropwise to a pre-cooled (0° C.) solution of mucobromic acid (25 g, 97 mmol) in anhydrous EtOH (75 mL). The reaction mixture was stirred for 1 h and then was concentrated in vacuo to 50 mL. The product crystallized from the concentrated solution upon storage at 4° C. for 3 days. The crystals were collected by filtration and rinsed with acetone and cold EtOH to yield the title compound 1-1 as an orange/yellow solid (24.2 g, 83%).

General Procedure II. Preparation of Pentamethine Cyanine Fluorophore (Cy5). Preparation of 2-[3-bromo-5-(1,3-dihydro-1,3,3-trimethyl-2H-indol-2-ylidene)-1,3-pentadien-1-yl]-1,3,3-trimethyl-3H-indolium iodide 1-2

A solution of compound 1-1 (1.01 g, 2.65 mmol), 1,2,3,3-tetramethyl-3H-indolium iodide (4.0 g, 13.3 mmol), and sodium acetate (2.16 g, 26.5 mmol) in acetic anhydride (40 mL) was heated at 80° C. for 20 min. The reaction was then diluted with DCM and washed with water and brine. The DCM layer was then dried over $MgSO_4$ and concentrated in vacuo. The residue was purified by flash chromatography ($SiO_2$, eluted with DCM and MeOH) to afford the title product 1-2 (758 mg, 48%).

General Procedure III. Suzuki-Miyaura Cross-Coupling with Pinacol Borate. Preparation of 2-[3-(4-aminomethylphenyl)-5-(1,3-dihydro-1,3,3-trimethyl-2H-indol-2-ylidene)-1,3-pentadien-1-yl]-1,3,3-trimethyl-3H-indolium iodide 1-3

In a flame-dried flask, intermediate 1-2 (758 mg, 1.28 mmol), 4-aminomethylphenylboronic acid pinacol ester hydrochloride (600 mg, 2.57 mmol), and cesium carbonate (1.25 g, 3.85 mmol) were mixed with EtOH (50 mL) and water (25 mL). The mixture was degassed by bubbling dry argon at 60° C. for 1 h. Palladium(II) acetate (60 mg, 0.128 mmol) and triphenylphosphine (200 mg, 0.514 mmol) were then added and the reaction mixture was stirred for 16 h at 60° C. under argon. Additional 4-aminomethylphenylboronic acid pinacol ester hydrochloride (90 mg, 0.386 mmol), Palladium(II) acetate (60 mg, 0.128 mmol), and triphenylphosphine (200 mg, 0.514 mmol) were then added and reaction was stirred for 16 h at 60° C. under Ar. The reaction mixture was then concentrated in vacuo, diluted with DCM and filtered through Celite®. The filtrate was washed with water and brine, then dried over $MgSO_4$, and concentrated in vacuo. The residue was purified by flash chromatography ($SiO_2$, eluted with 0.09% HCl in MeOH and DCM). The pure product was dissolved in DCM and washed with saturated $NaHCO_3$ 3 times. The DCM portion was then dried over $MgSO_4$ and concentrated in vacuo to yield product 1-3 (258 mg, 41%).

Preparation of N-{3-[(4-formylphenyl)methyl-amino]propyl}methacrylamide 1-4

A mixture of N-(3-aminopropyl)methacrylamide hydrochloride (APMA.HCl; 4.47 g, 25.1 mmol) and $K_2CO_3$ (13.8 g, 100.5 mmol) in anhydrous MeOH (10 mL) was stirred for 15 min and then diluted with anhydrous DCM (100 mL). 4-Bromomethyl-benzaldehyde (2 g, 10.0 mmol) and triethylamine (5 mL, 35.8 mmol) were added and the reaction mixture was stirred for 16 h. Then the mixture was filtered, a small amount of 4-methoxyphenol (MEHQ, polymerization inhibitor) was added to the filtrate, and it was concentrated in vacuo. Drying under high vacuum afforded the title compound 1-4 as a white solid (3.25 g, 124%).

General Procedure IV. Reductive Amination. Preparation of Compound 1-6

A solution of amine 1-3 (258 mg, 0.419 mmol), glacial acetic acid (0.15 mL, 2.50 mmol), and aldehyde 1-4 (319 mg, 1.20 mmol) in anhydrous MeOH (15 mL) and anhydrous DCE (5 mL) was stirred for 15 minutes over molecular sieves (3 Å, 200 mg). Then sodium triacetoxyborohydride (400 mg, 1.88 mmol) was added in three portions with 10 min intervals. Upon completion of the reaction, the slurry was filtered and the filtrate concentrated in vacuo to approximately 5 mL. The concentrate was diluted with DCM, washed with saturated $NaHCO_3$ and brine, dried over $MgSO_4$, and concentrated in vacuo. The residue was purified by flash chromatography ($SiO_2$, eluted with DCM and 0.05% HCl in MeOH). The purified product was dissolved in DCM, washed with sat. $NaHCO_3$ 3 times, dried over $MgSO_4$, and concentrated in vacuo to yield the title product 1-6 (198 mg, 55%).

General Procedure V. Alkylation with Unprotected 2-bromomethylphenylboronic acid. Preparation of Compound 1

To a solution of diamine 1-6 (198 mg, 0.23 mmol) in anhydrous DCM (15 mL) and anhydrous DMF (2 mL), $K_2CO_3$ (257 mg, 1.86 mmol), 2-bromomethylphenylboronic acid (300 mg, 1.4 mmol), and DIPEA (0.4 mL, 2.3 mmol) were added. The reaction mixture was stirred for 1 h and addition of 2-bromomethylphenylboronic acid (150 mg, 0.697 mmol) and DIPEA (0.081 mL, 0.465 mmol) was repeated. After 1 h, fresh portion of 2-bromomethylphenylboronic acid (450 mg, 2.8 mmol) was added and the mixture was stirred for 16 h. The crude product was precipitated by hexane, collected by centrifugation, and purified by flash chromatography ($SiO_2$, eluted with DCM and 0.05% HCl in MeOH. The pure product was dissolved in DCM, washed with saturated $NaHCO_3$ 3 times, dried over $MgSO_4$, and concentrated in vacuo to yield the title product compound 1 (78 mg, 30% yield). HPLC-MS: m/z 1000.7 (calcd. 1000.6 for $M^+$); $\lambda_{max}$=650 nm.

Preparation of Compound 2

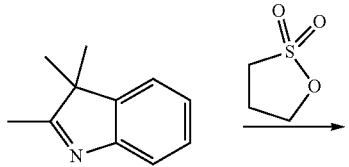

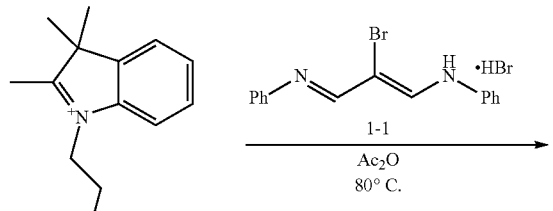

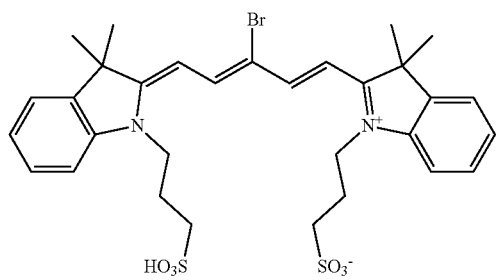
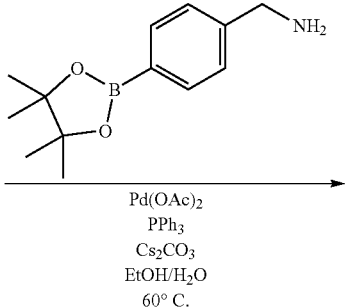
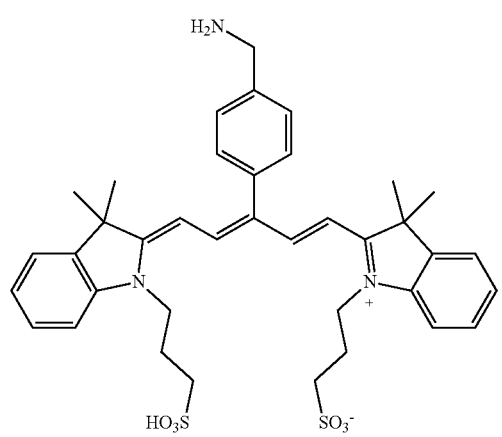
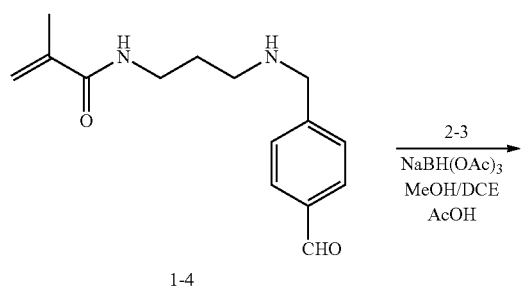
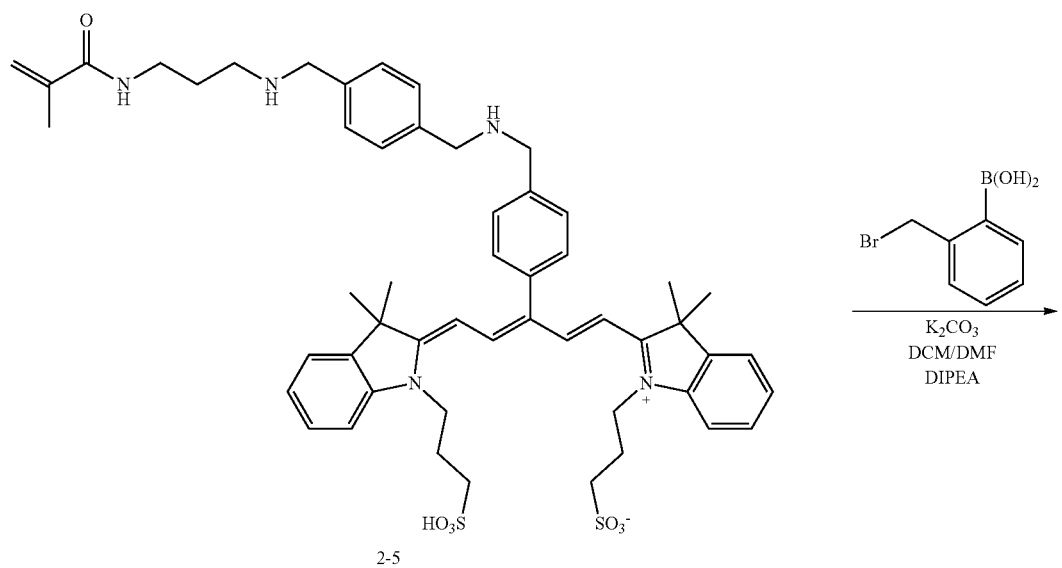
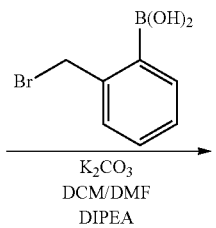

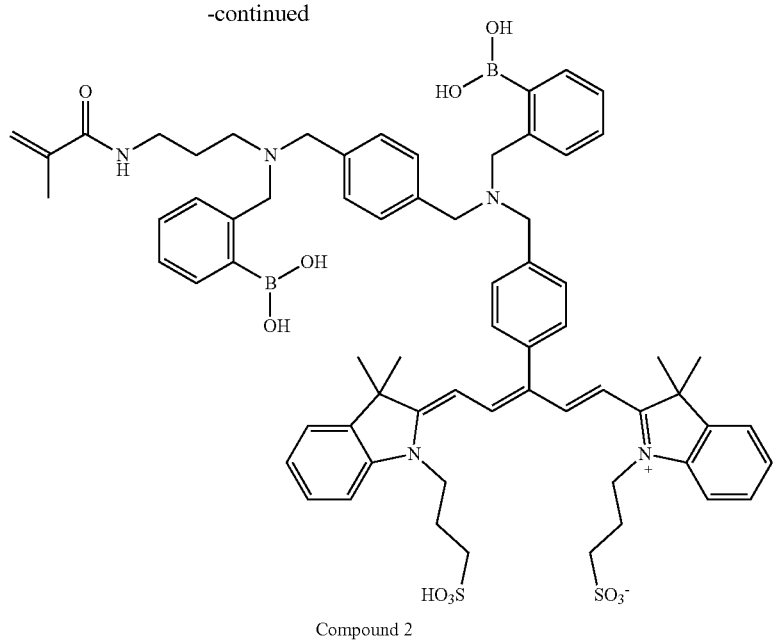

Compound 2

General Procedure VI. Alkylation of 2,3,3-trimethyl-3H-indole with sultone. Preparation of Compound 2-1

A mixture of 2,3,3-trimethyl-3H-indole (9.90 g, 62.3 mmol) and 1,3-propanesultone (11.4 g, 93.4 mmol) in anhydrous MeCN (150 mL) was heated at 90° C. in a sealed vessel overnight. Then the mixture was poured into diethyl ether (500 mL) under vigorous stirring and then filtered. The solid product was dried under high vacuum to afford the intermediate 2-1 as a pink solid (15 g, 86% yield).

Compound 2 was prepared from intermediate 2-1, following general procedures II, III, IV, and V, as outlined in the scheme above. HPLC-MS: m/z=1217.1 (calcd. 1216.5 for M$^+$); $\lambda_{max}$=650 nm.

Preparation of Compound 3

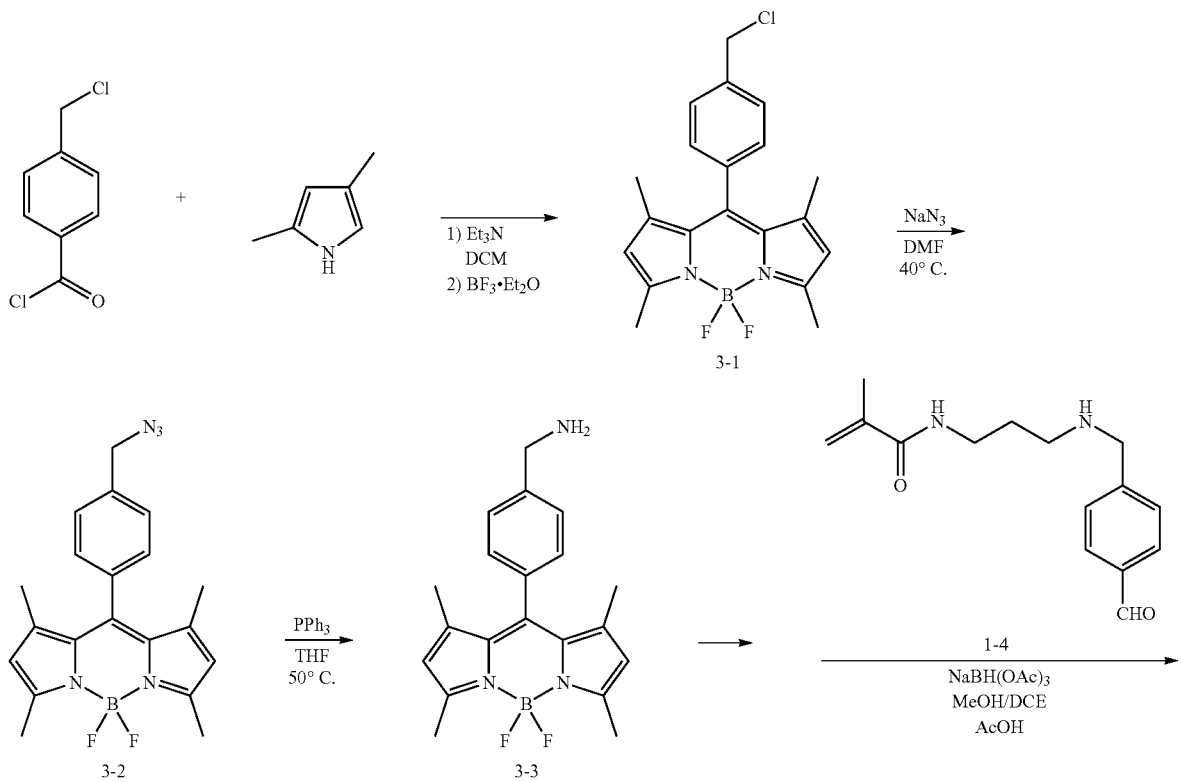

-continued

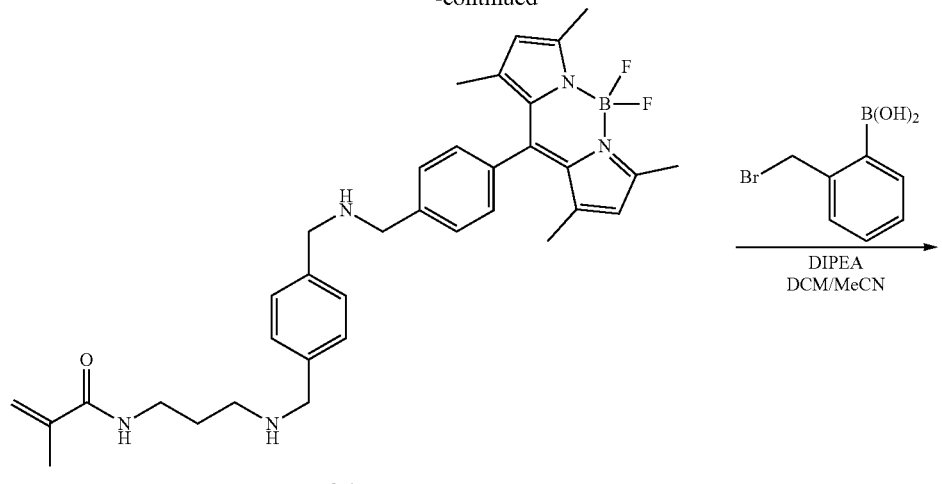

3-4

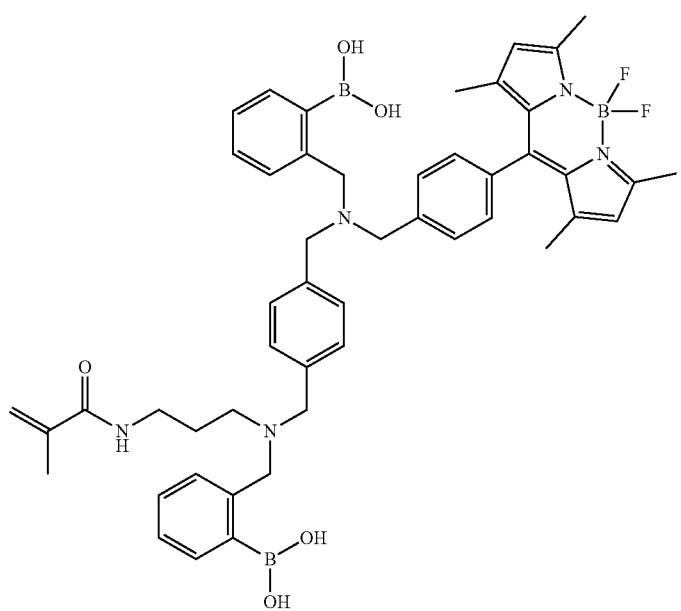

Compound 3

Preparation of Compound 3-1

To a stirred solution of 2,4-dimethylpyrrole (5.7 g, 60 mmol) in DCM (120 mL) p-(chloromethyl)benzoyl chloride (5.67 g, 30 mmo) was added dropwise at room temperature and under nitrogen atmosphere. The mixture was stirred for 12 h. Triethylamine (20 mL) was added, the reaction mixture was stirred for additional 1 h at room temperature, followed by addition of boron trifluoride diethyl etherate (20 mL). The reaction mixture was stirred for 2 h, and concentrated under reduced pressure. The residue was purified by column chromatography ($SiO_2$, eluted with hexanes/EtOAc=8:1) to give intermediate 3-1 (3.0 g, 27% yield) as orange solid.

Preparation of Compound 3-2

To a mixture of compound 3-1 (3.75 g, 10.0 mmol) in DMF (60 mL) was added sodium azide (0.98 g, 15.0 mmol) at room temperature. The resulting mixture was stirred at 40° C. overnight, then diluted with water (500 mL), and extracted with EtOAc (3×200 mL). The organic layers were combined, washed with brine (3×100 mL), dried over sodium sulfate, filtered, and concentrated to give compound 3-2 (2.6 g, 75% yield) as brown solid, which was used directly for the next step without further purification.

Preparation of Compound 3-3

To a solution of compound 3-2 (2.05 g, 5.78 mmol, 1.0 eq) in THF (100 mL) was added triphenylphosphine (2.07 g, 7.09 mmol) and water (10 mL) at room temperature. The resulting mixture was stirred at 50° C. overnight under nitrogen atmosphere. Then the mixture was concentrated under reduced pressure. The residue was purified by flash chromatography ($SiO_2$, eluted with DCM/EtOAc=1:1, then DCM/MeOH=10:1 to afford compound 3-4 (1.5 g, 81% yield) as brown solid.

Compound 3 was prepared from intermediate 3-3 following general procedures IV and V. HPLC-MS: m/z 867.2 (calcd. 866.5 for M+H$^+$); $\lambda_{max}$=502 nm.

Preparation of Compound 4
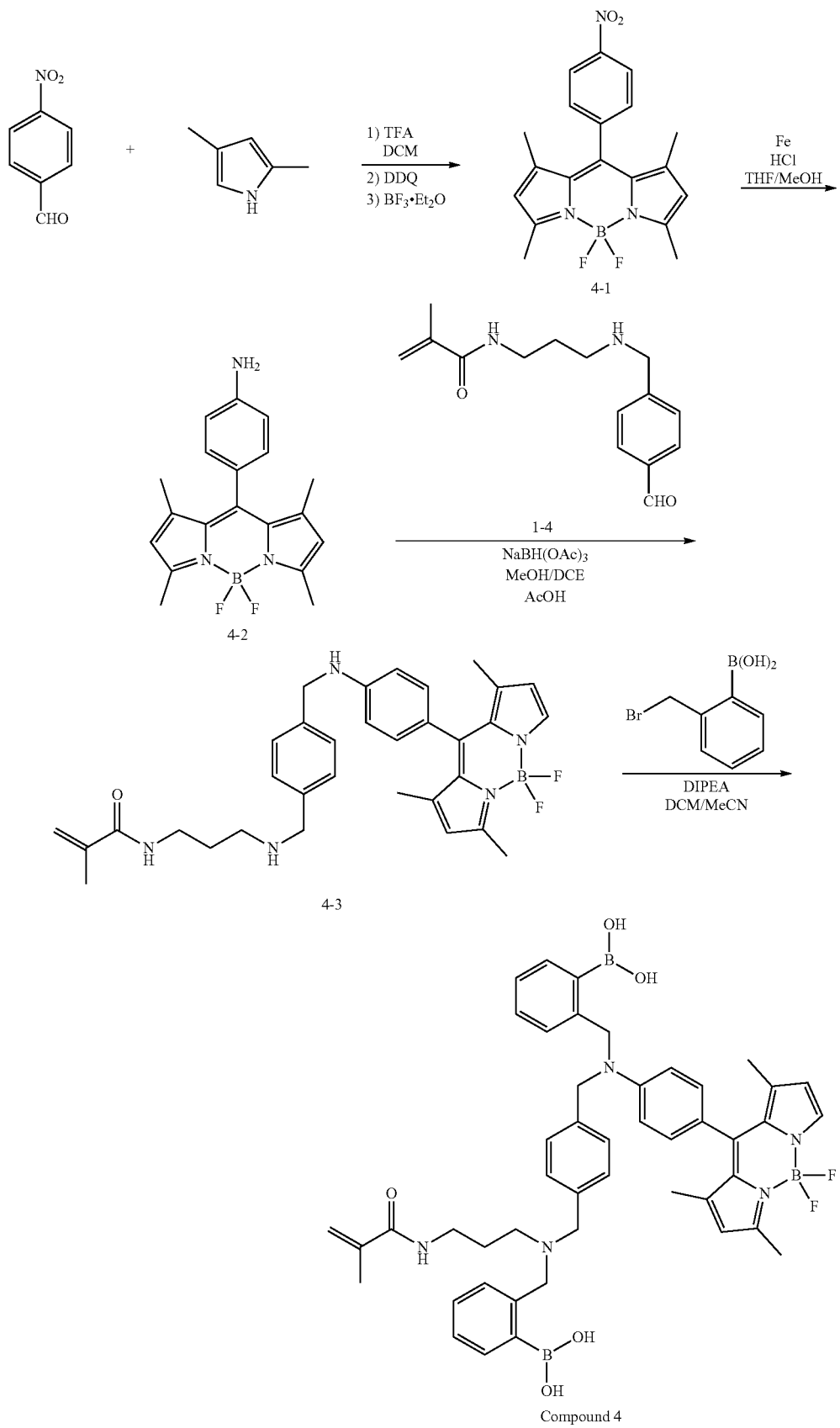

General Procedure VII. Preparation of BODIPY Fluorophore from Aldehyde and Pyrrole.
Preparation of Compound 4-1

A mixture of 4-nitrobenzaldehyde (1.20 g, 7.9 mmol), 2,4-dimethylpyrrole (1.6 mL, 15.9 mmol), and TFA (0.12 mL, 1.6 mmol) in anhydrous DCM (300 mL) was stirred at room temperature for 3 h. Then 2,3-dichloro-5,6-dicyano-1,4-benzoquinone (1.80 g, 7.9 mmol) was added and the darkened reaction mixture was stirred for 1 h. Triethylamine (11 mL, 79 mmol) and boron trifluoride diethyl etherate (12.7 mL, 103 mmol) were subsequently added and the mixture was stirred for 1 h. The reaction mixture was then washed with water (2×500 mL) and brine (250 mL). Organic layer was dried over anhydrous $Na_2SO_4$, filtered, and concentrated in vacuo. The residue was purified by flash chromatography ($SiO_2$, eluted with gradient of 0% to 30% EtOAc in hexanes). Yield: 0.60 g (21%).

Preparation of Compound 4-2

A mixture of intermediate 4-1 (1.23 g, 3.3 mmol), and iron powder (3.53 g, 63.3 mmol) in THF (75 mL), 0.5 M methanolic HCl (20 mL), and water (5 mL) was refluxed for 2 h. Then the reaction mixture was concentrated in vacuo, the residue was redissolved in DCM (100 mL), filtered, and concentrated again. The residue was purified by flash chromatography ($SiO_2$, eluted with gradient of 0% to 30% EtOAc in hexanes) yielding the title compound 4-2 (0.85 g, 76% yield) as a red-orange solid.

Compound 4 was prepared from intermediates 4-2 and 1-4 following general procedures IV and V. HPLC-MS: m/z 852.5 (calcd. 852.4 for M+H$^+$); $\lambda_{max}$=500 nm. H NMR (400 MHz, MeOH-d$_4$+NaOD) δ ppm 7.61 (d, J=7.6 Hz, 2H), 7.23-7.33 (m, 4H), 6.96-7.13 (m, 4H), 6.91-6.96 (m, 2H), 6.88 (d, J=8.7 Hz, 2H), 6.78 (d, J=8.7 Hz, 2H), 6.00 (s, 2H), 5.49 (s, 1H), 5.25 (q, J=1.1 Hz, 1H), 5.09 (br. s, 2H), 4.70 (br. s., 2H), 3.83 (br. s., 2H), 3.58 (br. s., 2H), 3.06 (t, J=6.5 Hz, 2H), 2.41 (t, J=7.0 Hz, 2H), 1.82 (q, J=1.1 Hz, 3H), 1.73 (quin, J=6.7 Hz, 2H), 1.50 (s, 6H). Six methyl protons from BODIPY overlapped with the solvent peak.

Preparation of Compound 6

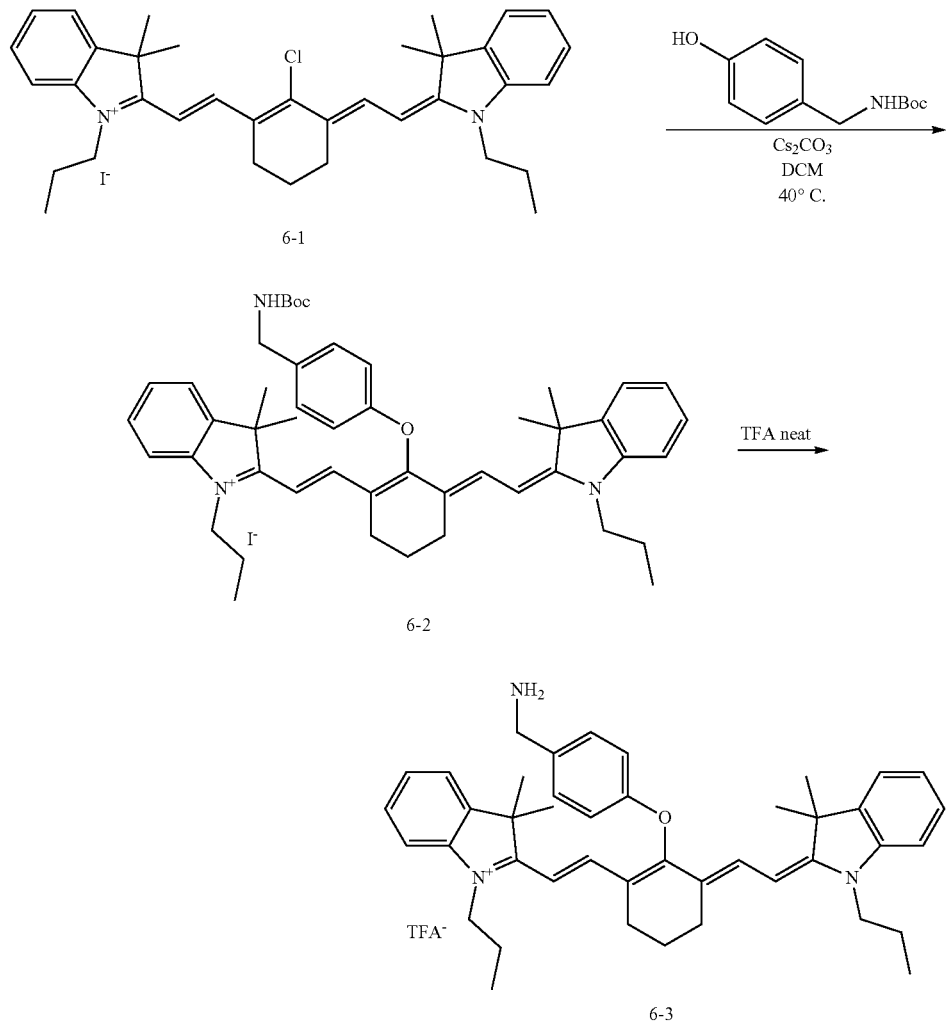

Scheme 4. Preparation of compound 6

-continued
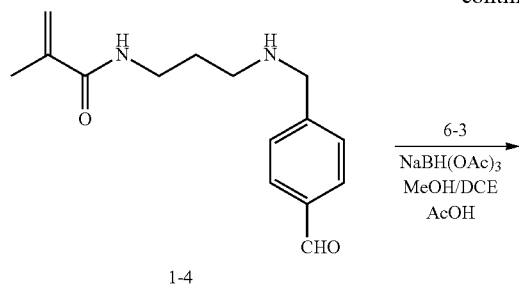
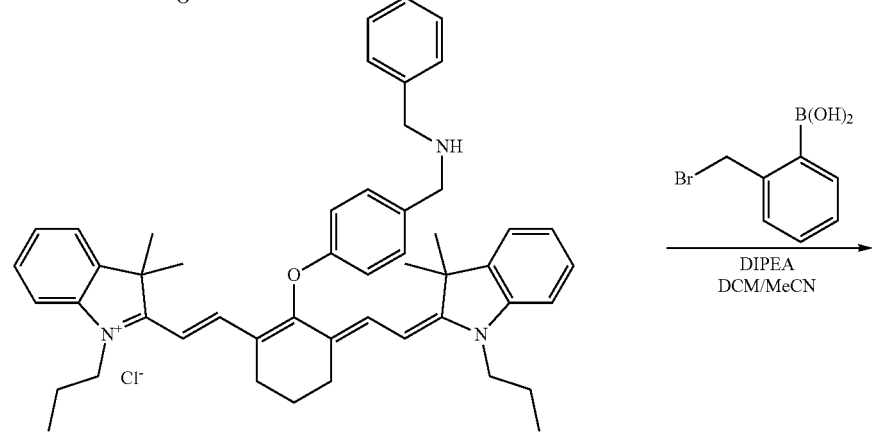
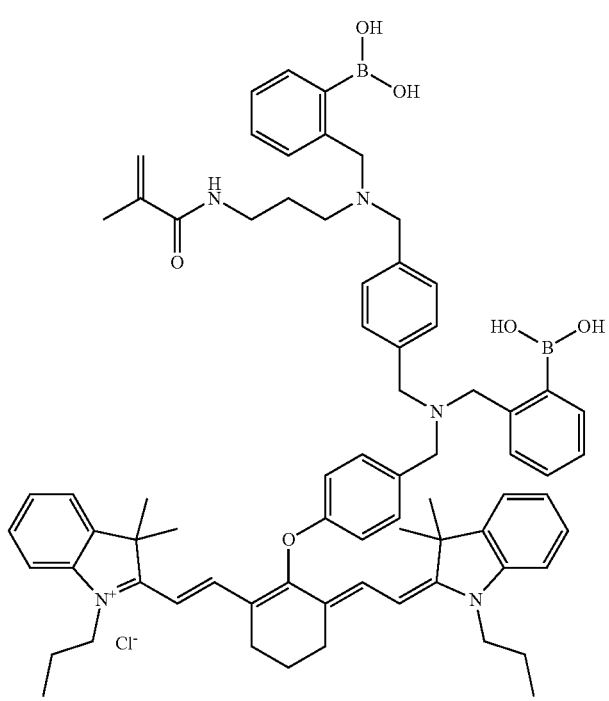
Compound 6

General Procedure VIII. Nucleophilic Substitution at Cy7 Fluorophore. Preparation of 2-(2-{2-chloro-3-[(1,3-dihydro-3,3-dimethyl-1-propyl-2H-indol-2-ylidene)ethylidene]-2-(4-tert-butylcarbamate aminomethylphenoxy)-1-cyclohexen-1-yl}ethenyl)-3,3-dimethyl-1-propylindolium iodide 6-2

A mixture of tert-butyl (4-hydroxyphenylmethyl)carbamate (348 mg, 1.5 mmol), IR-780 (6-1) (500 mg, 0.75 mmol), and cesium carbonate (487 mg, 1.5 mmol) in anhydrous DCM (50 mL) was stirred at 40° C. under argon. After 1 h, the reaction mixture was filtered through Celite® and the filtrate was concentrated in vacuo. The crude residue was purified by flash chromatography (SiO$_2$, eluted with DCM and MeOH) to yield the title product 6-2 (1.3 g, quant.).

General Procedure IX. Boc Deprotection. Preparation of 2-(2-{2-chloro-3-[(1,3-dihydro-3,3-dimethyl-1-propyl-2H-indol-2-ylidene)ethylidene]-2-(4-aminomethylphenoxy)-1-cyclohexen-1-yl}ethenyl)-3,3-dimethyl-1-propylindolium iodide 6-3

Intermediate 6-2 (625 mg, 0.73 mmol) was dissolved in neat TFA (10 mL) at 0° C. The reaction mixture was allowed to warm up to room temperature over 5 min while stirring under argon. Then the solution was concentrated in vacuo. The crude product was purified by flash chromatography (SiO$_2$, eluted with DCM and MeOH) to afford the pure product 6-3 (466 mg, 88%).

Preparation of Compound 6-4

To a solution of intermediate 6-3 (895 mg, 1.19 mmol) in anhydrous MeOH (40 mL) over molecular sieves (3 Å, 500 mg), glacial acetic acid (0.35 mL, 6.0 mmol) and intermediate 1-4 (752 mg, 1.49 mmol) were added. The reaction mixture was stirred for 15 min at room temperature, followed by portion-wise addition of sodium triacetoxyborohydride (3×277 mg, 3.90 mmol) with 10 min intervals. 15 min after the last addition, the reaction mixture was filtered and the filtrate was concentrated in vacuo. The residue was then diluted with DCM and washed with saturated NaHCO$_3$ and brine. The DCM layer was then dried over MgSO$_4$ and concentrated in vacuo. The crude product was purified by flash chromatography (SiO$_2$, eluted with DCM and MeOH) yielding the title compound 6-4 (415 mg, 35%).

Preparation of Compound 6

To a solution of intermediate 6-4 (400 mg, 0.40 mmol) in anhydrous DMF (4 mL) 2-bromomethylphenylboronic acid (600 mg, 2.8 mmol) and K$_2$CO$_3$ (1.35 g, 10.0 mmol) were added in three portions. The reaction mixture was stirred for 16 h at room temperature and then concentrated in vacuo. The residue was purified by flash chromatography (SiO$_2$, eluted with 0.05% HCl in MeOH and DCM). The pure product was taken up into DCM and washed with saturated NaHCO$_3$ three times. The DCM portion was then dried over MgSO$_4$ and concentrated in vacuo to yield the title compound 6 (90 mg, 18%). HPLC-MS: m/z 1138.5 (calcd. 1138.7 for M$^+$); $\lambda_{max}$=775 nm. $^1$H NMR (400 MHz, MeOH-d$_4$) δ ppm 7.96 (d, J=14.3 Hz, 1H), 7.63 (d, J=7.3 Hz, 1H), 7.36-7.44 (m, 6H), 7.32 (m, J=7.6, 7.6 Hz, 3H), 7.23-7.29 (m, 3H), 7.15-7.22 (m, 7H), 7.12 (m, J=7.3, 7.3 Hz, 4H), 6.14 (d, J=14.2 Hz, 2H), 5.52 (s, 1H), 5.22 (s, 1H), 4.13 (br. s., 2H), 4.04 (t, J=7.4 Hz, 4H), 4.03 (s, 2H), 3.65 (br. s., 2H), 3.52 (s, 2H), 3.50 (br. s, 2H), 3.35 (s, 1H), 3.10 (t, J=6.0 Hz, 2H), 2.74 (t, J=6.0 Hz, 4H), 2.54-2.68 (m, 2H), 2.04 (quin, J=6.0 Hz, 2H), 1.86-1.96 (m, 2H), 1.80 (m, J=7.7, 7.7, 7.7 Hz, 4H), 1.76 (s, 3H), 1.25 (s, 12H), 0.99 (t, J=7.4 Hz, 6H).

Preparation of Compound 5

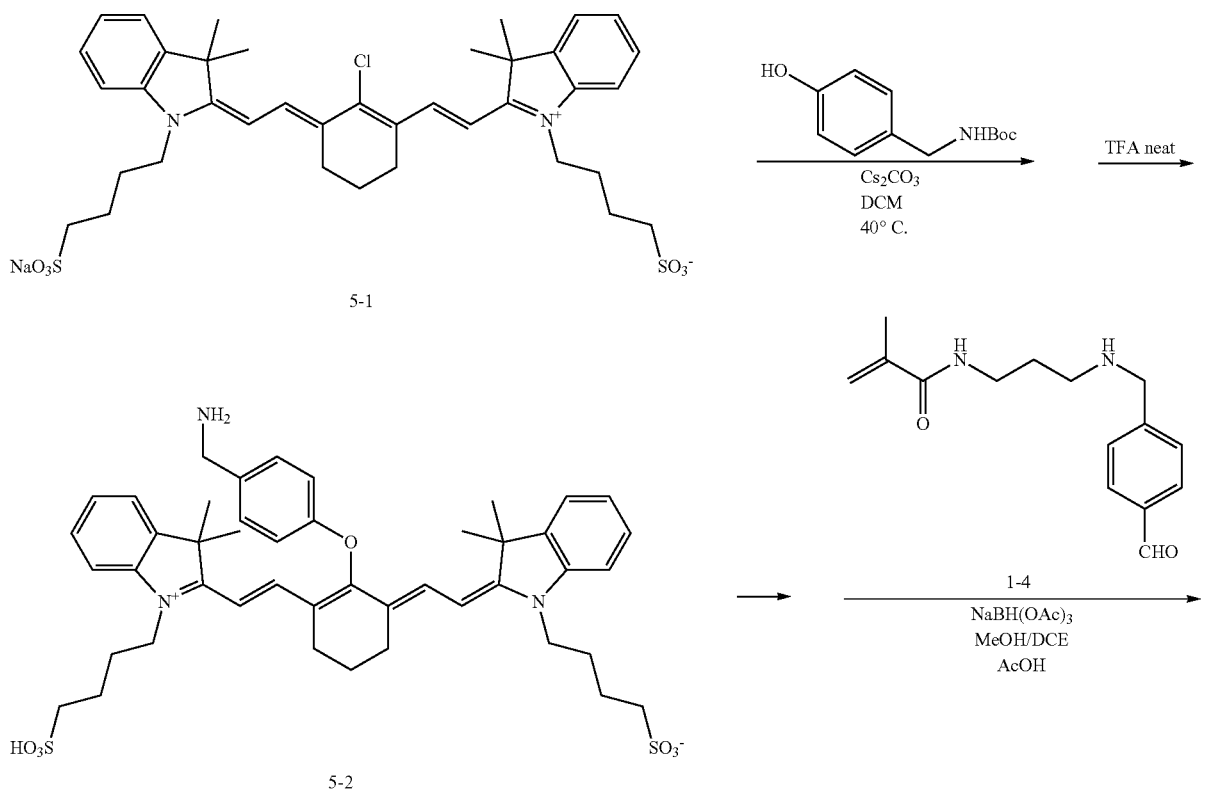

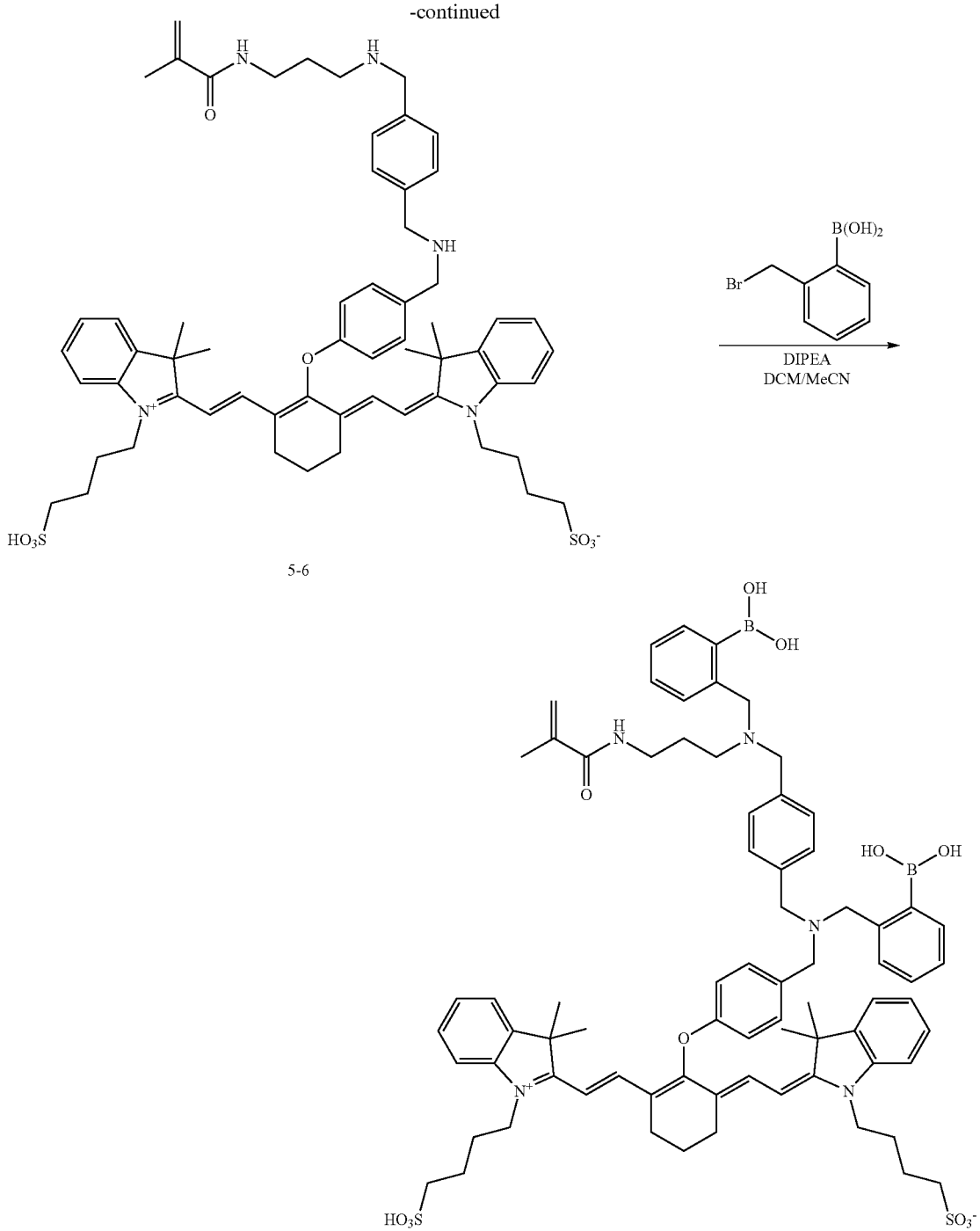

Compound 5

Preparation of 2-[2-(3-{2-[1,3-dihydro-3,3-dimethyl-1-(4-sulfobutyl)-2H-indol-2ylidene]ethylidene}-2-(4-aminomethylphenoxy)-1-cyclohexen-1-yl)ethenyl]-3,3-dimethyl-1-(4-sulfobutyl)-3H-indolium, monosodium salt (5-2)

A mixture of IR-783 (5-1) (4 g, 5.54 mmol), tert-butyl (4-hydroxyphenyl-methyl)carbamate (2.47 g, 11.1 mmol), and cesium carbonate (3.6 g, 11.1 mmol) in anhydrous DCM (100 mL) was stirred for 16 h at room temperature. The reaction mixture was filtered through Celite and the filtrate was concentrated in vacuo. The crude intermediate was dissolved in TFA (25 mL), the solution was stirred for 5 min and then concentrated in vacuo. The residue was purified by reversed-phase flash chromatography (C18 SiO$_2$, eluted with gradient of 0.09% HCl in MeOH). The pure product was isolated by basification of combined and concentrated fractions with saturated NaHCO$_3$, followed by triple extraction with DCM. The combined DCM layers were then dried over MgSO$_4$ and concentrated in vacuo to yield the title product 10-2 (5.4 g, quant.). HPLC-MS: m/z 1326.0 (calcd. 1326.6); $\lambda_{max}$=775 nm.

Preparation of Compound 7
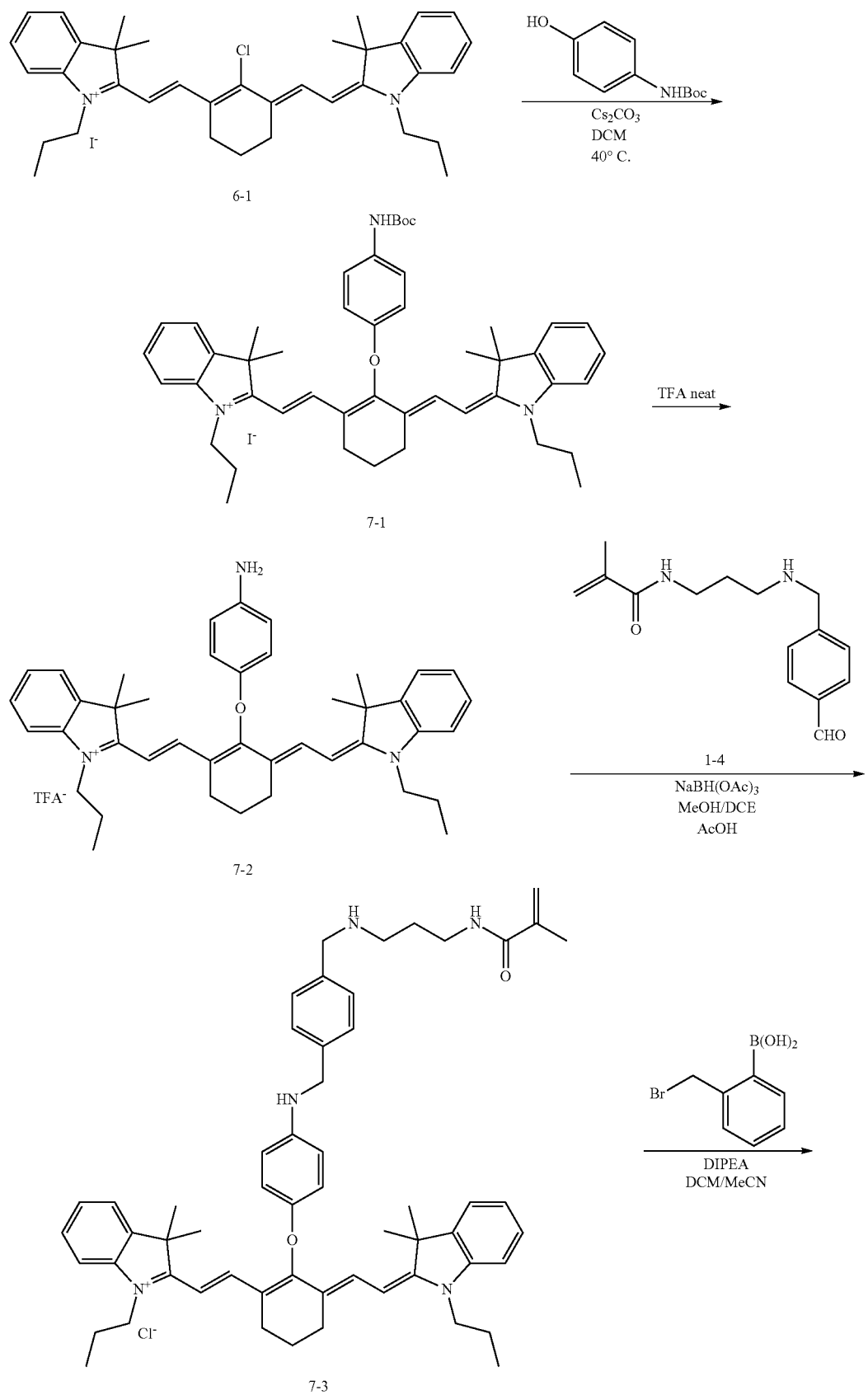

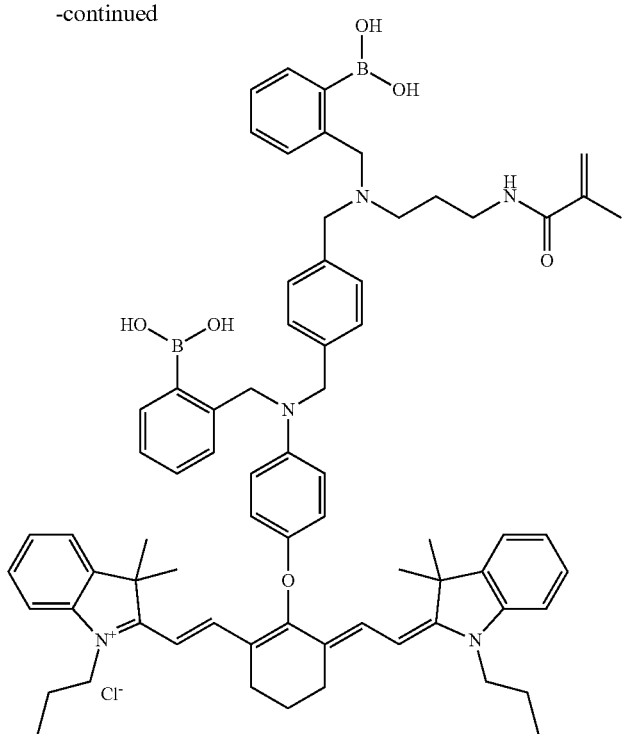
Compound 7
By analogy with compound 6, compound 7 was prepared from IR-780 and 4-N-Boc-aminophenol following general procedures VIII, IX, IV, and V. HPLC-MS: m/z 1124.5 (calcd. 1124.7); $\lambda_{max}$=775 nm. $^1$H NMR (400 MHz, MeOH-d$_4$) δ ppm 7.97 (d, J=14.2 Hz, 2H), 7.60 (br. s., 1H), 7.34-7.42 (m, 5H), 7.20-7.33 (m, 11H), 7.13-7.20 (m, 3H), 6.92 (s, 4H), 6.11 (d, J=14.2 Hz, 2H), 5.59 (s, 1H), 5.33 (s, 1H), 4.58 (s, 2H), 4.44 (s, 2H), 4.16 (br. s., 2H), 4.05 (t, J=7.4 Hz, 4H), 4.00 (br. s, 2H), 3.08 (t, J=6.2 Hz, 2H), 2.69 (t, J=6.0 Hz, 4H), 2.75 (br. s, 2H), 2.00 (m, J=6.4 Hz, 2H), 1.72-1.89 (m, 9H), 1.30 (s, 12H), 1.01 (t, J=7.4 Hz, 6H).
Preparation of Compound 10
Scheme 3. Preparation of compound 10
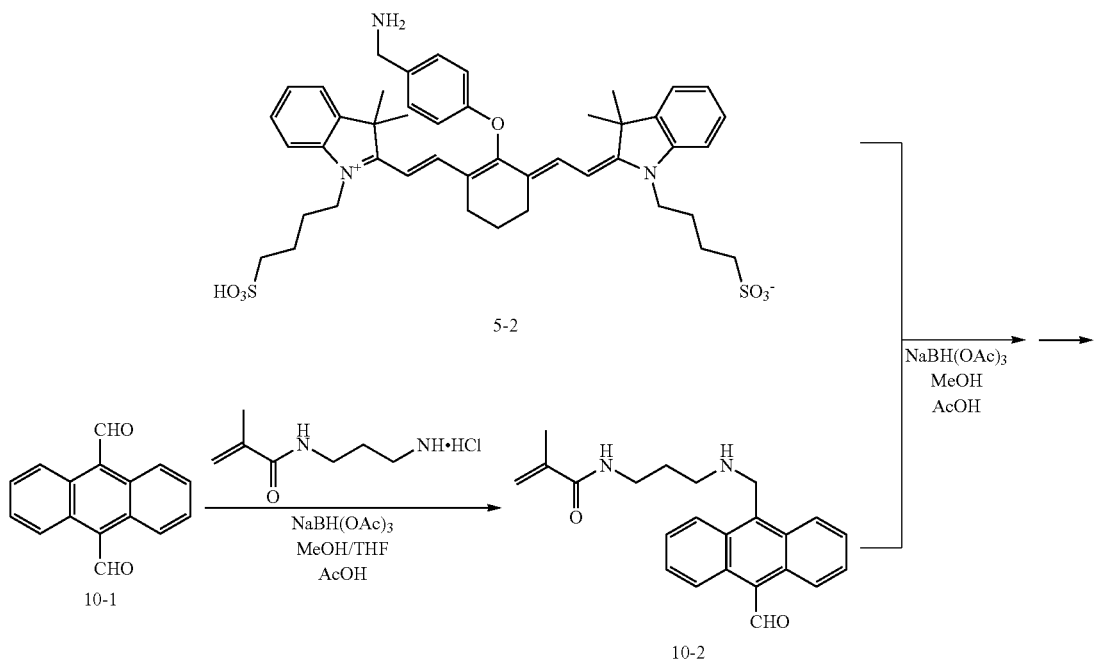

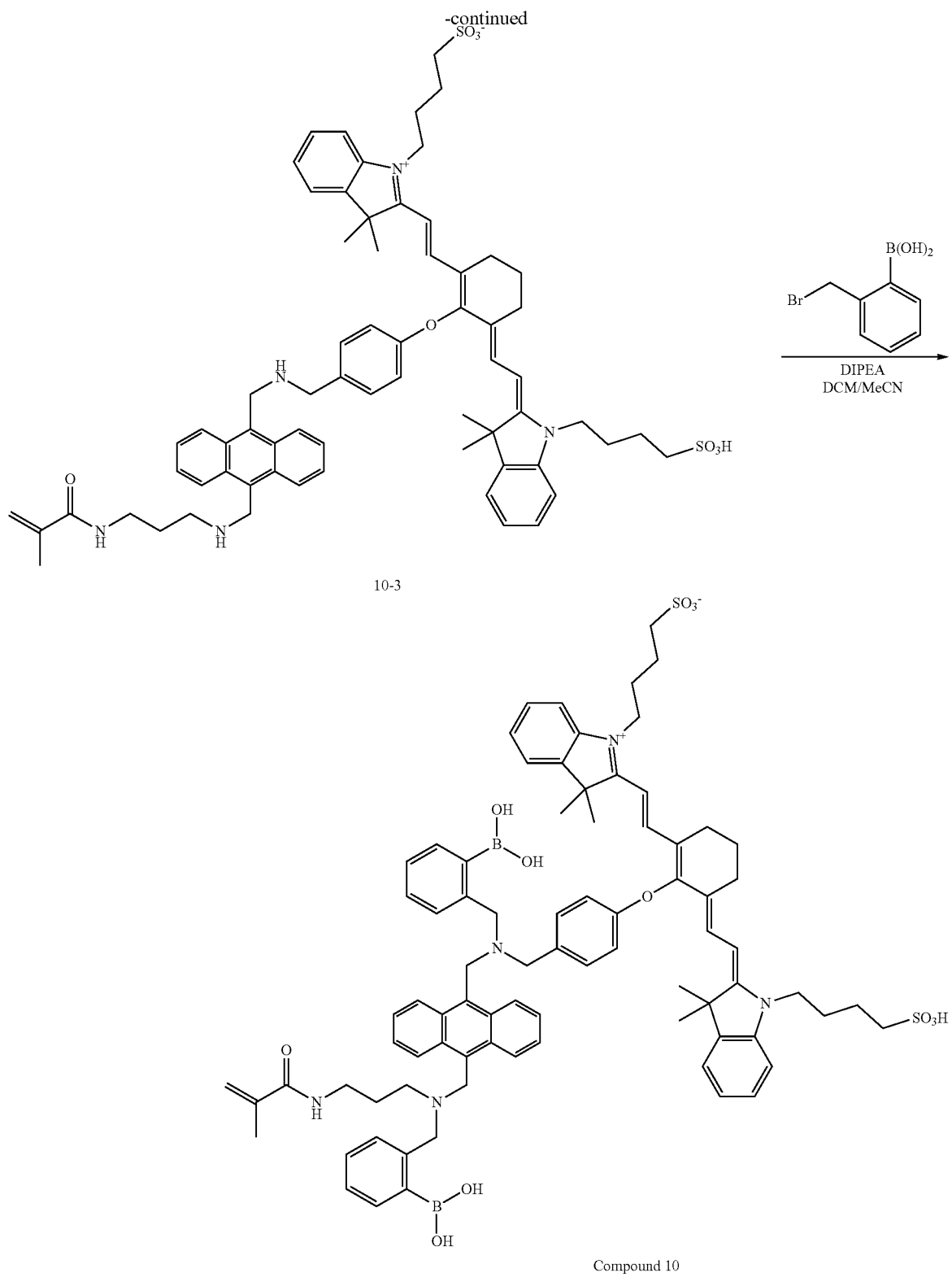

Compound 10

Preparation of 10-[(3-methacrylamidoprop-1-yl)aminomethyl]-9-anthracenecarboxaldehyde 10-2

To a solution of N-(3-aminopropyl)methacrylamide hydrochloride (1.00 g, 5.78 mmol) in anhydrous MeOH (5 mL), a solution of anthracene-9,10-dicarboxaldehyde (2.7 g, 11.56 mmol) in anhydrous DCM (10 mL) was added. The resulting mixture was diluted with anhydrous THF (150 mL) and acetic acid (0.52 mL, 8.6 mmol), followed by addition of sodium triacetoxyborohydride (2.45 g, 11.56 mmol). The mixture was stirred at room temperature. After 1 h, a second portion of sodium triacetoxyborohydride (1.2 g, 5.75 mmol) was added and the reaction was stirred at room temperature for 2 h. The reaction mixture was then diluted with DCM and washed with sat NaHCO₃ and brine. The DCM portion was then dried over MgSO₄ and concentrated in vacuo. The crude product was purified by flash chromatography (SiO₂, eluted with MeOH and DCM) to afford the title compound 10-2 (424 mg, 20%).

Preparation of Compound 10-3

A mixture of intermediate 5-2 (294 mg, 0.351), molecular sieves (3 Å), glacial acetic acid (200 µL, 1.4 mmol), and intermediate 10-2 (190 mg, 0.528 mmol) in anhydrous MeOH (10 mL) and DCE (5 mL) was stirred at room temperature for 15 minutes. Then sodium triacetoxyborohydride (112 mg, 0.528 mmol) was added and then the addition was repeated three more times over 20 h. The reaction was then concentrated in vacuo to approximately 2 mL, and basified by saturated NaHCO₃. The crude product was purified by reversed-phase flash chromatography three times (C18 SiO₂, eluted with gradient of water and MeOH with 0.1% TFA) to afford pure title product 10-3 (105 mg, 21.7%).

Preparation of Compound 10

A solution of intermediate 10-3 (90 mg, 0.065 mmol) and DIPEA (42.2 mg, 0.327 mmol) in anhydrous DCM (8 mL) was stirred for 10 min, followed by the addition of 2-bromomethylphenyl boronic acid (58.5 mg, 0.327 mmol). After 90 min, the reaction mixture was diluted with hexanes and centrifuged. The precipitate purified by reversed-phase flash chromatography (C18 SiO₂, eluted with gradient of water and MeOH). Pure title compound 10 was obtained by precipitating from concentrated DCM solution with diethyl ether (61 mg, 64%). HPLC-MS: m/z 1428.6 (calcd. 1426.7 for M+H⁺); $\lambda_{max}$=760 nm. ¹H NMR (400 MHz, MeOH-d₄) δ ppm 8.42 (d, J=8.2 Hz, 2H), 8.31 (d, J=8.8 Hz, 2H), 7.94 (d, J=14.2 Hz, 2H), 7.34-7.59 (m, 9H), 7.16-7.34 (m, 9H), 7.12 (d, J=8.5 Hz, 2H), 6.94-7.06 (m, 4H), 6.15 (d, J=14.2 Hz, 2H), 5.37 (s, 1H), 5.18 (quin, J=1.3 Hz, 1H), 4.41 (br. s., 2H), 4.13 (br. s., 2H), 4.06 (t, J=6.5 Hz, 4H), 3.60 (br. s., 2H), 3.53 (s, 2H), 2.99 (t, J=6.5 Hz, 2H), 2.86 (t, J=6.8 Hz, 4H), 2.66-2.80 (m, 6H), 2.04 (quin, J=6.5 Hz, 2H), 1.81-1.97 (m, 10H), 1.70 (s, 3H), 1.16 (s, 12H). One benzylic CH₂ group overlapped with the solvent signal.

Preparation of Compound 8

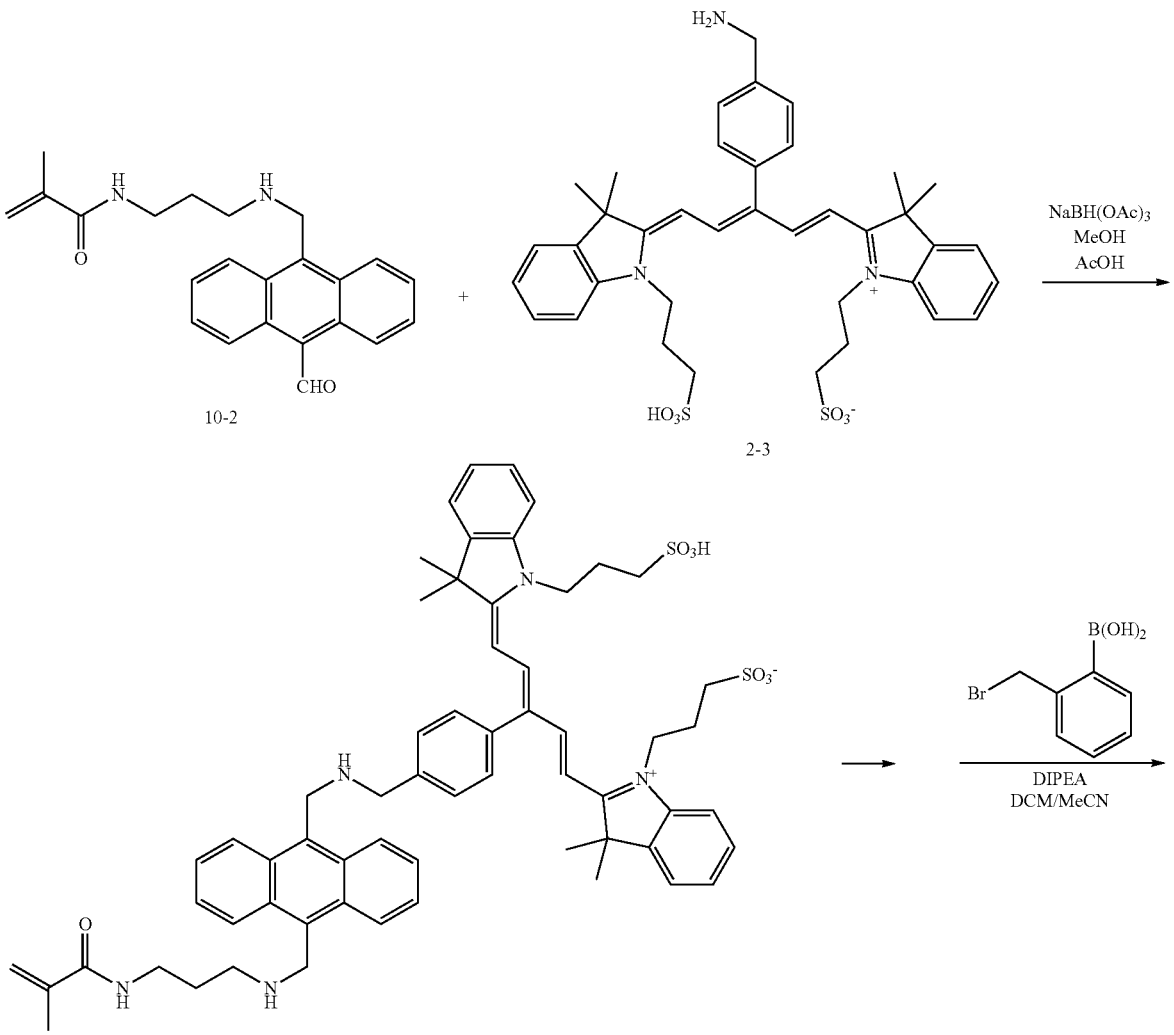

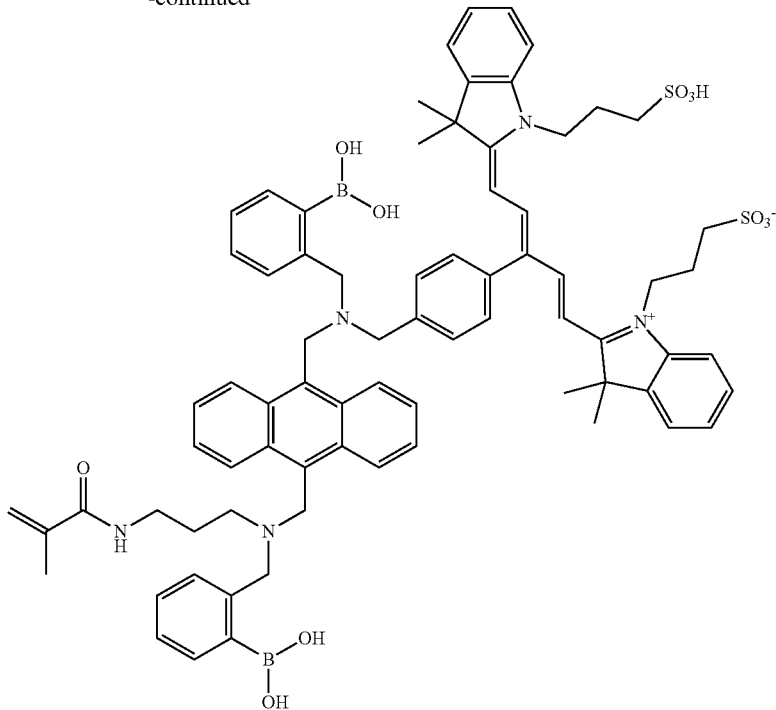

Compound 8

Preparation of Compound 8-1

By analogy with intermediate 10-3, anthacenecarboxaldehyde 10-2 (272 mg, 0.76 mmol) was coupled with Cy5-benzylamine 2-3 (500 mg, 0.69 mmol) under treatment of triacetoxyborohydride (726 mg, 3.4 mmol) and acetic acid (124 mg, 2.1 mmol). The desired product was isolated as a blue solid (13 mg, 2% yield) after purification by reversed phase flash chromatography (MeOH-water+0.25% HCl).

Preparation of Compound 8

By analogy with synthetic procedure for Compound 10, diamine 8-2 (13 mg, 0.012 mmol) was alkylated with 2-bromomethylphenylboronic acid (6.5 mg, 0.030 mmol) affording target product (7 mg, 44% yield) as a dark blue solid. HPLC-MS: m/z 1317.5 (calcd. 1316.6 for M+H$^+$); $\lambda_{max}$=640 nm.

Preparation of Compound 9

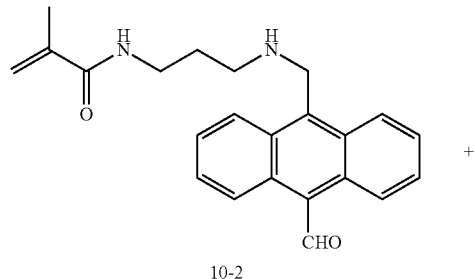

10-2

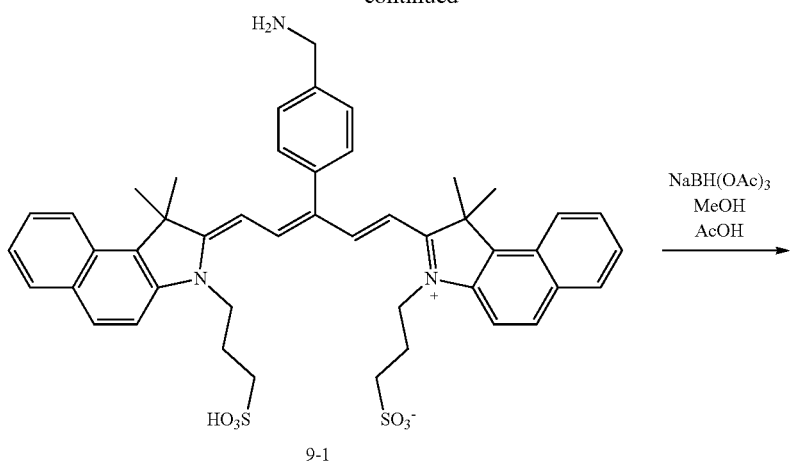
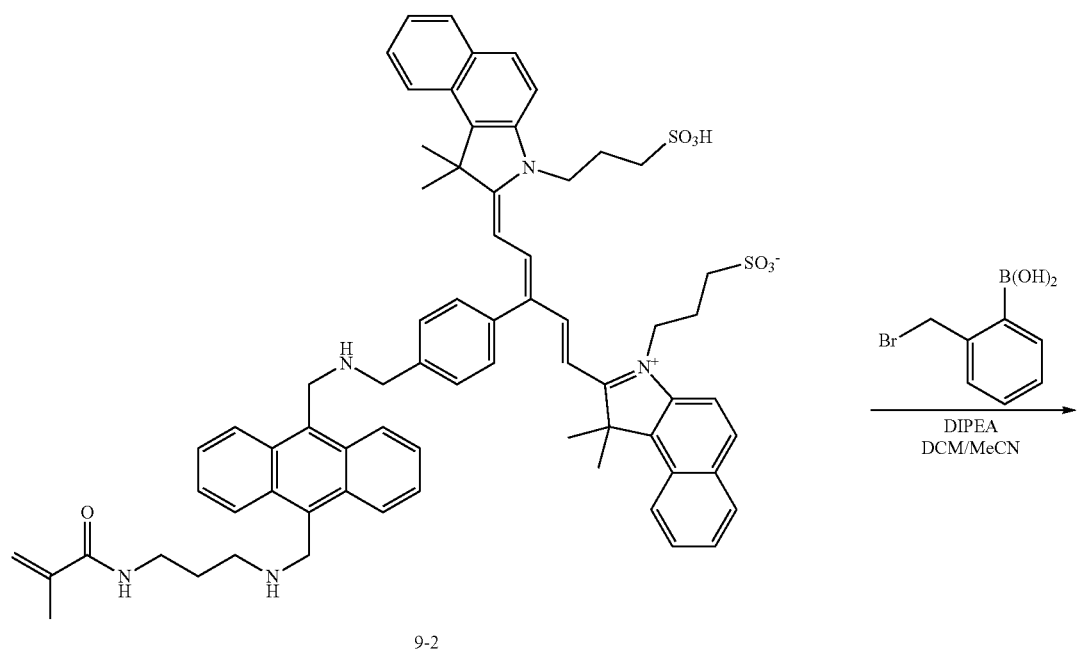

-continued

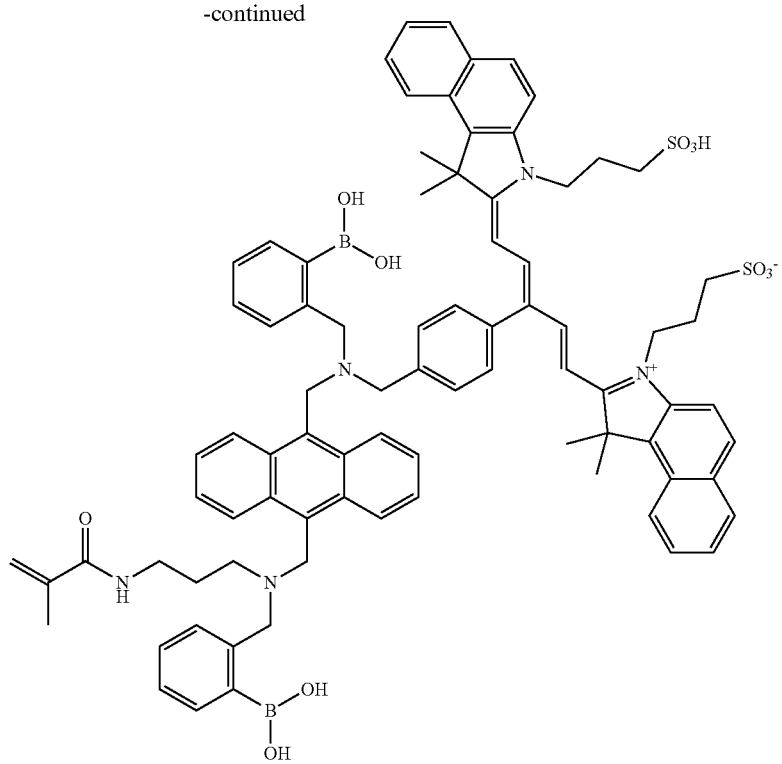

Compound 9

Intermediate 9-1 was prepared from 1,1,2-trimethyl-1H-benzo[e]indole following general procedures VI, II, and III (see intermediate 2-3). Compound 9 was then synthesized from intermediates 10-2 and 9-1 following analogous route as described for Compound 8, following general procedures IV and V. HPLC-MS: 1417.5 m/z (calcd. 1416.6 for M+H$^+$); $\lambda_{max}$=630, 685 nm.

Preparation of Compound 11

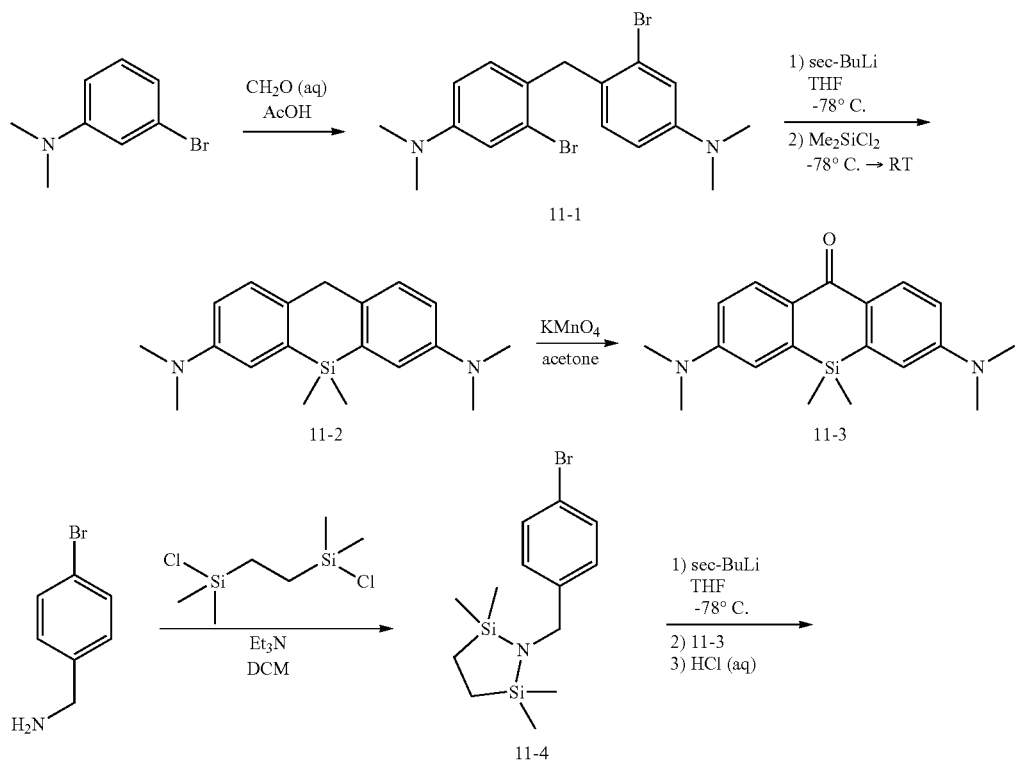

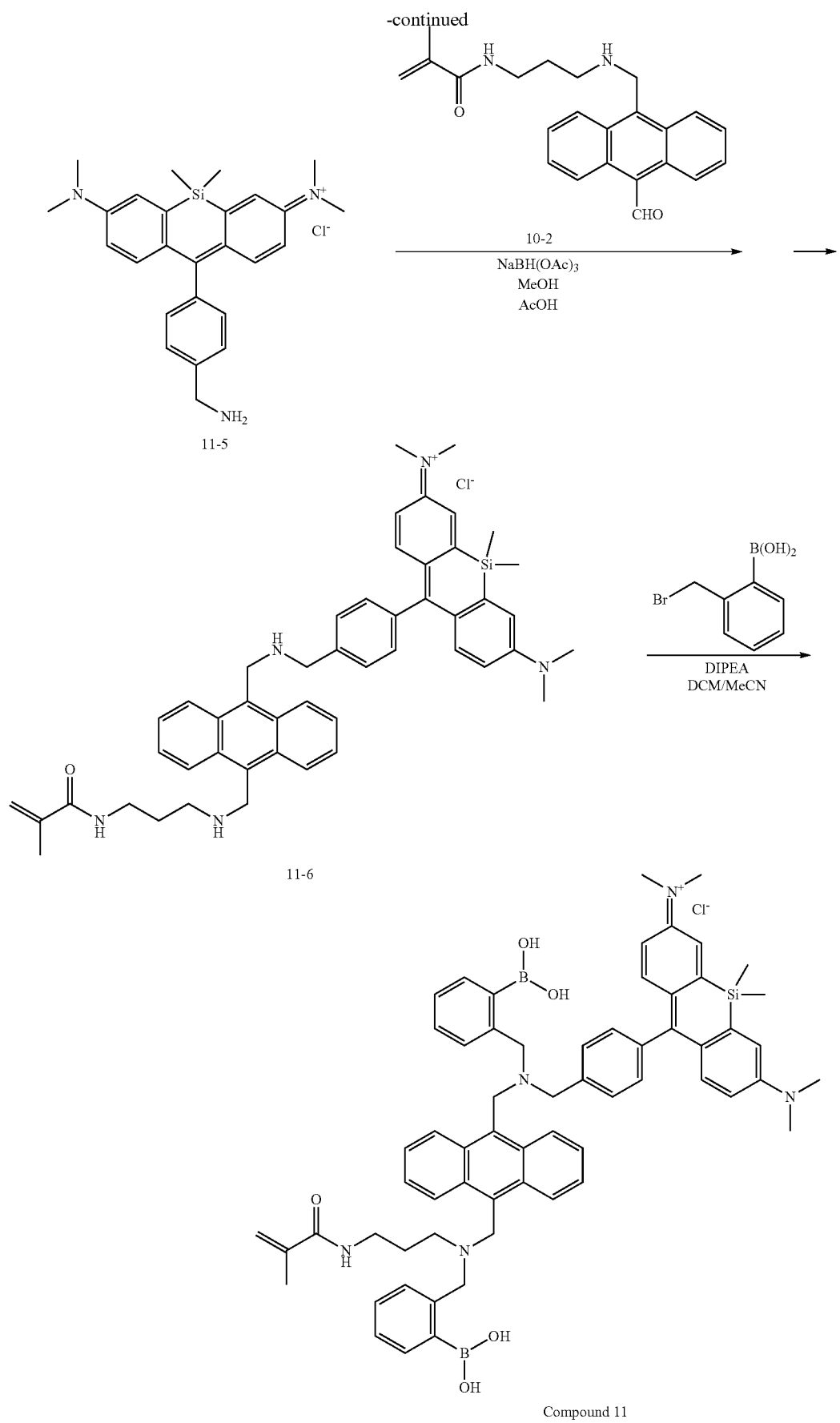
Compound 11

Preparation of Compound 11-1

Formaldehyde (63.52 g, 0.807 mol, as 38% in water), acetic acid (1500 mL), and 3-bromo-N,N-dimethylaniline (323 g, 1.615 mol) were combined and stirred at 60° C. under argon for 2 h. The reaction mixture was then concentrated under reduced pressure. The residue was dissolved in DCM (100 mL), washed with saturated NaHCO$_3$ and brine, dried over anhydrous Na$_2$SO$_4$, filtered, and concentrated under reduced pressure. The residue was purified by flash chromatography (SiO$_2$, eluent: DCM/hexanes 1:5). This afforded title intermediate 11-1 (216 g, 65% yield) as a pink solid.

Preparation of Compound 11-2

To a solution of intermediate 11-1 (30 g, 73 mmol) in anhydrous THF (200 mL) cooled to −78° C. under argon atmosphere, sec-butyllithium (1.3 M in cyclohexane, 168 mL, 218 mmol) was added dropwise over 30 minutes. The resulting mixture was stirred at 78° C. for 2 h, followed by addition of dichlorodimethyl silane (16.9 g, 131.1 mmol). The mixture was allowed to warm up to room temp over 2 h. The reaction was then quenched with 1 M HCl, pH was adjusted to 8 with NaOH, and the mixture was extracted with DCM (3×300 mL). Combined organic layers were washed with brine, dried over anhydrous Na$_2$SO$_4$, filtered, and concentrated under reduced pressure to give crude compound 11-2 (28 g) as a green solid. The crude product was used directly for the next step, without further purification.

Preparation of Compound 11-3

The crude compound 11-2 (28 g, theor. 73 mmol) was dissolved in acetone (300 mL) and cooled to −15° C. To this solution KMnO$_4$ (42.5 g, 271 mmol) was added portionwise over 30 minutes and the reaction mixture was stirred for 2 h at −15° C. Reaction then was allowed to warm up to room temperature, filtered through Celite®, and the filter cake was rinsed with acetone. The filtrate was concentrated under reduced pressure. The residue was purified by flash chromatography (SiO$_2$, eluent: DCM). This resulted in compound 11-3 (8 g, 26% yield) as a yellow-green solid.

Preparation of Compound 11-4

A mixture of 4-bromobenzylamine (1.0 g, 5.4 mmol), triethylamine (1.50 mL, 10.7 mmol) in anhydrous DCM (50 mL) was cooled to 0° C. under argon atmosphere. A solution of 1,2-bis(chlorodimetylsilyl)ethane (1.16 g, 5.4 mmol) in anhydrous DCM (20 mL) was added via cannula. The mixture was stirred for 1 h at 0° C. and then 1 h at room temperature. The solvent was removed in vacuo, the residue was suspended in hexanes and filtered. Filtrate was concentrated in vacuo and used in the next step without further purification.

General Procedure X. Preparation of Silicon Rosamine Fluorophore Via Lithium-Halogen Exchange with Sec-BuLi. Preparation of Compound 11-5

To a solution of arylbromide 11-4 (theor. 5.4 mmol) in anhydrous THF (20 mL) cooled to −78° C. under argon atmosphere, sec-butyllithium (c=1.4 M in cyclohexane, 5.76 mL, 8.1 mmol) was added dropwise. The mixture was stirred at −78° C. for 1 h. Then a solution of silaxanthone 11-3 (0.17 g, 0.5 mmol) in anhydrous THF (10 mL) was added via cannula, and the mixture was allowed to warm up to room temperature overnight. The reaction was quenched with 1 M HCl (10 mL) and stirred for 30 min to 3 h (monitored the progress by LCMS). The pH was adjusted to 8 with NaOH and the mixture was extracted with DCM. Combined organic layers were dried over anhydrous MgSO$_4$, filtered, and concentrated in vacuo. The residue was purified by reversed phase flash chromatography (C18 SiO$_2$, gradient elution with 0.25% HCl (aq) in MeOH). Yield: 250 mg (quant.) as a dark-blue solid.

Compound 11 was synthesized from intermediates 11-5 and 10-2, following general procedures IV and V. HPLC-MS: m/z 1027.1 (calcd. 1026.5 for M$^+$); $\lambda_{max}$=650 nm.

Preparation of Compound 12

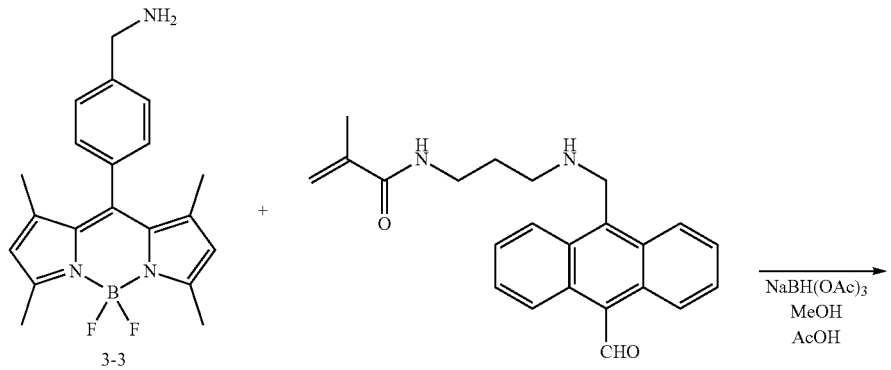

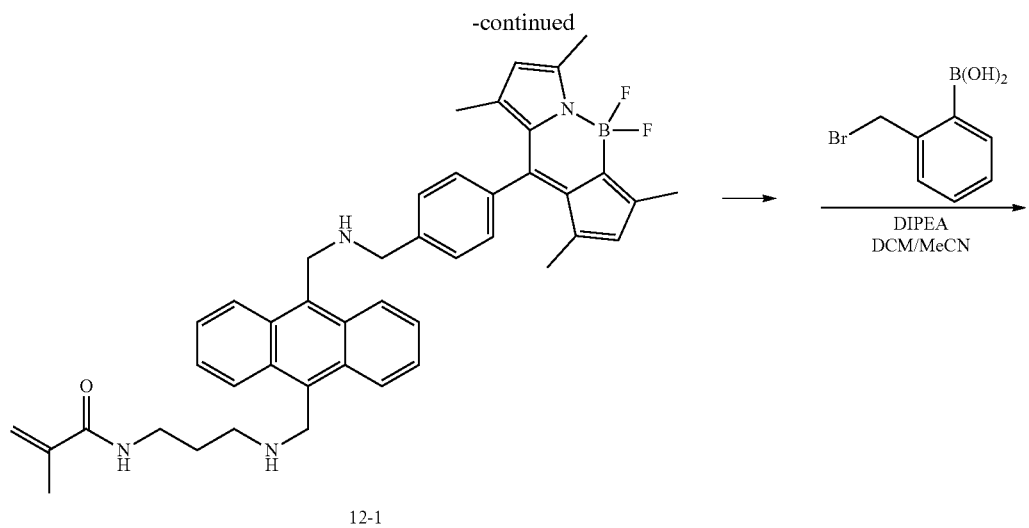
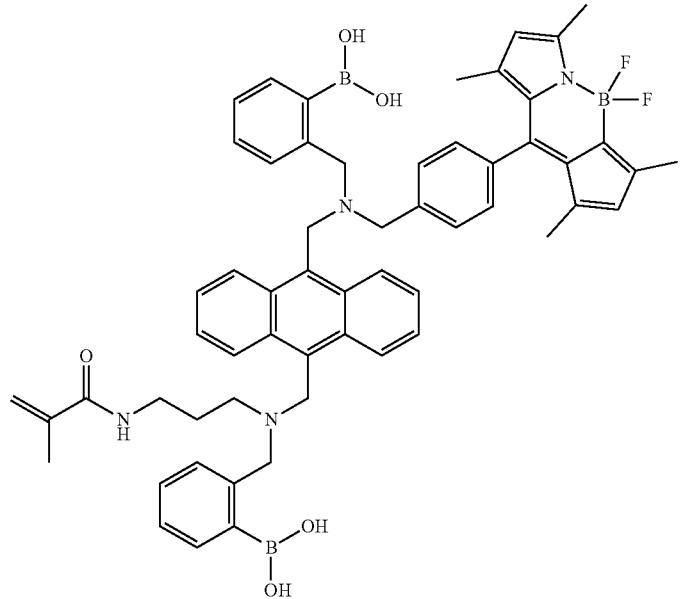
Compound 12 was synthesized form intermediates 3-3 and 10-2, following general procedures IV and V. HPLC-MS: m/z 967.4 (calcd. 966.5 for M+H⁺); $\lambda_{max}$=500 nm.
Preparation of Compound 13
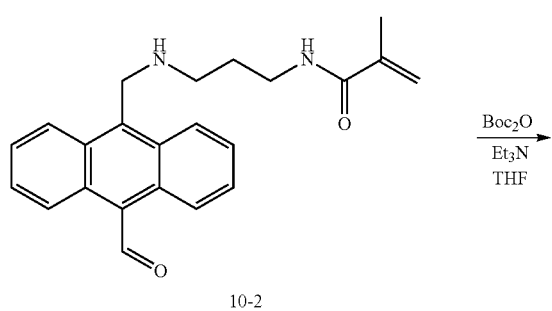

-continued
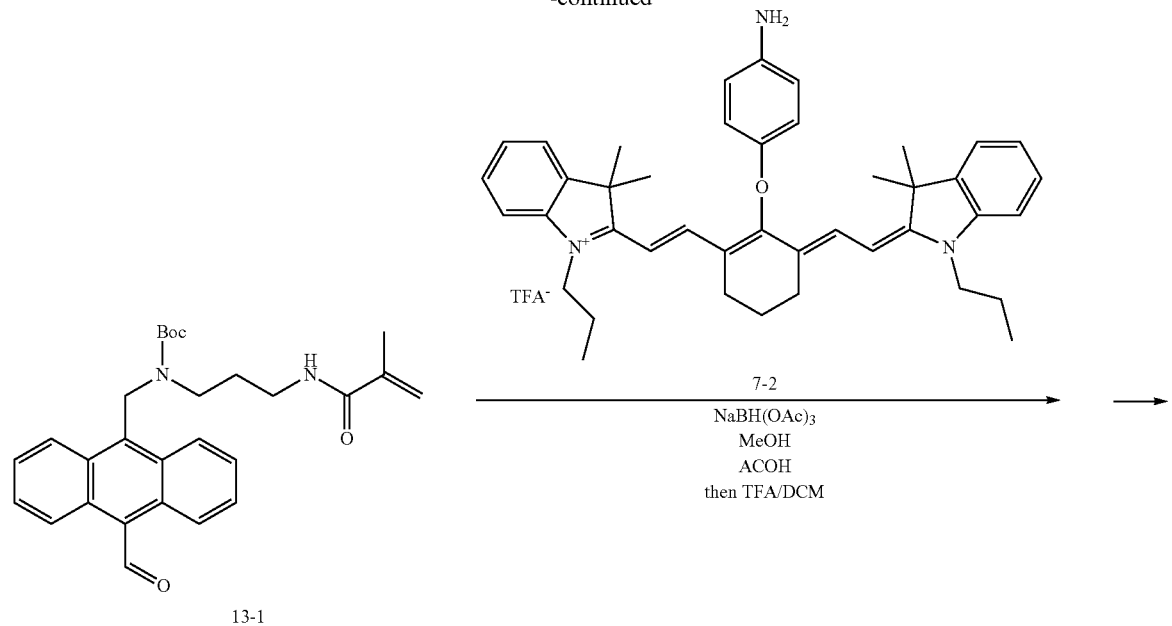
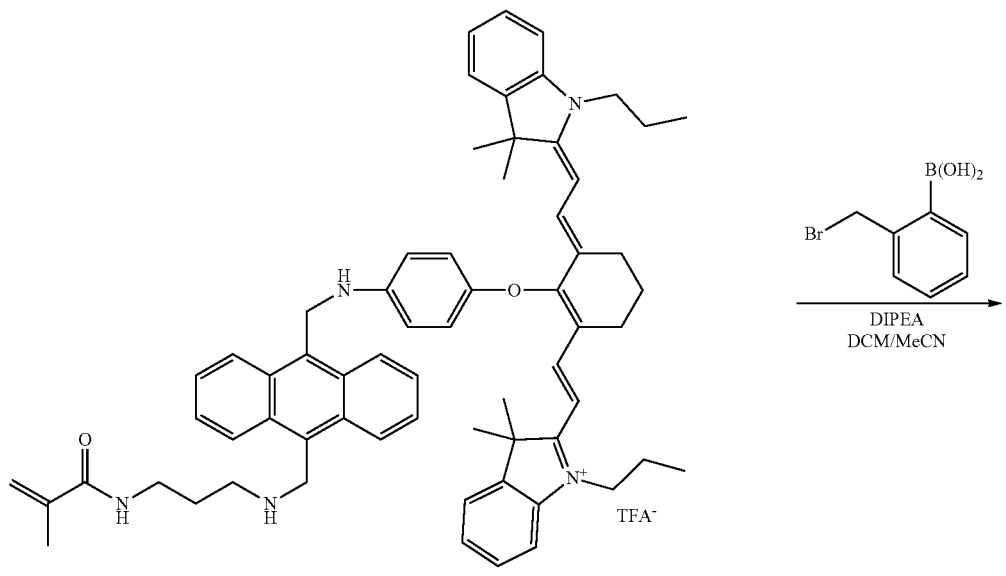

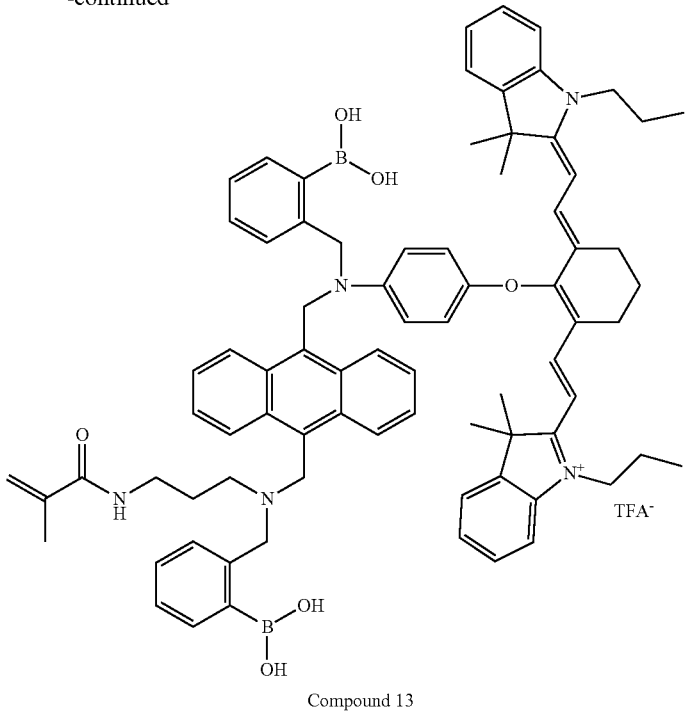

Compound 13

Preparation of Compound 13-1

A mixture of amine 10-2 (0.61 g, 1.69 mmol), triehylamine (0.55 mL, 3.9 mmol), and di-tert-butyl dicarbonate (0.70 g, 3.2 mmol) in THF (20 mL) was stirred at room temperature overnight. The solvent was removed in vacuo and the residue was purified by flash chromatography (SiO$_2$, eluted with 0 to 10% gradient of MeOH in DCM). Yield: 209 mg (27%) as yellow foam.

Compound 13 was synthesized from intermediates 7-2, and 13-1 following general procedures IV, IX, and V. HPLC-MS: m/z 1225.3 (calcd. 1224.7); $\lambda_{max}$=780 nm.

Preparation of Compound 14

Scheme 6. Preparation of compound 14

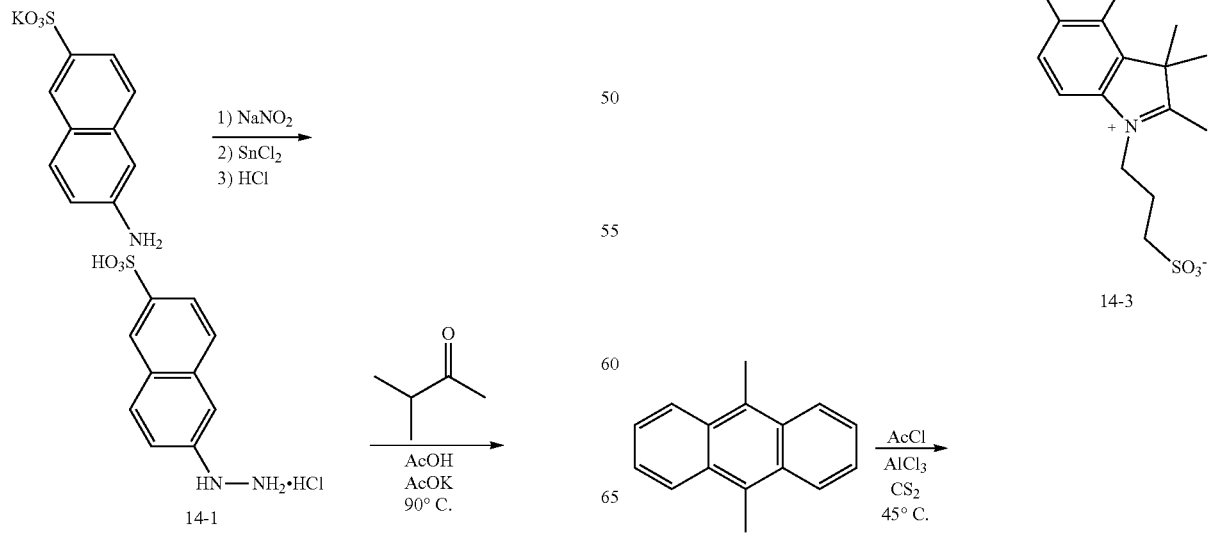

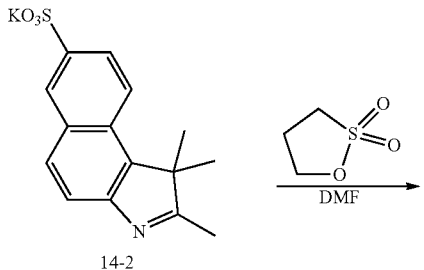

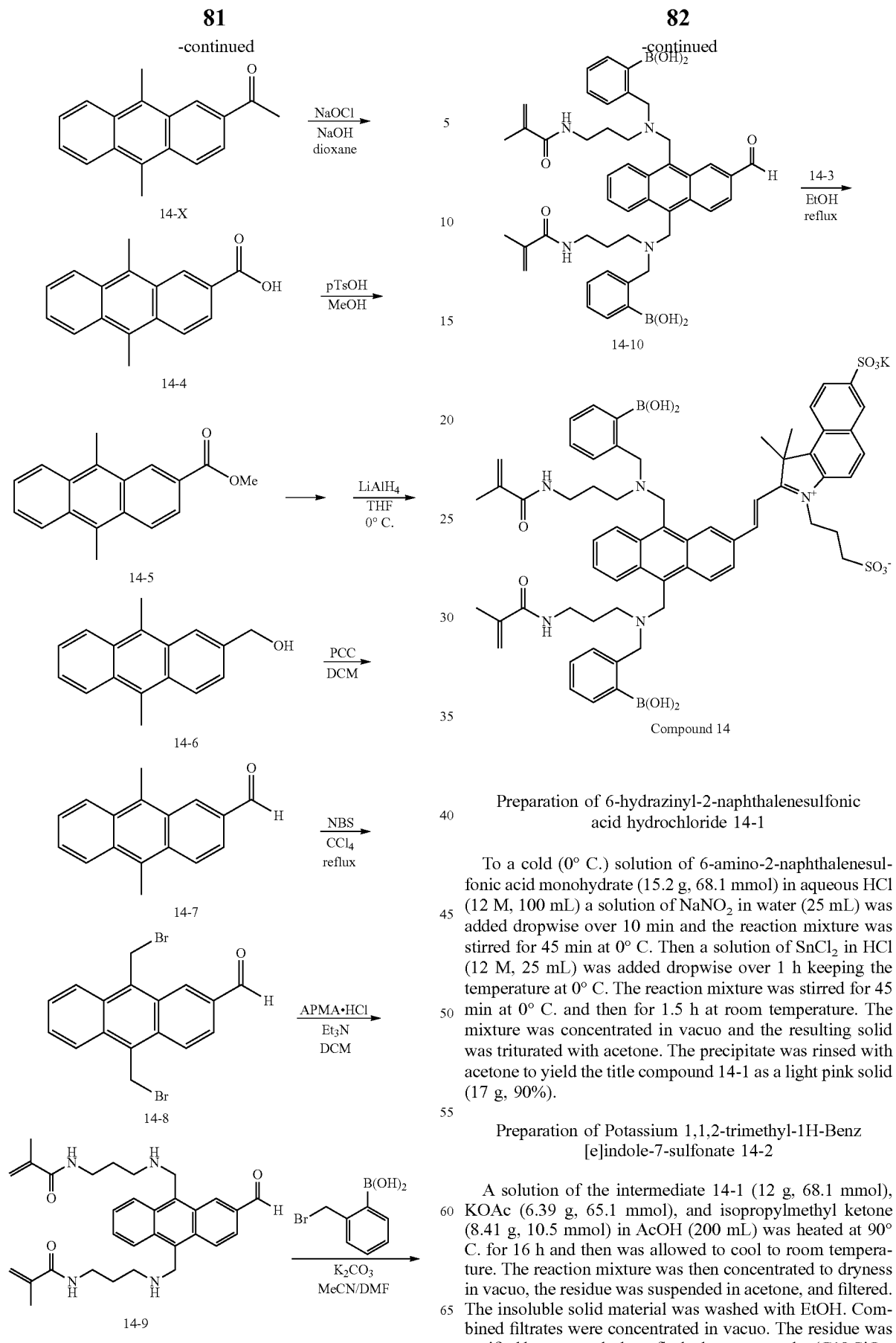

Preparation of 6-hydrazinyl-2-naphthalenesulfonic acid hydrochloride 14-1

To a cold (0° C.) solution of 6-amino-2-naphthalenesulfonic acid monohydrate (15.2 g, 68.1 mmol) in aqueous HCl (12 M, 100 mL) a solution of $NaNO_2$ in water (25 mL) was added dropwise over 10 min and the reaction mixture was stirred for 45 min at 0° C. Then a solution of $SnCl_2$ in HCl (12 M, 25 mL) was added dropwise over 1 h keeping the temperature at 0° C. The reaction mixture was stirred for 45 min at 0° C. and then for 1.5 h at room temperature. The mixture was concentrated in vacuo and the resulting solid was triturated with acetone. The precipitate was rinsed with acetone to yield the title compound 14-1 as a light pink solid (17 g, 90%).

Preparation of Potassium 1,1,2-trimethyl-1H-Benz[e]indole-7-sulfonate 14-2

A solution of the intermediate 14-1 (12 g, 68.1 mmol), KOAc (6.39 g, 65.1 mmol), and isopropylmethyl ketone (8.41 g, 10.5 mmol) in AcOH (200 mL) was heated at 90° C. for 16 h and then was allowed to cool to room temperature. The reaction mixture was then concentrated to dryness in vacuo, the residue was suspended in acetone, and filtered. The insoluble solid material was washed with EtOH. Combined filtrates were concentrated in vacuo. The residue was purified by reversed-phase flash chromatography (C18 $SiO_2$, eluted with gradient of acetonitrile in water) yielding the title compound 14-2 (7.5 g, 34%).

Preparation of Potassium 1,1,2-trimethyl-3-(3-sulfopropyl)-1H-Benz[e]indolium-7-sulfonate 14-3

To a solution of the intermediate 14-2 (5.7 g, 17.4 mmol) in anhydrous DMF (120 mL) 1,3-propanesultone (4.47 mL, 50.9 mmol) was added and the reaction mixture was stirred for 5 h at 100° C. and then was concentration in vacuo. The crude product was purified by reversed-phase flash chromatography (C18 $SiO_2$, eluted with water) yielding the title compound 14-3 as an orange foam (3.1 g, 40%).

Preparation of 2-acetyl-9,10-dimethylanthracene 14-X

To a solution of 9,10-dimethyl anthracene (10.0 g, 48.5 mmol) in carbon disulfide (300 mL), acetyl chloride (4.9 mL, 75.6 mmol) was added followed by aluminum trichloride (9.3 g, 69.8 mmol). The reddish-brown reaction mixture was stirred at room temperature overnight and then at 45° C. for 4 h. The reaction was quenched by addition of ice (50 g), conc. HCl (1 mL), and was stirred for 30 min. Then DCM (200 mL) was added until all black solid dissolved. The layers were separated, and the aqueous layer was additionally extracted with DCM. Combined organic layers were washed with water and dried over $MgSO_4$, filtered, concentrated in vacuo. The crude product was purified by flash chromatography ($SiO_2$, eluted with DCM). Obtained 6.7 g of the title product as a yellow solid (56%).

Preparation of 9,10-dimethyl-2-anthracenecarboxylic acid, 14-4

A solution of 9,10-dimethyl-2-acetylanthracene (7.6 g, 30.6 mmol) in dioxane (150 mL) was heated at 80° C., added to a solution of NaOCl (14.5%, 80 mL) and NaOH (6.7%, 50 mL), and stirred for 16 h at 80° C. Then the reaction mixture was diluted with water (100 mL) and acidified with HCl (1 M) until pH 1. The suspension was filtered, and the solid product was extensively washed with water to afford compound 14-4 as a yellow solid (6.3 g, 84%).

Preparation of 9,10-dimethyl-2-anthracenecarboxylic acid methyl ester, 14-5

A solution of compound 14-4 (6.3 g, 25.1 mmol) and p-toluenesulfonic acid (8.7 g, 50.3 mmol) in MeOH (100 mL) was refluxed for 22 h. The reaction was then concentrated in vacuo, diluted with DCM, and washed with saturated $NaHCO_3$, 1 M $NaHCO_3$, and brine. The organic layer was dried over anhydrous $MgSO_4$, filtered, and concentrated in vacuo to yield compound 14-5 as a yellow solid (6.13 g, 92%).

Preparation of 9,10-dimethyl-2-hydroxymethylanthracene, 14-6

A suspension of $LiAlH_4$ (2.63 g, 69.4 mmol) in anhydrous THF (100 mL) was cooled to 0° C. A solution of compound 14-5 (6.12 g, 23.1 mmol) in anhydrous THF (100 mL) was added dropwise over 15 min. After stirring at 0° C. for 45 min, the reaction was quenched by water (12 mL) and NaOH (15%, 3 mL) at 0° C. The reaction mixture was then diluted with diethyl ether (150 mL) and filtered. The solid was washed with ethyl acetate. Combined filtrate and washing were concentrated in vacuo, then the residue was dissolved in ethyl acetate and washed with brine. The organic layer was dried over anhydrous $MgSO_4$, filtered, and concentrated in vacuo to yield compound 14-6 as a yellow solid (4.6 g, 86%).

Preparation of 9,10-dimethyl-2-anthracenecarboxaldehyde, 14-7

In a flame dried 500 mL 3-neck flask potassium chlorochromate (5.48 g, 25.4 mmol) was suspended in anhydrous 1,2-dichloroethane (100 mL) under argon. Solution of compound 14-6 (4.62 mg, 19.5 mmol) in anhydrous 1,2-dichloroethane (150 mL) was added dropwise to the slurry over 20 min. After stirring at room temperature for 6 h, the reaction mixture was filtered through Celite and the plug was rinsed with DCM. The filtrate was concentrated in vacuo to yield compound 14-7 as a yellow solid (720 mg, 15%).

Preparation of 9,10-bis(bromomethyl)-2-anthracenecarboxaldehyde, 14-8

A mixture of compound 14-7 (720 mg, 3.1 mmol) and N-bromosuccinimide (1.20 g, 6.7 mmol) in anhydrous $CCl_4$ (50 mL) was refluxed for 1 h. The reaction mixture was then diluted with toluene (100 mL) and cooled to −20° C. for 3 days. The resulting yellow crystals were isolated by filtration and washed with MeOH to yield compound 14-8 as a yellow solid (830 mg, 69%).

Preparation of Compound 14-9

A mixture of N-(3-aminopropyl)methacrylamide hydrochloride (1.54 g, 8.6 mmol), triethylamine (1.25 mL, 8.67 mmol), and compound 14-8 in anhydrous DCM (75 mL) was refluxed for 16 h under argon. Then the reaction mixture was concentrated in vacuo and the residue was purified by flash chromatography ($SiO_2$, eluted with gradient of 0 to 100% MeOH in DCM). The product 14-9 was obtained as an amber oil (812 mg, 73%).

Preparation of Compound 14-10

To a solution of compound 14-9 in anhydrous acetonitrile (25 mL) and anhydrous DMF (3 mL), $K_2CO_3$ (821 mg, 4.39 mmol) and 2-bromomethylphenylboronic acid (519 mg, 2.41 mmol) was added. The reaction was stirred for 4 days at room temperature, filtered, and the filtrate was concentrated in vacuo. Toluene was then added to the residue and removed in vacuo to aid in removal of DMF, dilution-evaporation was repeated twice. The residue was dried under high vacuum and then purified by reversed-phase flash chromatography (C18 $SiO_2$, eluted with 0.1% TFA in MeCN). The pure product was isolated by basification of combined and concentrated fractions with saturated $NaHCO_3$, followed by triple extraction with DCM. The DCM portion was then dried over $MgSO_4$ and concentrated in vacuo to afford the title compound 14-10 as a yellow residue (280 mg, 32%).

Preparation of Compound 14

A solution of compounds 14-10 (260 mg, 0.33 mmol) and 14-3 (448 mg, 0.99 mmol) in ethanol (50 mL) was refluxed for 2 h. Then the reaction mixture was allowed to cool down to room temperature and was concentrated in vacuo. The residue was purified twice by reversed-phase flash chromatography (C18 SiO$_2$, eluted with MeCN and water). The pure product was obtained as a pink/red solid (125 mg, 28%) after lyophilization. HPLC-MS: m/z 1176.9 (calcd. 1176.5 for M+H$^+$); $\lambda_{max}$=655, 687 nm.

Preparation of Compound 15

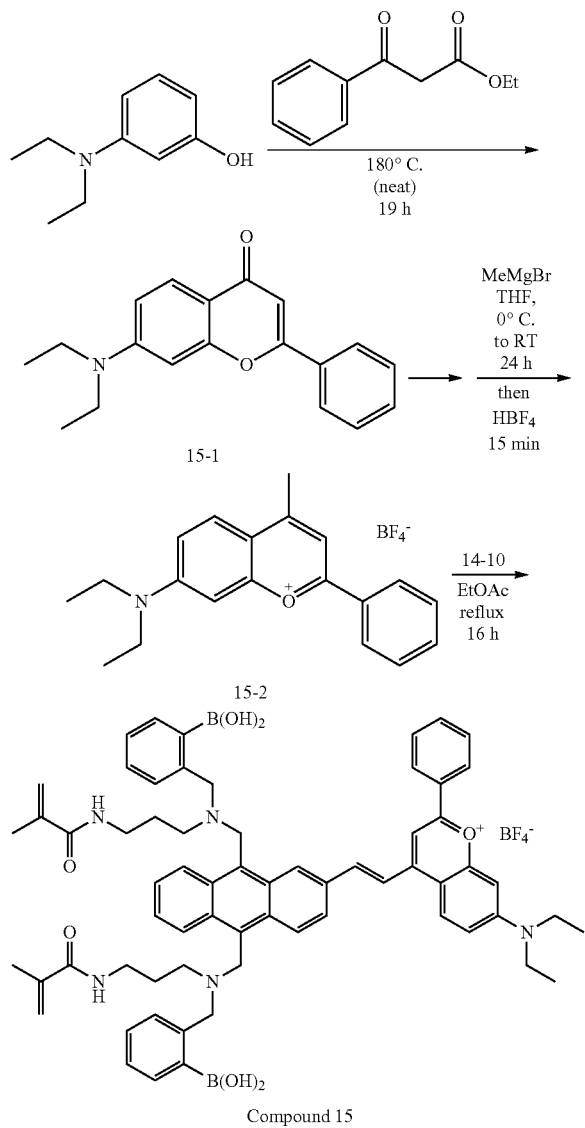

Scheme 9. Preparation of compound 15.

Compound 15

Preparation of 7-(diethylamino)-2-phenyl-4H-1-benzopyran-4-one (15-1)

A mixture of N,N-diethyl-3-aminophenol (4.0 g, 24.2 mmol) and ethyl benzoylacetate (9.30 g, 48.4 mmol) was heated at 180° C. under argon for 16 h. Then additional ethyl benzoylacetate (2.0 mL, 11 mmol) was introduced into the reaction mixture and it was stirred for 3 h followed by cooling to room temperature. The reaction mixture was diluted with ethyl acetate (20 mL) followed by the addition of hexanes, which produced precipitate. The suspension was centrifuged, and the supernatant was washed with 0.05 M HCl three times. The organic layer was dried over MgSO$_4$, filtered, and concentrated in vacuo. The residue was purified by flash chromatography (SiO$_2$, eluted with ethyl acetate and hexanes) to afford the compound 15-1 as a light yellow solid (773 mg, 10%).

Preparation of 7-(diethylamino)-4-methyl-2-phenyl-1-benzopyrylium tetrafluoroborate (15-2)

A solution of compound 15-1 (773 mg, 2.6 mmol) in anhydrous THF (10 mL) was cooled to 0° C. under argon. Methylmagnesium bromide (1.2 mL, 3.6 mmol) was added dropwise over 15 min. The flask was allowed to warm to room temperature and stirred for 24 h. Then 48% tetrafluoroboric acid (1.4 mL, 10.7 mmol) was added and the mixture was stirred for 15 min. The solution was then diluted with DCM and washed with water. The organic layer was dried over MgSO$_4$, filtered, and concentrated in vacuo. The residue was purified by flash chromatography (C18 SiO$_2$, eluted with water and MeOH). The fractions containing pure product were combined and concentrated in vacuo to remove MeOH. The aqueous residue was then extracted with DCM three times. Combined DCM layers were dried over MgSO$_4$, filtered, and concentrated in vacuo to yield compound 15-2 as a magenta solid (625 mg, 60%).

Preparation of Compound 15

A mixture of compounds 14-10 (100 mg, 0.12 mmol) and 15-2 (53.3 mg, 0.14 mmol) in ethyl acetate (5 mL) was heated at 75° C. for 16 h. The reaction mixture was concentrated in vacuo, and adsorbed on silica. The impurities were removed by washing the solids with a mixture of MeOH in DCM. The product was then recovered by sonicating the silica in DMSO followed by filtration. The filtrate was lyophilized to afford pure compound 15 (10 mg, 7%). HPLC-MS: m/z 1056 (calcd. 1056.6 for M$^+$); $\lambda_{max}$=530 nm (broad).

Preparation of Compound 17

Scheme 7. Preparation of compound 17.

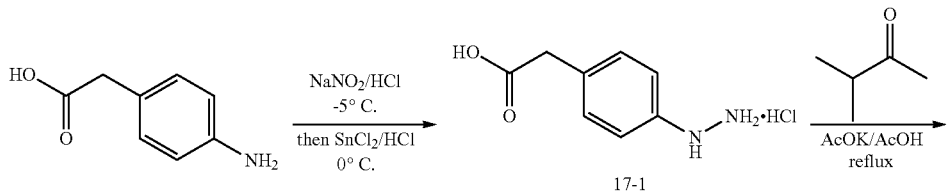

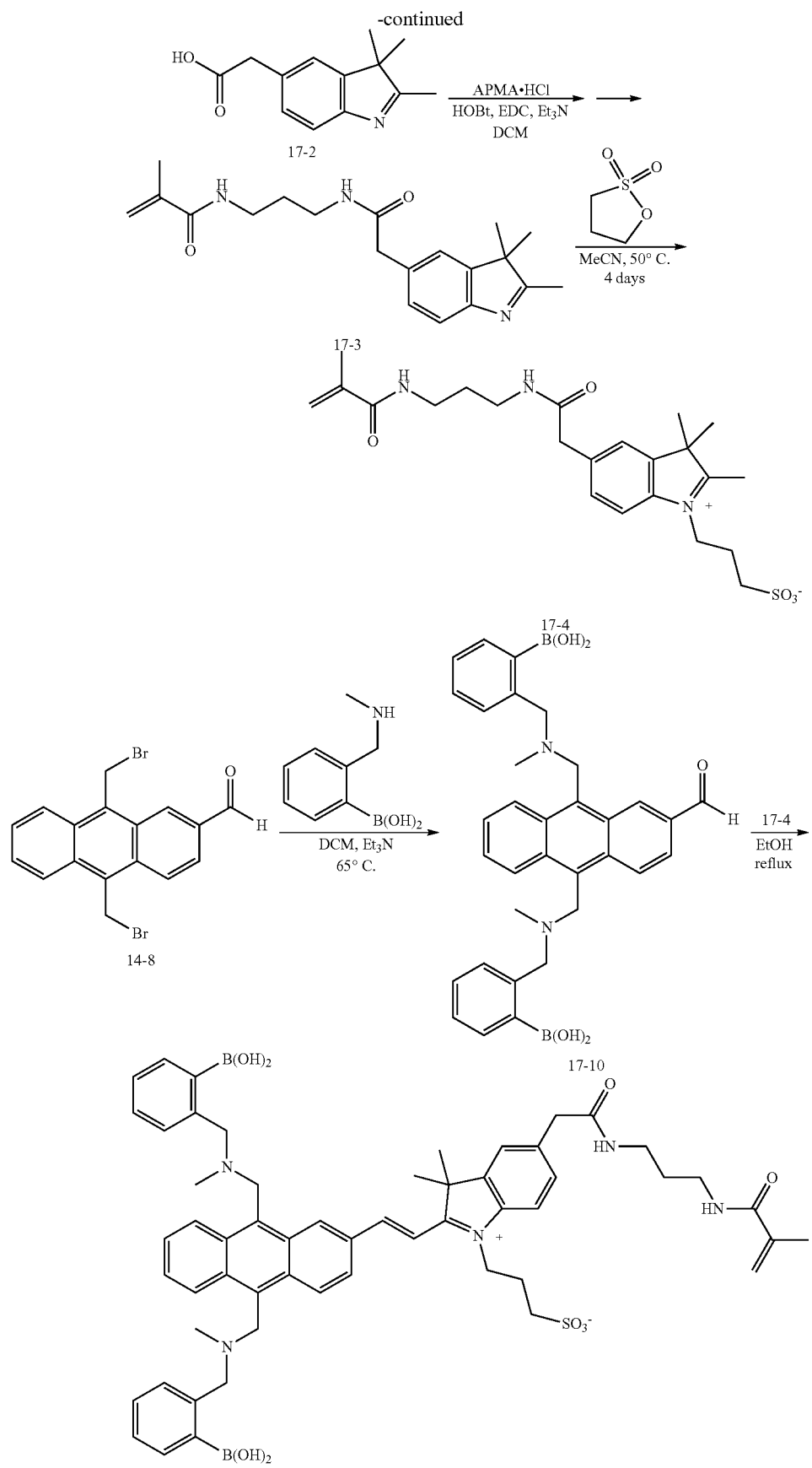
Compound 17

Preparation of (4-hydrazinylphenyl)acetic acid hydrochloride (17-1)

A mixture of 4-aminophenylacetic acid (6.86 g, 45.3 mmol) and HCl (12 M, 100 mL) was refluxed for 15 min. After heating, the solution was cooled to −5° C. and aqueous NaNO$_2$ (25 mL) was added dropwise over 10 min at 0° C. After stirring the reaction mixture for 20 min, SnCl$_2$ in HCl (12 M, 50 mL) was added dropwise over 10 min keeping the temperature below 0° C. The reaction mixture was then stirred for additional 2 h before it was filtered and the precipitate was washed with cold water (100 mL), cold ethanol (200 mL), and diethyl ether (50 mL). The solid was then dried under high vacuum to yield compound 17-1 as a beige solid (6.68 g, 73%).

Preparation of 2,3,3-trimethyl-3H-indole-5-acetic acid (17-2)

A mixture of compound 17-1 (6.6 g, 32.5 mmol), acetic acid (80 mL), potassium acetate (6.39 g, 65.1 mmol), and isopropylmethyl ketone (8.41 g, 10.5 mmol) was refluxed for 3 h and then cooled to room temperature. The solution was then concentrated in vacuo. The residue was dissolved in DCM and washed with brine, then dried over MgSO$_4$, filtered, and concentrated in vacuo. The resulting solid was purified by flash chromatography (SiO$_2$, eluted with 0 to 15% gradient of MeOH in DCM) yielding compound 17-2 as a light pink solid (4.9 g, 59%).

Preparation of Compound 17-3

A mixture of compound 17-2 (2.0 g, 7.8 mmol), N-(3-aminopropyl)methacrylamide hydrochloride (1.67 g, 9.39 mmol), HOBt (1.26 g, 9.39 mmol), EDC (2.25 g, 11.7 mmol), and triethylamine (3.39 mL, 23.5 mmol) in DCM (30 mL) was stirred at room temperature for 16 h and then concentrated in vacuo. The residue was purified by flash chromatography (SiO$_2$, eluted with MeOH and DCM) affording compound 17-3 (3.0 g, quant.).

Preparation of Compound 17-4

A solution of compound 17-3 (3.0 g, 8.7 mmol) and 1,3-propanesultone (7.7 mL, 87.8 mmol) in anhydrous acetonitrile (50 mL) was heated to 50° C. for 4 d. Then the reaction mixture was concentrated in vacuo to 10 mL. The concentrate was then diluted into with ether/acetone (40 mL) producing copious precipitate. The slurry was centrifuged and the supernatant was discarded. The solid was washed with acetone and dried in vacuo to yield compound 17-4 as a purple foam (3.5 g, 85%).

Preparation of Compound 17-10

A mixture of aldehyde 14-8 (250 mg, 0.63 mmol), 2-[(methylamino) methyl]phenylboronic acid (420.8 mg, 2.5 mmol) and triethylamine (0.367 mL, 2.5 mmol) in DCM (40 mL) and DMF (8 mL) was heated to reflux for 3 days. The reaction mixture was washed with water three times. The DCM layer was loaded onto silica column and eluted with gradient of 0-15% MeOH in DCM. The product 17-10 was obtained as a crude yellow oil (320 mg, 89%).

Preparation of Compound 17

A mixture of compounds 17-10 (318 mg, 0.56 mmol) and 17-4 (637 mg, 1.4 mmol) in ethanol (50 mL) was refluxed for 16 h. Then the reaction was concentrated in vacuo and the residue was purified by reversed-phase flash chromatography (C18 SiO$_2$, gradient elution with 0.25% HCl (aq) in MeOH). The product was isolated by basification of combined and concentrated pure fractions with saturated NaHCO$_3$, followed by triple extraction with DCM. The DCM portion was then dried over MgSO$_4$ and concentrated in vacuo to afford the title compound 17 after trituration with diethyl ether (150 mg, 26%) as a dark red solid. HPLC-MS: m/z 1006.6 (calcd. 1006.5 for M+H$^+$); $\lambda_{max}$=525 nm (broad).

Preparation of Compound 18

Scheme 8. Preparation of compound 18.

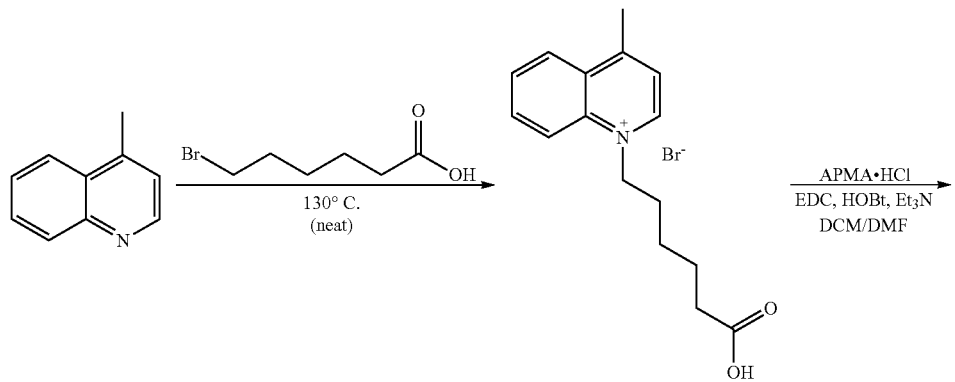

18-1

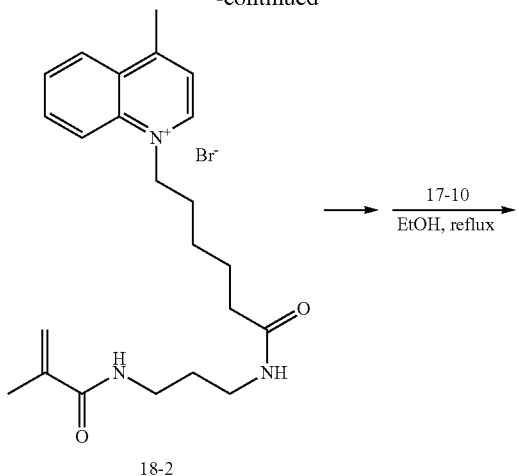

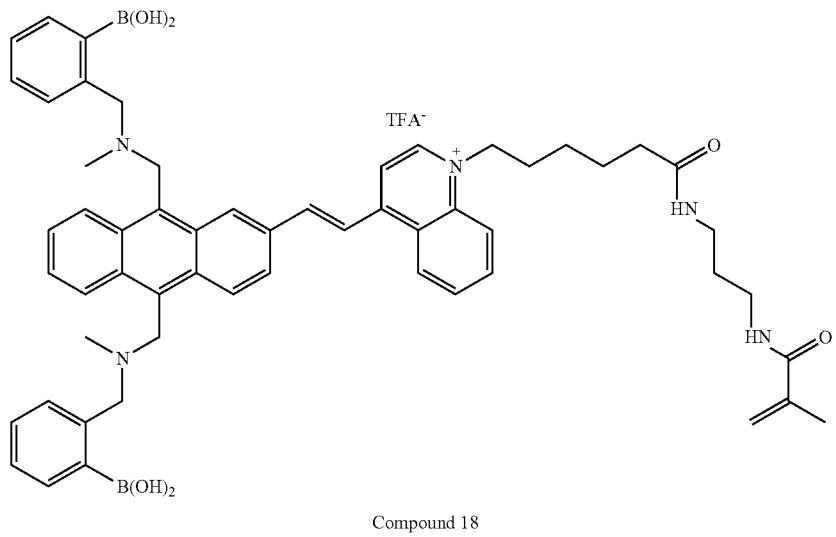

Compound 18

Preparation of 1-(5-carboxypentyl)-4-methylquinolinium bromide (18-1)

A mixture of lepidine (2.0 mL, 14.7 mmol) and 6-bromohexanoic acid (4.33 g, 22.2 mmol) was heated at 120° C. for 5 h and then at 130° C. for 16 h. The reaction mixture was then cooled to room temperature and sonicated with acetone for 15 min. The supernatant was decanted and the solid residue was additionally washed twice with fresh acetone under sonication yielding the compound 18-1 as a fine gray solid (2.4 g, 76%).

Preparation of Compound 18-2

In a dry 100 mL-flask compound 18-1 (1.0 g, 2.9 mmol) was dissolved in 3:1 DCM/DMF (50 mL) followed by the addition of N-(3-aminopropyl)methacrylamide hydrochloride (633 mg, 3.5 mmol), HOBt (598 mg, 4.4 mmol), EDC (849 mg, 4.4 mmol), and thriethylamine (0.857 mL, 5.9 mmol). The reaction mixture was stirred at room temperature for 16 h, followed by dilution with diethyl ether. The resulting suspension was centrifuged and the supernatant was discarded. The solid residue was purified by flash chromatography ($SiO_2$, eluted with MeOH and DCM) affording target compound 18-2 as a pink-red amorphous solid (884 mg, 65%).

Preparation of Compound 18

A mixture of compounds 17-10 (100 mg, 0.17 mmol) and 18-2 (200 mg, 0.43 mmol) in ethanol (10 mL) was refluxed for 5 h. Then the reaction mixture was cooled down to room temperature, and concentrated in vacuo. The residue was purified by flash chromatography ($SiO_2$, eluted with 0 to 30% gradient of MeOH in DCM, followed by 100% MeOH with 0.1% TFA). The resulting yellow oil was re-purified with same method. The pure product was dissolved in DCM and the solution was washed with saturated $NaHCO_3$, dried over anhydrous $MgSO_4$, filtered, and concentrated in vacuo. Pure compound 18 was obtained as an orange amorphous solid (9 mg, 5%). HPLC-MS: m/z 924.8 (calcd. 924.5 for $M^+$); $\lambda_{max}$=380 nm (broad).

Preparation of Compound 35
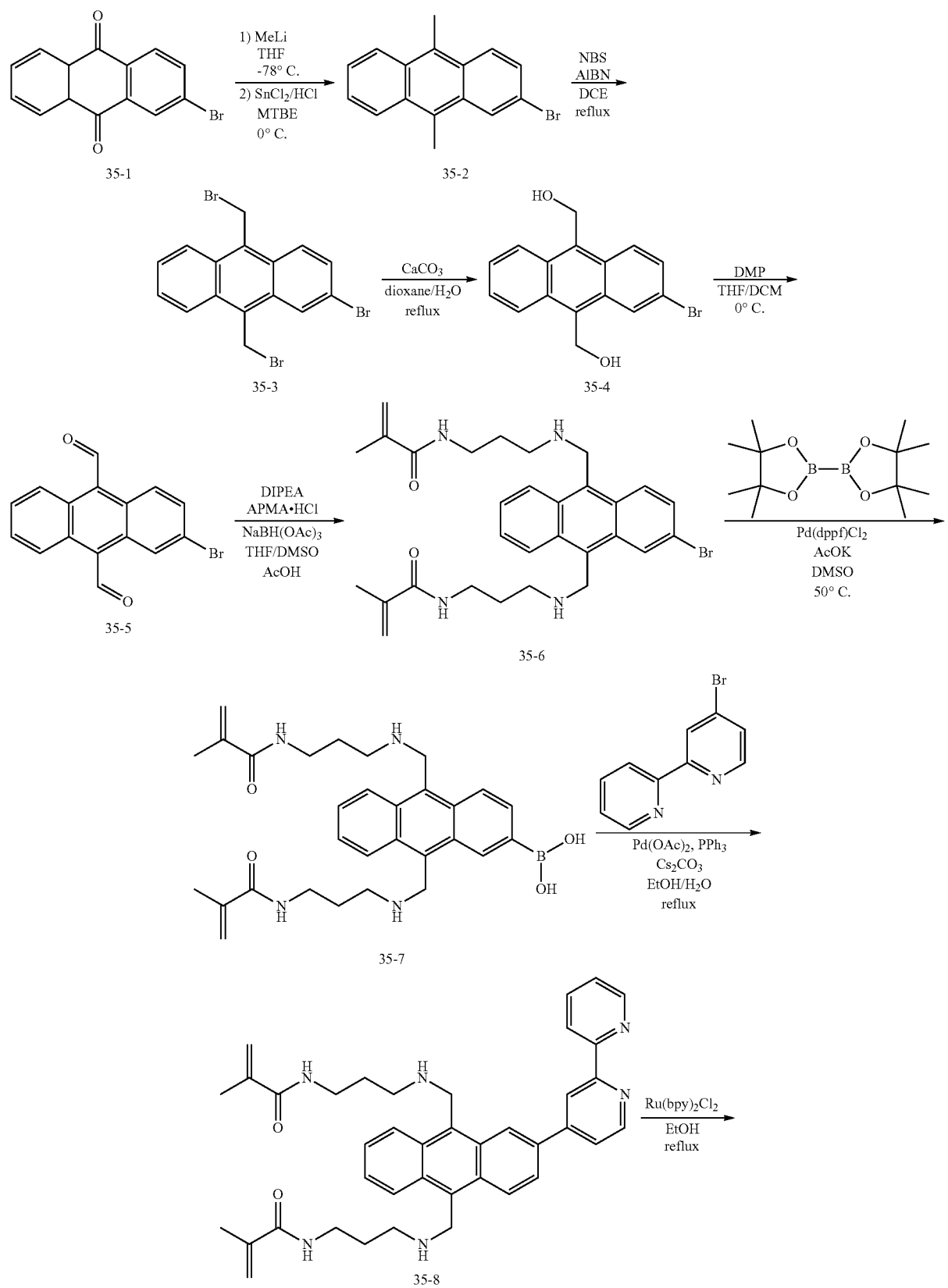
Scheme 1. Preparation of compound 35

-continued

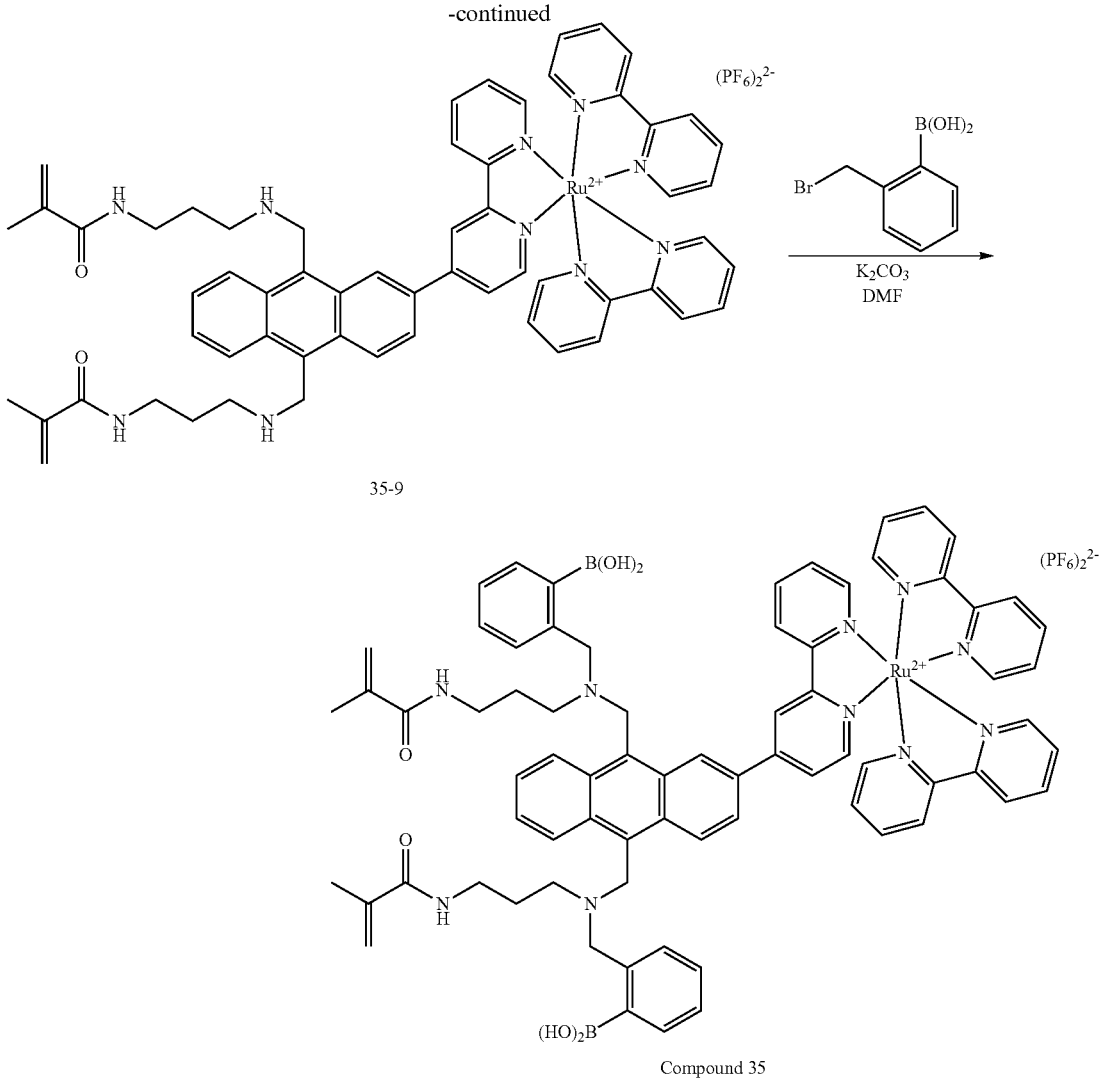

35-9

Compound 35

Preparation of 2-bromo-9,10-dimethylanthracene (35-2)

In a 4-neck 10 L flask, 2-bromoanthraquinone (compound 35-1, 500 g, 1.74 mole) was dissolved in anhydrous THF (6.5 L). The solution was cooled to −78° C. under nitrogen atmosphere and MeLi (2.39 L, 3.83 mole) was added dropwise over 2 h. The darkened reaction mixture was stirred for another 1 h at −78° C. and then was allowed to reach room temperature overnight. The reaction was quenched with saturated NH$_4$Cl (1.5 L). The organic layer was separated, washed with H$_2$O, dried over anhydrous Na$_2$SO$_4$, and concentrated under reduced pressure. The resulting yellow solid was then dissolved in MTBE (3.4 L). A solution of SnCl$_2$.2H$_2$O (2.12 kg, 9.40 mole) in concentrated HCl (1.67 L) was added under ice bath cooling over 30 min. The reaction mixture was stirred for 3 h at room temperature, then transferred to a separatory funnel, washed with H$_2$O, dried over anhydrous sodium sulfate, and concentrated under reduced pressure. The residue was purified by column chromatography (SiO$_2$, eluent: petroleum ether/DCM 20:1) to give the title compound 35-2 (220 g, 44%) as a yellow solid.

Preparation of 2-bromo-9,10-bis(bromomethyl)anthracene 35-3

A mixture of 2-bromo-9,10-dimethylanthracene 35-2 (6.89 g, 24.6 mmol) and N-bromosuccinimide (9.46 g, 53.15 mmol, 2.2 eq) in 1,2-dichloroethane (100 mL) was refluxed for 2 h. The solvent was removed in vacuo, and the residue was triturated with methanol (100 mL), filtered, rinsed thoroughly with methanol, and dried to give compound 35-3 as a yellow-orange solid (10.14 g, 95%).

General Procedure XI. Hydrolysis of bis-(bromomethyl)anthracenes. Preparation of 2-bromo-9,10-bis(hydroxymethyl)anthracene 35-4

A mixture of 2-bromo-9,10-bis(bromomethyl)anthracene 35-3 (22.9 g, 51.7 mmol) and anhydrous calcium carbonate (31.02 g, 310.2 mmol, 6 eq) in 2:1 1,4-dioxane/H$_2$O (250 mL) was stirred under reflux for 20 h. The reaction was then concentrated to remove dioxane, acidified with 1 M HCl (50 mL) and filtered. The collected solid was rinsed with water (3×50 mL), and dried under high vacuum yielding the product 35-4 as an orange-yellow solid (15.0 g, 92%).

Preparation of 2-bromoanthracene-9,10-dicarbaldehyde 35-5

Dess-Martin periodinane (3.3 g, 7.88 mmol) was added to a solution of 35-4 (1 g, 3.15 mmol) in 1:1 THF/DCM (250 mL) at 0° C. under nitrogen. The solution was stirred at room temperature for 3 h, then filtered, and diluted with saturated NaHCO$_3$. Resulting mixture was transferred to a separatory funnel and extracted with DCM three times. Combined DCM layers were dried over MgSO$_4$ and concentrated in vacuo. The residue was purified by flash chromatography (SiO$_2$, eluent: 100% DCM) affording 35-5 as an orange solid (440 mg, 44%).

Preparation of 2-bromo-9,10-bis[(3-methacrylamidopropyl)aminomethyl]anthracene 35-6

In a 1 L flame dried flask a mixture of APMA.HCl (5.75 g, 33.3 mmol) and DIPEA (5.8 mL, 33.3 mmol) in anhydrous THF (500 mL) was sonicated for 30 min. Then anhydrous DMSO was added until a clear solution was obtained (ca. 20 mL). Glacial acetic acid (0.48 mL, 8.3 mmol) and dialdehyde 35-5 (1.3 g, 4.2 mmol) were added to the solution, followed by stirring at room temperature for 45 min. Sodium triacetoxyborohydride (9.3 g, 44.4 mmol) was added in four equal portions over 2 h and the reaction mixture was stirred at room temperature for 16 h. The reaction mixture was then concentrated in vacuo, diluted with DCM and saturated NaHCO$_3$ and transferred to a separatory funnel. The aqueous layer was extracted with DCM 5 times. Combined DCM layers were then dried over MgSO$_4$ and concentrated in vacuo. The residue was purified by reversed-phase flash chromatography (C18 SiO$_2$, gradient elution with 0.25% HCl (aq) in MeOH). The pure product was obtained by lyophilization (0.29 g, 11%) as a pale yellow solid.

General Procedure XII. Pd-Catalyzed Borylation of Aryl Bromides. Preparation of {2-[9,10-bis(3-methacrylamidopropyl)aminomethyl]anthracene}boronic acid 35-7

A mixture of diamine 35-6 (2 g, 3.53 mmol), bis(pinacolato)diboron (1.8 g, 7.07 mmol), potassium acetate (2.1 g, 21.2 mmol), and Pd(dppf)Cl$_2$ was purged 5 times with dry argon. Then anhydrous DMSO (120 mL) was added and the reaction mixture was stirred at 50° C. under argon for 16 h. After consumption of the starting material, the reaction mixture was diluted with DCM (350 mL) and water (350 mL), stirred at room temperature for 20 minutes before transferring to a separatory funnel. The organic layer was discarded and the aqueous layer was additionally washed with DCM 4 times. Remaining aqueous layer was concentrated in vacuo and used for reversed-phase flash chromatography (C18 SiO$_2$, eluted with gradient of 0.09% HCl (aq) in MeOH). The pure product was collected by lyophilization to yield boronic acid 35-7 as a yellow-orange solid (558 mg, 30%).

Preparation of 4-{[9,10-bis(3-methacrylamidopropyl)aminomethyl]anthr-2-yl}-2,2'-bipyridine 35-8

In a flame dried 50-mL 3-neck flask fitted with a condenser, a mixture of anthraceneboronic acid 35-7 (522 mg, 0.985 mmol), 4-bromo-2,2'-bipyridine (154 mg, 0.657 mmol), and cesium carbonate (640 mg, 1.97 mmol) in EtOH (15 mL) and water (2 mL) was degassed by refluxing under argon stream for 75 minutes. Then Pd(OAc)$_2$ (29.7 mg, 0.131 mmol) and PPh$_3$ (138 mg, 0.526 mmol) were added in one portion. Refluxing under argon was continued until the reaction was complete in 90 minutes. The reaction mixture was then allowed to cool to room temperature and filtered; the solid residue was rinsed with DCM and MeOH. The filtrate was concentrated in vacuo, and the resulting residue was purified by reversed-phase flash chromatography (C18 SiO$_2$, eluted with gradient of 0.09% HCl in MeOH). The pure product was isolated by basification of combined and concentrated fractions with solid NaHCO$_3$ (200 mg) followed by extraction with DCM twice. The combined DCM layers were then dried over MgSO$_4$ and concentrated in vacuo to yield product as a yellow solid (316 mg, 50%).

Preparation of bis(2,2'-bipyridine)-4-{[9,10-bis(3-methacrylamidopropyl)aminomethyl]-anthr-2-yl}-2,2'-bipyridineruthenium bis(hexafluorophosphate) 35-9

To a degassed solution of diamine 35-8 (75 mg, 0.117 mmol) in EtOH (20 mL), Ru(bpy)$_2$Cl$_2$.2H$_2$O (57 mg, 0.117 mmol) was added and the reaction was refluxed under argon stream at 80° C. for 20 h, at which point the reaction was complete. The solvent was removed in vacuo, and the residue was purified by reversed-phase flash chromatography (C18 SiO$_2$, eluted with gradient of 0.09% HCl (aq) in acetonitrile). Combined fractions with pure product were concentrated in vacuo to remove acetonitrile. The product was then precipitated by addition of saturated solution of ammonium hexafluorophosphate (0.25 mL), collected by filtration, rinsed with water and diethyl ether, and dried in vacuo. Yield: 159 mg (quant.).

Preparation of Compound 35

A mixture of intermediate 35-9 (409 mg, 0.30 mmol) and K$_2$CO$_3$ (415 mg, 3 mmol) in anhydrous DMF (4 mL) was stirred at room temperature for 16 h under argon. 2-Bromomethylphenylboronic acid (259 mg, 1.2 mmol) was then added and the reaction mixture was stirred at room temperature for 4 h. The reaction mixture was separated with reversed-phase flash chromatography (C18 SiO$_2$, eluted with gradient of 0.09% HCl (aq) in acetonitrile). Combined fractions with pure product were concentrated in vacuo to remove acetonitrile. The product was then precipitated by addition of saturated solution of ammonium hexafluorophosphate (0.25 mL) to the aqueous solution, and collected by centrifuging. The supernatant was discarded and the precipitate was additionally washed with diethyl ether three times affording the title compound as an orange-red to dark red solid (123 mg, 65%). HPLC-MS: m/z 661.7 (calcd. 668.8 for M+$^2$); $\lambda_{max}$=465 nm (broad).

Preparation of Compound 19
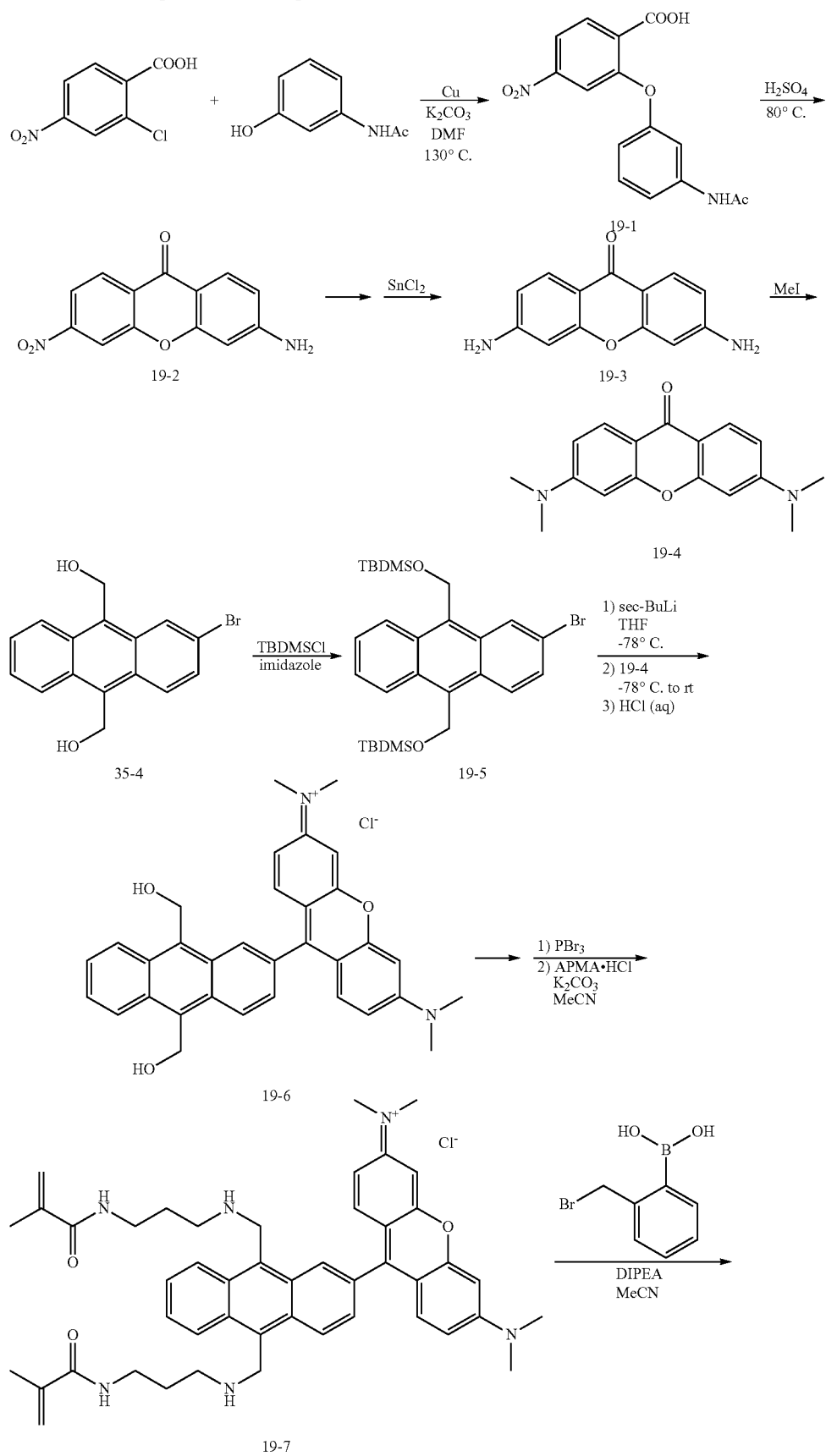

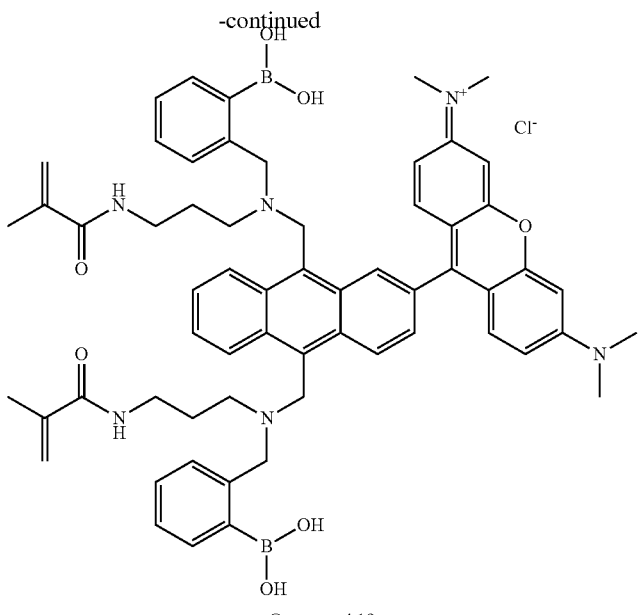

Compound 19

The intermediate 19-4 was synthesized following published protocol (Cui, J.; Jin, J.; Hsieh, Y.-H.; Yang, H.; Ke, B.; Damera, K.; Tai, P. C.; Wang, B. *Chem Med Chem* 2013, 8 (8), 1384-1393).

General Procedure XIII. TBDMS Protection. Preparation of Compound 19-5

A solution of diol 35-4 (81 g, 0.256 mol), tert-butyldimethylsilyl chloride (154 g, 1.02 mol), and imidazole (69.5 g, 1.02 mol) in anhydrous DCM (900 mL) was stirred for 3 h under argon. The reaction mixture was then filtered, and the filtrate was concentrated under reduced pressure to ~200 mL. The concentrate was passed through a silica plug (eluent: EtOAc/hexanes=1:1). Fractions containing main product (assessed by TLC) were collected and concentrated under reduced pressure. The residue was additionally purified by flash chromatography (SiO$_2$, eluent: gradient from 0 to 10% DCM in hexanes) to afford intermediate 19-5 (60 g, 43%) as a yellow solid.

Compound 19-6 was synthesized from intermediates 19-4 and 19-5, following the general procedure X.

General Procedure XIV. Double Amination of Anthracene Diol Via Dibromide Formation. Preparation of Compound 19-7

To a solution of diol 19-6 (560 mg, 1.11 mmol) in anhydrous DCM (100 mL), phosphorus tribromide (0.27 mL, 2.8 mmol) was added, and the mixture was stirred at room temperature for 15 min. Then the solvent was removed under reduced pressure. The residue was resuspended in anhydrous MeCN (10 mL) and transferred to a slurry of APMA·HCl (597 mg, 3.3 mmol) and K$_2$CO$_3$ (1.32 g, 6.7 mmol) in a mixture of anhydrous MeCN and DCM 1:1 (30 mL) that was pre-stirred at room temperature for at least 24 h. The reaction mixture was stirred for 2-16 h and then filtered. The filtrate was concentrated under reduced pressure, and the residue was purified by reversed phase flash chromatography (C18 SiO$_2$, eluted with gradient of MeOH in water+0.25% HCl) affording the title compound 19-7 (134 mg, 22% yield).

Compound 19 was synthesized from intermediate 19-7, following the general procedure V. HPLC-MS: m/z 1020.5 (calcd. 1019.5 for M$^+$); $\lambda_{max}$=565 nm. $^1$H NMR (400 MHz, MeOH-d$_4$) δ ppm 8.62 (d, J=9.7 Hz, 1H), 8.56 (t, J=8.0 Hz, 1H), 8.32 (dd, J=7.1, 2.9 Hz, 1H), 7.63-7.72 (m, 2H), 7.49-7.59 (m, 2H), 7.23-7.33 (m, 8H), 7.17-7.23 (m, 2H), 7.10 (d, J=2.3 Hz, 2H), 7.00 (dd, J=9.6, 2.2 Hz, 2H), 5.37 (s, 1H), 5.26 (s, 1H), 5.20 (quin, J=1.5 Hz, 1H), 5.13 (quin, J=1.5 Hz, 1H), 4.80 (br. s., 2H), 4.73 (br. s., 2H), 4.59 (s, 2H), 4.00 (s, 2H), 3.79 (s, 2H), 3.36 (s, 12H), 3.06 (t, J=6.7 Hz, 2H), 2.89 (t, J=6.8 Hz, 2H), 2.70 (t, J=7.6 Hz, 2H), 2.55 (t, J=7.4 Hz, 2H), 1.92-1.97 (m, 2H), 1.88-1.92 (m, 2H), 1.73 (dd, J=1.6, 1.0 Hz, 3H), 1.65 (dd, J=1.6, 1.0 Hz, 3H).

Preparation of Compound 20

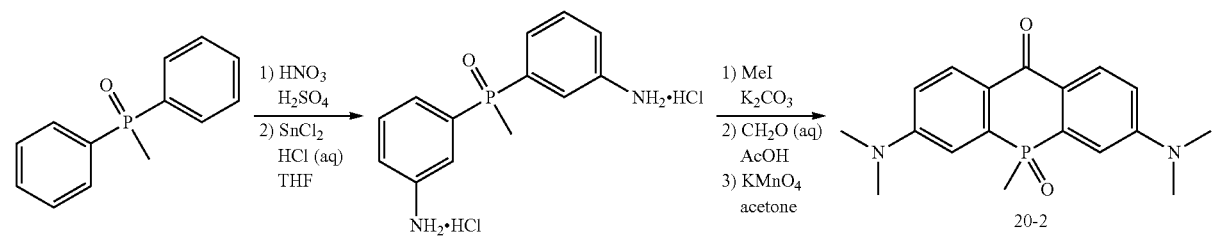

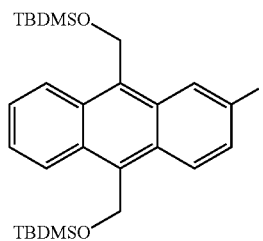
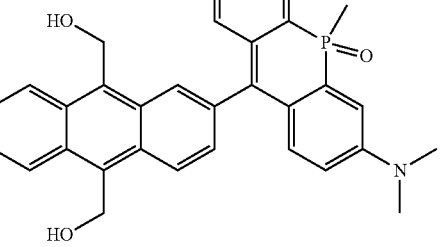
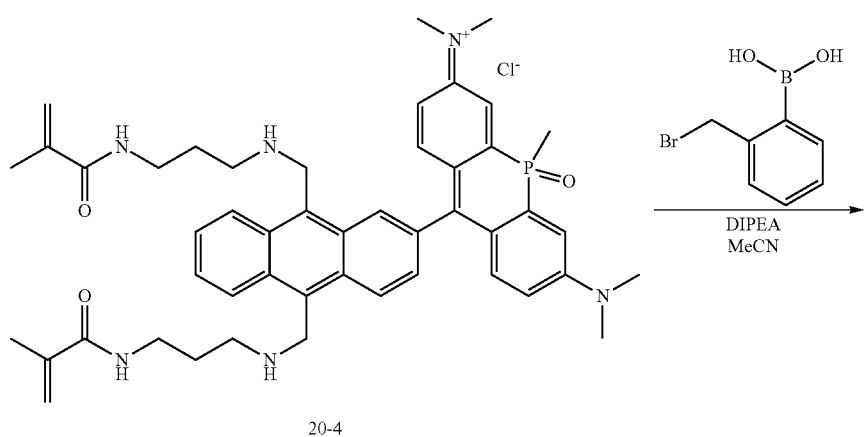
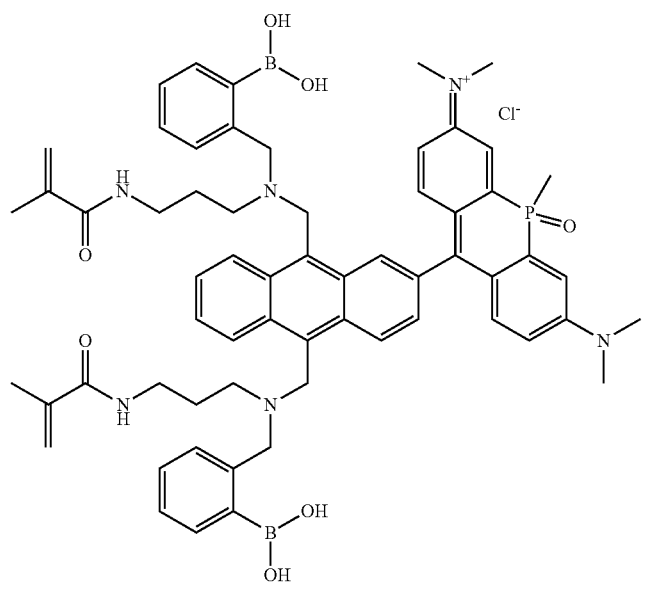
Compound 20
Intermediate 20-2 was prepared by analogy with published procedure (Cui, J.; Jin, J.; Hsieh, Y.-H.; Yang, H.; Ke, B.; Damera, K.; Tai, P. C.; Wang, B. *Chem Med Chem* 2013, 8 (8), 1384-1393).
Compound 20 was synthesized from intermediates 20-2 and 19-5, following general procedures X, XIV, and V. HPLC-MS: m/z 1066.1 (calcd. 1065.5 for M$^+$); $\lambda_{max}$=700 nm.

Preparation of Compound 21
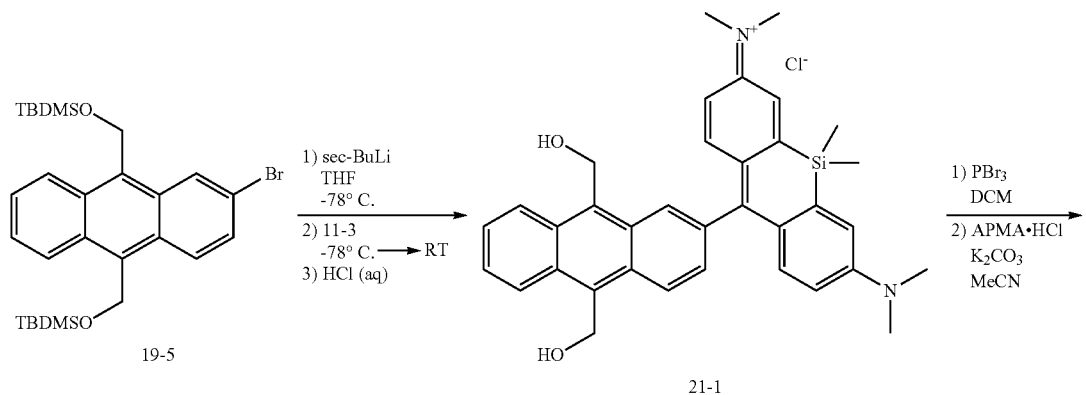
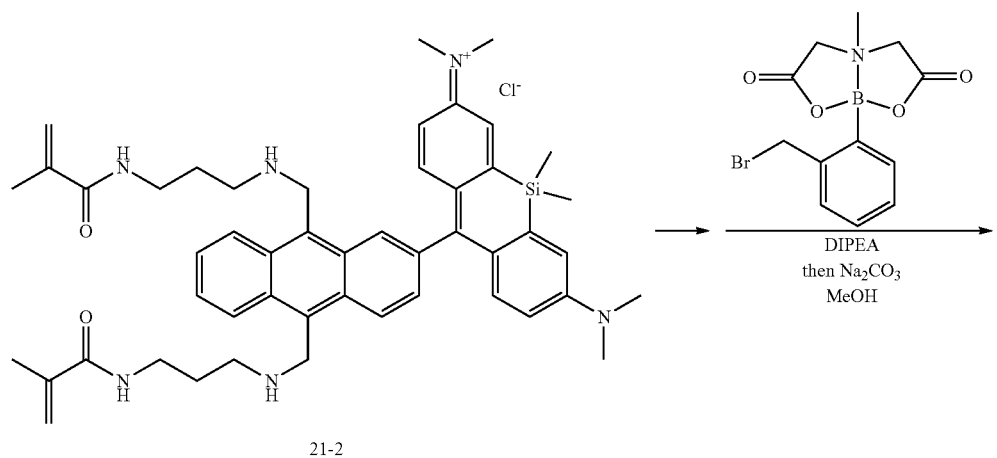
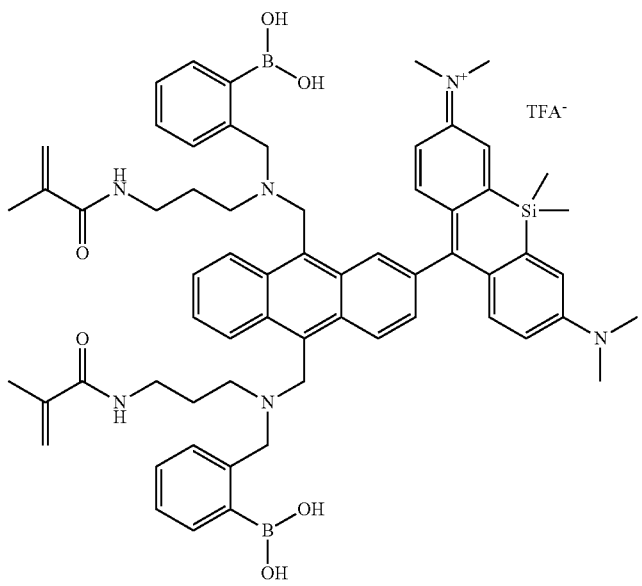
Intermediate 21-2 was synthesized from intermediates 19-5 and 11-3 following the general procedures X and XIV.

General Procedure XV. Alkylation with MIDA Boronate Followed by Deprotection. Preparation of Compound 21

Solution of the diamine 21-2 (1.5 g, 1.65 mmol), DIPEA (0.99 mL, 5.68 mmol), and 2-(bromomethyl)phenylboronic acid MIDA ester (1.7 g, 5.1 mmol) in a mixture of anhydrous DCM and acetonitrile (20 mL: 20 mL) was stirred at ambient temperature for 1 h. Then the solvent was removed under reduced pressure, the residue was dissolved in MeOH (25 mL), and treated with 2M aqueous Na$_2$CO$_3$ (15 mL). The mixture was stirred vigorously for 2 h. Then the suspension was filtered and rinsed with MeOH (150 mL). The filtrate was concentrated under reduced pressure, and the residue was partitioned between saturated NaHCO$_3$ (100 mL) and DCM (50 mL). The layers were separated and the aqueous layer was additionally extracted with DCM (3×30 mL). Combined DCM layers were dried over anhydrous Na$_2$SO$_4$, filtered, and concentrated under reduced pressure. The residue was purified by reversed phase flash chromatography (C18 SiO$_2$, eluted with 35% to 100% gradient of MeOH in water+0.05% TFA). Yield: 747 mg (39% yield as mono-TFA salt) as dark blue solid. HPLC-MS: m/z 1062.4 (calcd. 1061.6 for M$^+$). UV/Vis: $\lambda_{max}$=660 nm. $^1$H NMR (400 MHz, MeOH-d$_4$) δ ppm 0.67 (s, 3H) 0.86 (br. s., 3H) 1.67 (s, 3H) 1.69-1.73 (m, 2H) 1.74 (s, 3H) 1.85-2.00 (m, 2H) 2.61 (t, J=7.18 Hz, 2H) 2.70-2.78 (m, 2H) 2.93 (t, J=7.10 Hz, 2H) 3.08 (t, J=6.51 Hz, 2H) 3.37 (s, 12H) 3.86 (br. s., 2H) 4.06 (br. s., 2H) 4.56 (br. s., 2H) 4.84 (br. s., 2H) 5.15 (s, 1H) 5.21 (s, 1H) 5.29 (s, 1H) 5.38 (s, 1H) 6.67 (dd, J=9.50, 2.50 Hz, 2H) 6.83-6.97 (m, 1H) 7.10 (m, J=9.60 Hz, 1H) 7.19 (d, J=9.40 Hz, 2H) 7.24 (d, J=7.91 Hz, 1H) 7.26-7.34 (m, 4H) 7.37 (d, J=8.64 Hz, 1H) 7.42 (d, J=7.06 Hz, 1H) 7.47 (d, J=2.50 Hz, 2H) 7.51 (br. s., 1H) 7.61-7.70 (m, 2H) 8.43 (d, J=9.01 Hz, 1H) 8.48-8.60 (m, 2H).

Preparation of Compound 49

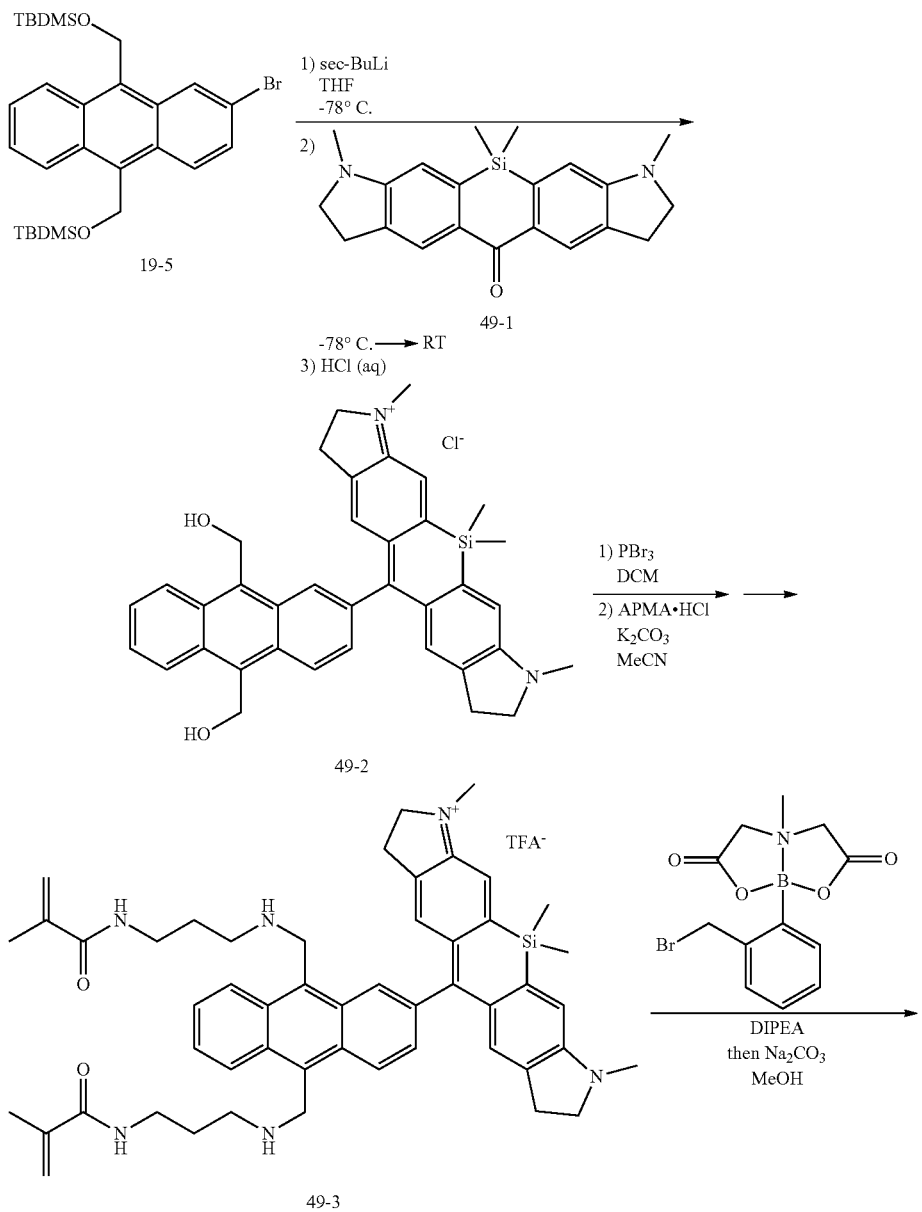

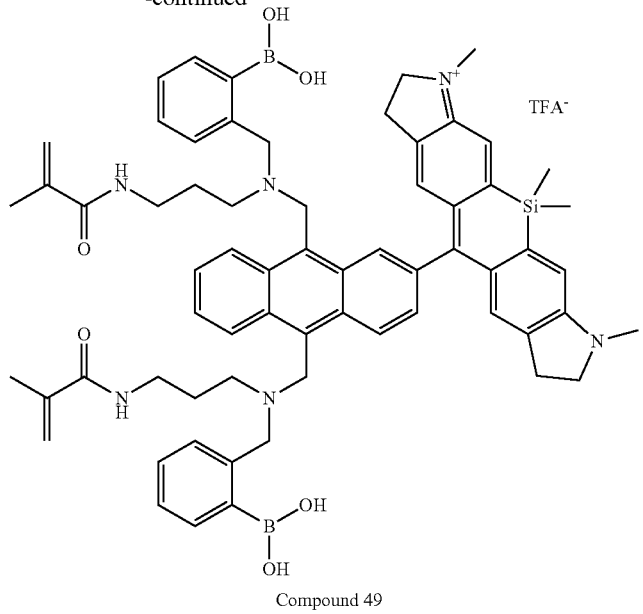
Compound 49
Intermediate 49-1 was synthesized following published procedure [ref: Koide, et al. *J. Am. Chem. Soc.*, 134(11), 5029-5031].
Compound 49 was synthesized from intermediate 49-1 and 19-5, following sequence of general procedures X, XIV, and XV. HPLC-MS: m/z 1086.2 (calcd. 1085.6 for M$^+$). UV/Vis: $\lambda_{max}$=705 nm.
Preparation of Compound 45
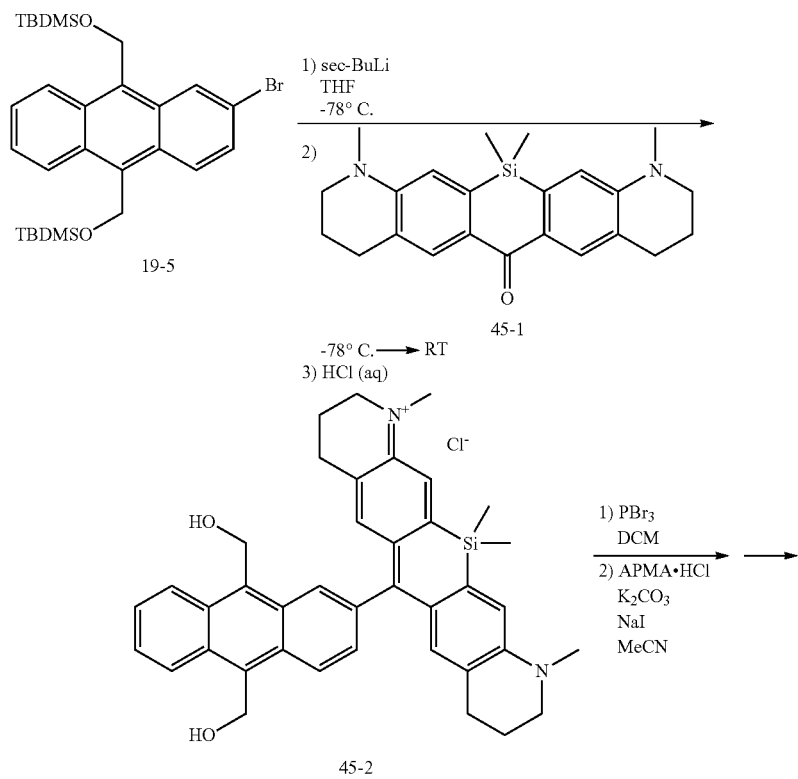

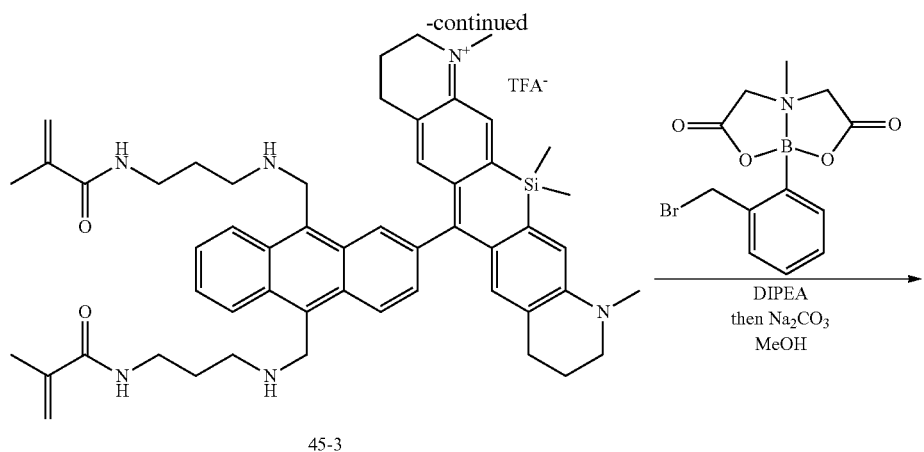

45-3

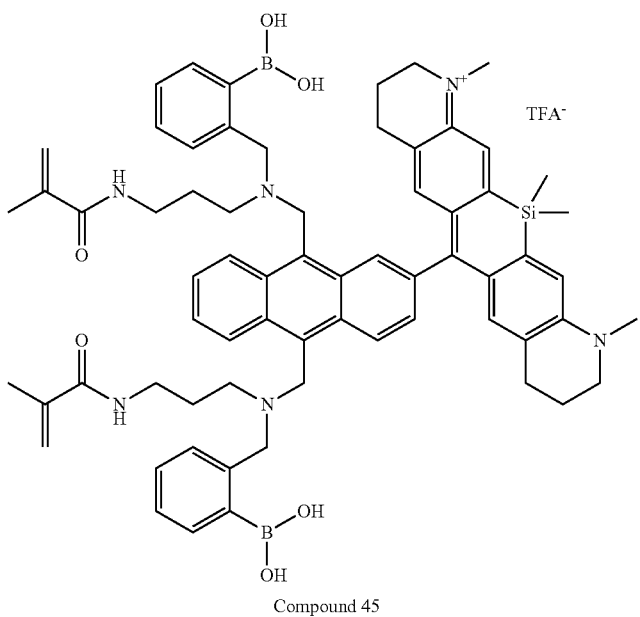

Compound 45

45

Intermediate 45-1 was synthesized from commercially available starting materials by analogy with 49-1, as described in literature (Koide, Y.; Urano, Y.; Hanaoka, K.; Piao, W.; Kusakabe, M.; Saito, N.; Terai, T.; Okabe, T.; Nagano, T. *J. Am. Chem. Soc.* 2012, 134 (11), 5029-5031).

Compound 45 was synthesized from intermediates 45-1 and 19-5, following general procedures X, XIV, and XV. HPLC-MS: m/z 1114.3 (calcd. 1113.6 for M$^+$). UV/Vis: $\lambda_{max}$=690 nm.

Preparation of Compound 48

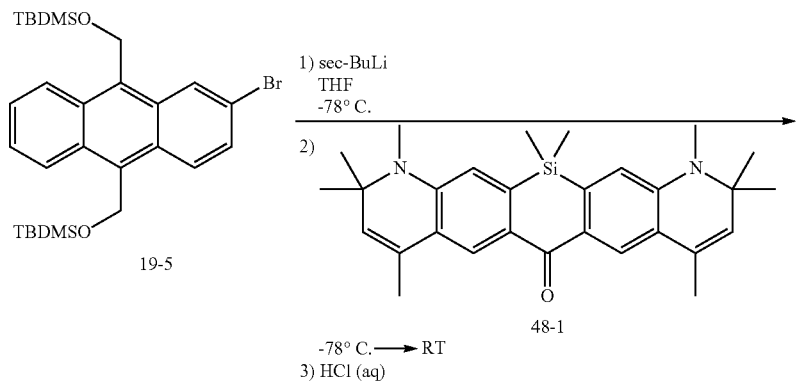

-continued
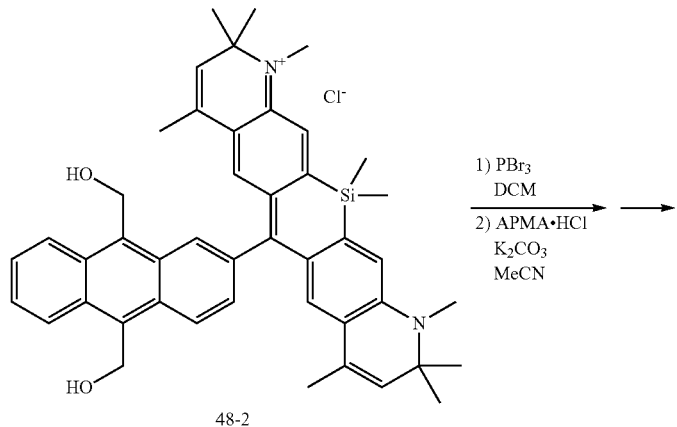
48-2
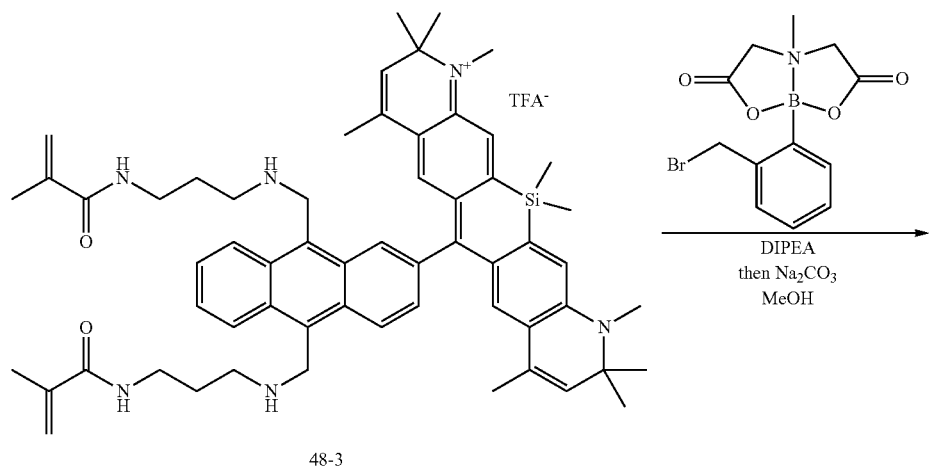
48-3
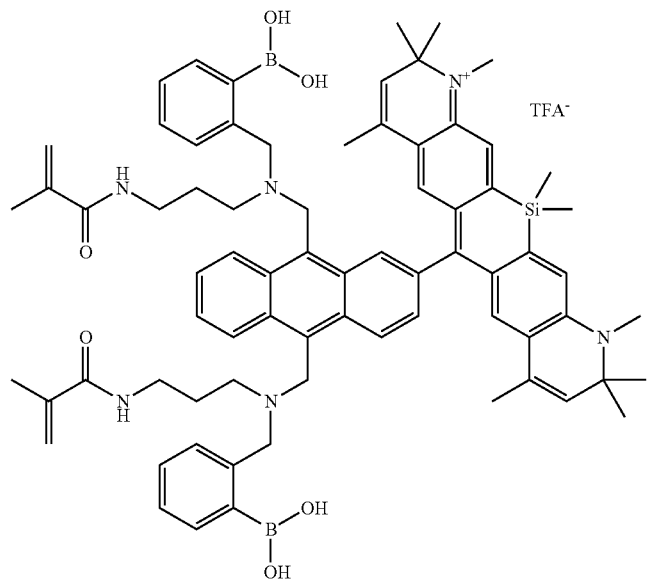
Compound 48

Silaxanthone 48-1 was synthesized from commercially available starting materials by analogy with 49-1, as described in literature (Koide, Y.; Urano, Y.; Hanaoka, K.; Piao, W.; Kusakabe, M.; Saito, N.; Terai, T.; Okabe, T.; Nagano, T. *J. Am. Chem. Soc.* 2012, 134 (11), 5029-5031).

Compound 48 was synthesized from silaxanthone 48-1 and bromoanthracene 19-5, following general procedures X, XIV, and XV. HPLC-MS: m/z 1194.3 (calcd. 1193.7 for M$^+$). UV/Vis: $\lambda_{max}$=740 nm.

Preparation of Compound 56

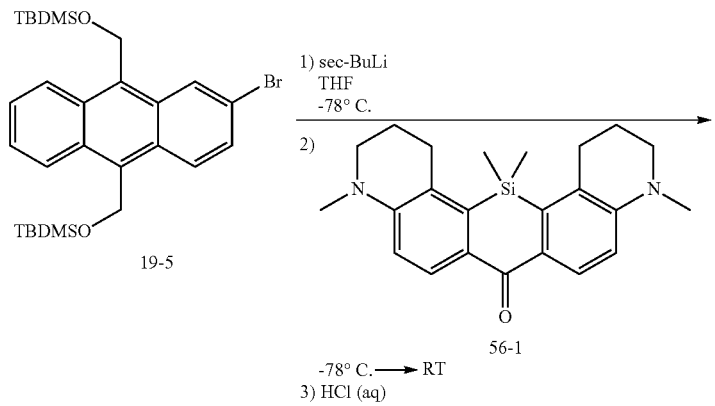

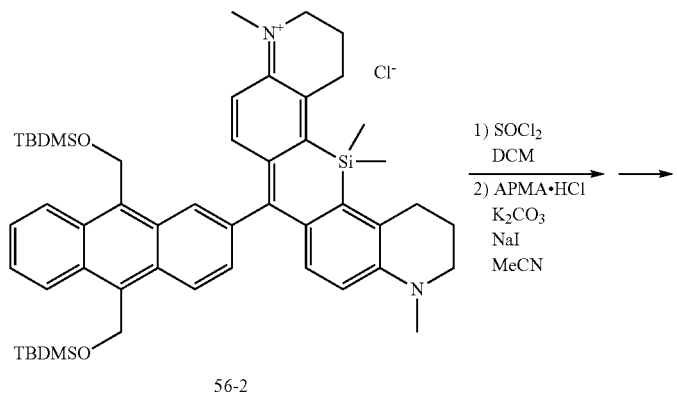

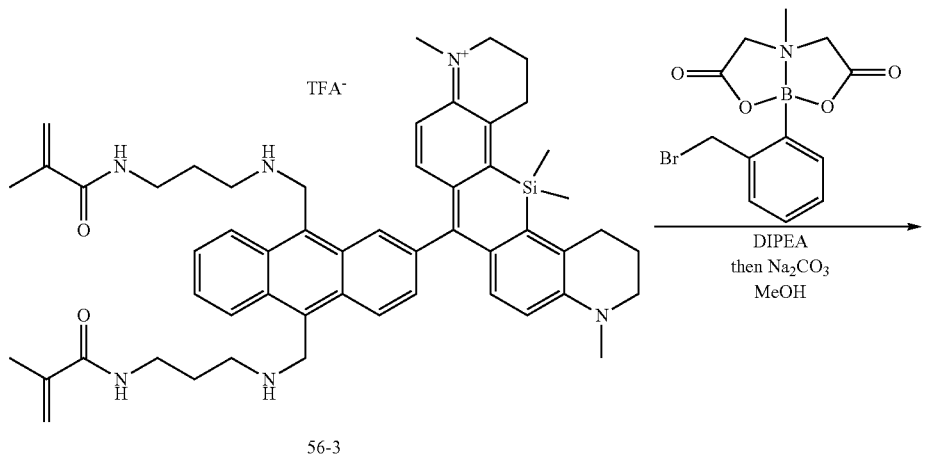

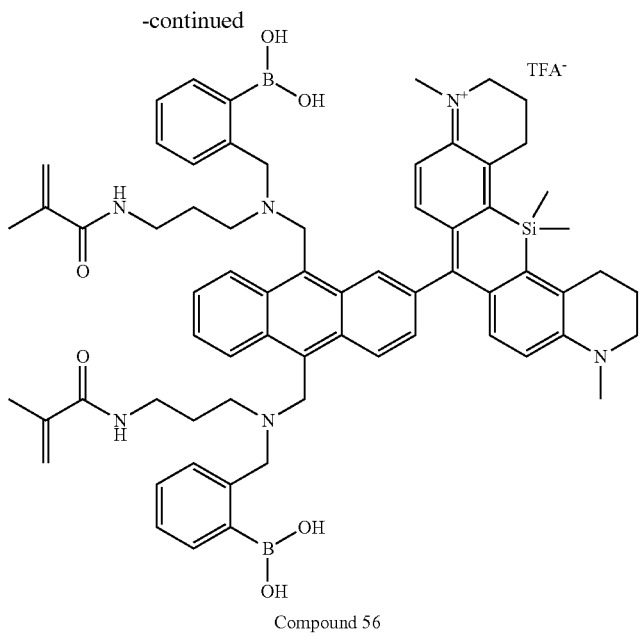

Compound 56

Intermediate 56-1 was synthesized from commercially available starting materials by analogy with 49-1, as described in literature (Koide, Y.; Urano, Y.; Hanaoka, K.; Piao, W.; Kusakabe, M.; Saito, N.; Terai, T.; Okabe, T.; Nagano, T. *J. Am. Chem. Soc.* 2012, 134 (11), 5029-5031).

General Procedure XVI. Preparation of Silicon Rosamine Fluorophore Via Lithium-Halogen Exchange with t-BuLi and TMEDA. Preparation of Compound 56-2

A solution of aryl bromide 19-5 (142 mg, 0.26 mmol) and TMEDA (0.02 mL, 0.13 mmol) in anhydrous THF (4 mL) was cooled to −78° C. under argon. A solution of tert-butyllithium in pentane (c=1.52 M, 0.19 mL, 0.29 mmol) was added dropwise and the mixture was stirred at −78° C. for 5-15 min, followed by rapid addition of silaxanthone 56-1 as a solution in anhydrous THF (c=0.075 M, 2.65 mL, 0.20 mmol). The mixture was stirred at −78° C. for 5-30 min and then was allowed to warm up to room temperature. After 1 h, the reaction was quenched with half-saturated NH$_4$Cl, acidified with 0.1 M HCl (1 mL) and extensively extracted with DCM until aqueous layer was colorless. Combined organic layers were dried over anhydrous Na$_2$SO$_4$, filtered and concentrated under reduced pressure. The residue was purified by flash chromatography (SiO$_2$, eluted with gradient from 2% to 25% MeOH in DCM) yielding bis-TBDMS diether 56-2 (83 mg, 27% yield, 56% b. r. s. m.) as a dark-blue solid.

General Procedure XVIIA. Double Amination of TBDMS Diether. Preparation of Compound 56-3

A solution of intermediate 56-2 (83 mg, 0.09 mmol) in anhydrous DCM (9 mL) was treated with 1 M thionyl chloride in DCM (0.5 mL, 0.5 mmol) for 16 h at room temperature. Then the solvent was removed in vacuo and the residue was rigorously dried under high vacuum to remove traces of thionyl chloride. This was dissolved in anhydrous MeCN (5 mL) and transferred to a slurry of APMA.HCl (330 mg, 1.85 mmol) and K$_2$CO$_3$ (511 mg, 3.7 mmol) in anhydrous MeCN (50 mL) that was pre-stirred at room temperature for at least 24 h. To the suspension NaI (8 mg, 0.05 mmol) was added, and the mixture was stirred at room temperature for 2 h and then filtered. Filtrate was concentrated in vacuo and the residue was purified by reversed phase flash chromatography (C18 SiO$_2$, eluted with gradient from 5% to 100% MeOH in water+0.05% TFA). Yield: 9 mg (10%) as blue oil.

Compound 56 was synthesized from intermediate 56-3 following general procedure XV. HPLC-MS: m/z 1114.3 (calcd. 1113.6 for M$^+$). UV/Vis: λ$_{max}$=665 nm.

Preparation of Compound 36

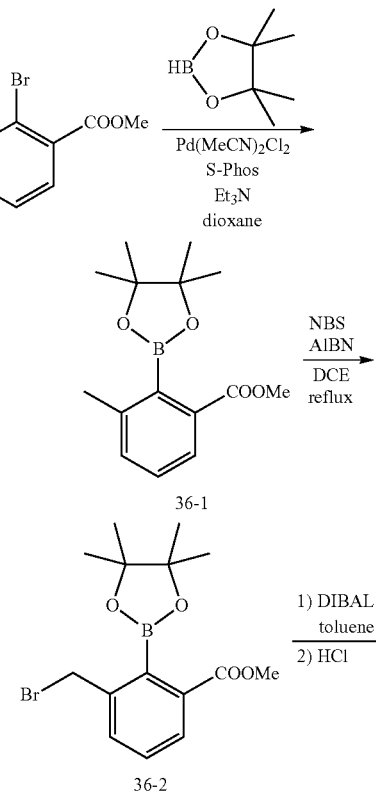

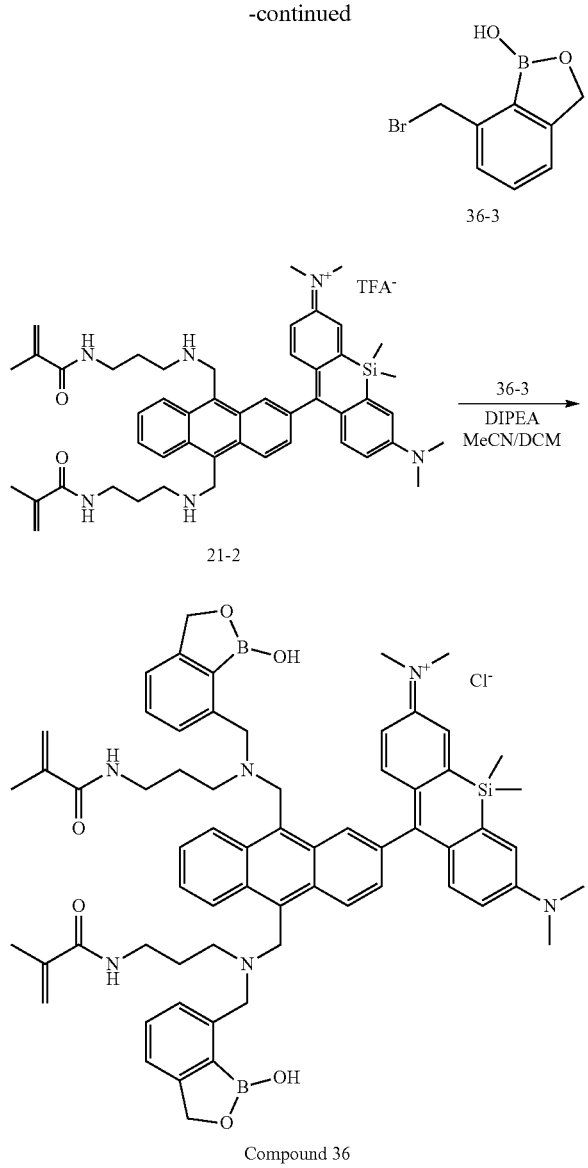

Preparation of Compound 36-1

A mixture of methyl 2-bromo-3-methylbenzoate (10 g, 43 mmol), pinacolborane (9.7 mL, 66 mmol), triethylamine (19 mL, 131 mmol), S-Phos (1.4 g, 3.5 mmol), and Pd(MeCN)Cl$_2$ (15.7 mg, 0.9 mmol) in degassed dioxane (200 mL) was heated at 60° C. under argon for 16 h. The reaction mixture was then filtered and concentrated under reduced pressure. The residue was purified by flash chromatography (SiO$_2$, eluted with gradient from 0% to 100% DCM in hexanes) affording the title compound 36-1 (11.2 g, 94% yield) as a white solid.

Preparation of Compound 36-2

A mixture of intermediate 36-1 (11.2 g, 40 mmol), N-bromosuccinimide (7.8 g, 44 mmol), AIBN (10 mg, 0.06 mmol) in 1,2-dichloroethane (180 mL) was refluxed for 16 h. Then the reaction mixture was concentrated under reduced pressure. The residue was triturated with cold (4° C.) EtOAc and insoluble solid was discarded. Solvent was removed under reduced pressure and the residue was purified by flash chromatography (SiO$_2$, eluted with gradient from 0% to 100% DCM in hexanes). This afforded title compound 36-2 (10.2 g, 72% yield) as a white solid.

Preparation of Compound 36-3

Solution of intermediate 36-2 (5.0 g, 14 mmol) in toluene (25 mL) was cooled to 0° C. under argon. Diisobutylaluminium hydride (c=1 M in THF, 29.5 mL, 29.5 mmol) was added dropwise over 30 min. The mixture was partitioned and the aqueous layer was exhaustively extracted with EtOAc. Combined organic layers were dried over anhydrous MgSO$_4$, filtered, and concentrated under reduced pressure. The residue was purified by flash chromatography (SiO$_2$, eluted with gradient from 0% to 10% MeOH in DCM). This afforded title compound 36-3 (2.2 g, 69%) as a colorless oil.

Compound 36 was prepared form intermediate 21-2 and 36-3 following the general procedure V. HPLC-MS: m/z 1086.4 (calcd. 1085.6 for M$^+$). UV/Vis: $\lambda_{max}$=660 nm.

Preparation of Compound 37

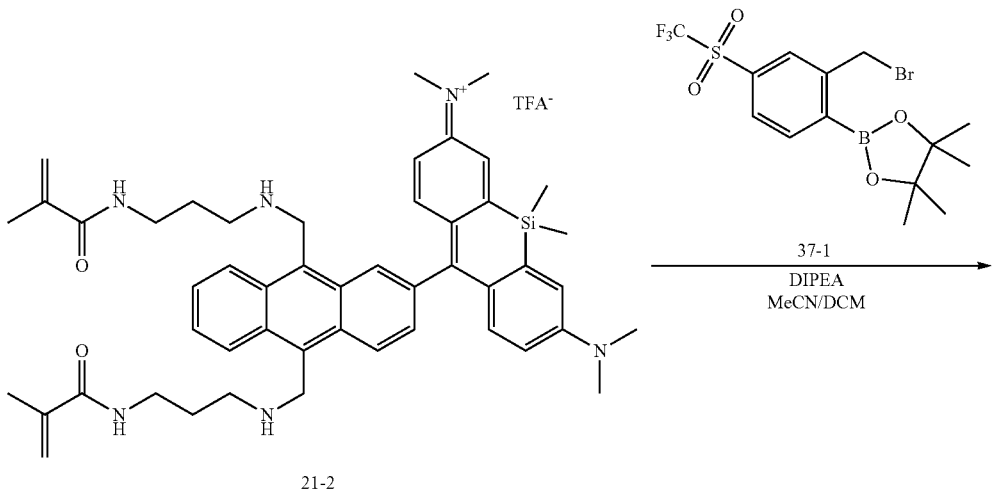

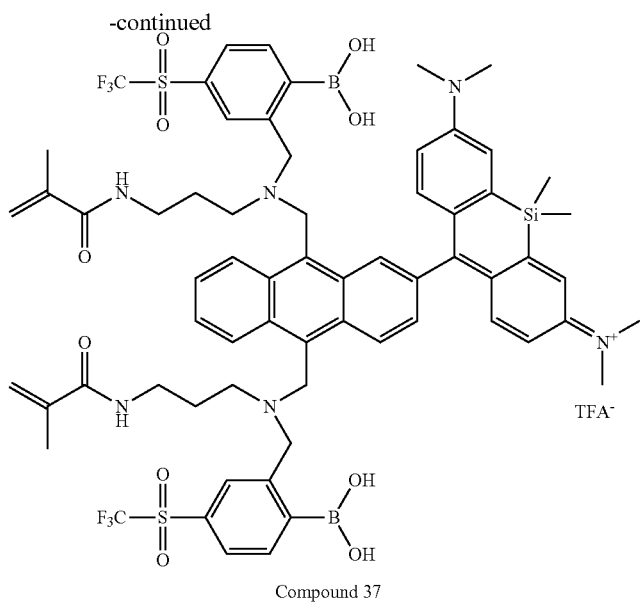
Compound 37
Intermediate 37-1 was synthesized following the published procedure (Colvin, et al., PCT Int. Appl. (2008), WO 2008066921 A2 Jun. 5, 2008).
Compound 37 was prepared from intermediates 21-2 and 37-1 following the general procedure V. HPLC-MS: m/z 1326.2 (calcd. 1325.5 for M$^+$). UV/Vis: $\lambda_{max}$=660 nm.
Preparation of Compound 46, 47, 51, 52, 53, 55, 57, 58, 60
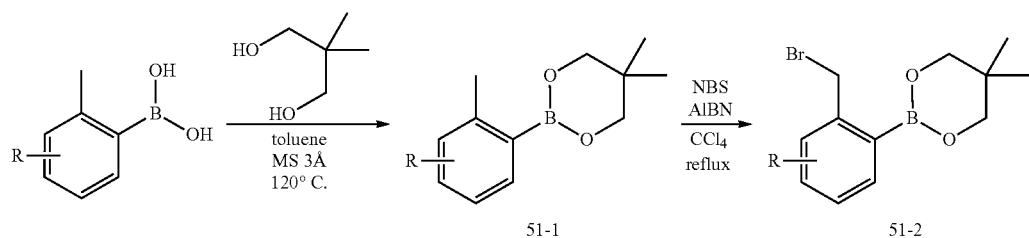
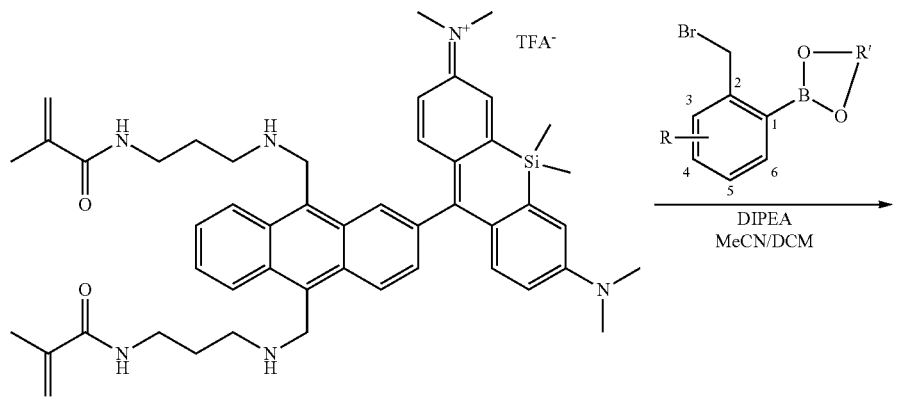

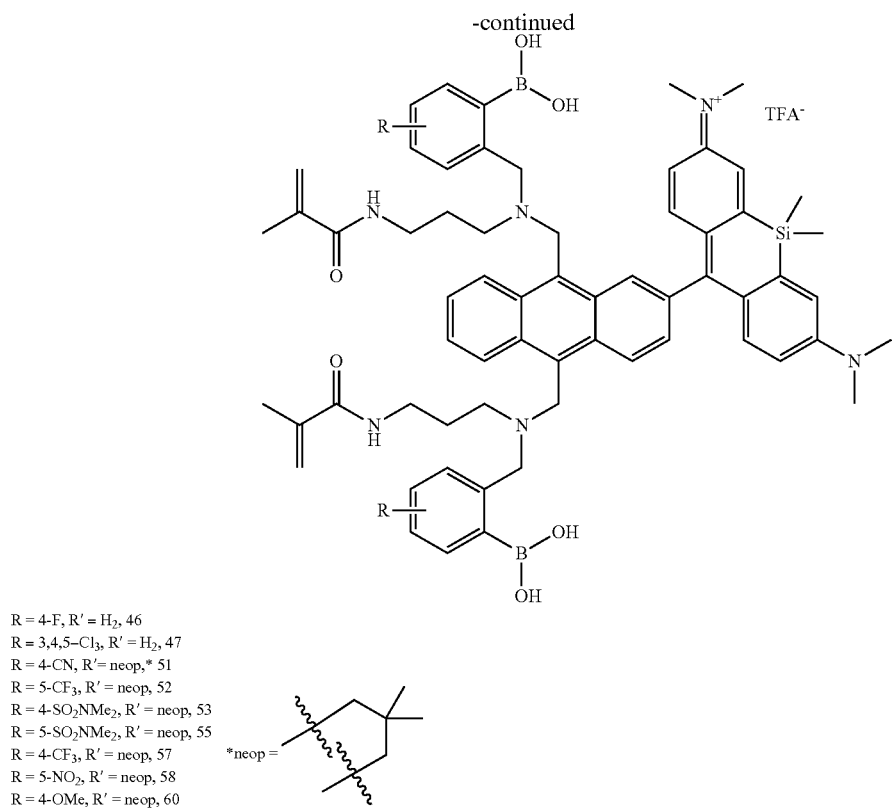

R = 4-F, R' = H₂, 46
R = 3,4,5-Cl₃, R' = H₂, 47
R = 4-CN, R'= neop,* 51
R = 5-CF₃, R' = neop, 52
R = 4-SO₂NMe₂, R' = neop, 53
R = 5-SO₂NMe₂, R' = neop, 55
R = 4-CF₃, R' = neop, 57
R = 5-NO₂, R' = neop, 58
R = 4-OMe, R' = neop, 60

General Procedure XVIII. Protection of Boronic Acids with Neopentyl Glycol. Preparation of Compound 51-1

A mixture of 4-cyano-2-methylphenylboronic acid (906 mg, 5.6 mmol), 2,2-dimetyl-1,3-propanediol (641 mg, 6.15 mmol) and 3 Å molecular sieves (1 g) in anhydrous toluene (10 mL) was heated at 120° C. for 1 h and then was allowed to cool to room temperature. The mixture was filtered and the filtrate was concentrated in vacuo. The residue was purified by flash chromatography (SiO₂, eluted with gradient from 20% to 60% EtOAc in hexanes). Yield: 1.054 g (82%) as yellowish solid.

General Procedure XIX. Radical Bromination. Preparation of Compound 51-2

A mixture of 4-cyano-2-methylphenylboronic acid neopentyl glycol ester 51-1 (229 mg, 1.0 mmol), N-bromosuccinimide (208 mg, 1.17 mmol), and AIBN (22 mg, 0.13 mmol) in CCl₄ (20 mL) was refluxed for 20-30 min. The progress was monitored by TLC (DCM:hexane=6:4). The reaction mixture was then filtered and the filtrate was concentrated under reduced pressure. The residue was purified by flash chromatography (SiO₂, eluted with 0% to 50% EtOAc in hexanes) affording the title compound 51-2 (312 mg, quant.) as a turbid oil which slowly crystallized upon storage at room temperature.

Compound 51 was prepared from intermediates 21-2 and 51-2 following the general procedure V. The neopentyl glycol protecting group was spontaneously removed during reversed phase purification. HPLC-MS: m/z 1112.2 (calcd. 1111.6 for M⁺). UV/Vis: $\lambda_{max}$=660 nm. ¹H NMR (400 MHz, MeOH-d₄; mixture of two rotamers) δ ppm 8.53 (m, J=9.4 Hz, 2H), 8.29-8.40 (m, 1H), 7.68-7.78 (m, 2H), 7.48-7.67 (m, 8H), 7.46 (d, J=2.7 Hz, 2H), 7.18 (d, J=9.1 Hz, 2H), 6.70 (dd, J=9.7, 2.8 Hz, 2H), 5.43 (s, 1H), 5.33 (s, 1H), 5.25 (quin, J=1.3 Hz, 1H), 5.18 (quin, J=1.3 Hz, 1H), 5.06 (br. s., 2H), 4.96 (br. s., 2H), 4.23 (br. s., 2H), 4.03 (br. s., 2H), 3.37 (s, 12H), 3.12 (t, J=6.1 Hz, 2H), 2.98 (t, J=6.2 Hz, 2H), 2.88 (dd, J=8.0, 6.6 Hz, 2H), 2.71 (dd, J=8.2, 6.6 Hz, 2H), 1.91-2.08 (m, 4H), 1.77 (s, 3H), 1.69 (s, 3H), 0.82 (br. s., 3H), 0.63 (s, 3H).

Compounds 46, 47, 52, 53, 55, 57, 58, 60 were prepared from intermediate 21-2 and corresponding boronic acid or neopentyl glycol boronates following general procedures XVIII, XIX, and V, as outlined in the Scheme above.

For compound 46: HPLC-MS: m/z 1098.3 (calcd. 1097.6 for M⁺). UV/Vis: $\lambda_{max}$=660 nm.

For compound 47: HPLC-MS: m/z 1268.0 (calcd. 1267.3 for M⁺). UV/Vis: $\lambda_{max}$=660 nm.

For compound 52: HPLC-MS: m/z 1198.2 (calcd. 1197.5 for M⁺). UV/Vis: $\lambda_{max}$=660 nm. ¹H NMR (400 MHz, MeOH-d₄; mixture of two rotamers) δ ppm 8.82 (s, 1H), 8.30 (d, J=7.9 Hz, 2H), 7.79-7.88 (m, 1H), 7.67-7.78 (m, 2H), 7.45-7.67 (m, 6H), 7.39-7.45 (m, 3H), 6.98 (d, J=2.7 Hz, 2H), 6.78 (dd, J=9.3, 2.7 Hz, 2H), 5.44 (s, 1H), 5.36 (s, 1H), 5.22 (quin, J=1.3 Hz, 1H), 5.18 (quin, J=1.3 Hz, 1H), 5.03 (br. s, 2H), 4.25 (br. s., 2H), 4.07 (br. s., 2H), 3.15 (t, J=6.6 Hz, 2H), 3.06 (t, J=6.6 Hz, 2H), 2.94 (s, 12H), 2.72-2.83 (m, 2H), 2.67 (dd, J=9.3, 7.2 Hz, 2H), 1.99-2.08 (m, 2H), 1.80 (s, 2H), 1.75 (s, 3H), 1.69 (s, 3H), 0.60 (s, 3H), 0.55 (s, 3H).

For compound 53: HPLC-MS: m/z 1276.2 (calcd. 1275.6 for M+). UV/Vis: $\lambda_{max}$=660 nm. $^1$H NMR (400 MHz, MeOH-d$_4$; mixture of two rotamers) δ ppm 8.83 (s, 1H), 8.47 (br. s., 1H), 8.14-8.26 (m, 1H), 7.76 (d, J=7.8 Hz, 1H), 7.60-7.73 (m, 6H), 7.48-7.54 (m, 2H), 7.36-7.47 (m, 3H), 6.98 (d, J=2.8 Hz, 2H), 6.81 (d, J=7.2 Hz, 2H), 5.48 (s, 1H), 5.41 (s, 1H), 5.25 (quin, J=1.3 Hz, 1H), 5.21 (quin, J=1.3 Hz, 1H), 4.92 (br. s., 2H), 4.76 (br. s., 2H), 4.29 (br. s, 2H), 4.17 (br. s., 2H), 3.16 (t, J=6.6 Hz, 2H), 3.10 (t, J=6.6 Hz, 2H), 2.95 (s, 12H), 2.76-2.84 (m, 2H), 2.65-2.73 (m, 2H), 2.64 (s, 6H), 2.48 (s, 6H), 2.00-2.11 (m, 2H), 1.82-1.90 (m, 2H), 1.79 (s, 3H), 1.73 (s, 3H), 0.61 (s, 3H), 0.55 (s, 3H).

For compound 55: HPLC-MS: m/z 1276.1 (calcd. 1275.6 for M+). UV/Vis: $\lambda_{max}$=660 nm. $^1$H NMR (400 MHz, MeOH-d$_4$; mixture of two rotamers) δ ppm 8.83 (br. s., 1H), 8.54 (d, J=9.1 Hz, 1H), 8.48 (d, J=8.6 Hz, 1H), 7.79-7.87 (m, 2H), 7.67-7.77 (m, 2H), 7.51-7.59 (m, 3H), 7.32-7.51 (m, 3H), 7.42 (d, J=2.7 Hz, 2H), 7.18 (d, J=9.7 Hz, 2H), 6.66 (dd, J=9.7, 2.5 Hz, 2H), 5.42 (s, 1H), 5.28 (s, 1H), 5.23 (s, 1H), 5.15 (s, 1H), 5.06 (br. s., 2H), 4.64 (br. s., 2H), 4.31 (br. s., 2H), 4.03 (br. s., 2H), 3.34 (s, 12H), 3.08-3.19 (m, 2H), 2.95 (s, 6H), 2.88 (t, J=6.6 Hz, 2H), 2.57-2.66 (m, 4H), 2.54 (s, 6H), 1.90-2.10 (m, 2H), 1.80-1.90 (m, 2H), 1.75 (s, 3H), 1.65 (s, 3H), 0.80 (br. s., 3H), 0.66 (s, 3H).

For compound 57: HPLC-MS: m/z 1198.1 (calcd. 1197.5 for M+). UV/Vis: $\lambda_{max}$=660 nm. $^1$H NMR (400 MHz, MeOH-d$_4$; mixture of two rotamers) δ ppm 8.50-8.60 (m, 2H), 8.47 (d, J=9.1 Hz, 1H), 8.28 (t, J=9.6 Hz, 1H), 7.58-7.75 (m, 5H), 7.50-7.57 (m, 2H), 7.47 (d, J=2.7 Hz, 2H), 7.36-7.49 (m, 2H), 7.14 (d, J=9.5 Hz, 2H), 6.65 (dd, J=9.5, 2.7 Hz, 2H), 5.35 (s, 1H), 5.27 (s, 1H), 5.19 (quin, J=1.2 Hz, 1H), 5.12 (quin, J=1.2 Hz, 1H), 4.92 (br. s., 2H), 4.60 (br. s., 2H), 4.19 (br. s., 2H), 4.01 (br. s., 2H), 3.36 (s, 12H), 3.07 (t, J=6.6 Hz, 2H), 2.95 (t, J=6.6 Hz, 2H), 2.74-2.83 (m, 2H), 2.61-2.74 (m, 2H), 1.87-2.03 (m, 2H), 1.73-1.82 (m, 2H), 1.71 (s, 3H), 1.64 (s, 3H), 0.88 (br. s., 3H), 0.64 (s, 3H).

For compound 58: HPLC-MS: m/z 1152.3 (calcd. 1151.5 for M+). UV/Vis: $\lambda_{max}$=660 nm. $^1$H NMR (400 MHz, MeOH-d$_4$; mixture of two rotamers) δ ppm 8.85 (br. s., 1H), 8.28-8.40 (m, 2H), 8.24 (dd, J=8.4, 2.7 Hz, 2H), 7.88 (d, J=8.4 Hz, 1H), 7.79 (d, J=9.1 Hz, 1H), 7.69-7.75 (m, 1H), 7.53-7.63 (m, 2H), 7.43 (d, J=9.0 Hz, 2H), 7.34-7.52 (m, 3H), 6.98 (d, J=2.7 Hz, 2H), 6.78 (dd, J=9.0, 2.7 Hz, 2H), 5.46 (s, 1H), 5.39 (s, 1H), 5.22 (quin, J=1.3 Hz, 1H), 5.19 (quin, J=1.3 Hz, 1H), 4.94 (br. s, 4H, overlaps with CD$_3$OH signal), 4.27 (br. s, 2H), 4.13 (br. s., 2H), 3.17 (t, J=6.6 Hz, 2H), 2.94 (s, 12H), 2.90-2.97 (m, 2H), 2.75-2.86 (m, 2H), 2.66-2.75 (m, 2H), 2.00-2.12 (m, 2H), 1.78-1.90 (m, 2H), 1.76 (s, 3H), 1.71 (s, 3H), 0.60 (s, 3H), 0.55 (s, 3H).

For compound 60: HPLC-MS: m/z 1122.2 (calcd. 1121.6 for M+). UV/Vis: $\lambda_{max}$=660 nm. $^1$H NMR (400 MHz, MeOH-d$_4$; mixture of two rotamers) δ ppm 8.50-8.61 (m, 2H), 8.39-8.50 (m, 1H), 7.58-7.69 (m, 2H), 7.45 (d, J=2.7 Hz, 2H), 7.36-7.49 (m, 2H), 7.32 (d, J=8.9 Hz, 1H), 7.15 (m, J=8.4 Hz, 3H), 6.84-6.93 (m, 2H), 6.75-6.83 (m, 2H), 6.65 (dd, J=9.7, 2.3 Hz, 2H), 5.38 (s, 1H), 5.29 (s, 1H), 5.21 (quin, J=1.3 Hz, 1H), 5.14 (quin, J=1.3 Hz, 1H), 4.73 (br. s., 2H), 4.54 (br. s., 2H), 3.87 (br. s, 2H), 3.75 (s, 3H), 3.68 (br. s, 2H), 3.35 (s, 12H), 3.08 (t, J=6.5 Hz, 2H), 2.95 (t, J=6.6 Hz, 2H), 2.93 (s, 3H), 2.65-2.71 (m, 2H), 2.57-2.65 (m, 2H), 1.84-1.94 (m, 2H), 1.75 (s, 3H), 1.69-1.74 (m, 2H), 1.67 (s, 3H), 0.87 (br. s, 3H), 0.63 (s, 3H).

Preparation of Compounds 39, 40, 43, 44

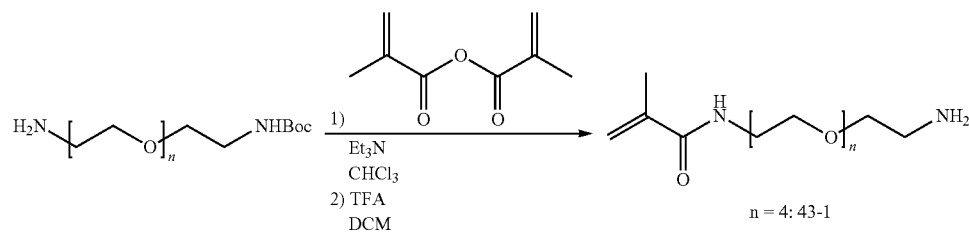

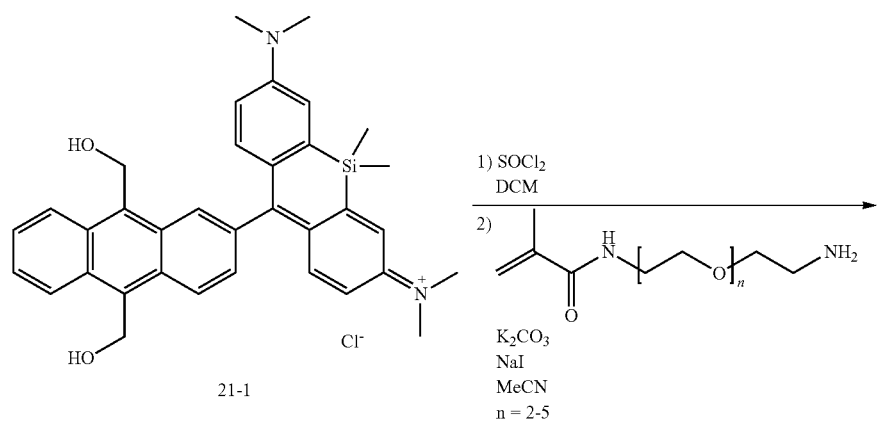

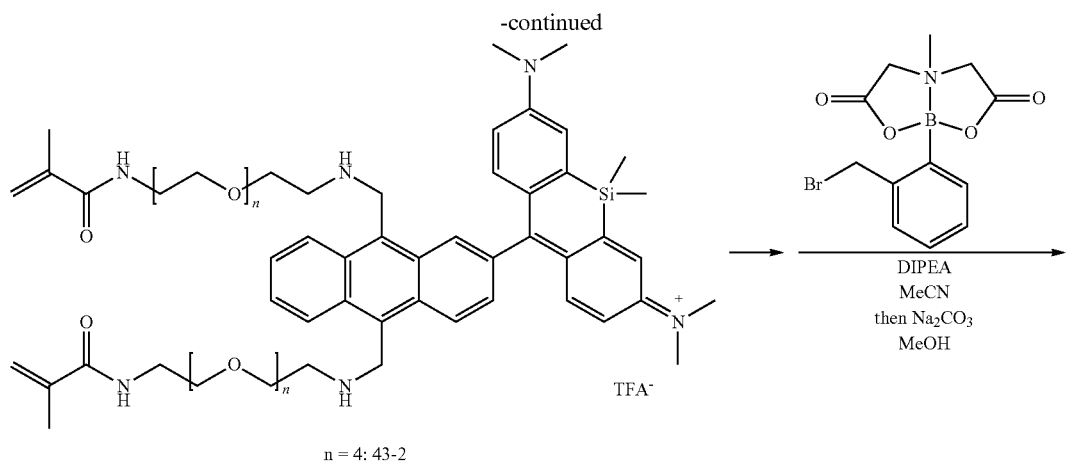

n = 4: 43-2

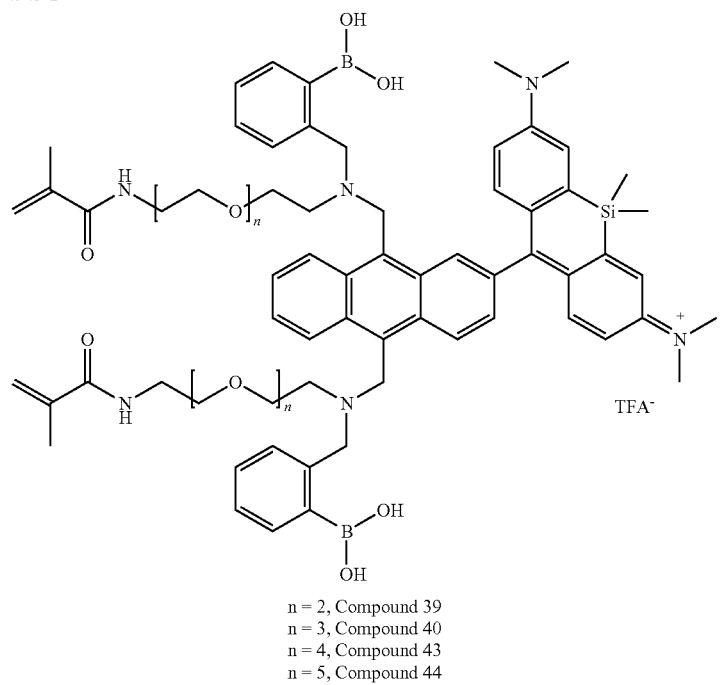

n = 2, Compound 39
n = 3, Compound 40
n = 4, Compound 43
n = 5, Compound 44

General Procedure XX. PEG Monomethacrylates. Preparation of Compound 43-1

To a solution of mono-Boc-protected PEG$_4$ diamine (1.0 g, 2.97 mmol) in chloroform (30 mL), methacrylic anhydride (0.55 mL, 3.46 mmol) and triethylamine (0.55 mL, 3.95 mmol) were successively added, and the reaction mixture was stirred at room temperature overnight. Then the reaction mixture was concentrated under reduced pressure and the residue was taken up into EtOAc (40 mL). The solution was washed with 1 N HCl (2×40 mL), saturated NaHCO$_3$ (40 mL), and brine (40 mL). The organic layer was dried over anhydrous Na$_2$SO$_4$, filtered, and concentrated under reduced pressure. The residue was purified by reversed phase flash chromatography (C18 SiO$_2$, eluted with gradient of MeOH in water+0.05% TFA) affording the desired intermediate (553 mg, 46% yield) as a colorless oil. The purified oil (553 mg, 1.37 mmol) was dissolved in DCM (5 mL) and treated with TFA (1 mL) for 3 h at room temperature, and then the reaction mixture was concentrated under reduced pressure. The residue was dried under high vacuum yielding desired PEG$_4$-mono-methacrylamide 43-1 (750 mg, quant., TFA salt) as amber oil. Intermediates 39-1, 40-1, and 44-1 were prepared from corresponding mono-Boc-protected oligo(ethyleneglycol)diamines following the general procedure XX.

Compounds 39, 40, 43, and 44 were prepared from corresponding amines 39-1, 40-1, 43-1, and 44-1, and common intermediate diol 21-1, following the general procedures XVIIA and XV, as outlined in the scheme above.

For compound 39: HPLC-MS: m/z 1210.5 (calcd. 1209.6 for M$^+$). UV/Vis: $\lambda_{max}$=660 nm. $^1$H NMR (400 MHz, DMSO-d$_6$) δ ppm 8.41-8.54 (m, 2H), 8.19 (br. s., 1H), 7.60-7.67 (m, 1H), 7.51-7.60 (m, 2H), 7.47 (d, J=2.8 Hz, 2H), 7.17-7.43 (m, 7H), 6.91-7.17 (m, 4H), 6.71 (dd, J=9.8, 2.7 Hz, 2H), 5.52-5.59 (m, 1H), 5.54 (s, 1H), 5.18-5.29 (m, 2H), 4.67 (br. s., 2H), 4.60 (br. s., 2H), 3.94 (br. s., 2H), 3.76 (br. s., 2H), 3.31-3.38 (m, 8H), 3.29 (s, 12H), 3.22 (t, J=6.5 Hz, 2H), 3.12-3.19 (m, 8H), 3.10 (t, J=6.5 Hz, 2H), 2.69-2.77 (m, 2H), 2.58-2.64 (m, 2H), 1.75 (s, 3H), 1.74 (s, 3H), 0.69 (s, 3H), 0.61 (s, 3H).

For compound 40: HPLC-MS: m/z 1297.7 (calcd. 1298.5 for M$^+$). UV/Vis: $\lambda_{max}$=660 nm.

For compound 43: HPLC-MS: m/z 1386.5 (calcd. 1385.8 for M$^+$). UV/Vis: $\lambda_{max}$=660 nm.

For compound 44: HPLC-MS: m/z 1474.4 (calcd. 1473.8 for M$^+$). UV/Vis: $\lambda_{max}$=660 nm.

Preparation of Compound 50
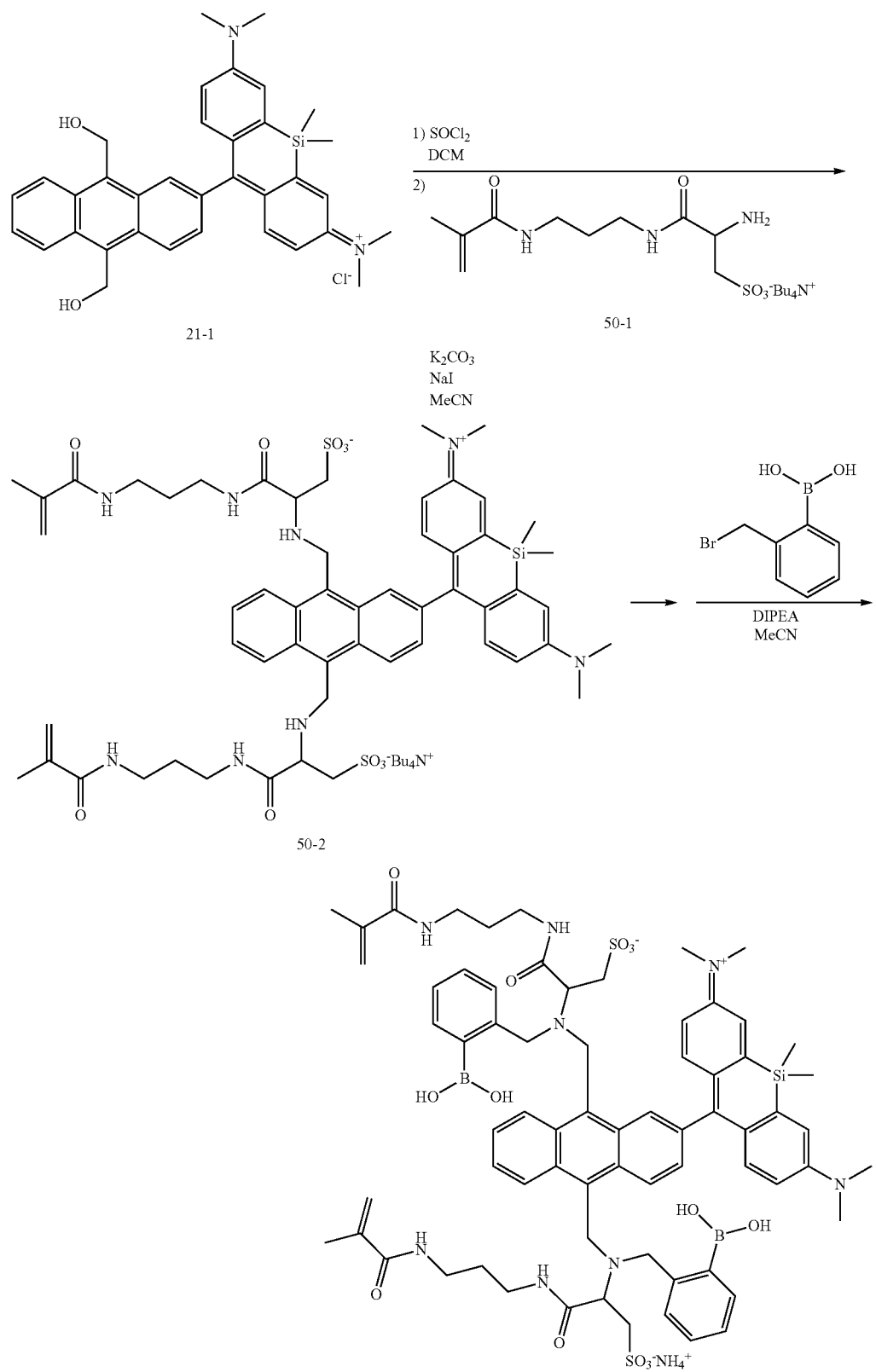

Intermediate 50-1 was prepared as described elsewhere (Suri, Jeff T. PCT Int. Appl., 2008014280, 31 Jan. 2008).

Compound 50 was prepared from intermediates 21-1 and 50-1, following general procedures XVIIA and V. The final compound was additionally purified with reversed phase flash chromatography (C18 SiO$_2$, eluted with gradient of MeCN in 10 mM aqueous NH$_4$HCO$_3$). HPLC-MS: m/z 1385.0 (calcd. 1385.5 for M+Na$^+$). UV/Vis: $\lambda_{max}$=655 nm.

Preparation of Compound 23

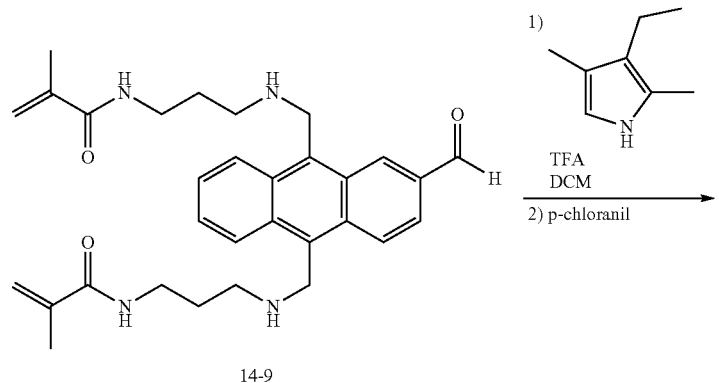

14-9

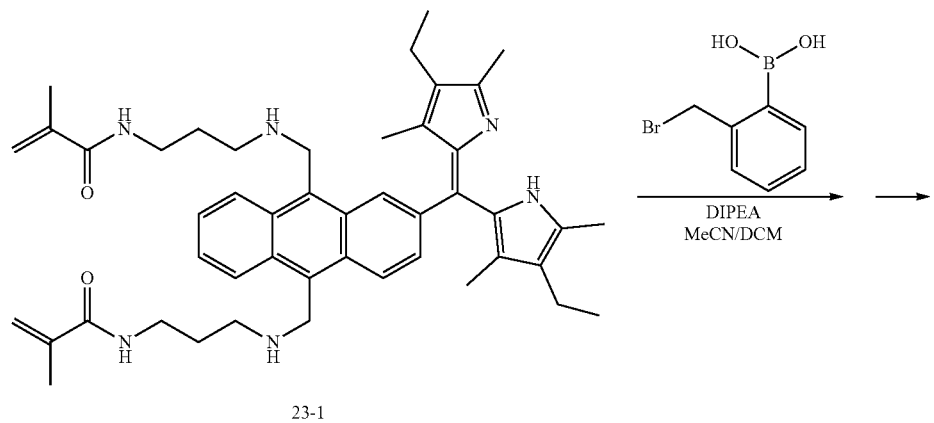

23-1

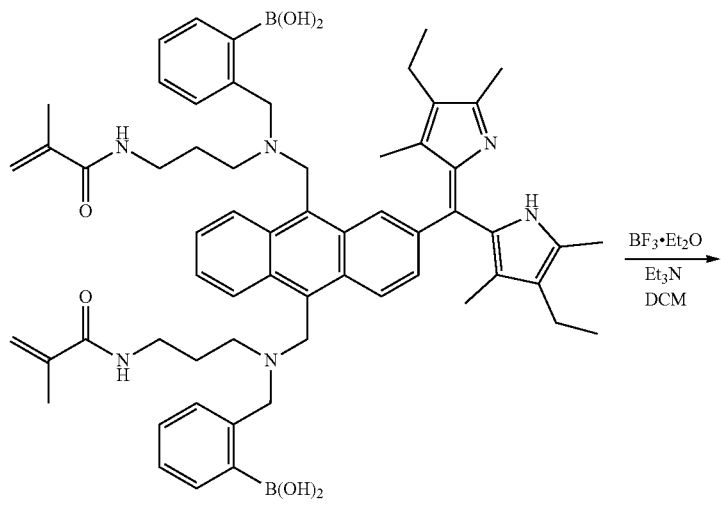

23-2

-continued
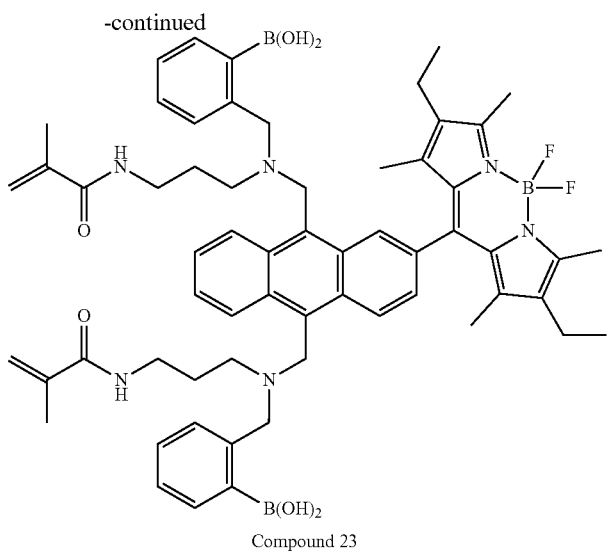
Compound 23
Compound 23 was synthesized from aldehyde 14-9 following the combination of general procedures VII and V as outlined in the scheme above. HPLC-MS: m/z 1057.0 (calcd. 1057.6 for M$^+$). UV/Vis: $\lambda_{max}$=560 nm.
Preparation of Compound 22
Scheme 2. Preparation of compound 22
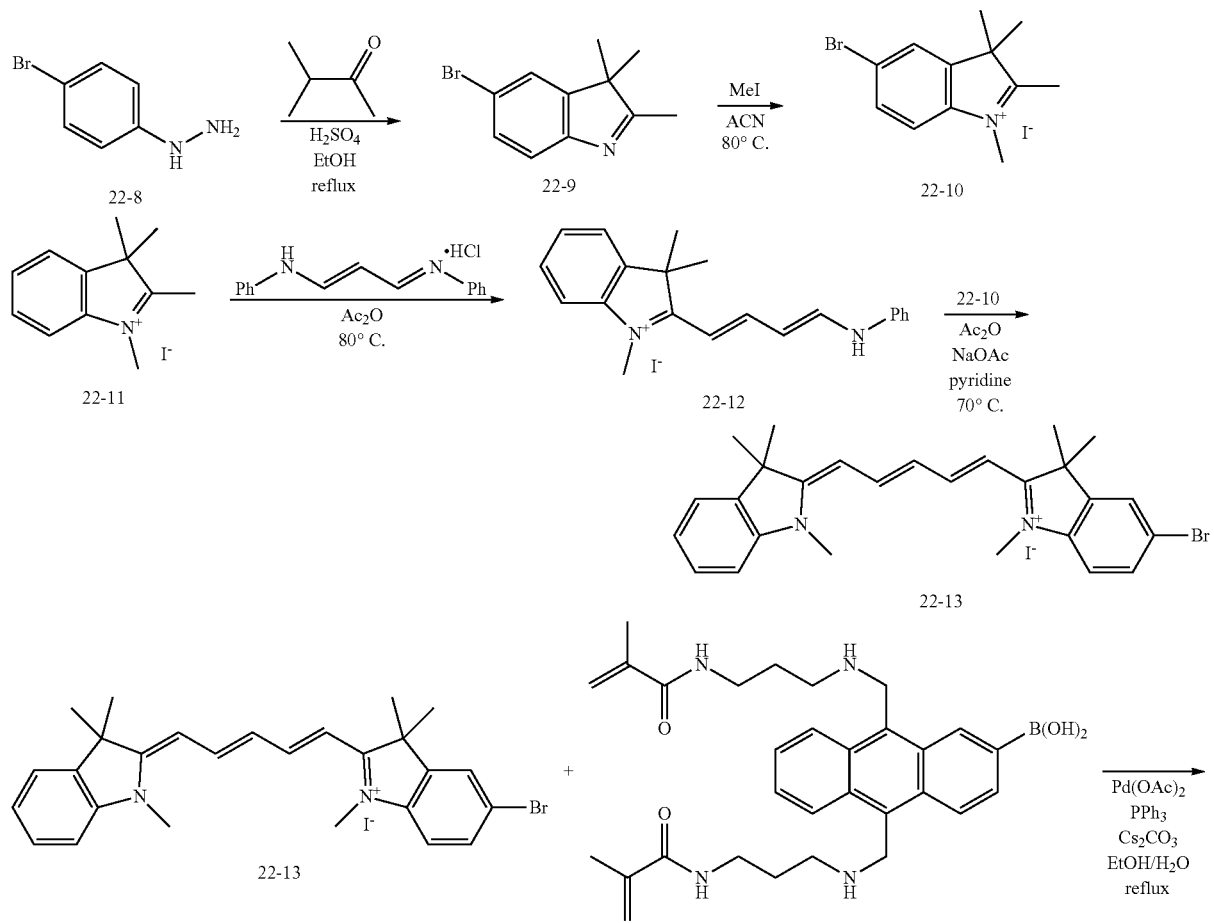

-continued

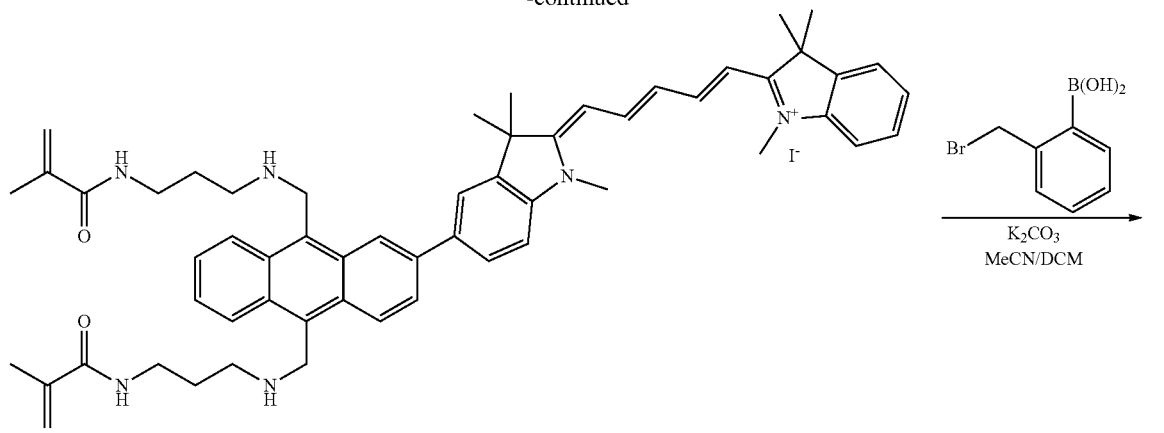

22-14

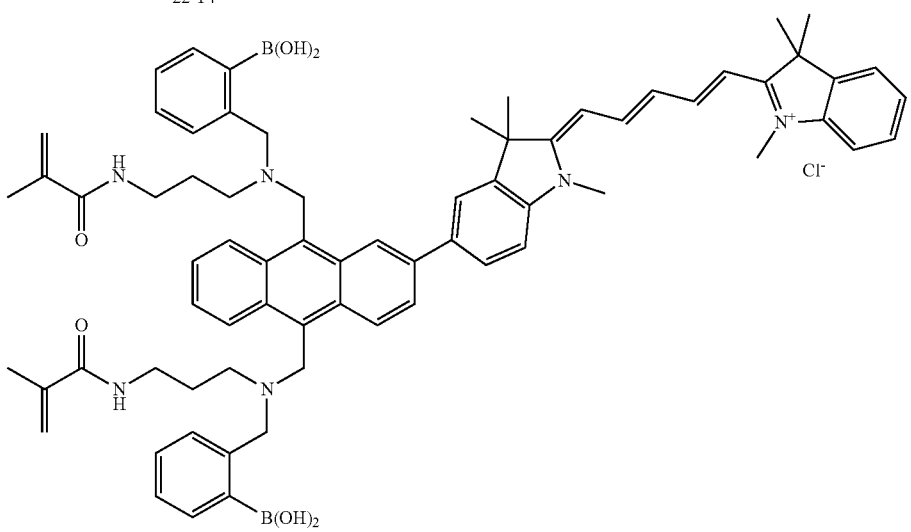

Compound 22

Preparation of 5-bromo-2,3,3-trimethylindolenine 22-9

A solution of 4-bromophenyl hydrazine (10 g, 44.7 mmol), 3-methyl-2-butanone (9.6 mL, 89.5 mmol) in anhydrous EtOH (160 mL), and conc. $H_2SO_4$ (5 mL) was refluxed for 1 h under argon. Then the reaction mixture was concentrated in vacuo to 80 mL, diluted with DCM, and transferred to a separatory funnel. Aqueous layer was discarded, and organic layer was washed three times with saturated $NaHCO_3$, water, and brine. The DCM portion was then dried over $MgSO_4$ and concentrated in vacuo to yield the title product (5.1 g, 48%).

Preparation of 5-bromo-1,2,3,3-tetramethyl-3H-indolium iodide 22-10

A mixture of intermediate 22-9 (5.1 g, 21.4 mmol) and iodomethane (3.96 mL, 64.3 mmol) in acetonitrile (40 mL) was heated to 80° C. in a pressure flask for 16 h producing light-yellow precipitate. The reaction mixture was allowed to cool to room temperature, diluted with diethyl ether and then cooled to −78° C. The product was collected by filtration, and rinsed with cold diethyl ether yielding the title product 22-10 (7.51 g, 93%).

Preparation of 1,3,3-trimethyl-2-[4-(phenylamino)-1,3-butadien-1-yl]-3H-indolium iodide 22-12

A mixture of N-(3-phenylimino-1-propen-1-yl)aniline hydrochloride (1.61 g, 6.2 mmol) and 1,2,3,3-tetramethyl-3H-indolium iodide (750 mg, 2.49 mmol) in acetic anhydride (40 mL) was heated to 80° C. under argon for 20 min. The reaction mixture was then diluted with DCM and transferred to a separatory funnel. The organic layer was washed with water and brine, then dried over $MgSO_4$ and concentrated in vacuo. The crude product was purified by flash chromatography ($SiO_2$, eluted with DCM and MeOH) yielding the title product 22-12 (439 mg, 41%).

Preparation of 5-bromo-2-[(5-(1,3-dihydro-1,3,3-trimethyl-2H-indol-2-ylidene)-1,3-pentadien-1-yl]-1,3,3-trimethyl-3H-indolium iodide 22-13

A mixture of sodium acetate (750 mg, 9.1 mmol), intermediates 22-12 (430 mg, 0.911 mmol) and 22-10 (1.03 g mg, 2.72 mmol), and pyridine (2 mL) in acetic anhydride (16 mL) was stirred for 1 h. The reaction mixture was diluted with DCM and neutralized with saturated $NaHCO_3$. The mixture was then partitioned and the DCM layer was washed with brine 2 times. The DCM portion was then dried over $MgSO_4$, and concentrated in vacuo. Crude product was purified by flash chromatrography (SiO$_2$, eluted with DCM and MeOH) affording the title product 22-13 (311 mg, 58%).

Preparation of 5-{[9,10-bis(3-methacrylamidopropyl)aminomethyl]anthr-2-yl}-2-[(5-(1,3-dihydro-1,3,3-trimethyl-2H-indol-2-ylidene)-1,3-pentadien-1-yl]-1,3,3-trimethyl-3H-indolium iodide 22-14

To a mixture of intermediates 35-7 (200 mg, 0.339 mmol), 22-13 (215 mg, 0.406 mmol), and cesium carbonate (331 mg, 1.01 mmol) in degassed EtOH (15 mL) and water (1 mL), palladium(II) acetate (7.6 mg, 0.034 mmol) and triphenylphosphine (36 mg, 0.136 mmol) were added. The reaction mixture was refluxed for 16 h under argon then concentrated in vacuo. The residue was dissolved in DCM and washed with saturated NaHCO$_3$ and brine. The DCM layer was dried over MgSO$_4$ and concentrated in vacuo. Crude product was purified by reversed-phase flash chromatography (C18 SiO$_2$, eluted with gradient of 0.09% HCl in MeOH). The pure product was isolated by basification of combined and concentrated fractions with saturated NaHCO$_3$ followed by triple extraction with DCM. The combined DCM layers were then dried over MgSO$_4$ and concentrated in vacuo to yield the title product 22-14 (92 mg, 27%).

Preparation of Compound 22

To a mixture of intermediate 22-14 (85 mg, 0.085 mmol) and K$_2$CO$_3$ (118 mg, 0.85 mmol) in anhydrous acetonitrile (6 mL) and anhydrous DCM (4 mL), 2-bromomethylphenylboronic acid (55 mg, 0.256 mmol) was added. The reaction was stirred under argon at room temperature for 40 min, then more 2-bromomethylphenylboronic acid (36 mg, 0.168 mmol) was added with anhydrous MeOH (2 mL) and the resulting mixture was stirred for 2 h. The reaction mixture was then concentrated in vacuo to 10 mL and filtered. The precipitate was additionally washed with DCM. The filtrate was concentrated in vacuo. The crude product was purified by reversed-phase flash chromatography (C18 SiO$_2$, eluted with gradient of 0.09% HCl in MeOH). The pure product was isolated by basification of combined and concentrated fractions with saturated NaHCO$_3$, followed by triple extraction with DCM. The combined DCM layers were then dried over MgSO$_4$ and concentrated in vacuo. The title compound 22 was precipitated by hexanes and dried in vacuo (55 mg, 51%). HPLC-MS: m/z 1135.3 (calcd. 1135.6 for M$^+$). UV/Vis: $\lambda_{max}$=660 nm.

Preparation of Compound 80

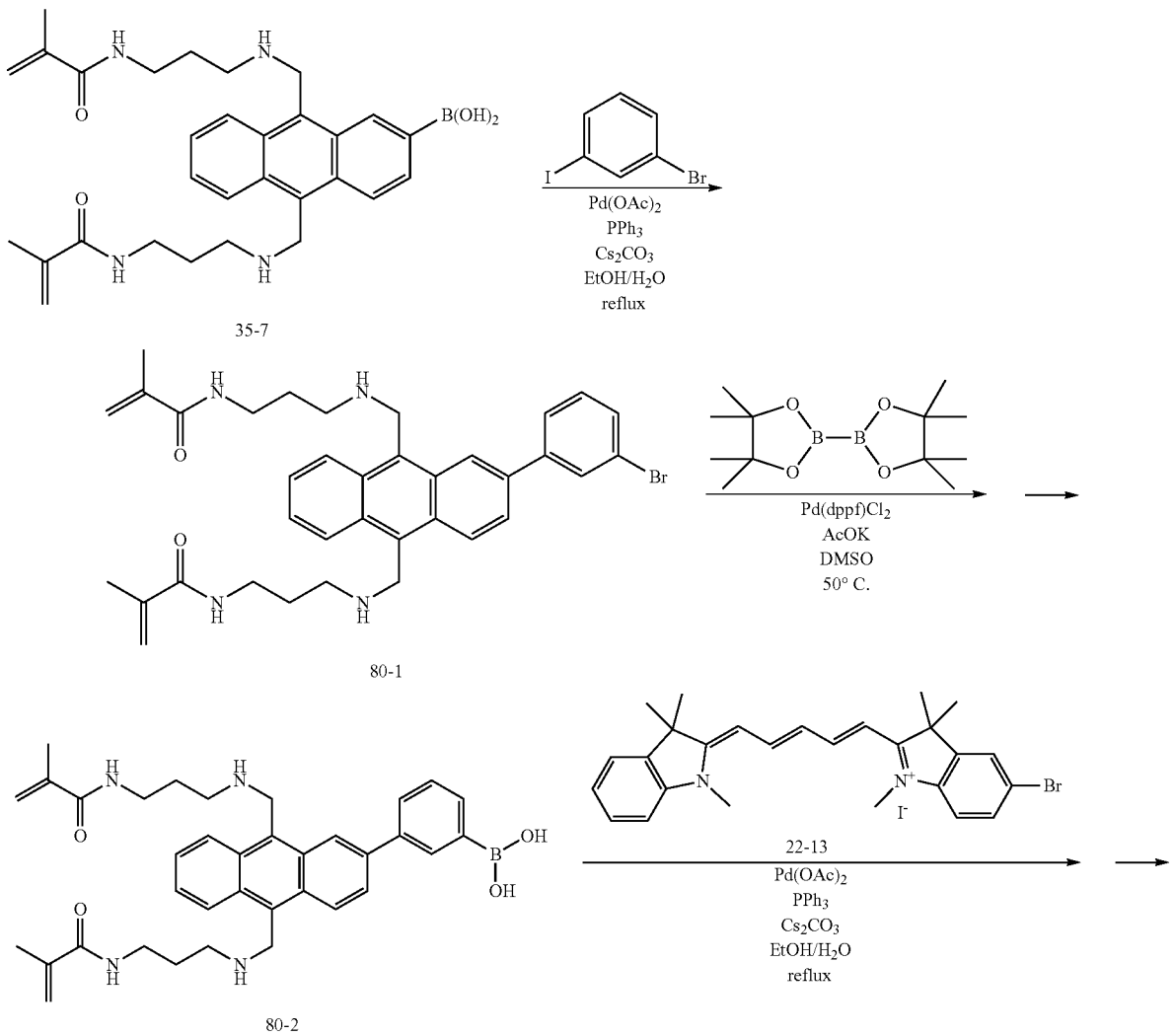

-continued
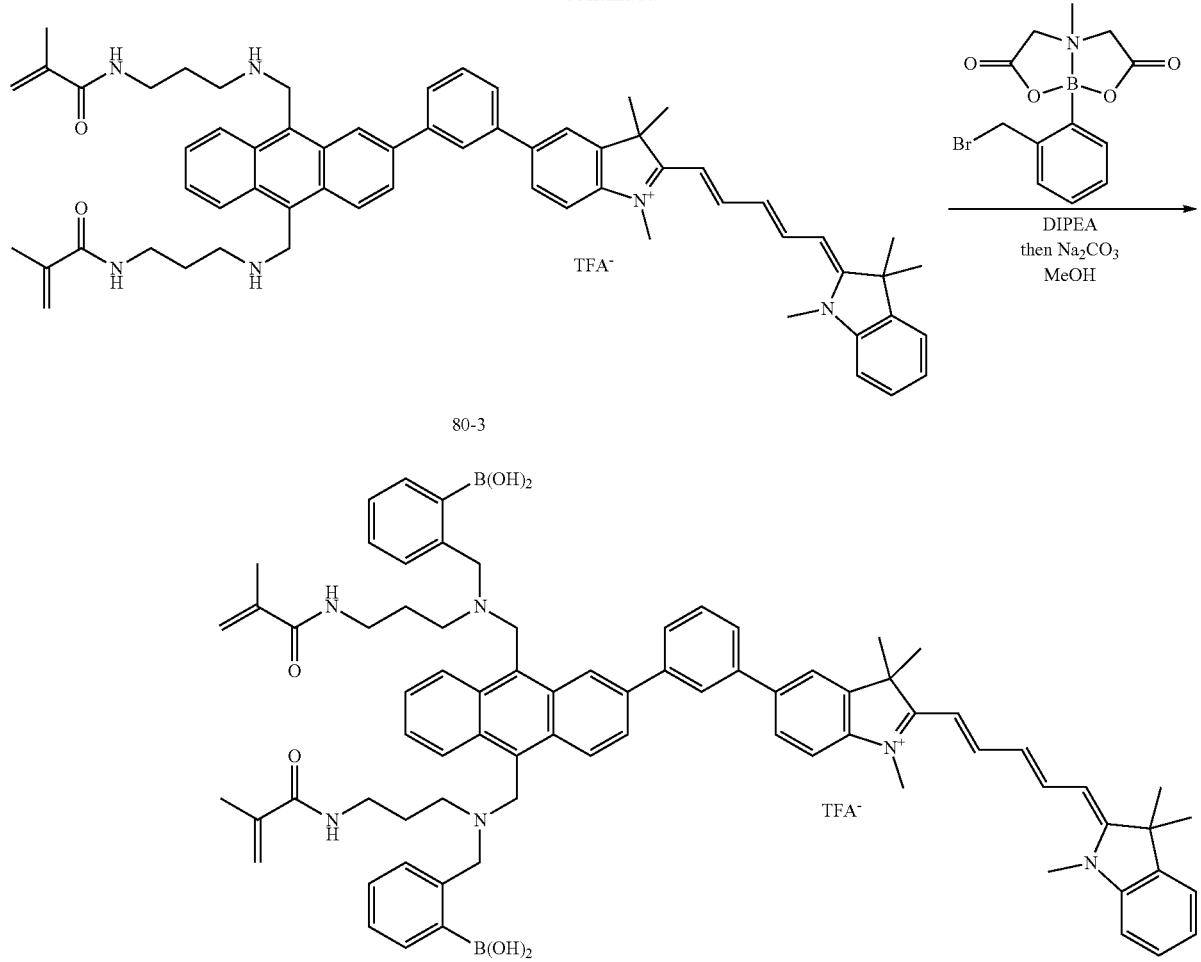
80-3
Compound 80
Compound 80 was synthesized from intermediates 35-7 and 22-13, following general procedures III, XII, III, and XV, as outlined in the scheme above. HPLC-MS: m/z 1212.4 (calcd. 1211.7 for M+H⁺). UV/Vis: $\lambda_{max}$=650 nm.
Preparation of Compound 24
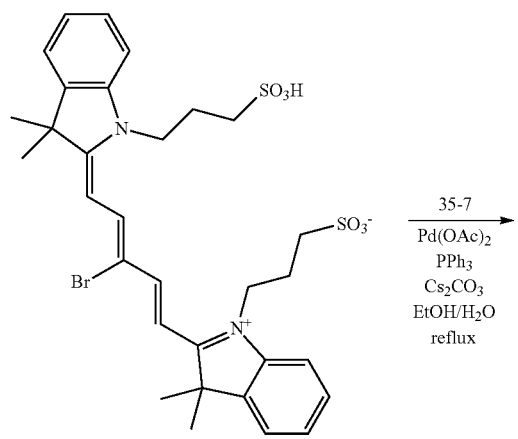
2-2

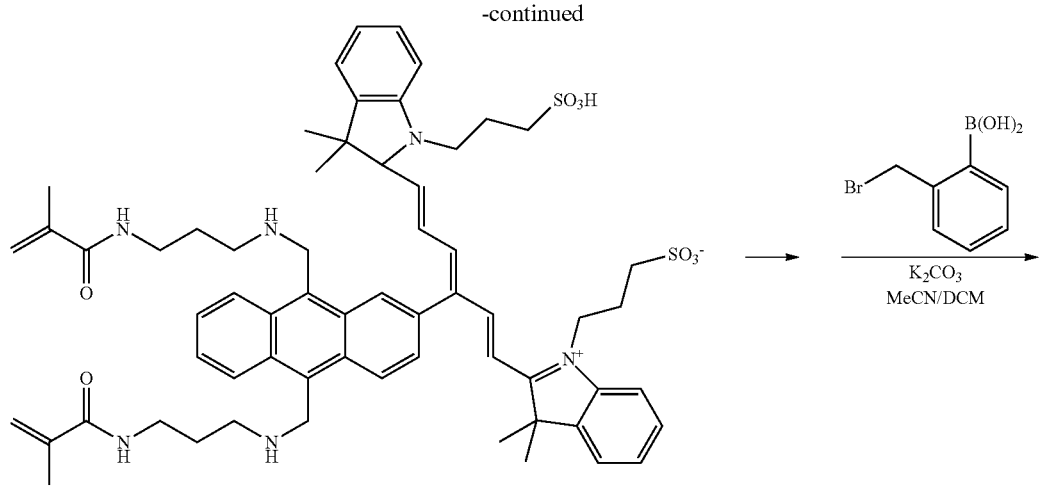

24-1

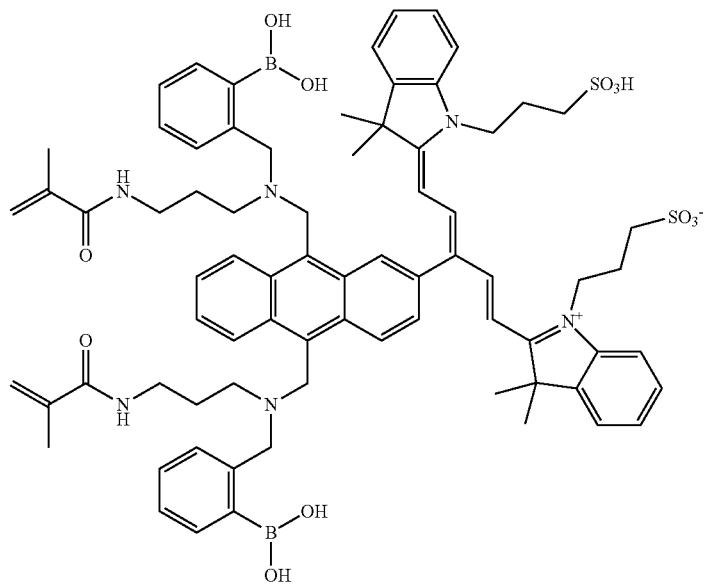

Compound 24

Compound 24 was synthesized from intermediates 2-2 and 35-7, following general procedures III and V with K$_2$CO$_3$ instead of DIPEA as a base in the last step. HPLC-MS: m/z 1352.6 (calcd. 1351.6 for M+H$^+$). UV/Vis: λ$_{max}$=650 nm. $^1$H NMR (400 MHz, DMSO-d$_6$; some integrals were broadened and not resolved) δ ppm 8.66 (s, 2H), 8.59 (br. s., 1H), 8.55 (br. s., 2H), 8.44 (d, J=8.9 Hz, 1H), 8.36 (m, J=8.9 Hz, 1H), 7.70 (d, J=6.0 Hz, 1H), 7.58-7.67 (m, 4H), 7.55 (m, J=8.3 Hz, 1H), 7.46-7.53 (m, 2H), 7.43 (d, J=7.4 Hz, 1H), 7.30-7.41 (m, 6H), 7.20-7.30 (m, 3H), 7.09-7.20 (m, 2H), 5.43 (br. s, 1H), 5.39 (br. s, 1H), 5.14 (quin, J=1.5 Hz, 1H), 5.10 (quin, J=1.5 Hz, 1H), 4.50 (br. s., 4H), 3.95 (br. s., 2H), 3.78 (br. s., 2H), 2.80 (m, J=6.9 Hz, 4H), 2.19 (br. s., 4H), 1.68 (s, 3H), 1.63-1.83 (m, 20H), 1.62 (s, 3H).

Preparation of Compound 78

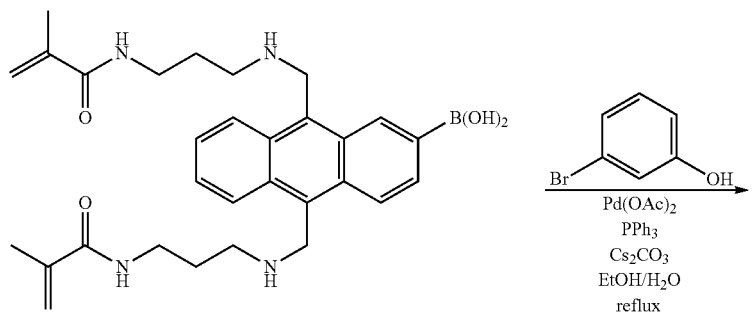

35-7

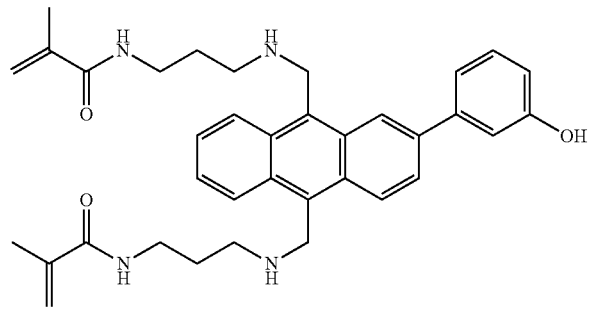
78-1
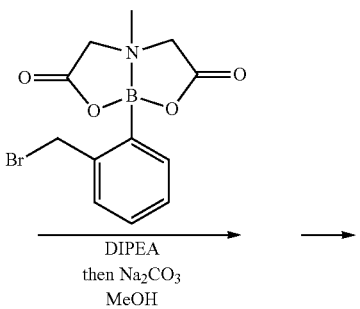
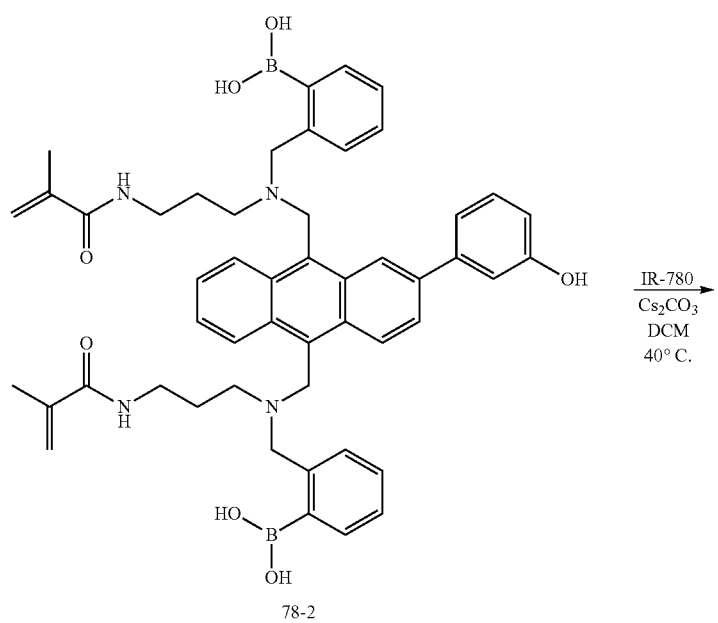
78-2
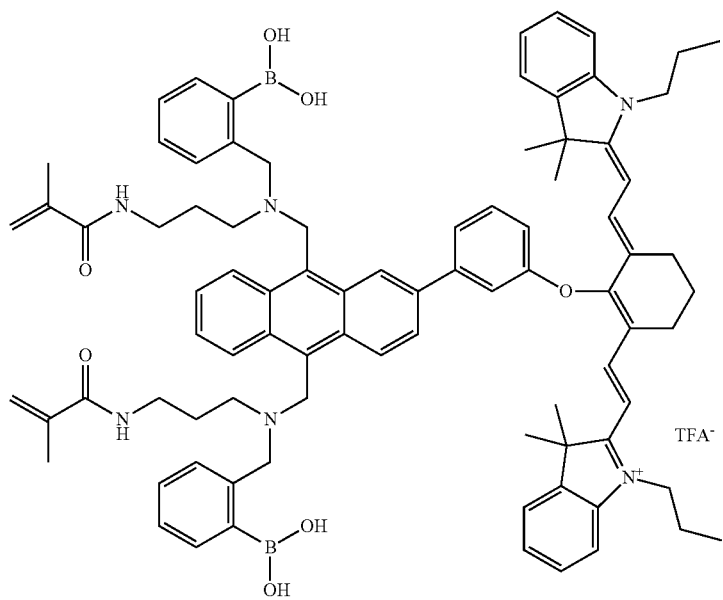
Compound 78

Compound 78 was synthesized from intermediate 35-7, 3-bromophenol, and IR-780 following general procedures III, XV, and VIII, as outlined in the scheme above. HPLC-MS: m/z 1350.7 (calcd. 1349.8 for M+). UV/Vis: $\lambda_{max}$=780 nm. $^1$H NMR (400 MHz, MeOH-d$_4$) δ ppm 8.71 (br. s., 1H), 8.43-8.55 (m, 1H), 8.38 (d, J=7.2 Hz, 2H), 8.11 (d, J=14.4 Hz, 2H), 7.76 (d, J=9.4 Hz, 1H), 7.54-7.66 (m, 4H), 7.46-7.54 (m, 2H), 7.40-7.45 (m, 1H), 7.36 (t, J=7.4 Hz, 2H), 7.33 (d, J=7.4 Hz, 2H), 7.26 (m, J=7.9 Hz, 5H), 7.20-7.24 (m, 2H), 7.18 (t, J=7.1 Hz, 2H), 7.04-7.14 (m, 2H), 6.22 (d, J=14.2 Hz, 2H), 5.35 (s, 1H), 5.31 (s, 1H), 5.14 (quin, J=1.3 Hz, 1H), 5.15 (quin, J=1.3 Hz, 1H), 4.91 (br. s., 2H), 4.78 (br. s., 2H), 4.20 (br. s., 2H), 4.08 (t, J=7.2 Hz, 4H), 3.84 (br. s., 2H), 3.01 (t, J=6.5 Hz, 2H), 3.04 (t, J=6.7 Hz, 2H), 2.80 (t, J=6.1 Hz, 4H), 2.71-2.78 (m, 2H), 2.63 (dd, J=9.1, 6.1 Hz, 2H), 2.09 (quin, J=5.7 Hz, 2H), 1.79-1.94 (m, 8H), 1.66 (s, 3H), 1.67 (s, 3H), 1.40 (s, 12H), 1.01 (t, J=7.4 Hz, 6H).

Preparation of Compound 79

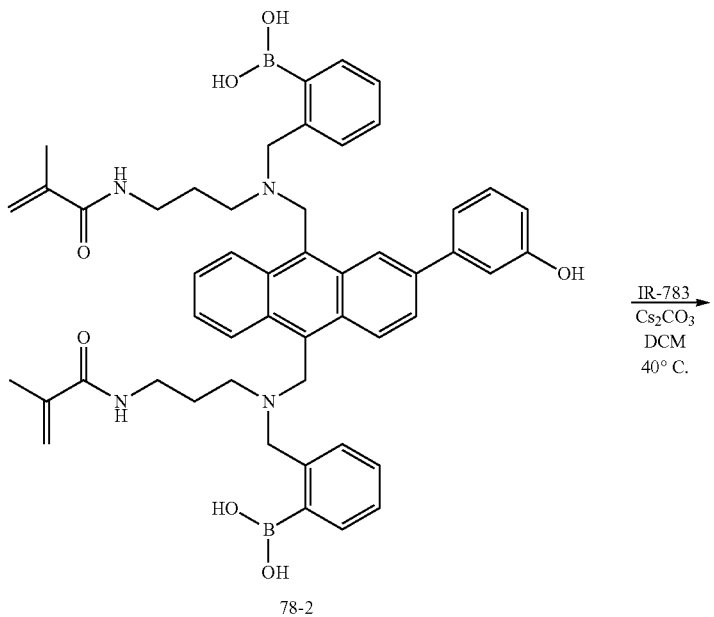

78-2

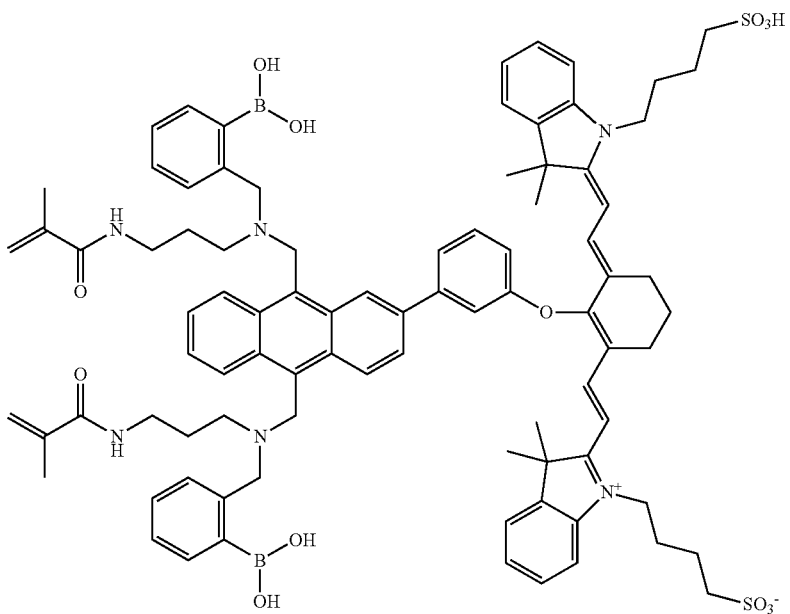

Compound 79

Compound 79 was synthesized from intermediate 78-2 and IR-783 following general procedure VIII, as outlined in the scheme above. HPLC-MS: m/z 769.5 (calcd. 769.4 for [M+H]$^{2+}$). UV/Vis: $\lambda_{max}$=785 nm. $^1$H NMR (400 MHz, MeOH-d$_4$; an extra set of Cy7 signals was present in the spectrum) δ ppm 8.65 (br. s., 1H), 8.49 (d, J=8.6 Hz, 1H), 8.38-8.47 (m, 1H), 8.44 (d, J=14.1 Hz, 2H), 8.14-8.26 (m, 1H), 8.10 (d, J=14.1 Hz, 2H), 7.79 (d, J=9.1 Hz, 1H), 7.64 (t, J=7.9 Hz, 1H), 7.52-7.61 (m, 4H), 7.51 (d, J=7.3 Hz, 2H), 7.45-7.49 (m, 1H), 7.42 (t, J=7.5 Hz, 2H), 7.34-7.40 (m, 3H), 7.22-7.34 (m, 11H), 7.16 (t, J=7.4 Hz, 4H), 6.33 (d, J=14.1 Hz, 2H), 6.26 (d, J=14.1 Hz, 2H), 5.33 (s, 1H), 5.31 (s, 1H), 5.13 (s, 1H), 5.11 (s, 1H), 4.97 (br. s., 2H), 4.31 (br. s., 2H), 4.22 (t, J=7.1 Hz, 4H), 4.14 (t, J=6.3 Hz, 4H), 3.92 (br. s., 2H), 3.35 (s, 3H), 3.04 (t, J=6.2 Hz, 2H), 3.01 (t, J=6.6 Hz, 2H), 2.88 (s, 12H), 2.79-2.83 (m, 4H), 2.76 (t, J=5.6 Hz, 4H), 2.67 (m, J=8.4 Hz, 2H), 2.02-2.13 (m, 2H), 1.81-2.02 (m, 22H), 1.71-1.77 (m, 12H), 1.65 (s, 3H), 1.64 (s, 3H), 1.39 (s, 12H)

Preparation of Compound 84

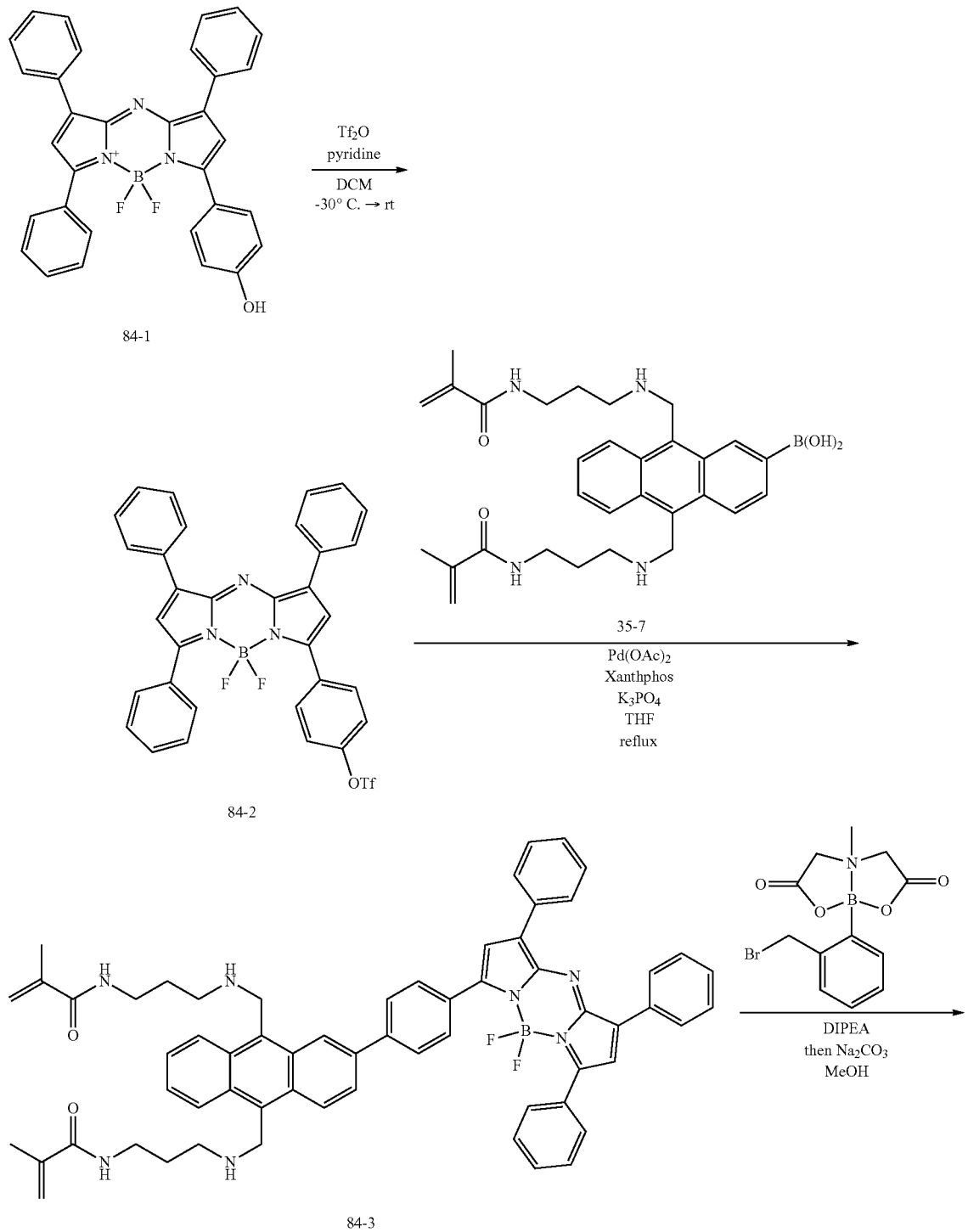

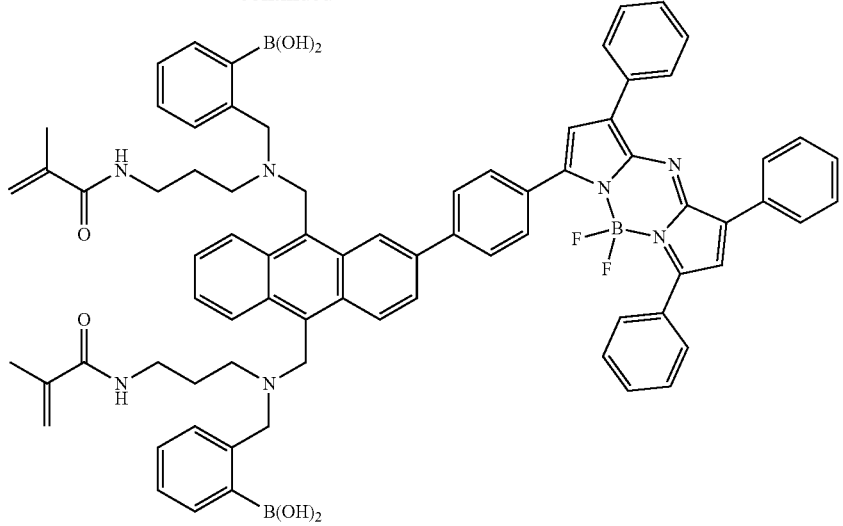

Compound 84

Aza-BODIPY monophenol 84-1 was prepared as described elsewhere (Jokic, T.; Borisov, S. M.; Saf, R.; Nielsen, D. A.; Kühl, M.; Klimant, I. *Anal. Chem.* 2012, 84 (15), 6723-6730).

General Procedure XXI. Conversion of Phenols into Aromatic Triflates. Preparation of Compound 84-2

Solution of aza-BODIPY phenol 84-1 (250 mg, 0.49 mmol) and pyridine (0.08 mL, 1.0 mmol) in anhydrous DCM (8 mL) was cooled to −30° C. under argon atmosphere. Triflic anhydride (0.11 mL, 0.66 mmol) was added and the reaction mixture was stirred at −30° C. for 30 min. Then the reaction mixture was quenched with 0.1 M HCl (5 mL) and saturated $NH_4Cl$ (5 mL), diluted with water (10 mL) and partitioned with additional DCM (20 mL). Aqueous layer was discarded. Organic extract was washed with half-saturated $NH_4Cl$ (20 mL), dried over anhydrous $Na_2SO_4$, filtered, and concentrated under reduced pressure. The residue was purified by flash chromatography ($SiO_2$, eluted with gradient from 10% to 40% DCM in hexanes). Obtained the desired triflate 84-2 (228 mg, 72% yield) as a dark-purple solid.

General Procedure XXII. Suzuki-Miyaura Coupling with Aromatic Triflates. Preparation of Compound 84-3

A mixture of aza-BODIPY triflate 84-2 (68 mg, 0.105 mmol), anthracene boronic acid 35-7 (173 mg, 0.33 mmol), $K_3PO_4$ (134 mg, 0.63 mmol), $Pd(OAc)_2$ (5.6 mg, 0.025 mmol), and XantPhos (15 mg, 0.026 mmol) in degassed anhydrous THF (20 mL) was refluxed under argon atmosphere for 16 h. Then the reaction mixture was cooled down to ambient temperature, filtered through Celite® (washed with MeOH), filtrate was concentrated, and the residue was purified by reversed-phase flash chromatography (C18 $SiO_2$, eluted with gradient from 60% to 100% of MeOH in water+0.05% TFA). Obtained the desired product (11.6 mg, 11%) as a dark-blue solid.

Compound 84 was prepared from the intermediate 84-3, following the general procedure XV. HPLC-MS: m/z 1251.4 (calcd. 1250.6 for M+H⁺). UV/Vis: $\lambda_{max}$=665 nm.

Preparation of Compound 85

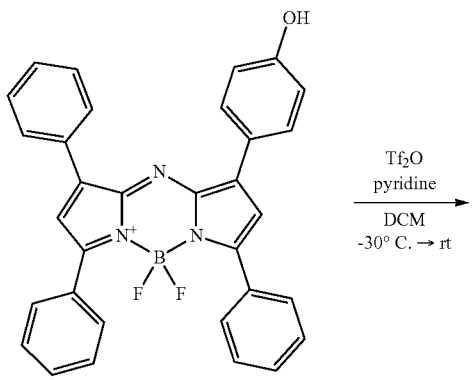

85-1

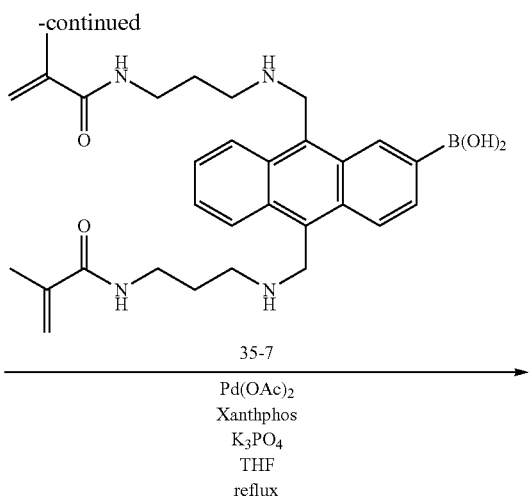
-continued
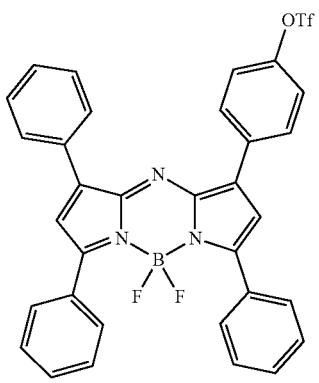
85-2
35-7
Pd(OAc)₂
Xanthphos
K₃PO₄
THF
reflux
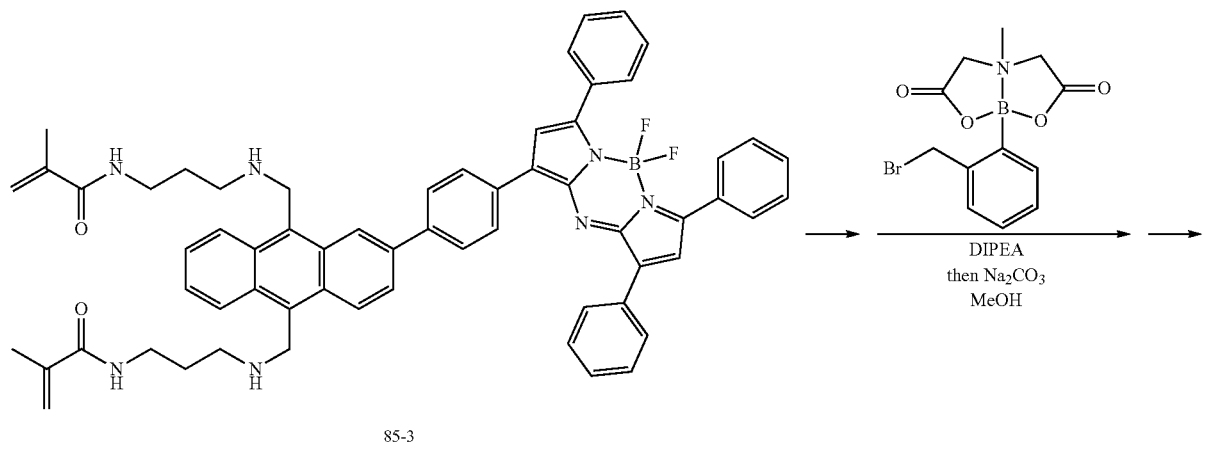
85-3
DIPEA
then Na₂CO₃
MeOH
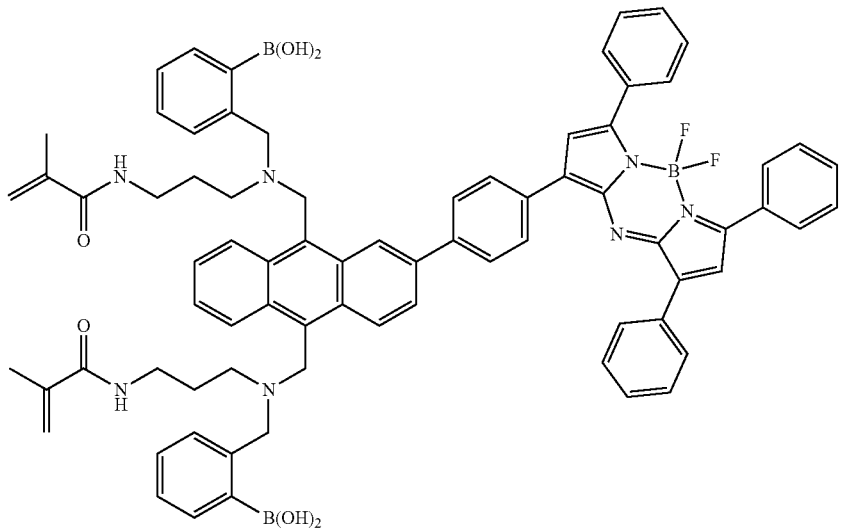
Compound 85

Aza-BODIPY monophenol 85-1 was prepared as described elsewhere (Jokic, T.; Borisov, S. M.; Saf, R.; Nielsen, D. A.; Kühl, M.; Klimant, I. *Anal. Chem.* 2012, 84 (15), 6723-6730).
Compound 85 was prepared from 85-1, following the general procedures XXI, XXII, and XV, as outlined in the scheme above, by analogy with the preparation of compound 85. HPLC-MS: m/z 1251.4 (calcd. 1250.6 for M+H$^+$). UV/Vis: $\lambda_{max}$=660 nm.
Preparation of Compound 26
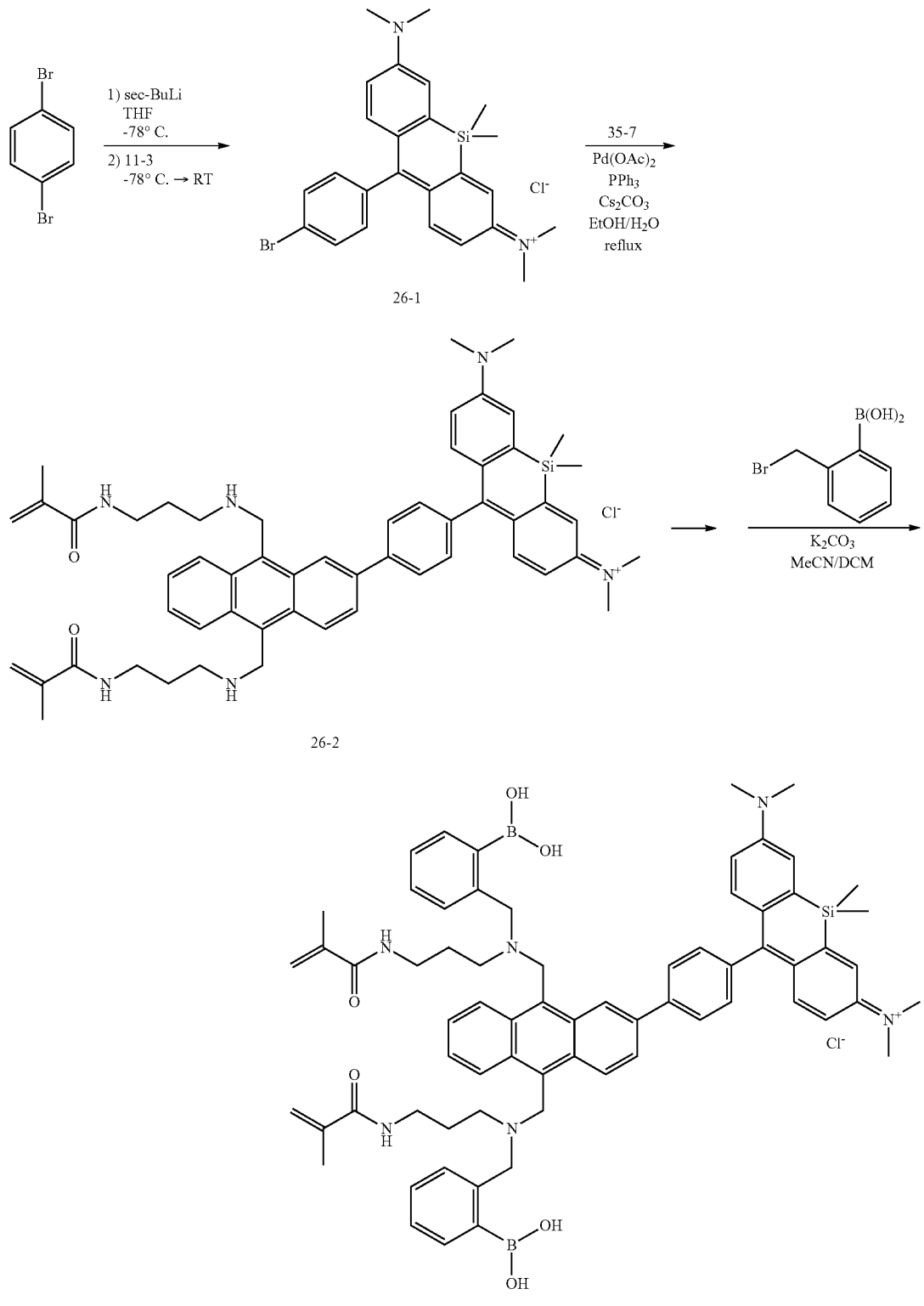

Compound 26 was prepared from 1,4-dibromobenzene and intermediates 11-3 and 35-7 via general procedures X, III, and V as outlined in the scheme above. HPLC-MS: m/z 1138.5 (calcd. 1137.6 for M$^+$). UV/Vis: $\lambda_{max}$=650 nm.
Preparation of Compound 27
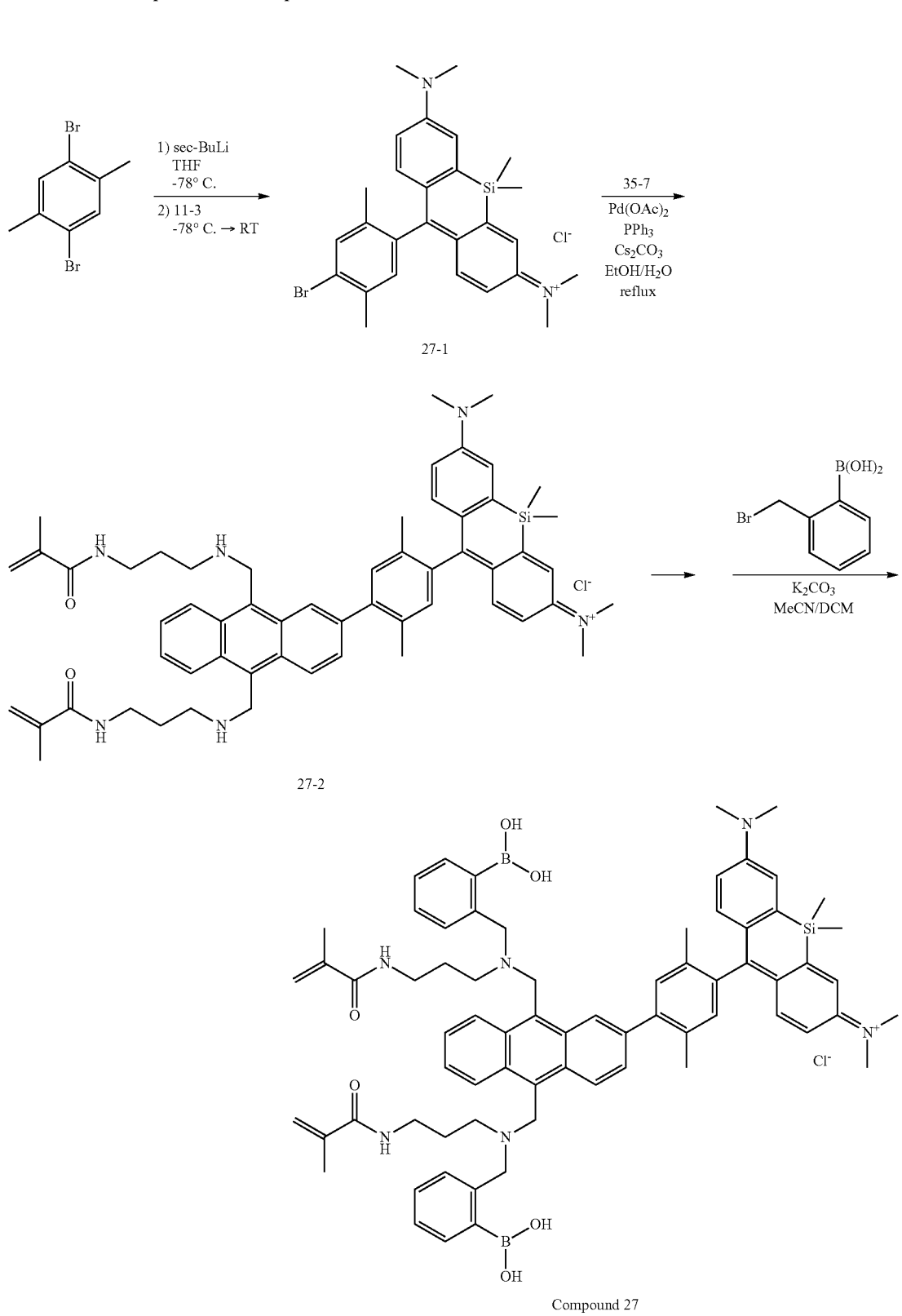
Compound 27

Compound 27 was prepared from 1,4-dibromo-2,5-dimethylbenzene and intermediates 11-3 and 35-7 via general procedures X, III, and V as outlined in the scheme above. HPLC-MS: m/z 1166.5 (calcd. 1165.6 for M$^+$). UV/Vis: $\lambda_{max}$=655 nm.
Preparation of Compound 28
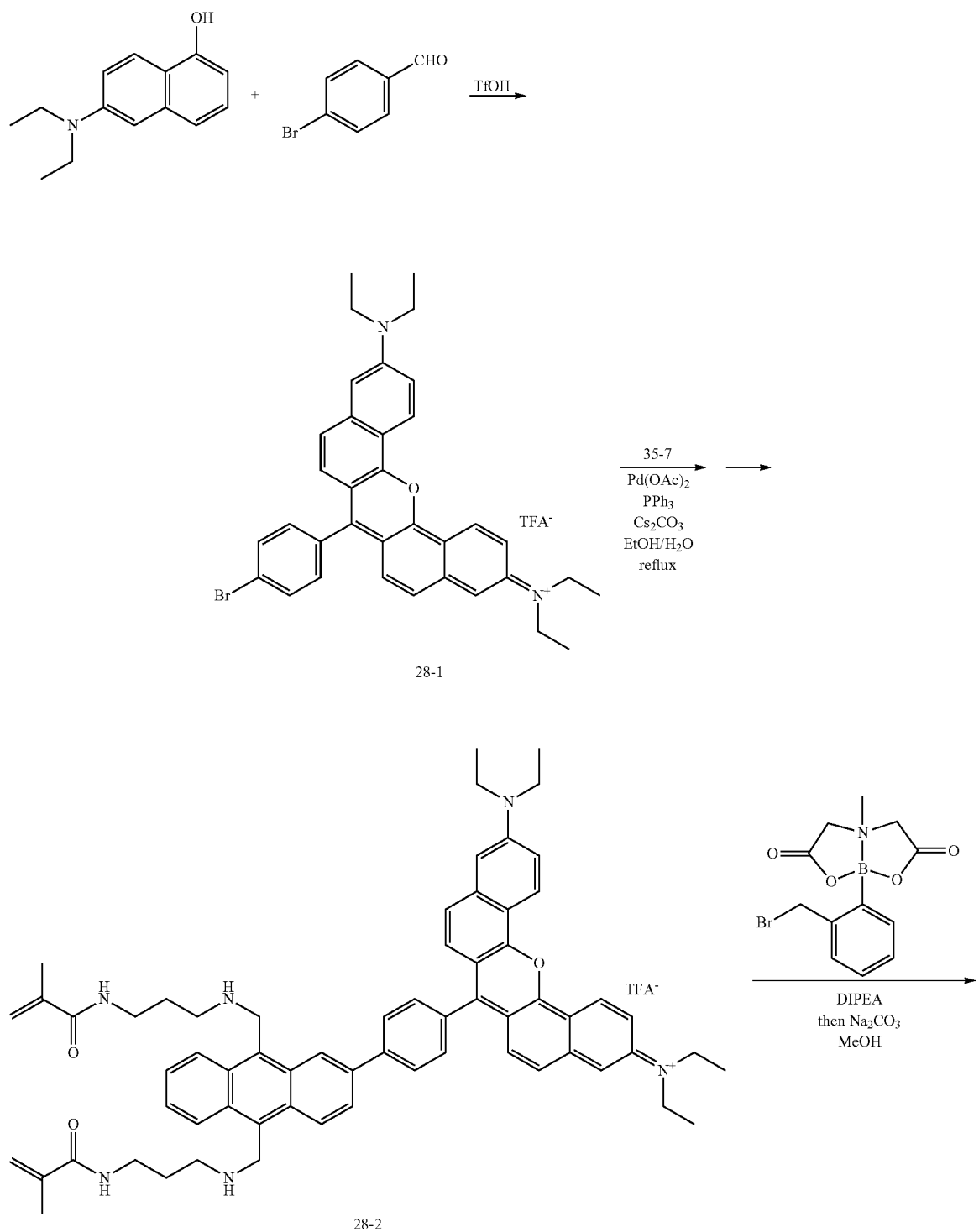

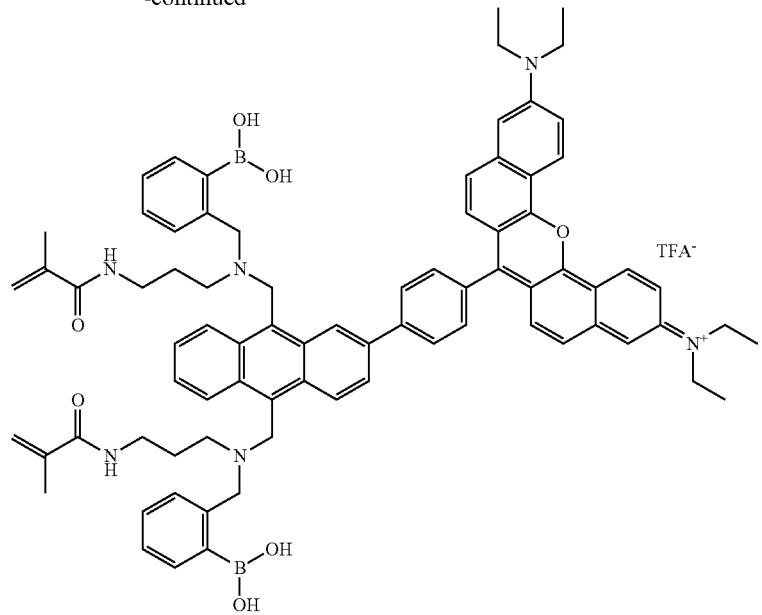

Compound 28

Preparation of Compound 28-1

A mixture of 6-diethylaminonaphth-1-ol (174 mg, 0.81 mmol) and 4-bromobenzaldehyde (75 mg, 0.0.41 mmol) in neat triflic acid (2 mL) was heated in a closed vial at 105° C. for 2 h. Then the reaction mixture was allowed to cool down to room temperature and diluted with DCM:water=1:1 (50 mL). The layers were separated and aqueous layer was additionally extracted with DCM (3×15 mL). Combined organic layers were dried over anhydrous $Na_2SO_4$, filtered and concentrated under reduced pressure. The residue was purified by reversed phase flash chromatography (C18 $SiO_2$, eluted with 80% MeOH in water+0.05% TFA). Yield: 50 mg (8.5%) as dark-blue powder.

Compound 28 was synthesized from intermediate 28-1 and 35-7 following the general procedures III and XV as outlined in the scheme above. HPLC-MS: m/z 1252.3 (calcd. 1251.7 for M$^+$). UV/Vis: $\lambda_{max}$=685 nm.

Preparation of Compound 33

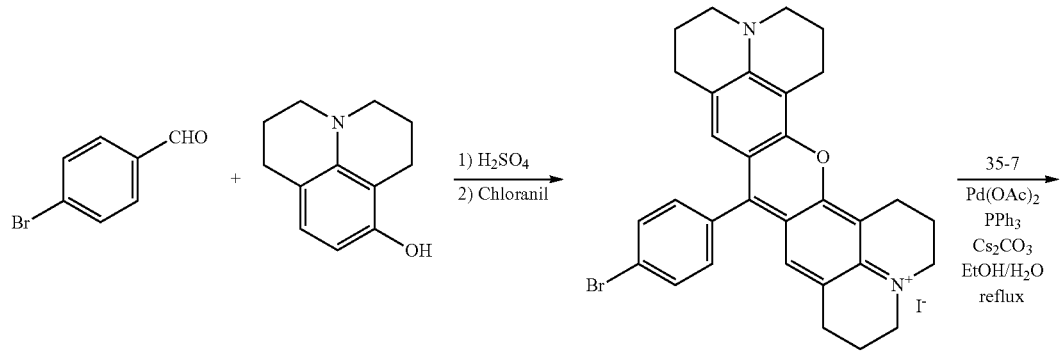

33-1

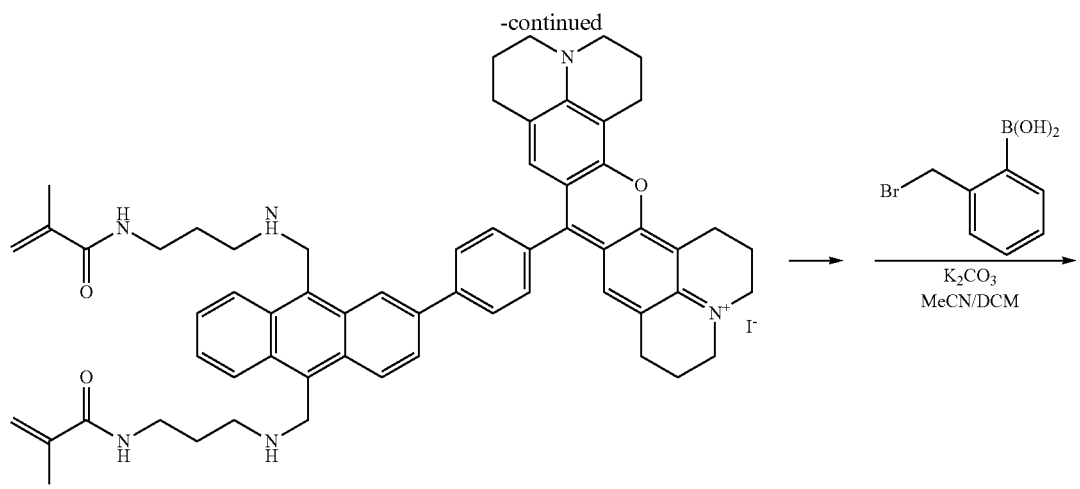

33-2

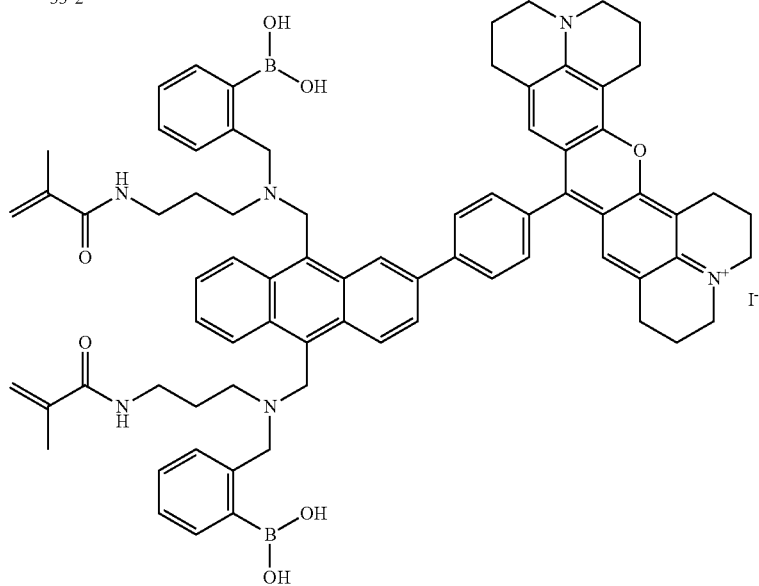

Compound 33

Intermediate 33-1 was synthesized as described in literature (Cherevatskaya, M. et al. *Angew. Chem. Int. Ed.*, 51(17), 4062-4066, 2012).

Compound 33 was synthesized form intermediates 33-1 and 35-7, following general procedures III and V, as outlined in the scheme above. HPLC-MS: m/z 1200.4 (calcd. 1199.6 for M+). UV/Vis: $\lambda_{max}$=585 nm. $^1$H NMR (400 MHz, CDCl$_3$) δ ppm 8.35 (d, J=9.3 Hz, 1H), 8.26 (d, J=8.8 Hz, 1H), 7.70-7.85 (m, 3H), 7.59-7.68 (m, 4H), 7.51-7.58 (m, 2H), 7.31-7.51 (m, 8H), 7.20 (s, 2H), 5.37 (s, 1H), 5.34 (s, 1H), 5.13 (s, 1H), 5.11 (s, 1H), 4.58 (br. s., 2H), 4.53 (s, 2H), 3.94 (br. s., 2H), 3.58 (t, J=5.5 Hz, 4H), 3.54 (t, J=5.5 Hz, 4H), 3.39-3.42 (m, 2H), 3.09 (t, J=6.3 Hz, 4H), 2.82 (t, J=5.8 Hz, 4H), 2.57 (t, J=7.5 Hz, 2H), 2.48 (t, J=7.5 Hz, 2H), 2.15 (quin, J=6.0 Hz, 4H), 2.00 (quin, J=6.0 Hz, 4H), 1.72 (s, 3H), 1.70 (s, 3H), 1.56-1.64 (m, 2H), 1.45-1.54 (m, 2H), 1.21-1.31 (m, 4H).

Preparation of Compound 42

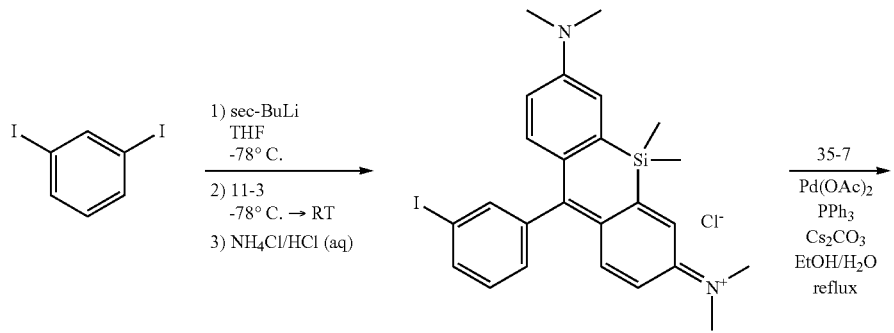

42-1

-continued

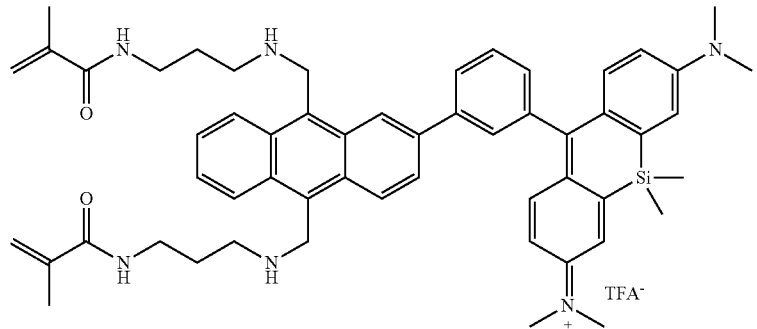

42-2

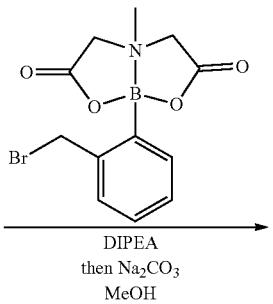

DIPEA
then Na₂CO₃
MeOH

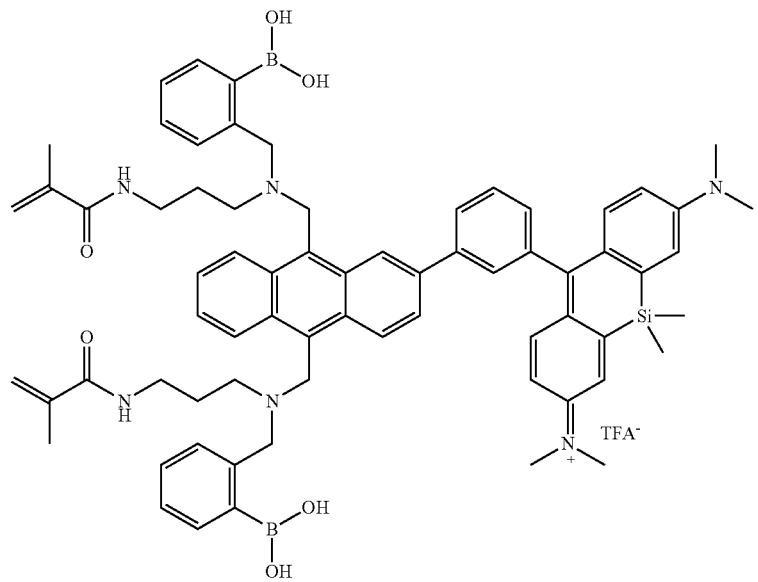

Compound 42

Compound 42 was synthesized form 1,3-diiodobenzene and intermediate 11-3 following general procedures X, III, and XV, as outlined in the scheme above. HPLC-MS: m/z 1138.3 (calcd. 1137.6 for M⁺). UV/Vis: $\lambda_{max}$=650 nm. ¹H NMR (400 MHz, MeOH-d₄) δ ppm 8.39 (d, J=9.0 Hz, 1H), 8.36 (d, J=8.7 Hz, 1H), 8.22-8.33 (m, 2H), 7.89 (d, J=7.9 Hz, 1H), 7.71-7.84 (m, 2H), 7.52-7.70 (m, 5H), 7.25-7.47 (m, 11H), 7.08-7.25 (m, 3H), 6.97 (d, J=2.9 Hz, 1H), 6.79 (dd, J=9.7, 2.9 Hz, 2H), 5.38 (s, 1H), 5.34 (s, 1H), 5.20 (quin, J=1.4 Hz, 1H), 5.14 (quin, J=1.4 Hz, 1H), 4.79 (s, 4H), 4.15 (br. s., 2H), 3.89 (br. s., 2H), 3.33 (s, 12H), 2.65-2.75 (m, 2H), 2.58 (m, J=7.6 Hz, 2H), 1.74-1.89 (m, 4H), 1.72 (s, 3H), 1.67 (s, 3H), 0.63 (s, 6H).

Preparation of Compound 59

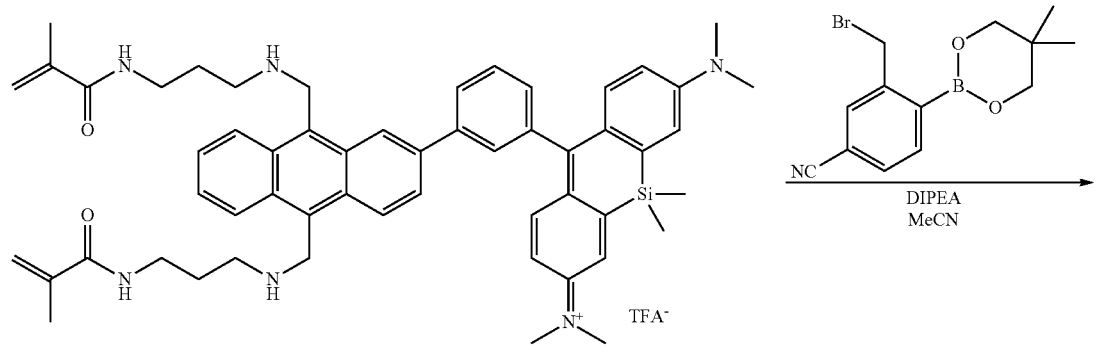

42-2

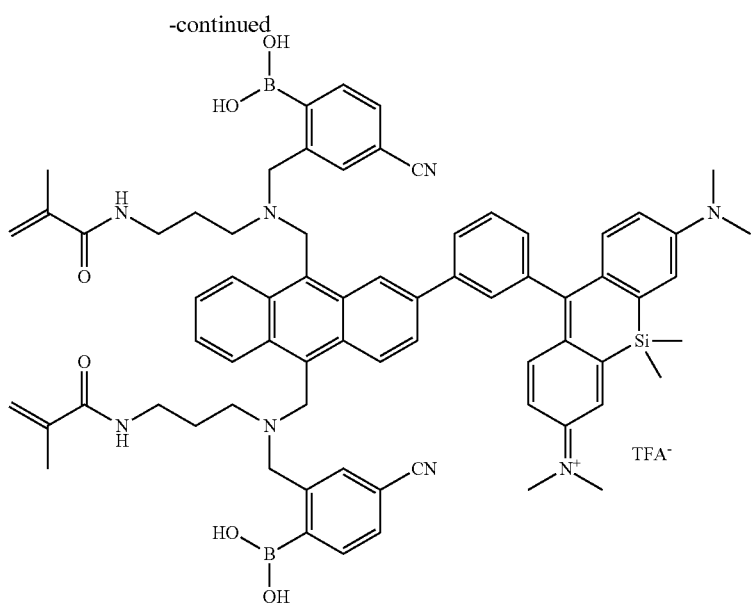
Compound 59
Compound 59 was synthesized from intermediates 42-2 and 51-2 following the general procedure V. HPLC-MS: m/z 1188.2 (calcd. 1187.6 for M+). UV/Vis: $\lambda_{max}$=650 nm.
Preparation of Compound 61
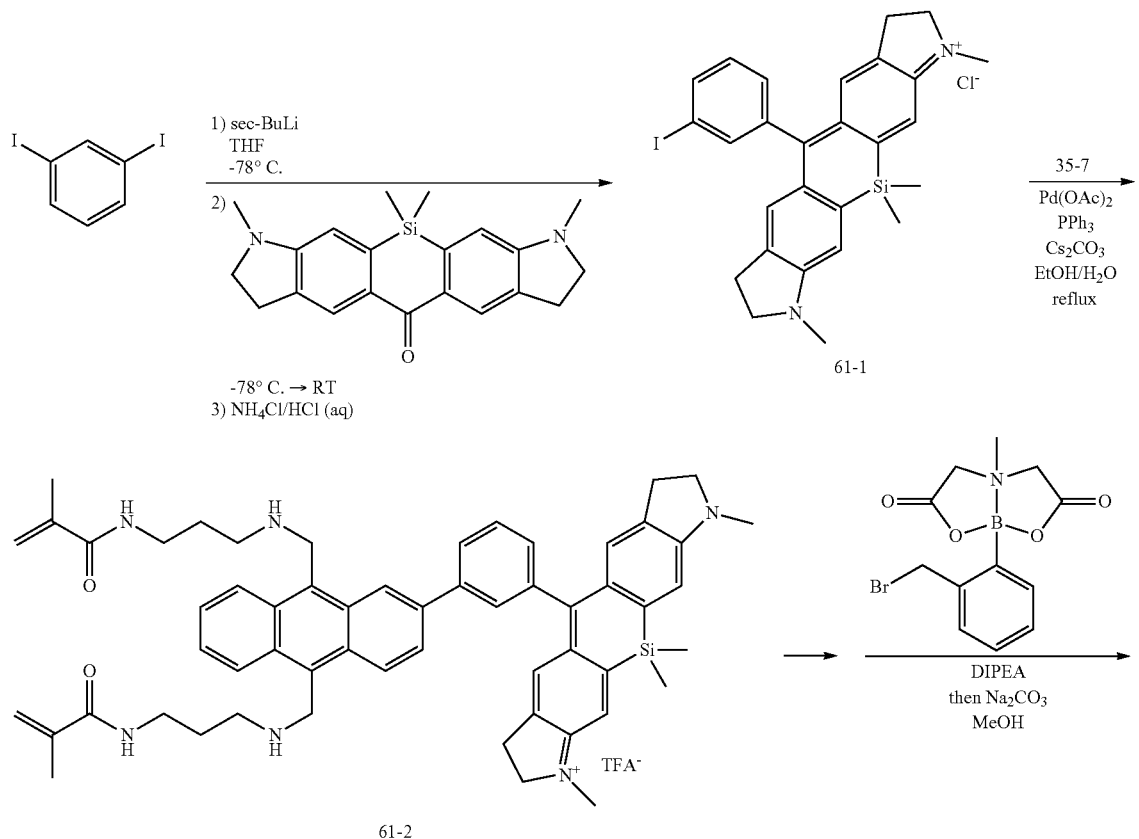

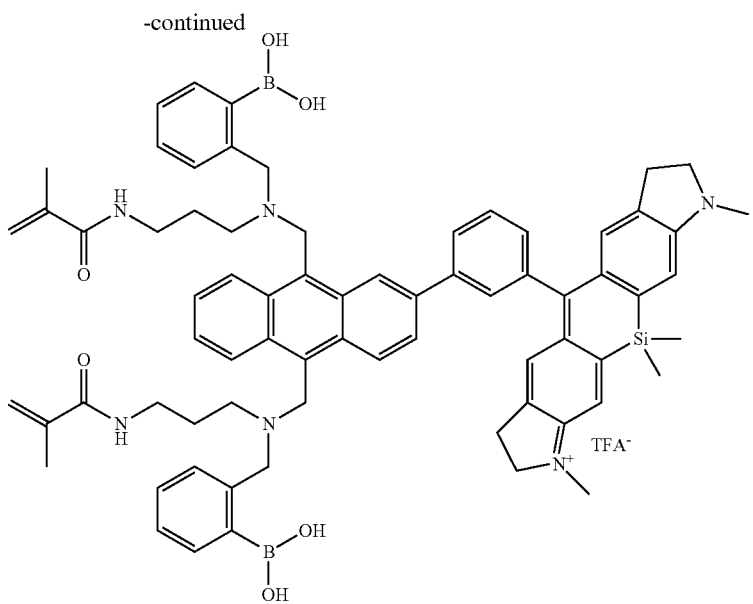
Compound 61
Compound 61 was synthesized form 1,3-diiodobenzene and intermediates 49-1 and 35-7 following general procedures X, III, and XV, as outlined in the scheme above.
HPLC-MS: m/z 1162.2 (calcd. 1161.6 for M$^+$). UV/Vis: $\lambda_{max}$=705 nm.
Preparation of Compound 62
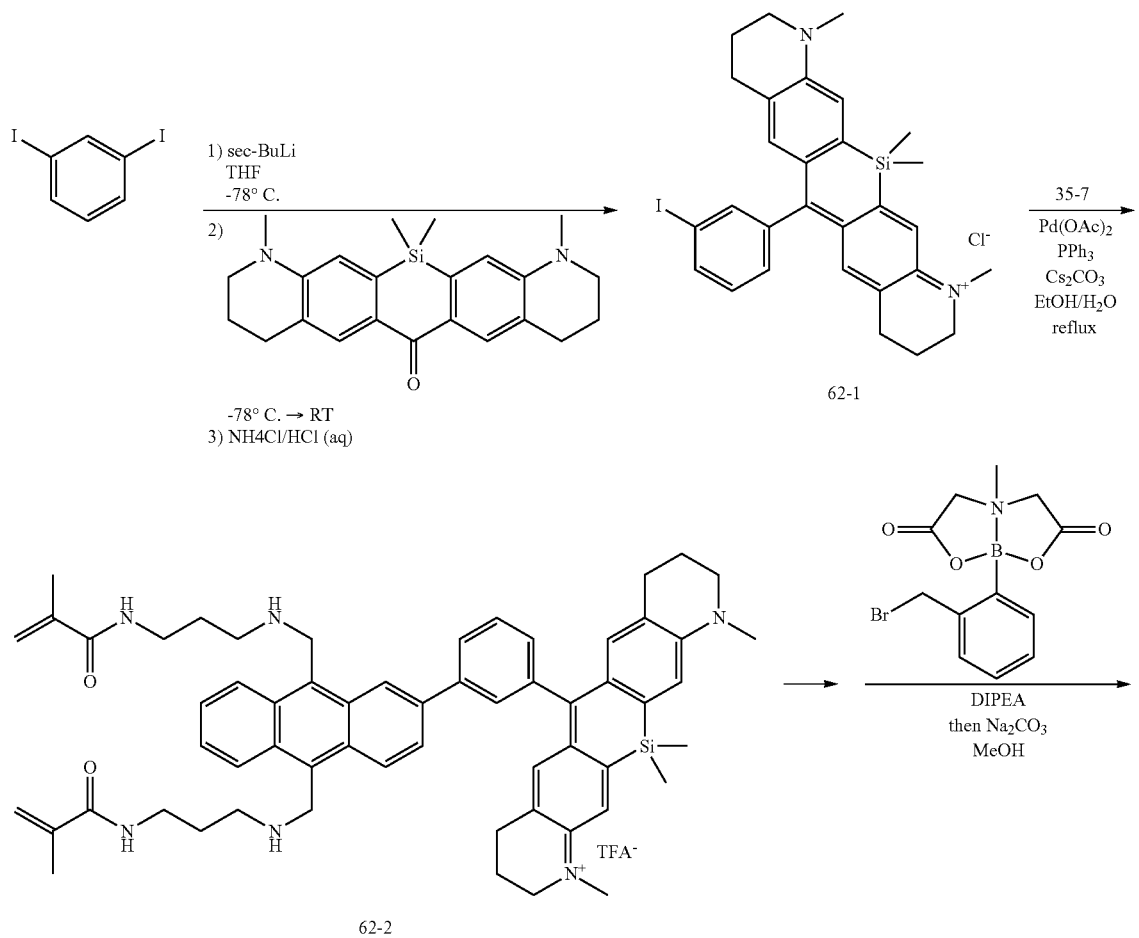

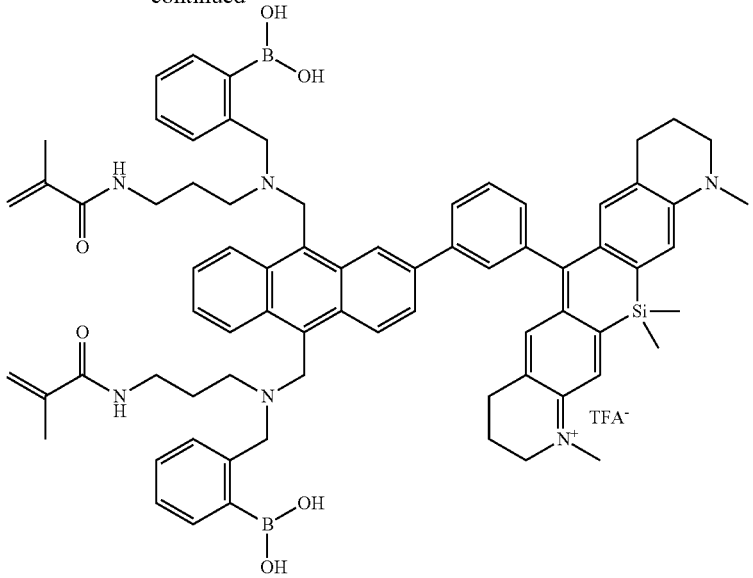
Compound 62
Compound 62 was synthesized form 1,3-diiodobenzene and intermediates 45-1 and 35-7 following general procedures X, III, and XV, as outlined in the scheme above. HPLC-MS: m/z 1190.3 (calcd. 1189.6 for M$^+$). UV/Vis: $\lambda_{max}$=680 nm.
Preparation of Compounds 54 and 71
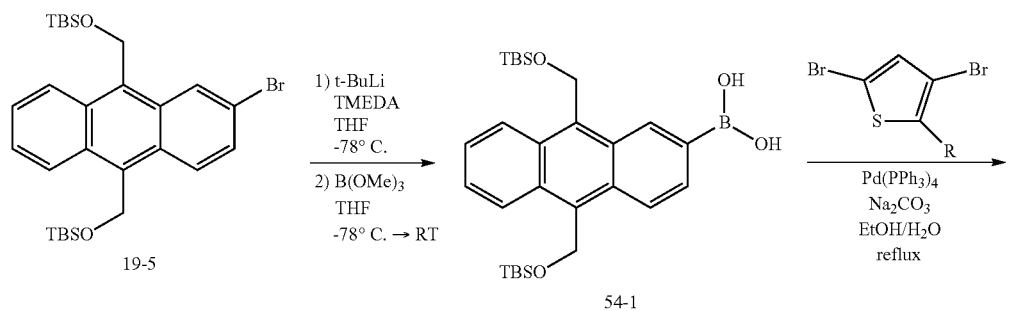
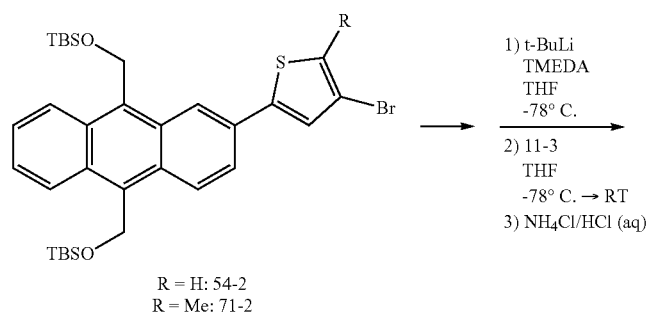
R = H: 54-2
R = Me: 71-2

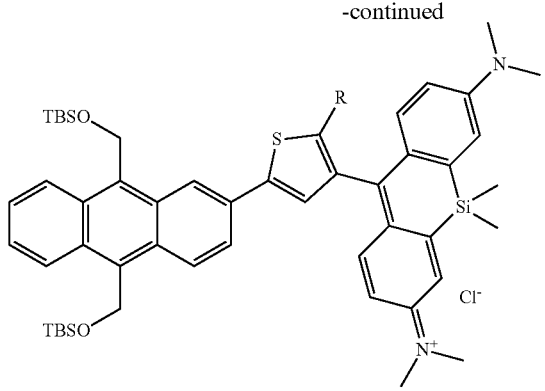

R = H: 54-3
R = Me: 71-3

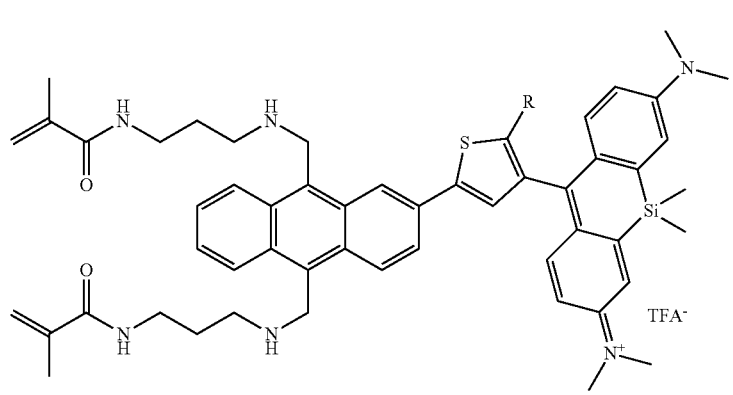

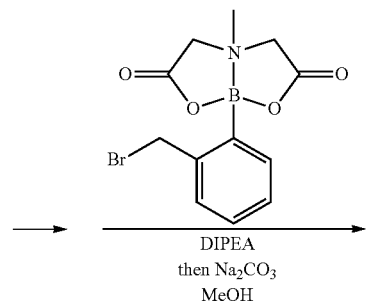

R = H: 54-4
R = Me: 71-4

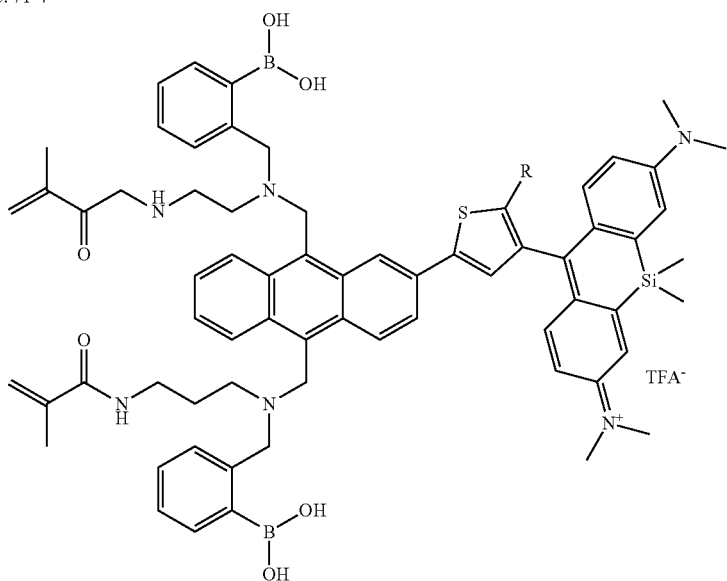

R = H: compound 54
R = Me: compound 71

Preparation of Compound 54-1

A solution of aryl bromide 19-5 (6.0 g, 11 mmol) and TMEDA (0.8 mL, 5.3 mmol) in anhydrous THF (100 mL) was cooled to −78° C. under argon. To this solution tert-BuLi (c=1.52 M in pentane, 8 mL, 12 mmol) was added dropwise over 5 min and the mixture was stirred at −78° C. for 5 min, followed by rapid addition of trimethylborate (1.6 mL, 14.4 mmol). The reaction mixture was allowed to warm up to room temperature and then quenched with MeOH (5 mL). The solvents were removed under reduced pressure and the residue was purified by flash chromatography (SiO$_2$, eluted with gradient from 5% to 20% EtOAc in hexanes). Desired boronic acid 54-1 was obtained (4.87 g, 87% yield) as a pale yellow solid.

General Procedure XXIII. Suzuki-Miyaura Coupling with Dihaloarenes. Preparation of Compound 54-2

Suspension of anthracene boronic acid 54-1 (1.0 g, 2.0 mmol) and 2,4-dibromothiophene (0.17 mL, 1.5 mmol) in degassed EtOH (80 mL) was refluxed under argon until all solids were dissolved. Pd(PPh$_3$)$_4$ (50 mg, 0.043 mmol) and 2 M aqueous Na$_2$CO$_3$ (2.1 mL, 4.2 mmol) were added and refluxing was continued under argon for 4 h. Then the solvent was removed under reduced pressure, the residue was dissolved in DCM (50 mL) and filtered through Celite®. Filtrate was concentrated and the residue was purified by flash chromatography (SiO$_2$, gradient elution from 10% to 40% DCM in hexanes). Title compound 54-2 was obtained (565 mg, 60% yield) as a bright yellow solid.

Compound 54 was prepared from intermediate 54-2 and 11-3 following general procedures XVI, XVIIA, and XV, as outlined in the scheme above. HPLC-MS: m/z 1144.1 (calcd. 1143.6 for M$^+$). UV/Vis: $\lambda_{max}$=660 nm. $^1$H NMR (400 MHz, MeOH-d$_4$) δ ppm 8.34 (d, J=8.6 Hz, 1H), 8.27 (d, J=8.6 Hz, 1H), 8.19 (d, J=8.2 Hz, 1H), 7.82 (d, J=9.0 Hz, 1H), 7.58-7.64 (m, 2H), 7.53-7.58 (m, 4H), 7.46-7.53 (m, 1H), 7.41 (d, J=2.8 Hz, 2H), 7.38-7.44 (m, 2H), 7.29-7.38 (m, 4H), 7.16-7.24 (m, 1H), 7.08 (t, J=7.2 Hz, 1H), 6.86 (dd, J=9.8, 2.9 Hz, 2H), 5.35 (s, 1H), 5.36 (s, 1H), 5.17 (quin, J=1.3 Hz, 2H), 4.68 (br. s, 2H), 4.65 (br. s, 2H), 4.09 (br. s., 2H), 3.91 (br. s., 2H), 3.36 (s, 12H), 3.02 (t, J=6.5 Hz, 2H), 2.92-2.99 (m, 2H), 2.65-2.74 (m, 2H), 2.53-2.65 (m, 2H), 1.77-1.89 (m, 2H), 1.67-1.76 (m, 2H), 1.70 (s, 6H), 0.65 (s, 6H).

Compound 71 was prepared from intermediate 54-1 and 2,4-dibromo-5-methylthiophene, following the same sequence of reactions as outlined for compound 54. HPLC-MS: m/z 1158.2 (calcd. 1157.6 for M$^+$). UV/Vis: $\lambda_{max}$=660 nm. $^1$H NMR (400 MHz, MeOH-d$_4$) δ ppm 8.35 (d, J=8.9 Hz, 1H), 8.23 (d, J=8.8 Hz, 1H), 8.28 (d, J=9.1 Hz, 1H), 7.78 (d, J=9.4 Hz, 1H), 7.49 (d, J=9.8 Hz, 2H), 7.47-7.60 (m, 4H), 7.41 (d, J=2.8 Hz, 2H), 7.37-7.43 (m, 1H), 7.28-7.37 (m, 4H), 7.17-7.25 (m, 2H), 7.10 (td, J=7.5, 1.1 Hz, 1H), 6.89 (dd, J=9.6, 2.8 Hz, 2H), 5.36 (s, 2H), 5.17 (quin, J=1.3 Hz, 2H), 4.70 (br. s., 4H), 4.09 (br. s., 2H), 3.92 (br. s, 2H), 3.37 (s, 12H), 3.02 (t, J=6.6 Hz, 2H), 2.94-3.00 (m, 2H), 2.65-2.72 (m, 2H), 2.62 (m, J=5.6 Hz, 2H), 2.28 (s, 3H), 1.81-1.89 (m, 2H), 1.70 (s, 6H), 1.65-1.75 (m, 2H), 0.66 (s, 3H), 0.64 (s, 3H).

Preparation of Compound 63

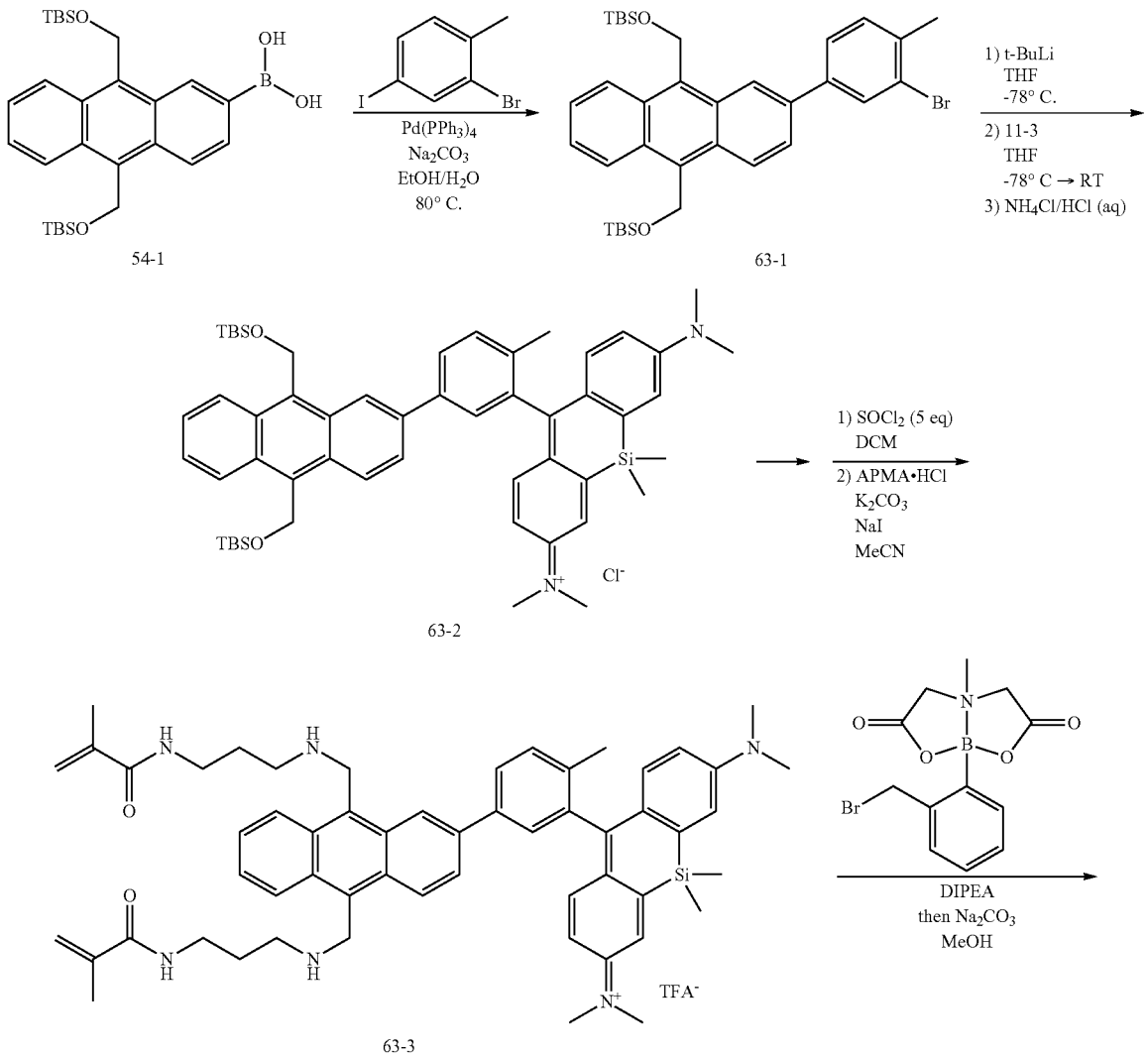

-continued

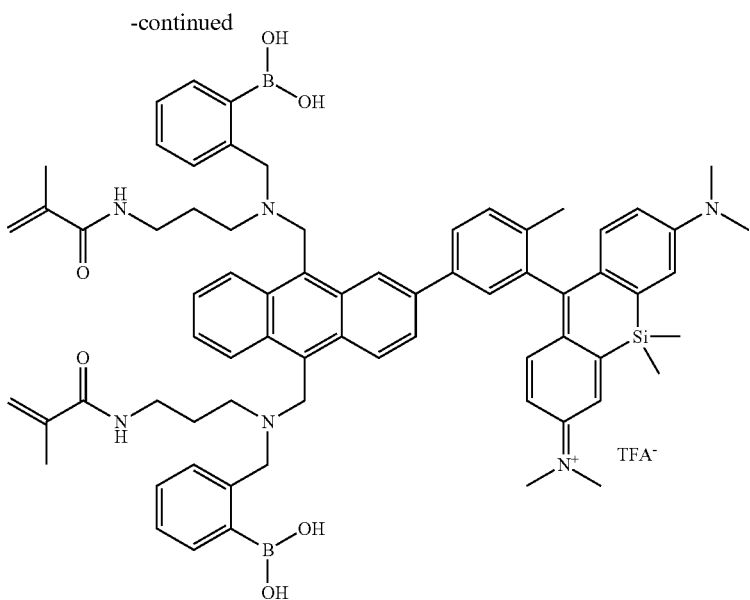

Compound 63

Compound 63 was prepared from 2-bromo-4-iodotoluene and intermediates 54-1, and 11-3 following general procedures XXIII, XVI, XVIIA, and XV, as outlined in the scheme above. HPLC-MS: m/z 1152.3 (calcd. 1151.6 for M+). UV/Vis: $\lambda_{max}$=650 nm. $^1$H NMR (400 MHz, MeOH-d$_4$) d ppm 8.47 (br. s., 1H), 8.14-8.30 (m, 2H), 8.04 (d, J=7.9 Hz, 1H), 7.81 (d, J=7.7 Hz, 1H), 7.71 (d, J=9.5 Hz, 1H), 7.58 (d, J=1.8 Hz, 1H), 7.51 (d, J=8.2 Hz, 1H), 7.31-7.51 (m, 5H), 7.29 (d, J=2.8 Hz, 2H), 7.15-7.23 (m, 2H), 7.18 (d, J=9.6 Hz, 2H), 7.03-7.15 (m, 3H), 6.70 (dd, J=9.7, 2.9 Hz, 2H), 5.29 (quin, J=0.8 Hz, 1H), 5.22 (quin, J=0.8 Hz, 1H), 5.10 (quin, J=1.3 Hz, 1H), 5.02 (quin, J=1.3 Hz, 1H), 4.58 (br. s, 2H), 4.54 (br. s, 2H), 3.98 (br. s., 2H), 3.74 (s, 2H), 3.23 (s, 12H), 2.89 (t, J=6.6 Hz, 2H), 2.74 (t, J=6.9 Hz, 2H), 2.51-2.62 (m, 2H), 2.37-2.49 (m, 2H), 2.05 (s, 3H), 1.65-1.76 (m, 4H), 1.63 (m, J=1.5, 0.7 Hz, 3H), 1.55 (dd, J=1.5, 1.0 Hz, 3H), 0.54 (s, 3H), 0.53 (s, 3H).

Preparation of Compound 64

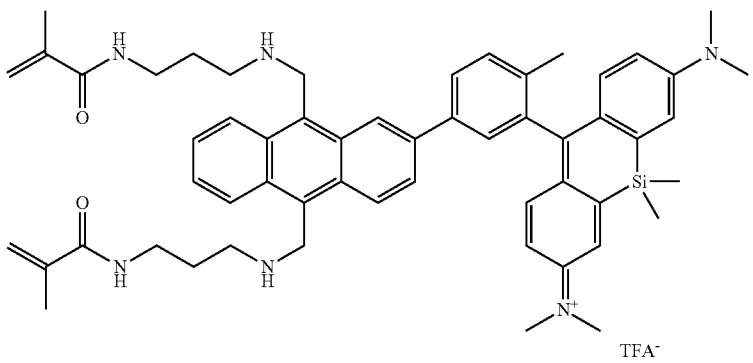 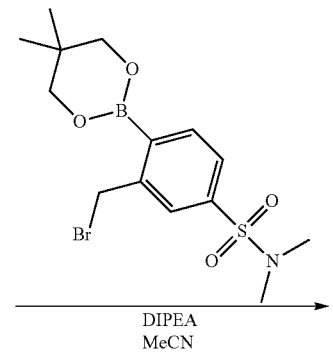

63-3

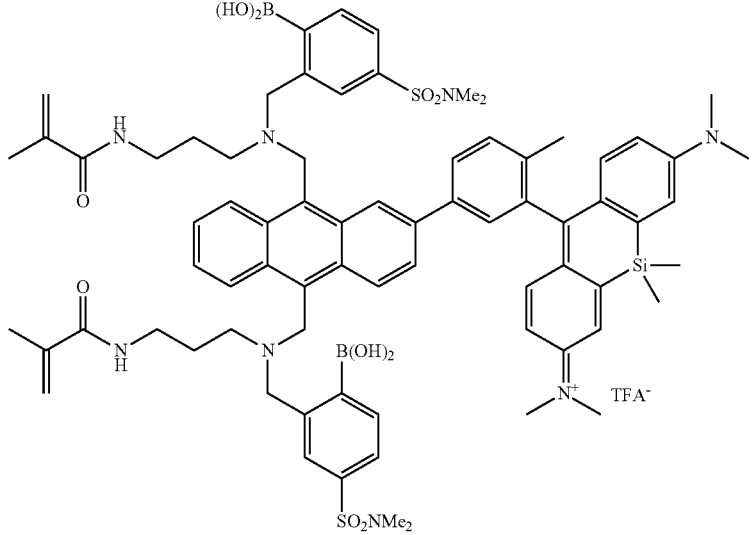
Compound 64
Compound 64 was prepared from intermediates 63-3 and 53-2 following the general procedure V. HPLC-MS: m/z 1366.3 (calcd. 1365.6 for M+). UV/Vis: $\lambda_{max}$=650 nm. $^1$H NMR (600 MHz, MeOH-d$_4$; mixture of two rotamers) δ ppm 8.12-8.31 (m, 2H), 7.86-8.03 (m, 3H), 7.71-7.77 (m, 2H), 7.60-7.71 (m, 6H), 7.53-7.60 (m, 3H), 7.47-7.53 (m, 1H), 7.36-7.44 (m, 2H), 7.30-7.36 (m, 2H), 6.88 (d, J=8.3 Hz, 1H), 5.47 (s, 1H), 5.35 (s, 1H), 5.26 (s, 1H), 5.14 (s, 1H), 4.70 (br. s, 4H), 3.36 (s, 12H), 3.08 (br. s., 2H), 2.96 (br. s., 2H), 2.69-2.77 (m, 4H), 2.67-2.69 (m, 4H), 2.65 (br. s, 6H), 2.48 (br. s, 6H), 1.87-1.98 (m, 2H), 1.79-1.85 (m, 2H), 1.78 (s, 3H), 1.71 (s, 3H), 1.66 (s, 3H), 0.68 (s, 3H), 0.64 (s, 3H).
Preparation of Compound 65
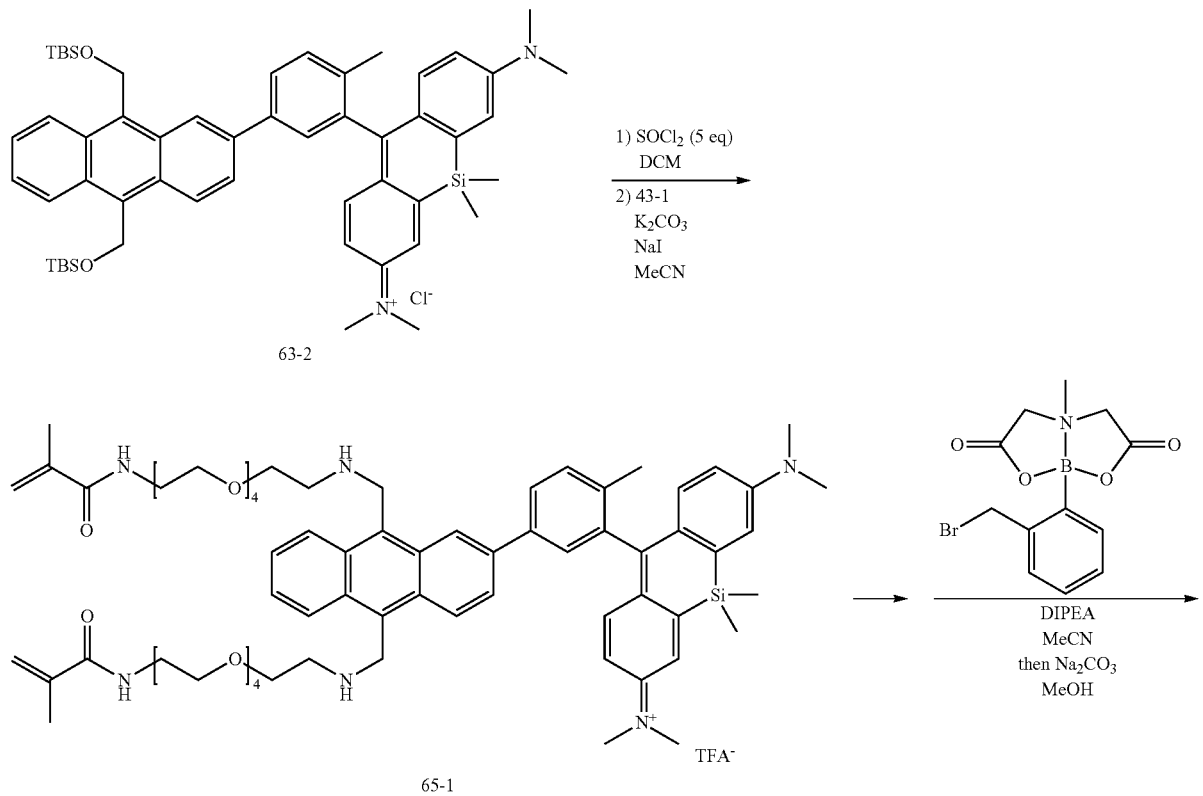

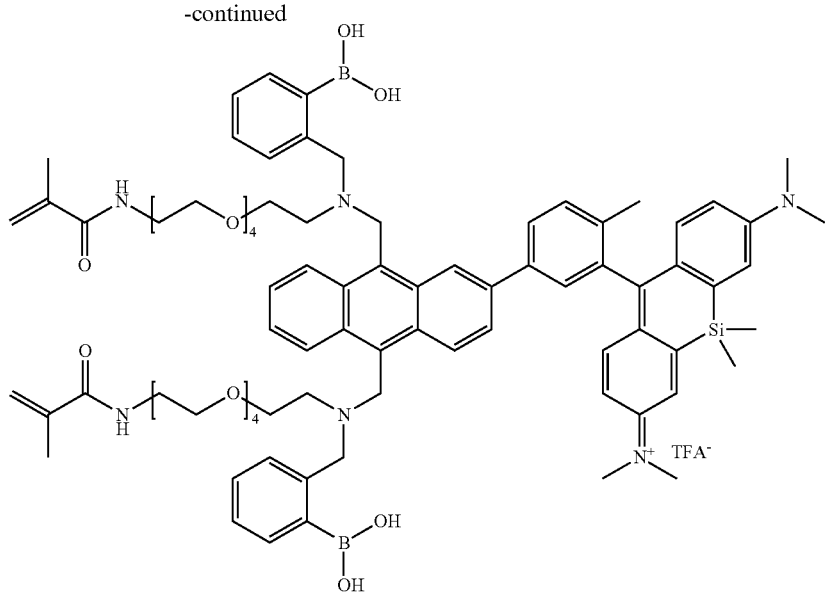
Compound 65
Compound 65 was prepared from intermediates 63-2 and 43-1, following the general procedures XVIIA and XV, as outlined in the scheme above. HPLC-MS: m/z 1476.3 (calcd. 1475.8 for M$^+$). UV/Vis: $\lambda_{max}$=650 nm.
Preparation of Compound 69
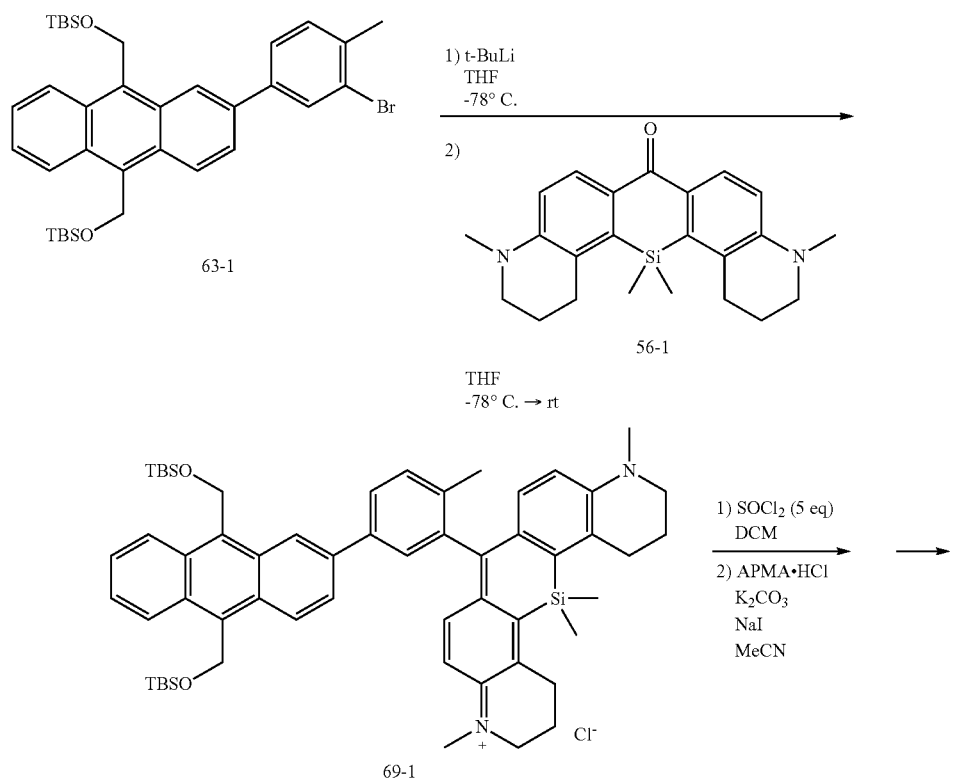

-continued
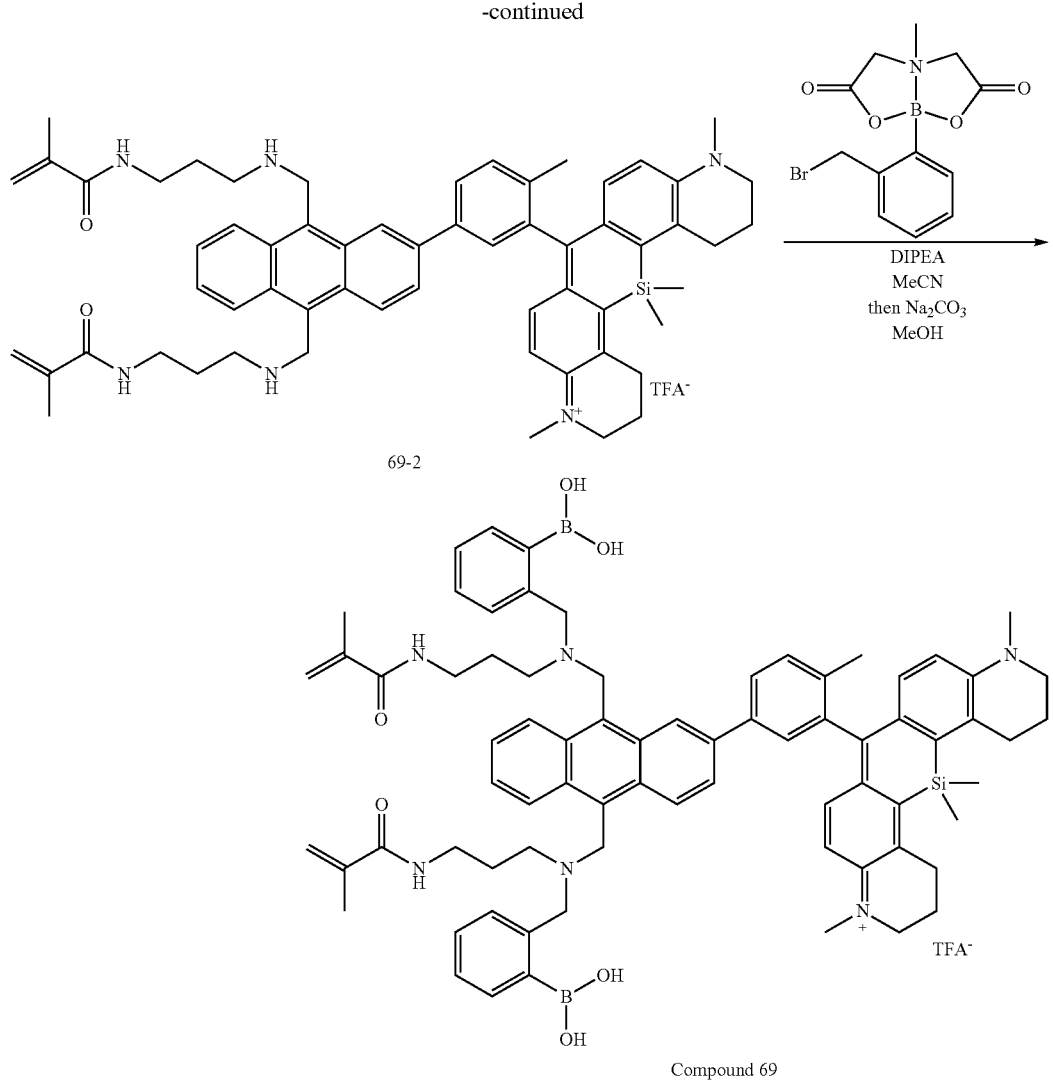
69-2
Compound 69
Compound 69 was prepared from intermediates 63-1 and 56-1, following the general procedures XVI, XVIIA, and XV, as outlined in the scheme above. HPLC-MS: m/z 1204.3 (calcd. 1203.7 for M$^+$). UV/Vis: $\lambda_{max}$=660 nm. $^1$H NMR (400 MHz, MeOH-d$_4$) δ ppm 8.15-8.44 (m, 2H), 7.94-8.05 (m, 1H), 7.85-7.94 (m, 2H), 7.78-7.85 (m, 1H), 7.69-7.78 (m, 3H), 7.54-7.69 (m, 8H), 7.27-7.38 (m, 1H), 7.19 (d, J=10.3 Hz, 2H), 6.75 (d, J=9.7 Hz, 2H), 5.28 (br. s, 1H), 5.29 (br. s, 1H), 5.14 (br. s, 1H), 5.10 (br. s., 1H), 4.80 (br. s., 2H), 3.69 (t, J=6.1 Hz, 4H), 3.18-3.27 (m, 2H), 3.23 (s, 6H), 3.00-3.16 (m, 8H), 2.94 (t, J=6.6 Hz, 2H), 2.18 (s, 3H), 2.06-2.15 (m, 4H), 1.90-2.06 (m, 2H), 1.74-1.90 (m, 2H), 1.58 (s, 3H), 1.59 (s, 3H), 0.80 (s, 3H), 0.80 (s, 3H).
Preparation of Compound 82
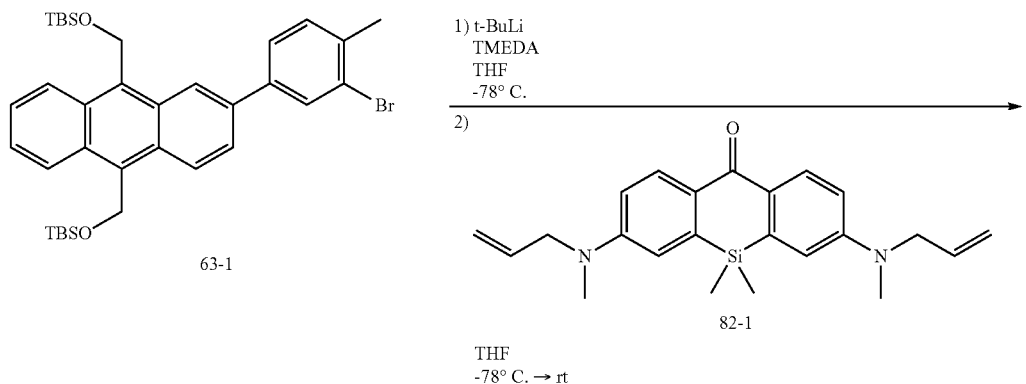

-continued
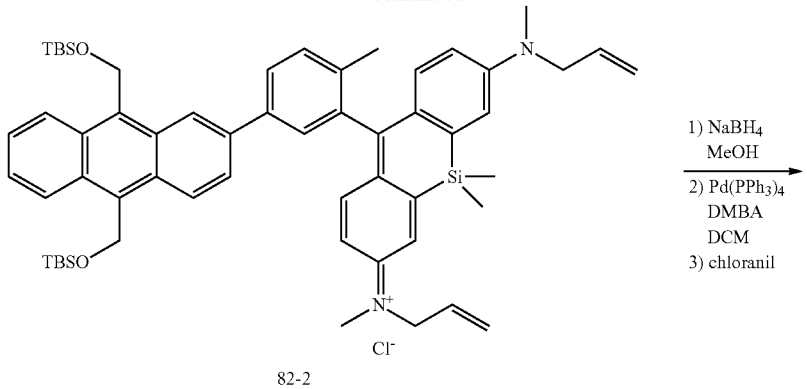
82-2
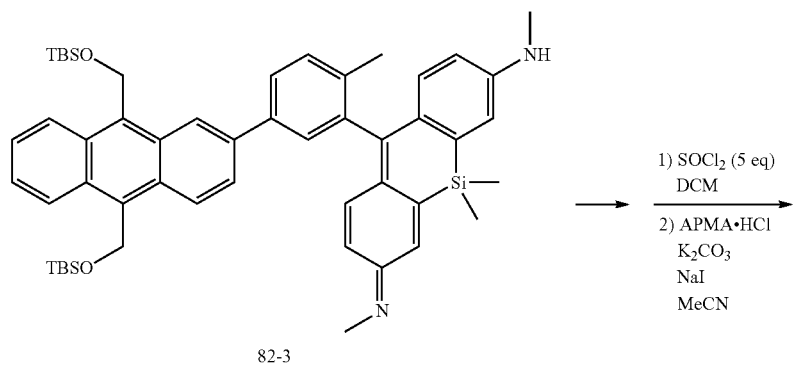
82-3
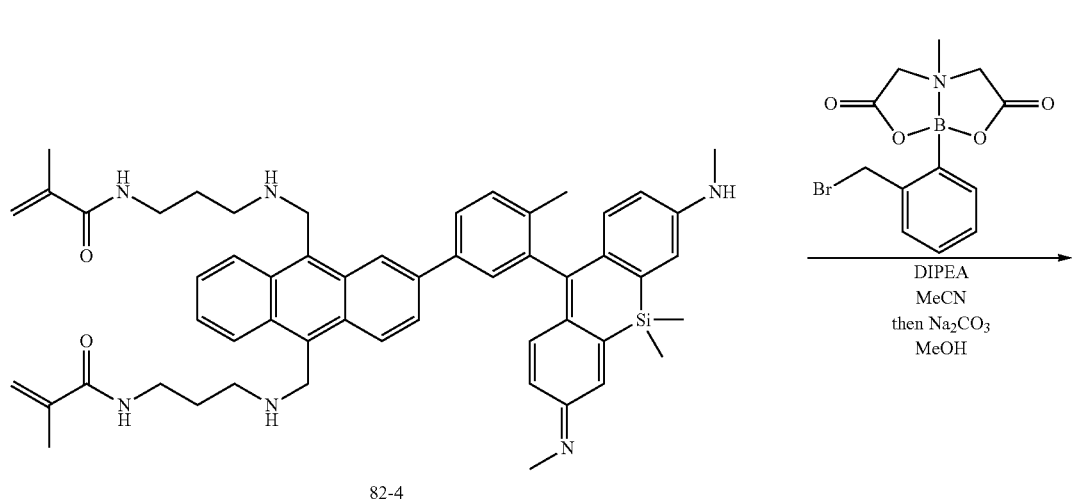
82-4

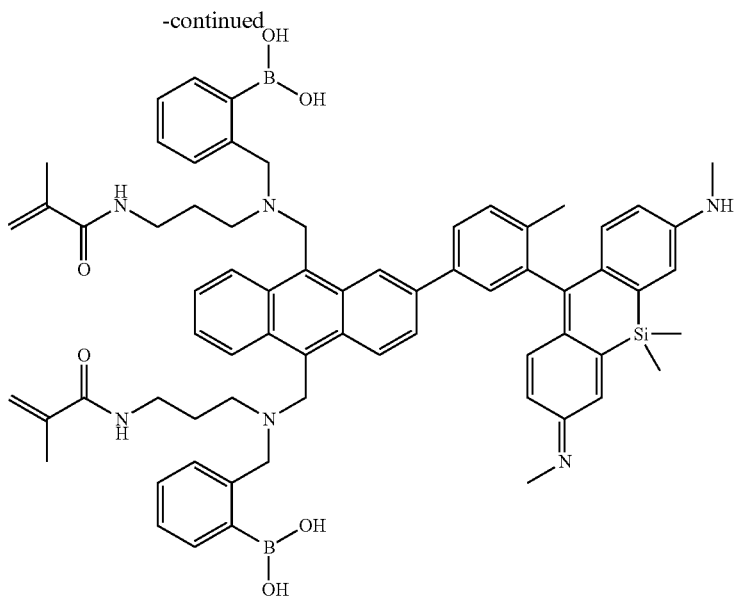

Compound 82

Silaxanthone 82-1 was prepared as described in the literature (Umezawa, K.; Yoshida, M.; Kamiya, M.; Yamasoba, T.; Urano, Y. *Nat. Chem.* 2016, 9 (3), 279-286).

Intermediate 82-2 was prepared from intermediates 63-1 and 82-1 following the general procedure XVI.

Preparation of Compound 82-3

General method of deallylation of silicon-substituted xanthene dyes was described in literature (Umezawa, K.; Yoshida, M.; Kamiya, M.; Yamasoba, T.; Urano, Y. *Nat. Chem.* 2016, 9 (3), 279-286). According to this method, bis-allyl intermediate 82-2 (158 mg, 0.166 mmol) was dissolved in MeOH (5 mL) and treated with the excess of solid $NaBH_4$ until the color turned yellow-green (gas released upon addition of $NaBH_4$). The mixture was stirred for additional 10 min, and then the mixture was quenched with water and the resulting slurry was partitioned with EtOAc. Aqueous layer was discarded, organic layer was washed with brine, dried over anhydrous $Na_2SO_4$, filtered, and concentrated under reduced pressure. The residue was dissolved in degassed DCM (10 mL). 1,3-Dimethylbarbituric acid (DMBA; 245 mg, 1.57 mmol) and $Pd(PPh_3)_4$ (43 mg, 0.037 mmol) were added, and the mixture was stirred at ambient temperature for 16 h. Then chloranil (49 mg, 0.20 mmol) was added, and after 20 min of stirring the reaction mixture was filtered through Celite®. The filtrate was concentrated under reduced pressure, and the residue was purified by flash chromatography ($SiO_2$, eluted with gradient from 2% to 30% MeOH in DCM). Desired intermediate 82-3 was obtained as a dark-blue solid (150 mg, quant. yield).

Compound 82 was prepared from intermediate 82-3, following the general procedures XVIIA and XV, as outlined in the scheme above. HPLC-MS: m/z 1124.1 (calcd. 1123.6 for M+H⁺). UV/Vis: $\lambda_{max}$=625 nm.

Preparation of Compound 83

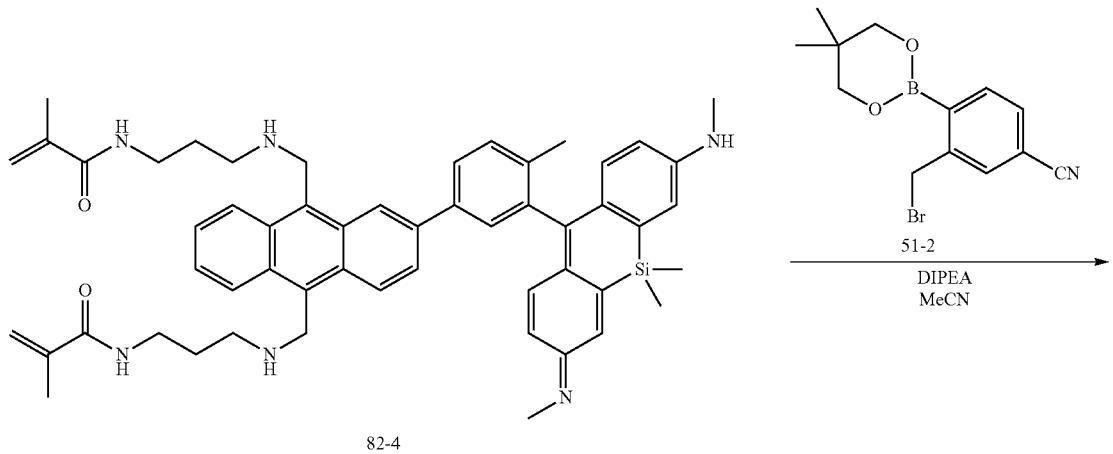

82-4

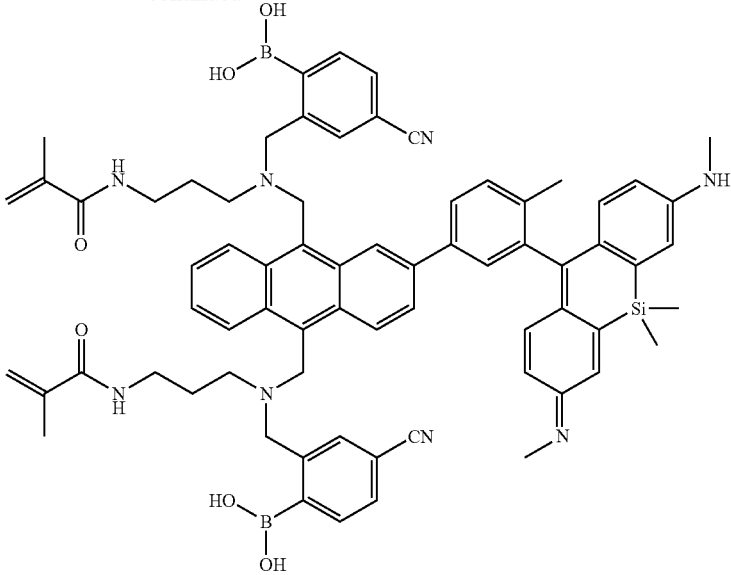

Compound 83

Compound 83 was prepared from the intermediates 82-4 and 51-2, following the general procedure V. The neopentyl glycol protecting group was spontaneously removed during reversed phase purification. HPLC-MS: m/z 1174.1 (calcd. 1173.6 for M+H$^+$). UV/Vis: $\lambda_{max}$=625 nm. $^1$H NMR (400 MHz, MeOH-d$_4$) δ ppm 8.66 (br. s., 1H), 8.41 (d, J=9.5 Hz, 1H), 8.45 (d, J=8.4 Hz, 1H), 8.30 (d, J=7.8 Hz, 1H), 8.06 (d, J=1.3 Hz, 1H), 8.01 (s, 1H), 7.96 (m, J=8.7 Hz, 2H), 7.47-7.73 (m, 7H), 7.32-7.46 (m, 3H), 7.23 (d, J=2.3 Hz, 2H), 6.66 (dd, J=9.4, 2.3 Hz, 2H), 5.48 (s, 1H), 5.41 (s, 1H), 5.27 (quin, J=1.3 Hz, 1H), 5.20 (quin, J=1.3 Hz, 1H), 4.98 (br. s., 2H), 4.59 (br. s, 2H), 4.29 (br. s., 2H), 4.05 (br. s., 2H), 3.35 (s, 6H), 3.04-3.12 (m, 2H), 2.99 (t, J=6.5 Hz, 2H), 2.83-2.92 (m, 2H), 2.72-2.83 (m, 2H), 2.16 (s, 3H), 1.87-1.98 (m, 4H), 1.79 (s, 3H), 1.72 (s, 3H), 0.60 (s, 3H), 0.58 (s, 3H).

Preparation of Compound 66

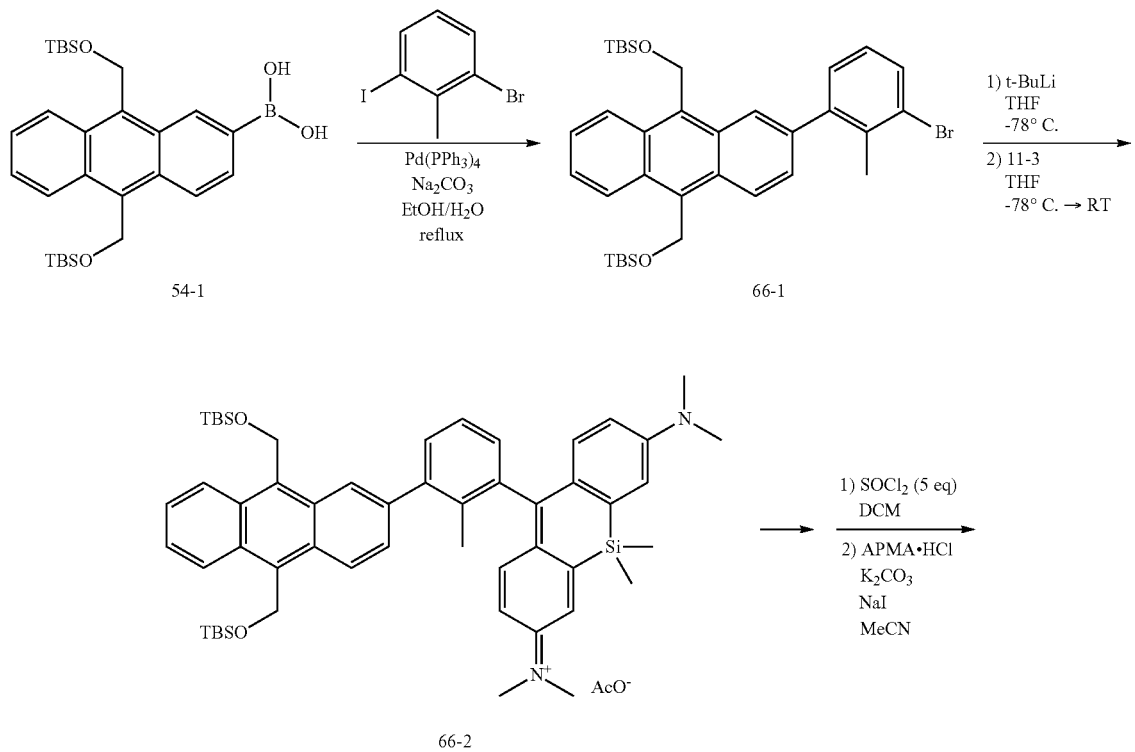

-continued

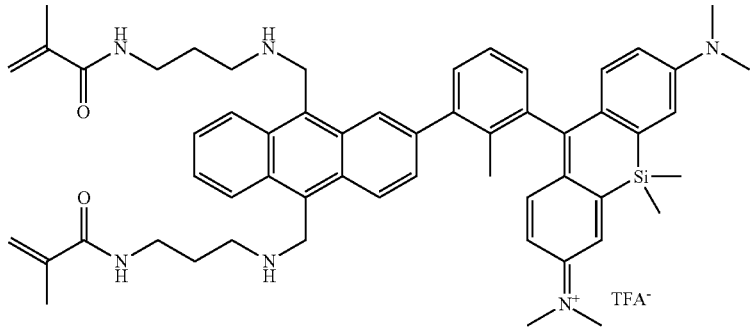 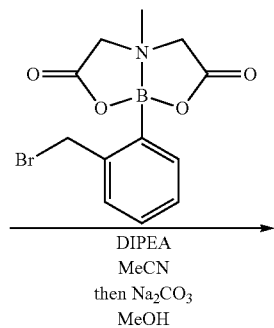

66-3

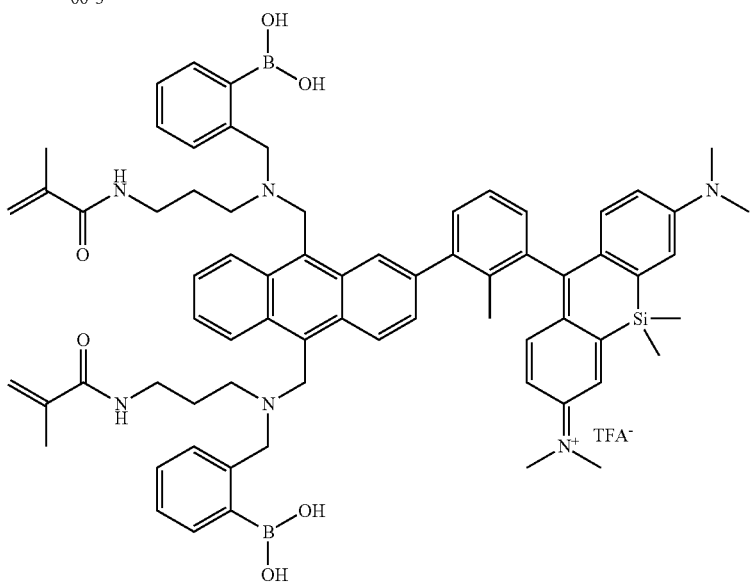

Compound 66

Compound 66 was prepared from 2-bromo-6-iodotoluene and intermediates 54-1 and 11-3, following the general procedures XXIII, XVI, XVIIA, and XV, as outlined in the scheme above. HPLC-MS: m/z 1152.3 (calcd. 1151.6 for M$^+$). UV/Vis: $\lambda_{max}$=650 nm. $^1$H NMR (400 MHz, MeOH-d$_4$) δ ppm 8.51 (s, 1H), 8.40-8.47 (m, 1H), 8.38 (d, J=10.0 Hz, 1H), 7.50-7.65 (m, 6H), 7.36-7.45 (m, 2H), 7.40 (d, J=3.2 Hz, 2H), 7.21-7.36 (m, 5H), 7.31 (d, J=9.5 Hz, 2H), 7.17 (m, J=6.7 Hz, 2H), 6.87 (dd, J=9.8, 2.7 Hz, 2H), 5.37 (s, 1H), 5.34 (s, 1H), 5.18 (m, J=1.7, 1.7, 1.7, 1.7 Hz, 2H), 4.94 (br. s, 2H), 4.82 (br. s., 2H), 4.17 (br. s, 2H), 3.95 (br. s, 2H), 3.37 (s, 12H), 3.04 (t, J=6.9 Hz, 2H), 3.00 (t, J=6.4 Hz, 2H), 2.73-2.82 (m, 2H), 2.57-2.71 (m, 2H), 2.04 (s, 3H), 1.88-1.97 (m, 2H), 1.79-1.88 (m, 2H), 1.70 (s, 6H), 0.65 (s, 3H), 0.61 (s, 3H).

Preparation of Compound 67

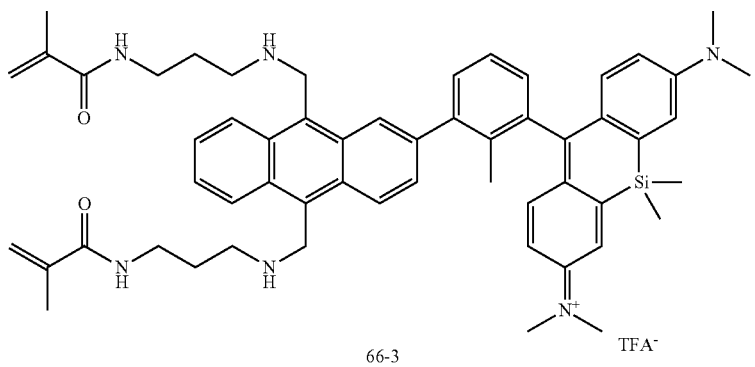 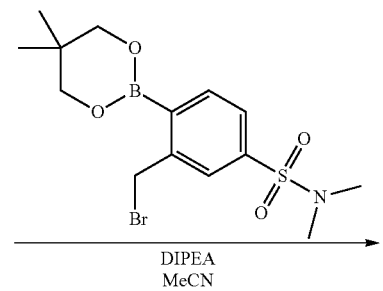

66-3

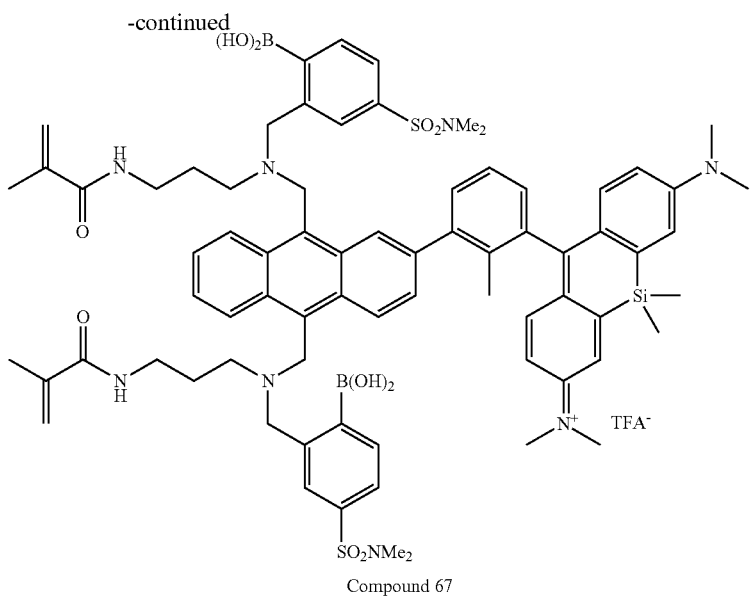
Compound 67
Compound 67 was prepared from intermediates 66-3 and 53-2 following the general procedure V. HPLC-MS: m/z 1366.4 (calcd. 1365.6 for M$^+$). UV/Vis: $\lambda_{max}$=650 nm.
Preparation of Compound 73
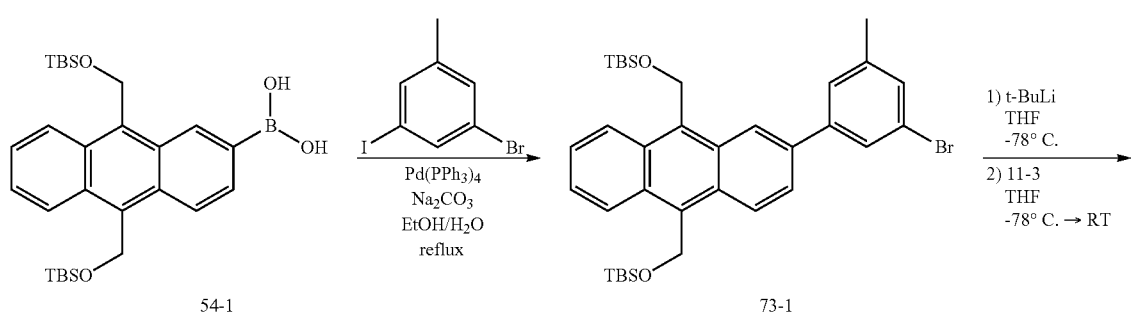
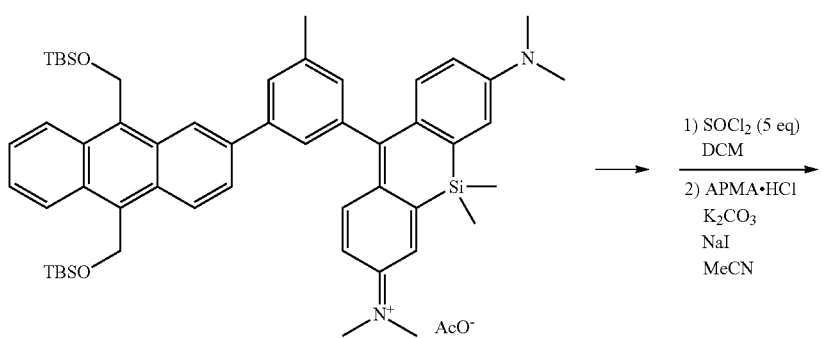

-continued

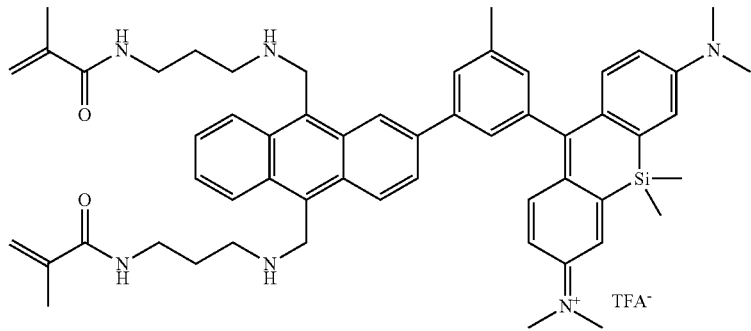 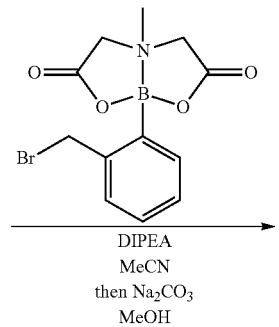

73-3

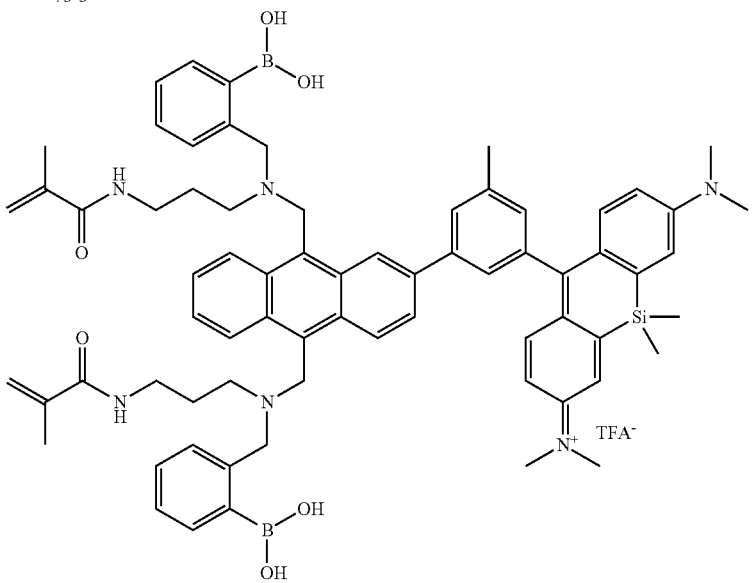

Compound 73

Compound 73 was prepared from 3-bromo-5-iodotoluene and intermediates 54-1 and 11-3, following the general procedures XXIII, XVI, XVIIA, and XV, as outlined in the scheme above. HPLC-MS: m/z 1152.3 (calcd. 1151.6 for M+). UV/Vis: $\lambda_{max}$=650 nm. ¹H NMR (400 MHz, MeOH-d₄; mixture of two rotamers) δ ppm 8.25-8.39 (m, 2H), 8.07-8.20 (m, 2H), 7.75-7.84 (m, 2H), 7.61 (m, J=5.0 Hz, 2H), 7.47-7.54 (m, 1H), 7.39-7.46 (m, 3H), 7.37 (m, J=3.2 Hz, 3H), 7.26-7.34 (m, 3H), 7.18-7.25 (m, 3H), 7.15 (d, J=5.6 Hz, 1H), 6.78 (dd, J=9.7, 2.9 Hz, 2H), 5.36 (s, 1H), 5.34 (s, 1H), 5.17-5.21 (m, 1H), 5.11-5.16 (m, 1H), 4.61 (br. s., 4H), 4.06 (br. s, 2H), 3.83 (br. s, 2H), 2.97-3.03 (m, 2H), 2.90-2.95 (m, 12H), 2.85 (t, J=6.3 Hz, 2H), 2.63-2.70 (m, 2H), 2.61 (s, 3H), 2.49-2.59 (m, 2H), 1.78-1.85 (m, 2H), 1.73-1.78 (m, 2H), 1.65-1.69 (m, 6H), 0.63 (s, 6H).

Preparation of Compound 74

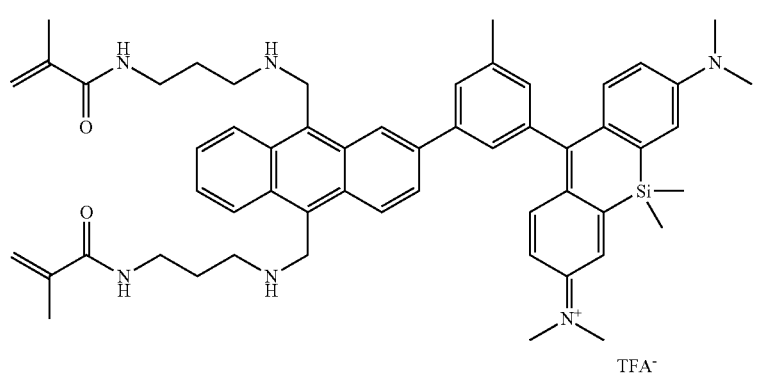 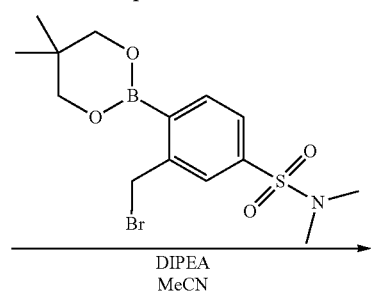

73-3

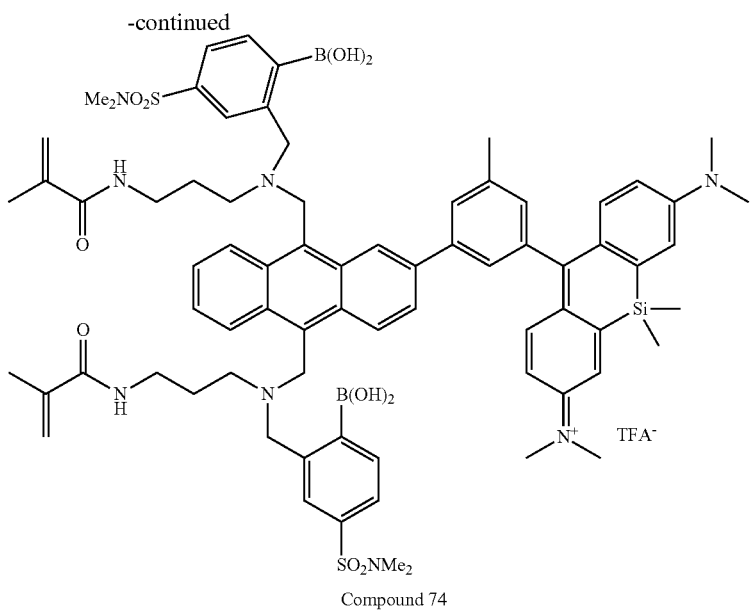
Compound 74
Compound 74 was prepared from intermediates 73-3 and 53-2 following the general procedure V. HPLC-MS: m/z 1366.6 (calcd. 1365.6 for M$^+$). UV/Vis: $\lambda_{max}$=650 nm. $^1$H NMR (400 MHz, MeOH-d$_4$) δ ppm 8.23 (s, 1H), 8.16-8.26 (m, 1H), 8.06-8.15 (m, 1H), 7.96-8.06 (m, 1H), 7.52-7.79 (m, 11H), 7.41 (d, J=3.0 Hz, 2H), 7.45 (d, J=9.9 Hz, 2H), 7.25 (s, 1H), 6.89 (d, J=9.3 Hz, 2H), 5.45 (s, 1H), 5.34 (br. s., 1H), 5.24 (s, 1H), 5.13 (br. s., 1H), 4.48-4.70 (m, 4H), 4.38 (br. s, 2H), 3.91 (br. s., 2H), 3.36 (s, 12H), 3.00 (s, 3H), 2.95-3.05 (m, 2H), 2.85-2.95 (m, 2H), 2.65-2.74 (m, 4H), 2.63 (br. s., 6H), 2.47 (br. s, 6H), 1.84-1.94 (m, 2H), 1.77 (s, 3H), 1.72-1.84 (m, 2H), 1.66 (s, 3H), 0.68 (s, 3H), 0.65 (s, 3H).
Preparation of Compound 75
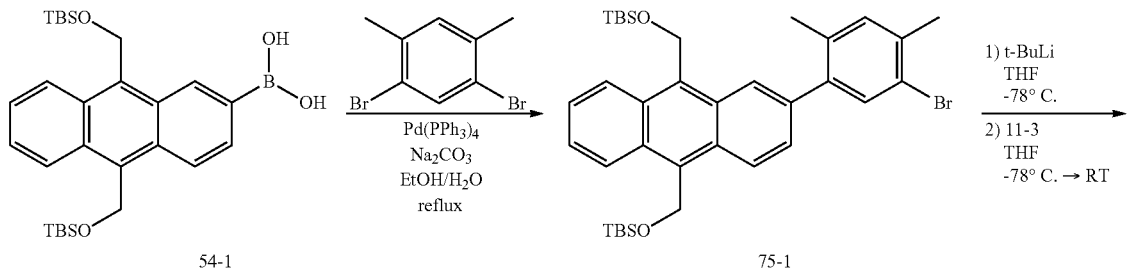
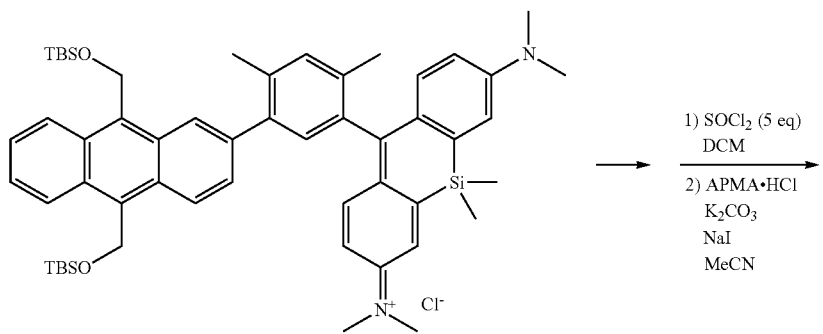

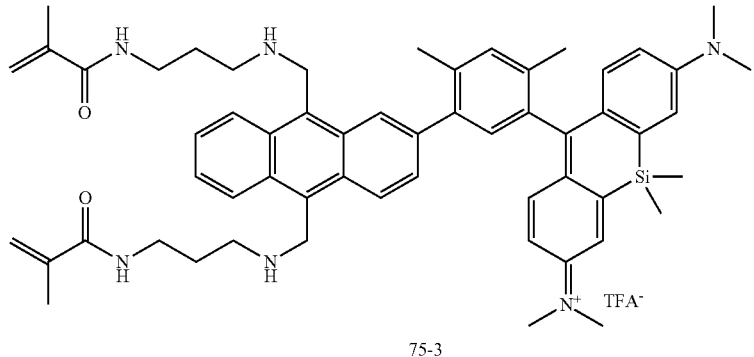

75-3

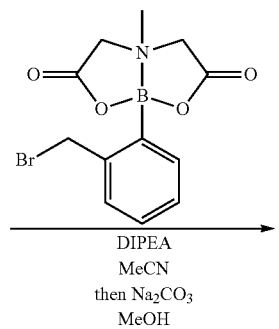

DIPEA
MeCN
then Na₂CO₃
MeOH

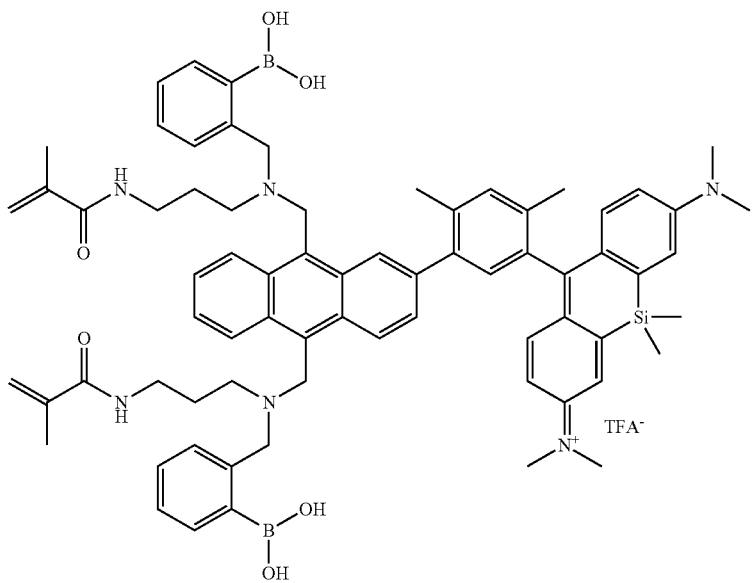

Compound 75

Compound 75 was prepared from 1,5-dibromo-2,4-dimethylbenzene and intermediates 54-1 and 11-3, following the general procedures XXIII, XVI, XVIIA, and XV, as outlined in the scheme above. HPLC-MS: m/z 1166.4 (calcd. 1165.6 for M⁺). UV/Vis: $\lambda_{max}$=650 nm. ¹H NMR (400 MHz, MeOH-d₄; mixture of two rotamers) δ ppm 8.45-8.53 (m, 2H), 8.25-8.44 (m, 2H), 7.63 (d, J=9.3 Hz, 1H), 7.52-7.60 (m, 2H), 7.49 (d, J=6.8 Hz, 1H), 7.44 (s, 1H), 7.40 (dd, J=6.8, 2.0 Hz, 1H), 7.37 (d, J=2.9 Hz, 2H), 7.33 (d, J=9.7 Hz, 2H), 7.17-7.31 (m, 4H), 7.06-7.17 (m, 3H), 6.84 (dd, J=9.7, 2.9 Hz, 2H), 5.36 (br. s., 1H), 5.35 (s, 1H), 5.19 (quin, J=1.3 Hz, 1H), 5.15 (quin, J=1.3 Hz, 1H), 4.91 (br. s., 2H), 4.75 (br. s., 2H), 4.18 (br. s., 2H), 3.83 (br. s, 2H), 3.34 (s, 12H), 3.03 (t, J=6.5 Hz, 2H), 2.91 (t, J=6.4 Hz, 2H), 2.76 (dd, J=9.0, 6.7 Hz, 2H), 2.58 (dd, J=8.5, 6.7 Hz, 2H), 2.49 (s, 3H), 2.11 (s, 3H), 1.84-1.96 (m, 2H), 1.75-1.84 (m, 2H), 1.72 (s, 3H), 1.68 (s, 3H), 0.61 (s, 3H), 0.58 (s, 3H).

Preparation of Compound 76
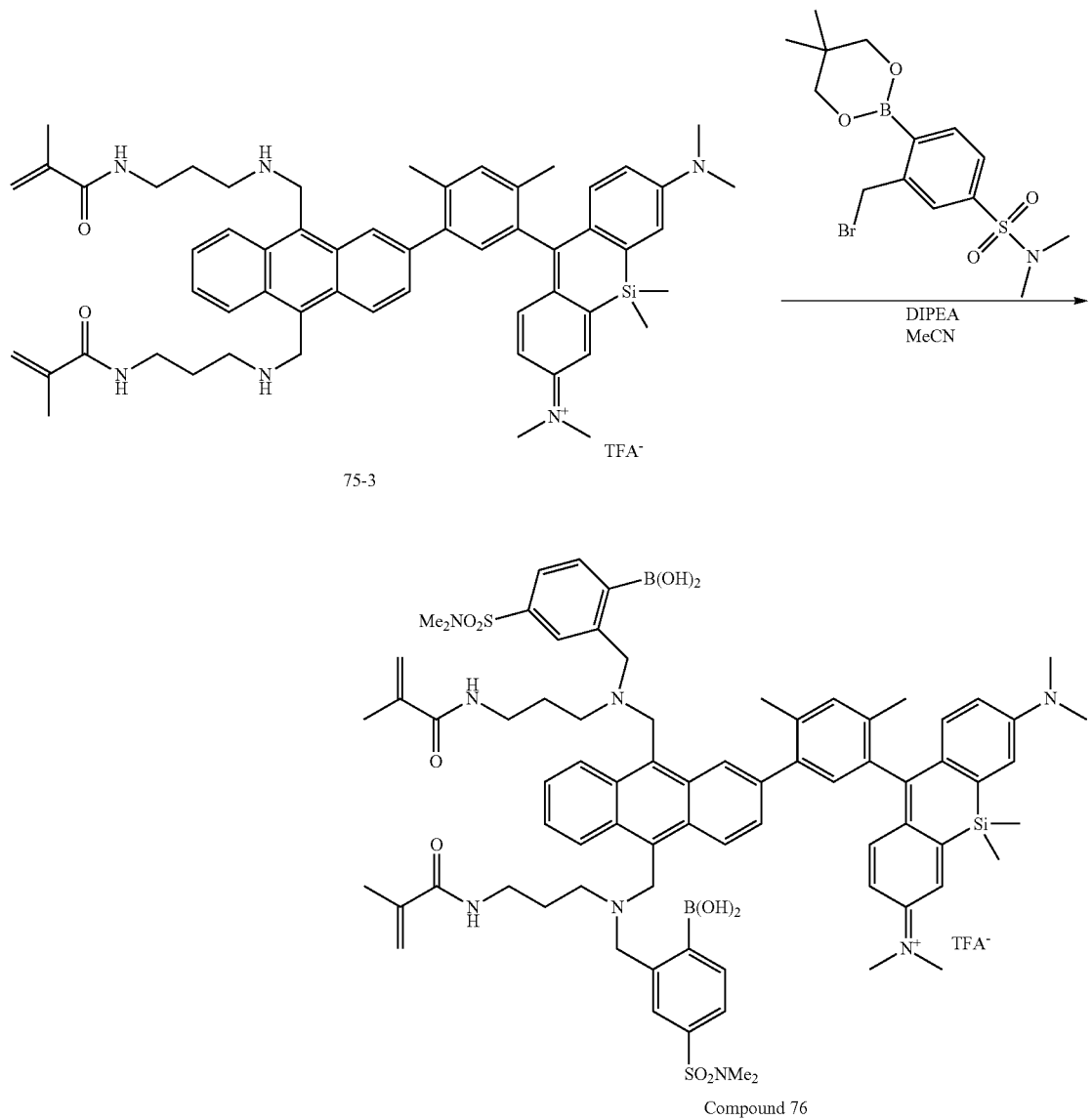
Compound 76 was prepared from intermediates 75-3 and 53-2 following the general procedure V. HPLC-MS: m/z 1380.4 (calcd. 1379.6 for M$^+$). UV/Vis: $\lambda_{max}$=650 nm. $^1$H NMR (400 MHz, MeOH-d$_4$) δ ppm 8.46 (br. s., 1H), 8.34-8.41 (m, 1H), 8.22-8.30 (m, 1H), 7.74-7.78 (m, 1H), 7.63-7.72 (m, 3H), 7.47-7.62 (m, 6H), 7.44 (s, 1H), 7.35-7.38 (m, 2H), 7.30-7.35 (m, 1H), 7.34 (s, 1H), 7.28 (br. s, 1H), 6.88 (dd, J=9.6, 2.7 Hz, 2H), 5.40 (s, 1H), 5.40 (s, 1H), 5.22 (quin, J=1.3 Hz, 1H), 5.18 (quin, J=1.3 Hz, 1H), 4.91 (br. s., 2H), 4.27 (br. s., 2H), 4.08 (br. s., 2H), 3.36 (s, 12H), 3.05 (t, J=6.6 Hz, 2H), 2.94 (t, J=6.7 Hz, 2H), 2.77-2.86 (m, 2H), 2.68-2.73 (m, 2H), 2.55 (s, 6H), 2.52 (s, 3H), 2.47 (s, 6H), 2.12 (s, 3H), 1.80-1.95 (m, 4H), 1.73 (s, 3H), 1.71 (s, 3H), 0.61 (s, 6H).

Preparation of Compound 77
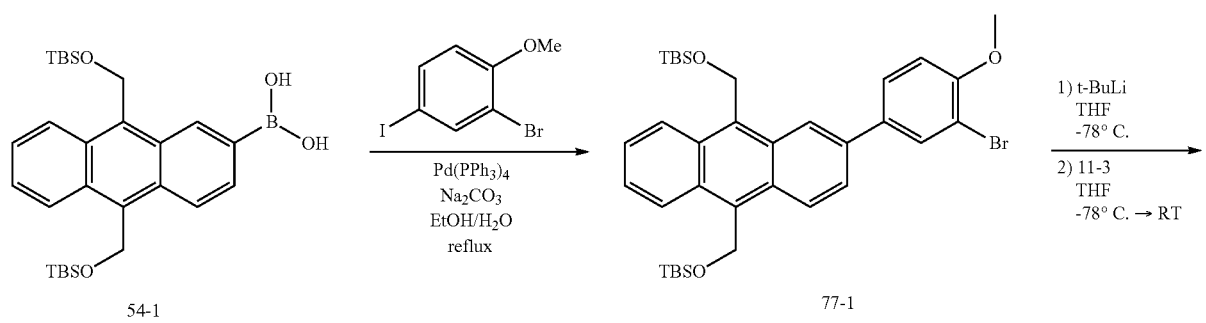
54-1 → 77-1
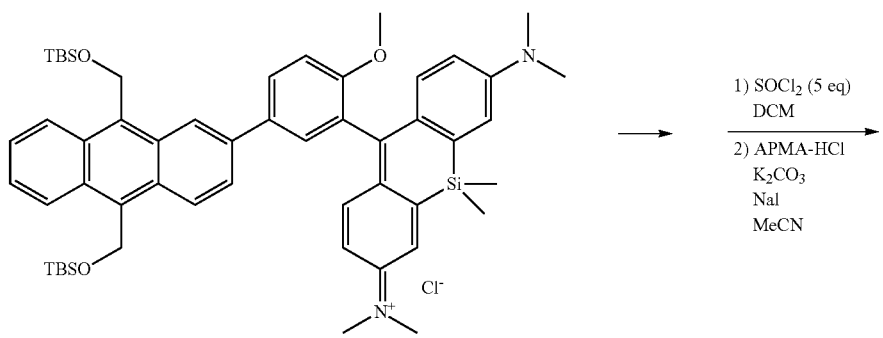
77-2
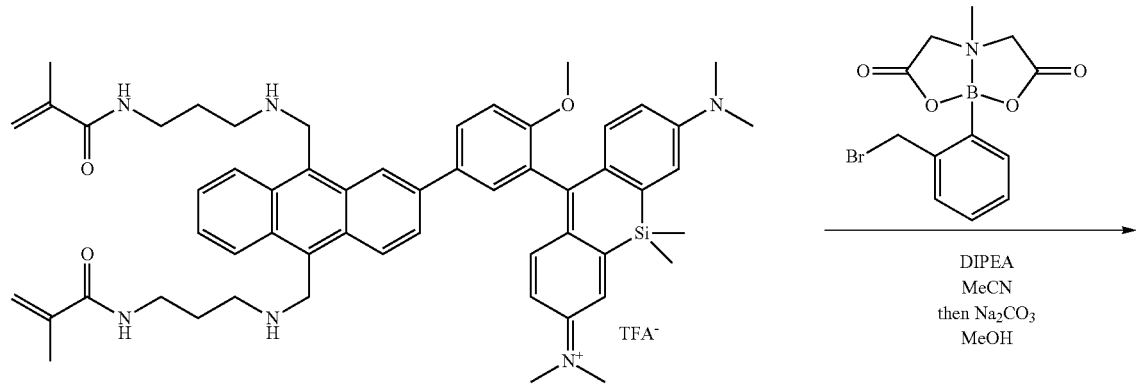
77-3

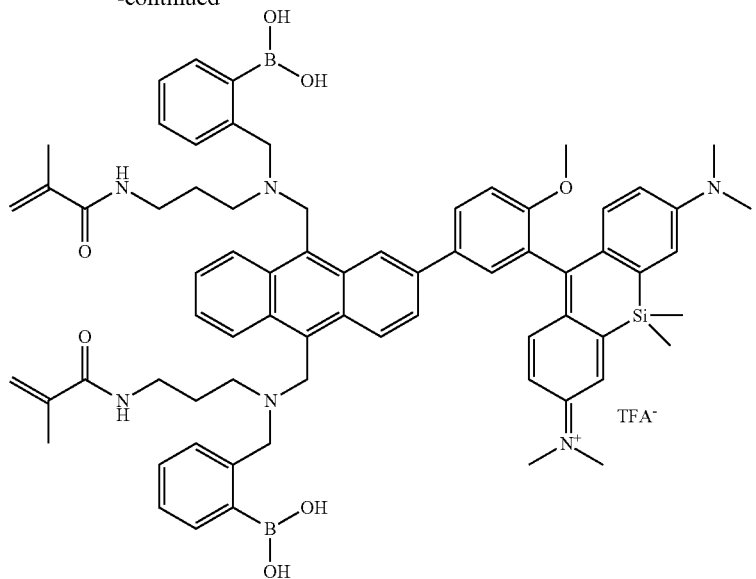

Compound 77

Compound 77 was prepared from 2-bromo-4-iodoanisole and intermediates 54-1 and 11-3, following the general procedures XXIII, XVI, XVIIA, and XV, as outlined in the scheme above. HPLC-MS: m/z 1168.4 (calcd. 1167.6 for M⁺). UV/Vis: $\lambda_{max}$=650 nm. ¹H NMR (400 MHz, MeOH-$d_4$) δ ppm 8.77 (d, J=2.4 Hz, 1H), 8.38-8.49 (m, 2H), 8.26 (m, J=8.0 Hz, 1H), 8.05 (d, J=9.5 Hz, 1H), 7.62-7.69 (m, 1H), 7.49-7.62 (m, 3H), 7.47 (d, J=8.0 Hz, 1H), 7.42 (m, J=8.7 Hz, 1H), 7.26-7.39 (m, 4H), 7.17-7.24 (m, 2H), 7.14 (d, J=8.7 Hz, 2H), 6.93 (d, J=2.9 Hz, 2H), 6.85 (d, J=8.6 Hz, 1H), 6.71 (dd, J=8.6, 2.9 Hz, 2H), 5.38 (s, 2H), 5.18 (s, 2H), 4.94 (br. s., 4H), 4.29 (br. s., 2H), 4.02 (s, 2H), 3.20 (s, 3H), 3.02-3.10 (m, 4H), 2.93 (s, 12H), 2.79-2.86 (m, 2H), 2.70-2.78 (m, 2H), 1.98-2.08 (m, 2H), 1.90-1.96 (m, 2H), 1.71 (s, 3H), 1.70 (s, 3H), 0.57 (s, 3H), 0.45 (s, 3H).

Preparation of Compound 86

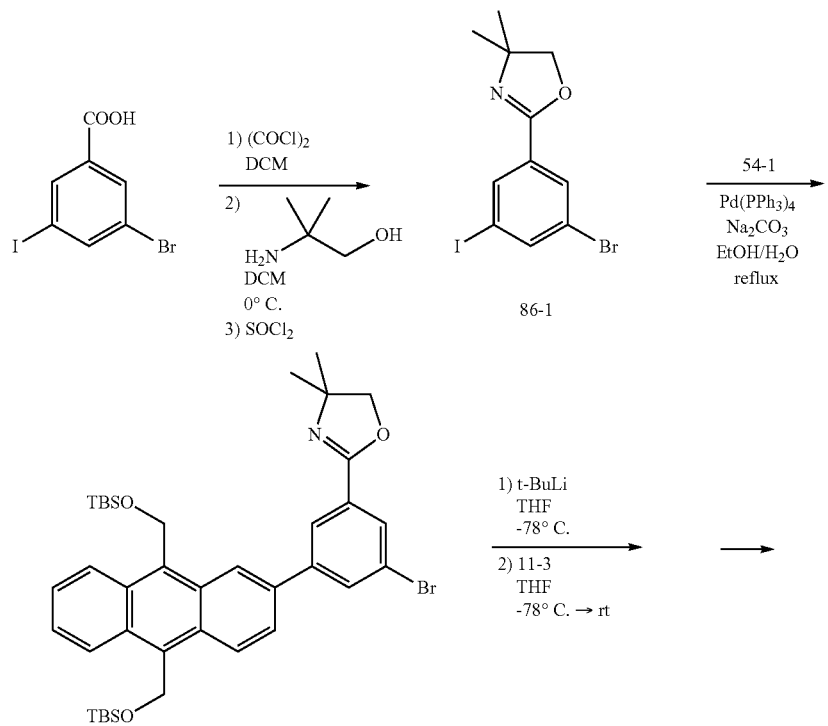

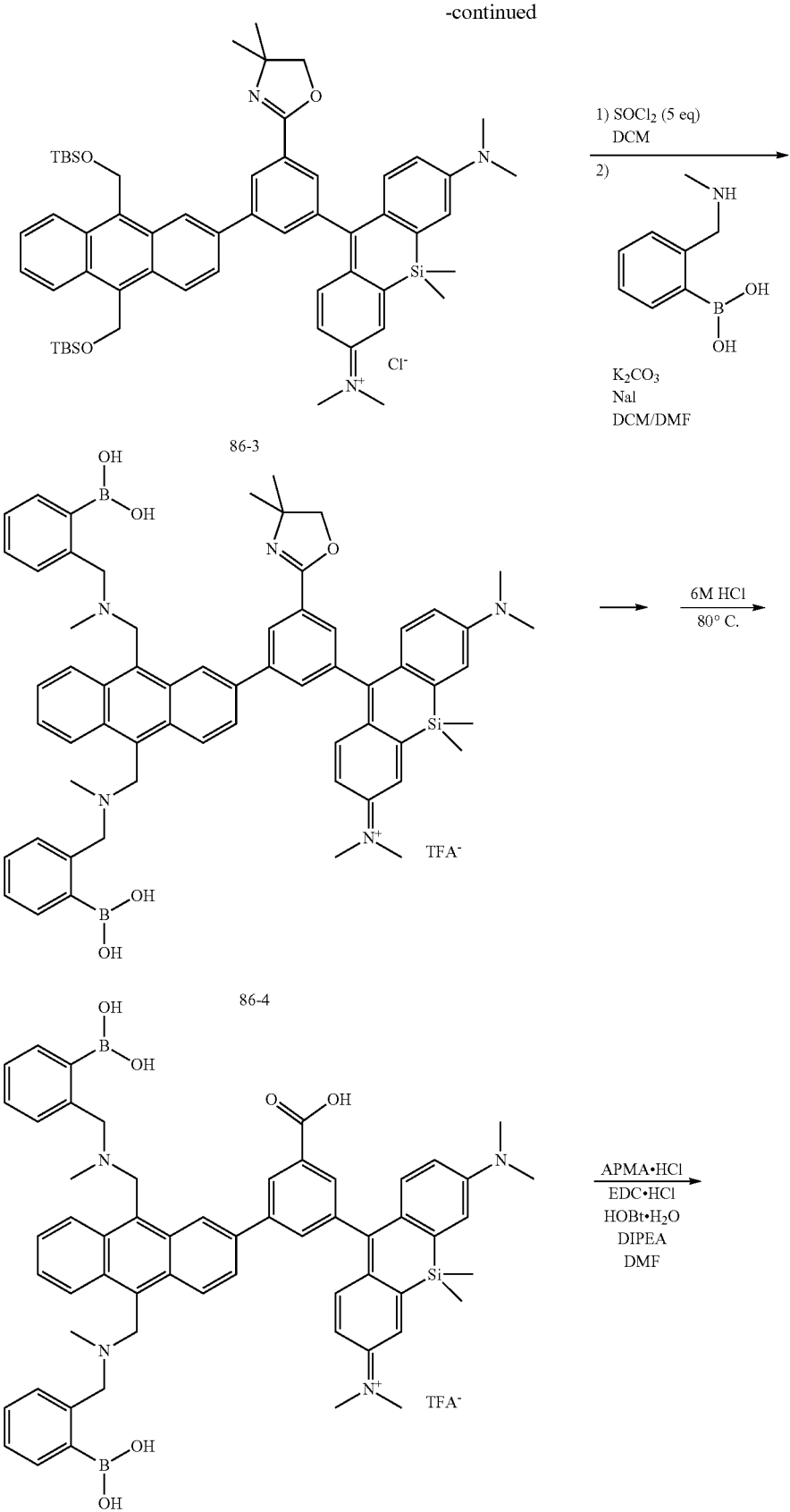

-continued

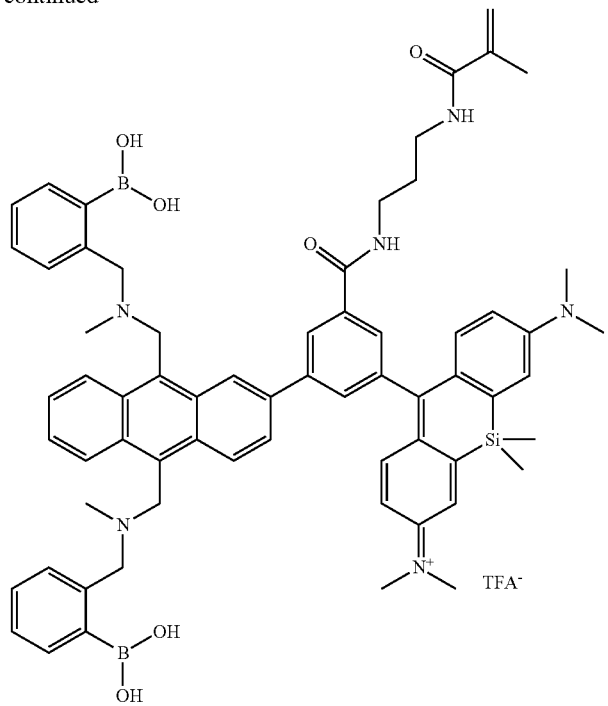

Compound 86

Preparation of Compound 86-1

To a suspension of 3-bromo-5-iodobenzoic acid (6.0 g, 18.4 mmol) in anhydrous DCM (20 mL) oxalyl chloride (6.5 mL, 75.8 mmol) was added dropwise, followed by catalytic amount of DMF (5 drops; gas release was observed shortly after addition of DMF). The reaction mixture was stirred at ambient temperature for 30 min, after which the suspension became clear orange solution. The solvent was removed under reduced pressure. The residue was extensively dried under high vacuum, and then redissolved in anhydrous DCM (30 mL) and added dropwise to a mixture of 2-amino-2-methylpropan-1-ol (5.05 g, 56.7 mmol) and anhydrous DCM (20 mL), while cooling the reaction mixture with ice/water bath (0° C.). The reaction mixture was allowed to reach ambient temperature and stirred for 3 h. The resulting suspension was filtered and the white precipitate was additionally washed with DCM (30 mL). Combined filtrate and washing were concentrated under reduced pressure to afford crude amide intermediate as a red oil. This was dissolved in neat thionyl chloride (13 mL) and the mixture was stirred at ambient temperature for 2 h. Then excess of thionyl chloride was removed in vacuo and resulting residue was purified by flash chromatography ($SiO_2$, eluted with gradient from 5% to 10% of EtOAc in hexanes). The product (6.16 g, 89% yield) was obtained as a white crystalline solid.

Compound 86-3 was obtained from oxazoline 86-1, anthracene boronic acid 54-1, and silaxanthone 11-3, following the general procedures XXIII, and XVI (no TMEDA added for the latter), as outlined in the scheme above.

General Procedure XVIIB. Double Amination of TBDMS Diether. Preparation of Compound 86-4

A solution of bis-TBDMS ether 86-3 (40 mg, 0.041 mmol) in anhydrous DCM (2 mL) was treated with 1 M $SOCl_2$ in DCM (0.25 mL, 0.25 mmol) at ambient temperature for 16 h. The solvent was then removed under reduced pressure, and the residue was extensively dried under high vacuum. The crude residue was dissolved in anhydrous DCM (2 mL) and added dropwise to a mixture of 2-(methylaminomethyl)-phenylboronic acid (110 mg, 0.67 mmol), $K_2CO_3$ (100 g, 0.72 mmol), and NaI (6 mg, 0.04 mmol) in anhydrous DMF (3 mL). The mixture was stirred at ambient temperature for 16 h. Then the mixture was filtered, the filtrate was concentrated under reduced pressure, and the residue was purified by reversed-phase flash chromatography (C18 $SiO_2$, eluted with gradient from 5% to 75% MeOH in water+0.05% TFA). The title compound (24 mg, 52% yield) was obtained as a dark-blue oil.

Preparation of Compound 86-5

Oxazoline 86-4 (24 mg, 0.021 mmol) was dissolved in 6 N HCl (5 mL), and the mixture was heated at 80° C. for 16 h. Then the reaction mixture was diluted with saturated $NH_4Cl$ and neutralized with 25% $NH_3$ (aq) to pH ~3-4. Aqueous mixture was extracted with DCM, combined extracts were dried over anhydrous $Na_2SO_4$, filtered and concentrated under reduced pressure. The residue was additionally purified by reversed phase flash chromatography (C18 $SiO_2$, eluted with gradient from 5% to 75% MeOH in water+0.05% TFA) yielding the title compound (11.7 mg, 52% yield) as a dark-blue solid.

Preparation of Compound 86

A mixture of carboxylic acid 86-5 (11.7 mg, 0.011 mmol), EDC.HCl (7.5 mg, 0.04 mmol), HOBt hydrate (2.15 mg, 0.014 mmol), APMA.HCl (6.5 mg, 0.036 mmol), and DIPEA (0.02 mL, 0.11 mmol) in anhydrous DMF (1 mL) was stirred at ambient temperature for 16 h. Then the reaction mixture was diluted with water, acidified with TFA and directly loaded onto C18 $SiO_2$ column for flash chromatography purification (eluted with gradient from 5% to 100% MeOH in water+0.05% TFA). The title compound (8.2 mg, 62% yield) was obtained as a dark-blue amorphous solid. HPLC-MS: m/z 1084.1 (calcd. 1083.6 for $M^+$).

UV/Vis: λ$_{max}$=650 nm. $^1$H NMR (400 MHz, MeOH-d$_4$) δ ppm 8.35 (br. s., 2H), 8.02-8.15 (m, 2H), 7.97 (br. s., 1H), 7.84-7.93 (m, 2H), 7.72-7.82 (m, 2H), 7.67 (m, J=6.1 Hz, 3H), 7.56-7.63 (m, 3H), 7.46-7.56 (m, 2H), 7.43 (d, J=2.9 Hz, 2H), 7.30 (d, J=9.7 Hz, 2H), 7.22-7.36 (m, 1H), 6.84 (dd, J=9.7, 2.8 Hz, 2H), 5.70 (s, 1H), 5.59 (br. s, 2H), 5.55 (br. s, 2H), 5.35 (quin, J=1.3 Hz, 1H), 4.81 (br. s, 2H), 4.84 (br. s, 2H), 3.56 (t, J=5.7 Hz, 2H), 3.39 (t, J=6.5 Hz, 2H), 3.36 (s, 12H), 2.83 (s, 3H), 2.78 (s, 3H), 1.91-1.95 (m, 2H), 1.92 (s, 3H), 0.66 (s, 3H), 0.65 (s, 3H).
Preparation of Compound 25
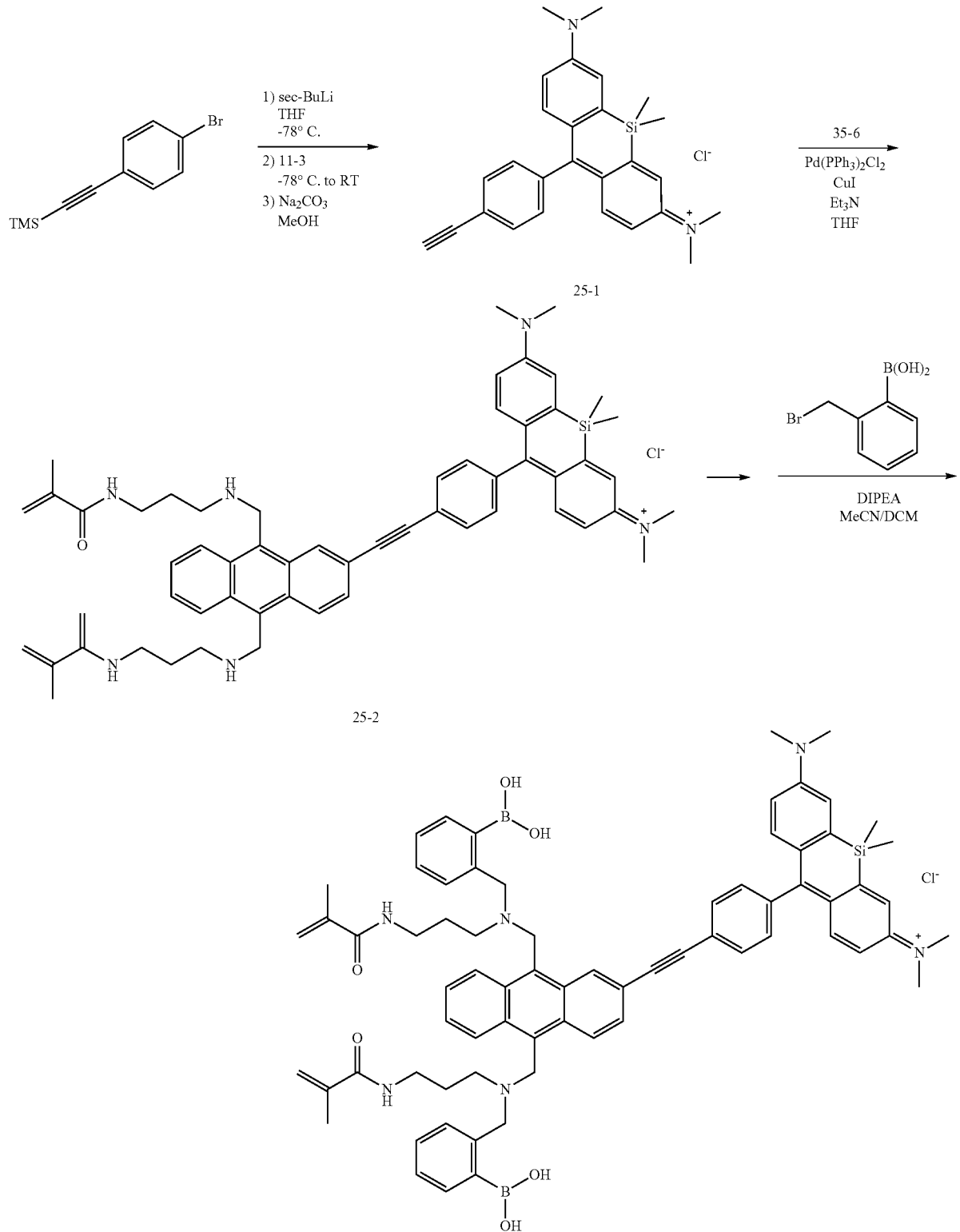
Compound 25

Intermediate 25-1 was prepared from, 1-bromo-4-[2-(trimethylsilyl)-ethynyl]benzene and intermediate 11-3 per the general procedure X followed by a basic workup.

General Procedure XXIV. Sonogashira Coupling. Preparation of Compound 25-2

A mixture of aryl alkyne 25-1 (250 mg, 0.61 mmol), aryl bromide 35-6 (374 mg, 0.73 mmol), Pd(PPh₃)₂Cl₂ (43 mg, 0.06 mmol), copper(I) iodide (12 mg, 0.06 mmol), and triethylamine (2 mL) in degassed THF (15 mL) was refluxed under argon for 16 h. Then the reaction mixture was concentrated under reduced pressure, the residue was dissolved in MeOH, and filtered through Celite®. Filtrate was concentrated again and the residue was purified by reversed phase flash chromatography (C18 SiO$_2$, eluted with gradient of MeOH in water+0.25% HCl) affording the title compound 25-2 (78 mg, 15%) as a brown oil.

Compound 25 was prepared from the intermediate 25-2 following the general procedure V, as outlined in the scheme above. HPLC-MS: m/z 1162.4 (calcd. 1161.6 for M⁺). UV/Vis: $\lambda_{max}$=650 nm.

Preparation of Compound 81

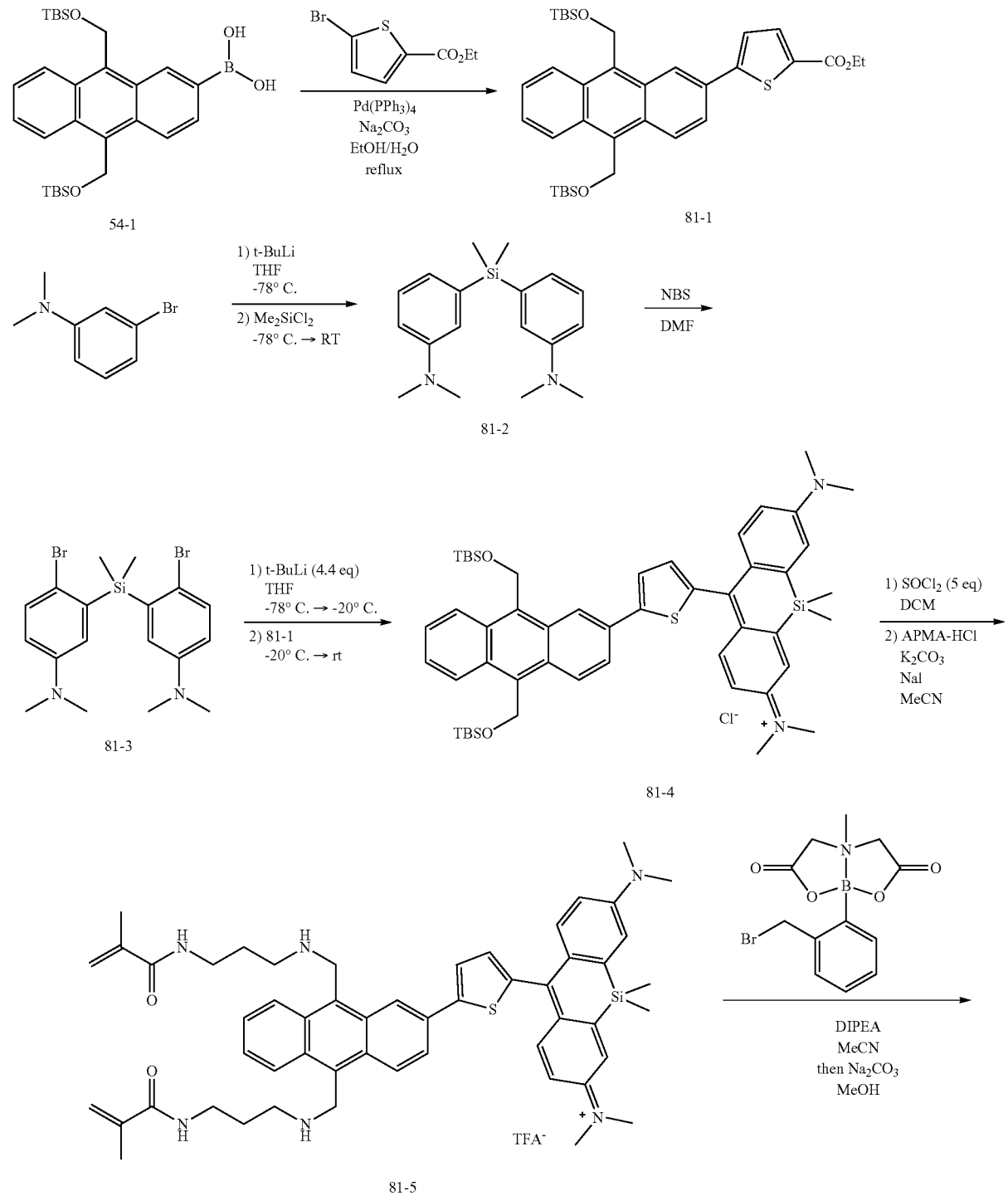

-continued

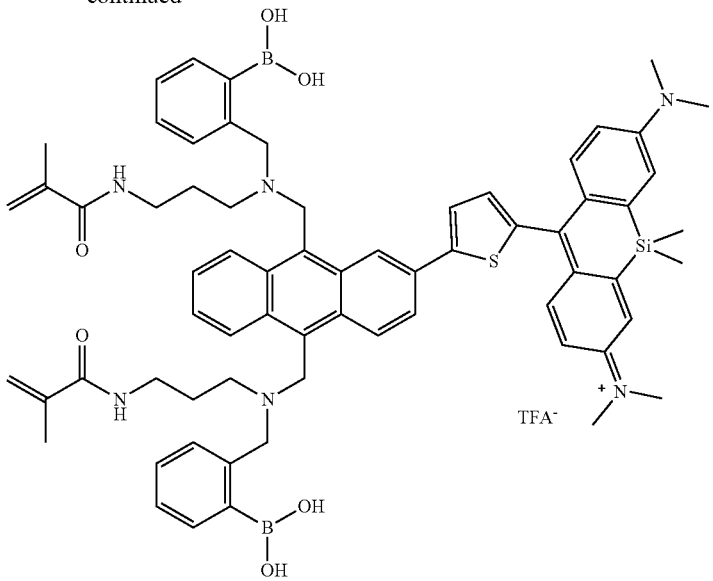

Compound 81

Intermediate 81-1 was prepared from intermediate 54-1 and ethyl 5-bromo-2-thiophenecarboxylate following the general procedure XXIII. Intermediate 81-3 was prepared following the published procedure (Grimm, J. B.; Brown, T. A.; Tkachuk, A. N.; Lavis, L. D. *ACS Cent. Sci.* 2017, 3 (9), 975-985).

Preparation of Compound 81-4

According to general method described in literature (Grimm, J. B.; Brown, T. A.; Tkachuk, A. N.; Lavis, L. D. *ACS Cent. Sci.* 2017, 3 (9), 975-985), solution of intermediate 81-3 (46.7 mg, 0.10 mmol) in anhydrous THF (3 mL) was cooled to −78° C. under argon atmosphere. To the solution, tert-BuLi (1.52 M in pentane, 0.29 mL, 0.44 mmol) was added dropwise. The bright-yellow reaction mixture was stirred at −78° C. for 30 min and then warmed up to −20° C. Solution of ethyl ester 81-1 (140 mg, 0.225 mmol) in anhydrous THF (3 mL) was added slowly and the reaction mixture was allowed to warm up to ambient temperature and stirred for 16 h. The reaction was quenched with half-saturated NH$_4$Cl, acidified with 1 M HCl until dark-green color, and extracted with DCM (3×). Combined organic extracts were dried over anhydrous Na$_2$SO$_4$, filtered, and concentrated under reduced pressure. The residue was purified by flash chromatography (SiO$_2$, eluted with gradient from 0 to 25% MeOH in DCM) yielding the desired product (28 mg, 32%) as a dark-green solid.

Compound 81 was prepared form intermediate 81-4, following general procedures XVIIA and XV. HPLC-MS: m/z 1144.1 (calcd. 1143.6 for M$^+$). UV/Vis: $\lambda_{max}$=670 nm.

Preparation of Compound 68

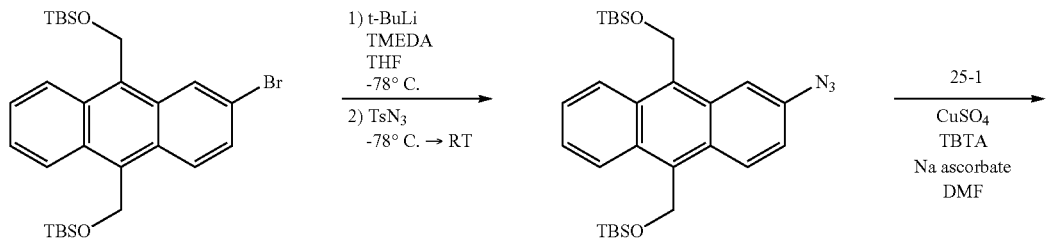

-continued

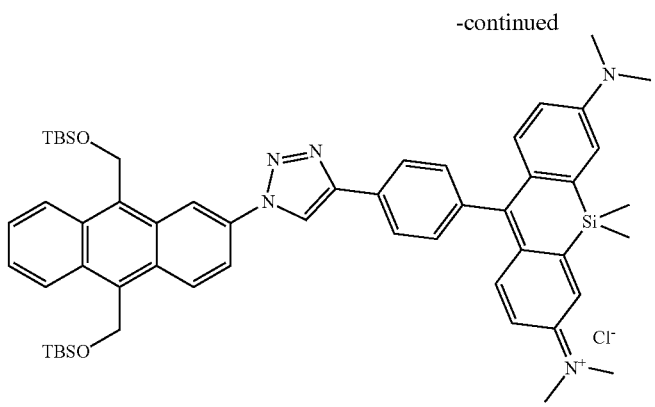

68-2

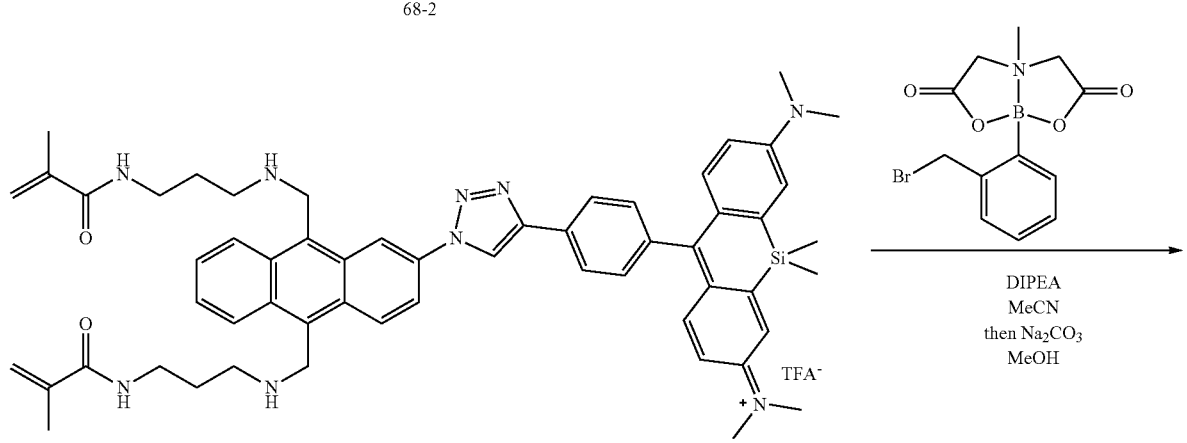

68-3

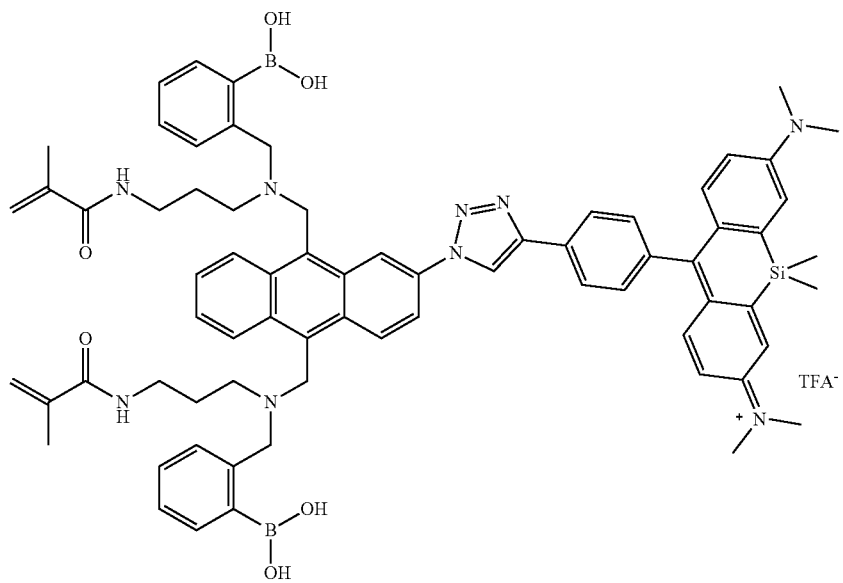

Compound 68

Preparation of Compound 68-1

Solution of aryl bromide 19-6 (555 mg, 1.02 mmol) and TMEDA (0.17 mL, 1.14 mmol) in anhydrous THF (4 mL) was cooled to −78° C. under argon. To this solution t-BuLi (c=1.52 M in cyclohexane, 0.74 mL, 1.12 mmol) was added dropwise. After 5 min, tosyl azide (13.6% w/w in toluene, 1.6 mL, 0.99 mmol) was added dropwise over 2 min. The reaction mixture was stirred at −78° C. for 30 min and then was quenched by water (10 mL) and was allowed to warm up to room temperature. Saturated NH₄Cl (10 mL) and DCM (15 mL) were added under vigorous stirring and then the layers were separated. Aqueous layer was discarded and organic layer was additionally washed with saturated NaHCO₃ and brine. Then the solution was dried over anhydrous Na₂SO₄, filtered, and concentrated under reduced pressure. The residue was purified by flash chromatography (SiO₂, eluted with gradient from 2% to 30% DCM in hexanes) affording 2-azidoanthracene 68-1 (442 mg, 85% yield) as a yellow solid. The product was stored under argon at −20° C. in the dark.

General Procedure XXV. Copper-Catalyzed Alkyne-Azide Cycloaddition. Preparation of Compound 68-2

A mixture of aryl alkyne 25-1 (86 mg, 0.19 mmol), aryl azide 68-1 (97 mg, 0.19 mmol), copper(II) sulfate pentahydrate (9.5 mg, 0.038 mmol), TBTA (20 mg, 0.038 mmol), and sodium (L)-ascorbate (15 mg, 0.075 mmol) in anhydrous DMF (10 mL) was stirred at room temperature for 16 h. Then the reaction mixture was diluted with ethyl acetate (75 mL) and washed with aqueous NH₄Cl (saturated solution diluted 1:10 with water, 100 mL), 5% w/w aqueous LiCl (100 mL) and brine (50 mL). Organic layer was dried over anhydrous Na₂SO₄, filtered, and concentrated under reduced pressure. The residue was purified by flash chromatography (SiO₂, eluted with gradient from 2% to 10% MeOH in DCM). This afforded title intermediate 68-2 (78 mg, 43% yield) as dark blue solid.

Compound 68 was prepared from intermediate 68-2 following general procedures XVIIA and XV, as outlined in the scheme above. HPLC-MS: m/z 1205.3 (calcd. 1204.6 for M⁺). UV/Vis: $\lambda_{max}$=650 nm.

Preparation of Compound 29

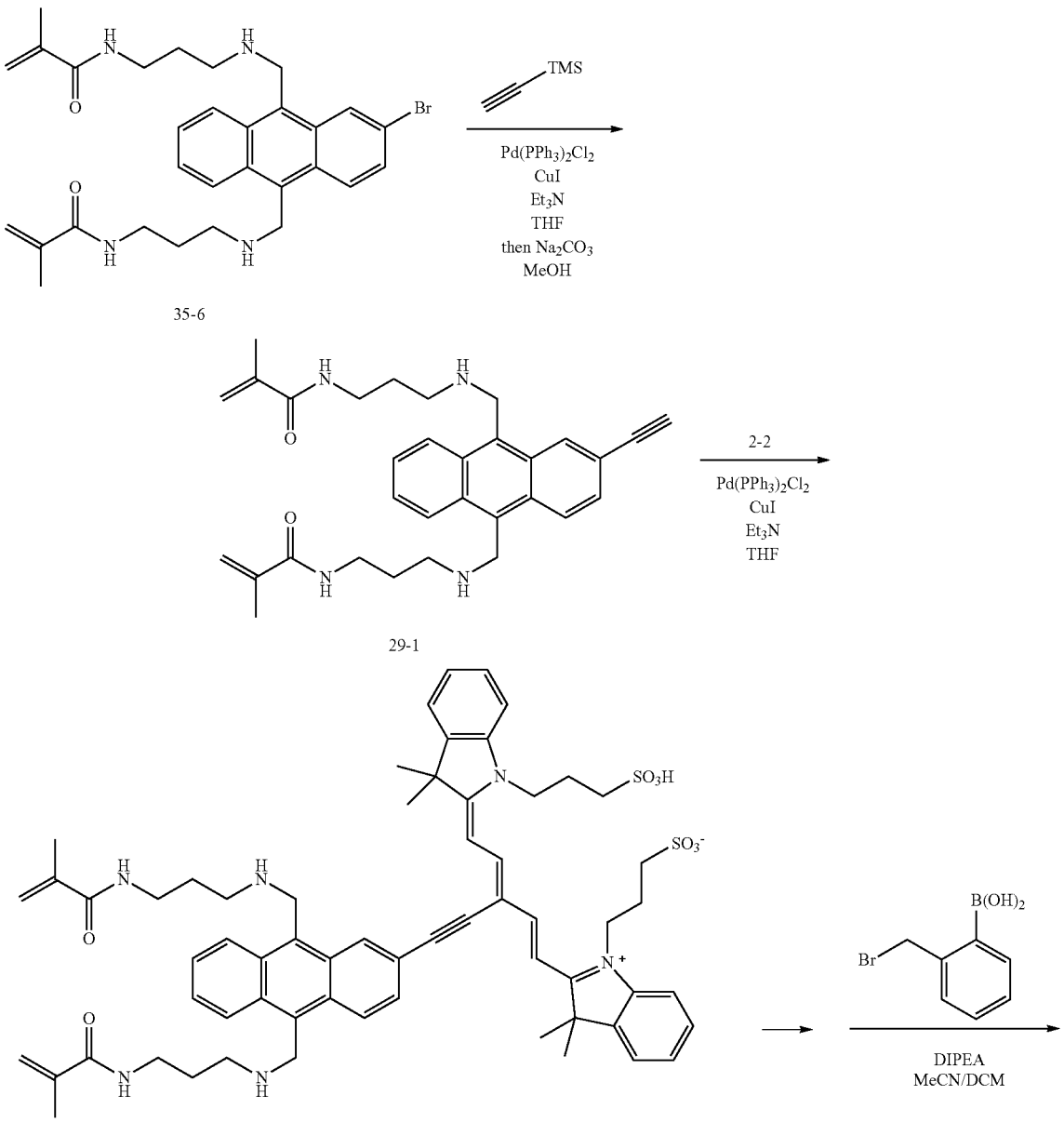

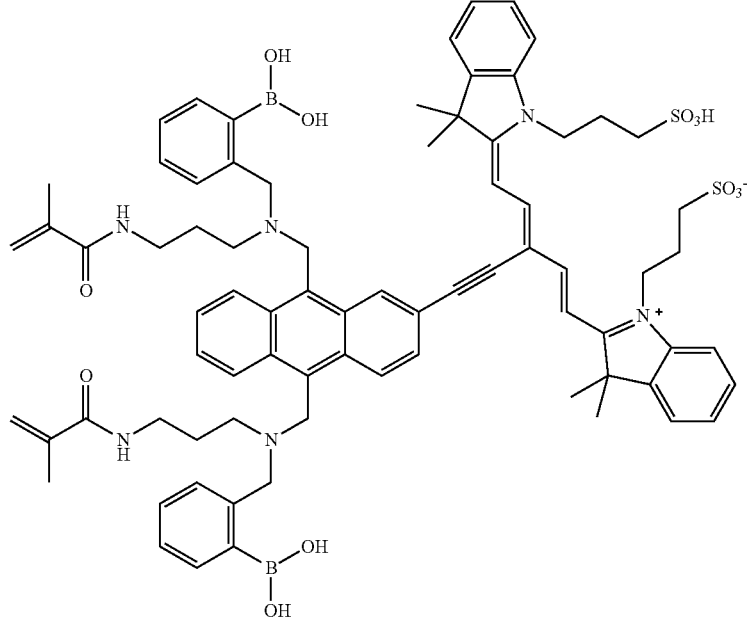
Compound 29
Intermediate 29-1 was prepared from intermediate 35-6 and ethynyltrimethylsilane following the general procedure XXIV followed by basic workup.
Compound 29 was prepared from intermediates 29-1 and 2-2 following the general procedures XXIV and V, as outlined in the scheme above. HPLC-MS: m/z 1376.6 (calcd. 1375.6 for M+H$^+$). UV/Vis: $\lambda_{max}$=650 nm.
Preparation of Compound 70
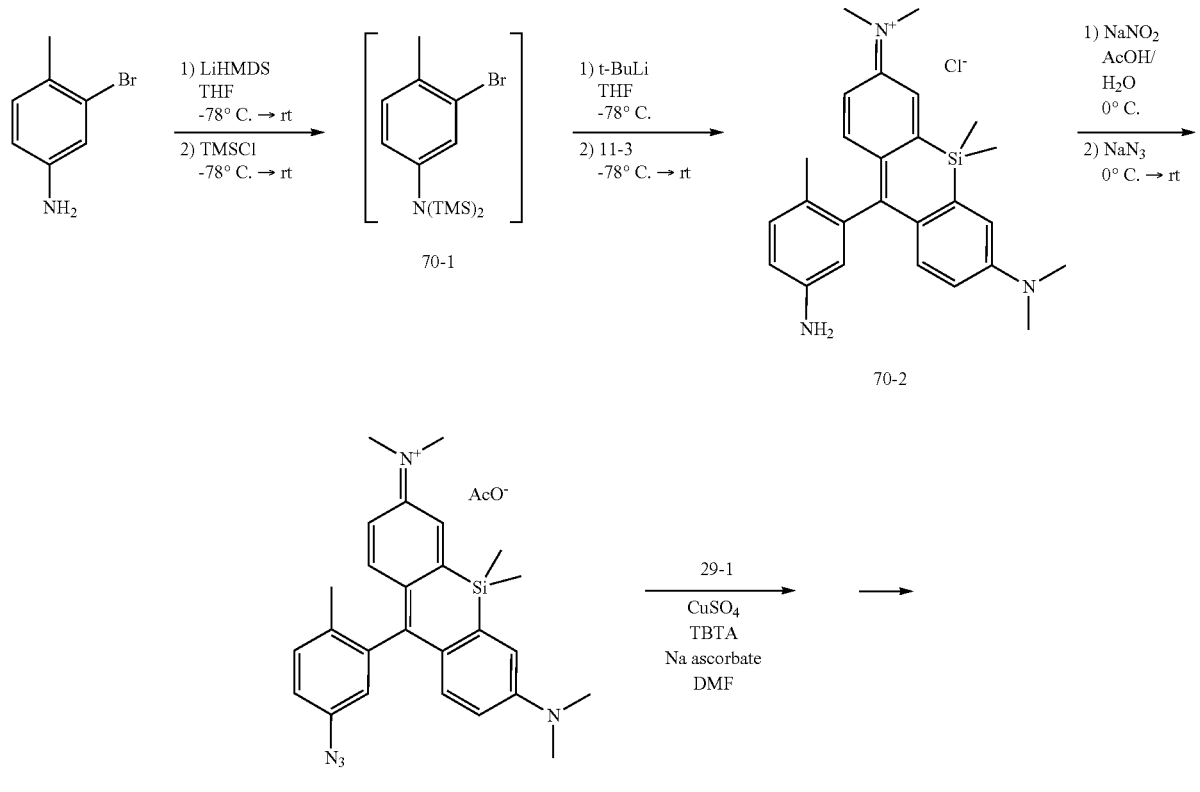

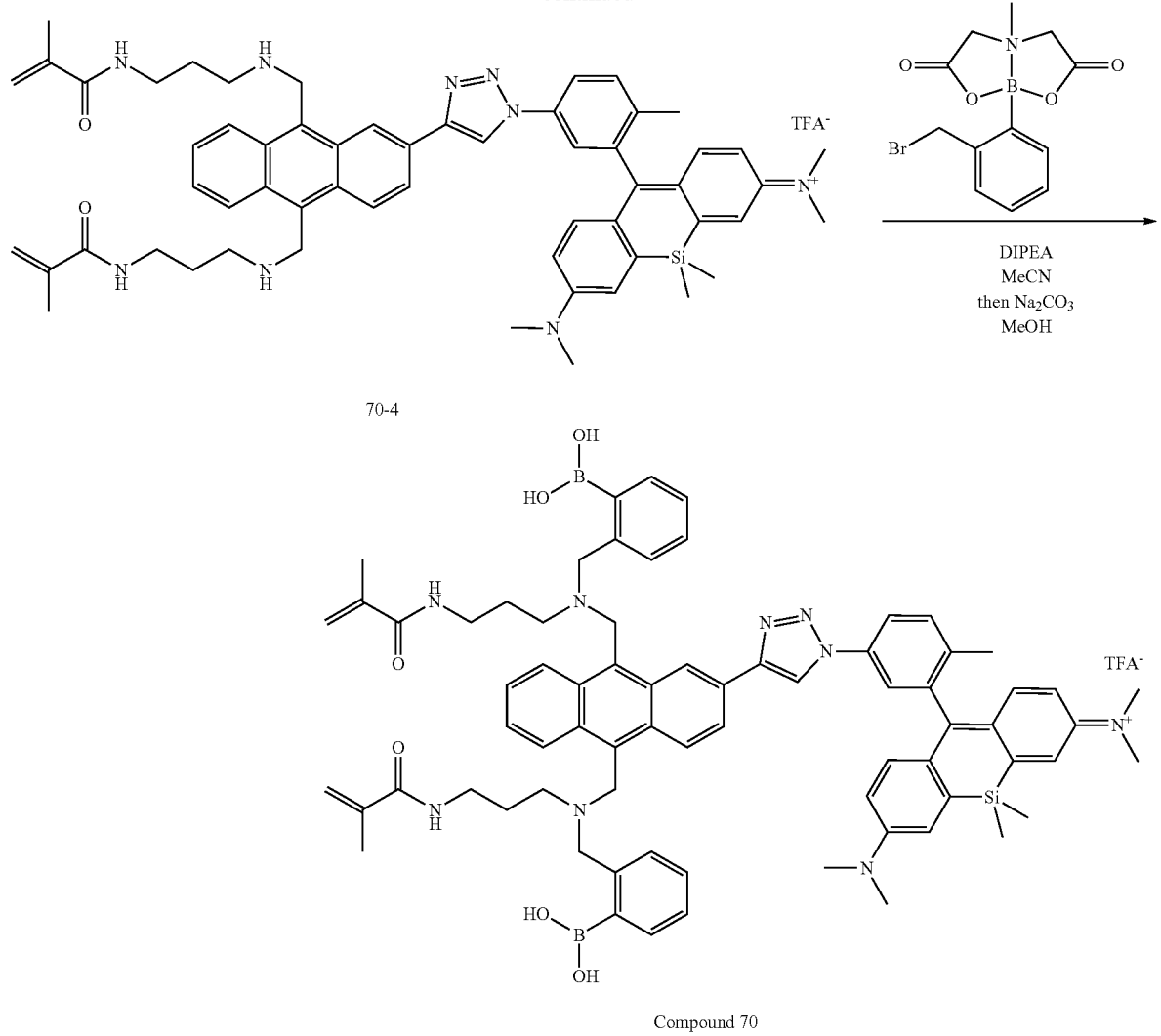

70-4

Compound 70

The preparation of intermediate 70-1 was accomplished based on the procedures reported for analogous compounds (Bertozzi, C. R.; Shieh, P. U.S. Pat. No. 9,410,958).

Preparation of Compound 70-1

Solution of 3-bromo-4-methylaniline (1.10 g, 5.9 mmol) in anhydrous THF (30 mL) was cooled to −78° C. under argon atmosphere. LiHMDS (1.05 M in THF, 11.8 mL, 12.4 mmol) was added dropwise over 10 min. The reaction mixture was allowed to warm up to ambient temperature, stirred for 15 min, and then was cooled back to −78° C. under argon atmosphere. Chlorotrimethylsilane (1.6 mL, 12.6 mmol) was added dropwise over 10 min, and the reaction mixture was allowed to warm up to ambient temperature and stirred for 1 h. Then the solvent was removed under reduced pressure. The resulting residue was suspended in hexanes, filtered, and the filtrate was concentrated under reduced pressure. The crude product 70-1 (1.85 g, 95% yield) was obtained as a brown-orange liquid after thorough drying under high vacuum. The product was used in the next step without further purification.

Preparation of Compound 70-2

Crude TMS-protected aniline 70-1 (1.85 g, 5.6 mmol) was dissolved in anhydrous THF (15 mL), and the solution was cooled to −78° C. under argon atmosphere. tert-BuLi (1.52 M in pentane, 4.5 mL, 6.84 mmol) was added dropwise and the solution was stirred at −78° C. for 30 min. Then solution of silaxanthone 11-3 (0.075 M in THF, 55 mL, 4.13 mmol) was quickly added, and the reaction mixture was allowed to warm up to ambient temperature. After 1 h of stirring, the reaction was quenched with 1 M HCl (16 mL) and the mixture was concentrated under reduced pressure. The residue was neutralized with saturated NaHCO$_3$ (100 mL) and then aqueous slurry was extracted with DCM (5×25 mL). Combined organic extracts were dried over anhydrous Na$_2$SO$_4$, filtered, and concentrated under reduced pressure. The residue was purified by flash chromatography (SiO$_2$, eluted with gradient from 2 to 20% of MeOH in DCM), affording the desired Si-rhodamine 70-2 (0.75 g, 40% yield) as a blue solid.

Preparation of Compound 70-3

A solution of aniline 70-2 (0.20 g, 0.44 mmol) in a mixture of glasial acetic acid and water 2:1 (v/v) was cooled to 0° C. To this mixture NaNO$_2$ (46 mg, 0.67 mmol) was added as solid, and the mixture was stirred at 0° C. for 5 min, followed by addition of NaN$_3$ (60 mg, 0.92 mmol). The reaction mixture was allowed to warm up to ambient temperature over 1.5 h, at which point the reaction was complete. The reaction mixture was slowly poured into 20% (w/v) aqueous Na$_2$CO$_3$ (100 mL) and the resulting slurry was extracted with DCM (3×). Combined organic extracts were dried over anhydrous Na$_2$SO$_4$, filtered, and concentrated under reduced pressure. Desired product 70-3 was obtained as a dark-blue solid without purification (190 mg, 86%).

Compound 70 was prepared from intermediates 70-3 and 29-1 in accordance with general procedures XXV and XV as outlined in the scheme above. HPLC-MS: 1219.3 (calcd. 1218.6 for M$^+$). UV/Vis: $\lambda_{max}$=650 nm. $^1$H NMR (400 MHz, MeOH-d$_4$) δ ppm 9.05 (br. s., 1H), 8.62 (br. s., 1H), 8.04-8.32 (m, 4H), 7.85-8.02 (m, 2H), 7.71 (d, J=8.8 Hz, 1H), 7.42-7.50 (m, 3H), 7.37-7.42 (m, 3H), 7.26-7.37 (m, 5H), 7.24 (d, J=9.6 Hz, 2H), 7.14 (t, J=6.6 Hz, 1H), 6.82 (d, J=9.1 Hz, 2H), 5.36 (s, 1H), 5.30 (s, 1H), 5.15 (quin, J=1.3 Hz, 1H), 5.10 (quin, J=1.2 Hz, 1H), 4.42-4.71 (m, 4H), 4.00 (br. s., 4H), 3.33 (s, 12H), 2.92-3.03 (m, 2H), 2.84-2.92 (m, 2H), 2.60-2.68 (m, 2H), 2.54-2.60 (m, 2H), 2.18 (s, 3H), 1.77-1.84 (m, 2H), 1.75 (s, 2H), 1.69 (s, 3H), 1.64 (s, 3H), 0.63 (s, 3H), 0.65 (s, 3H).

Preparation of Compound 72

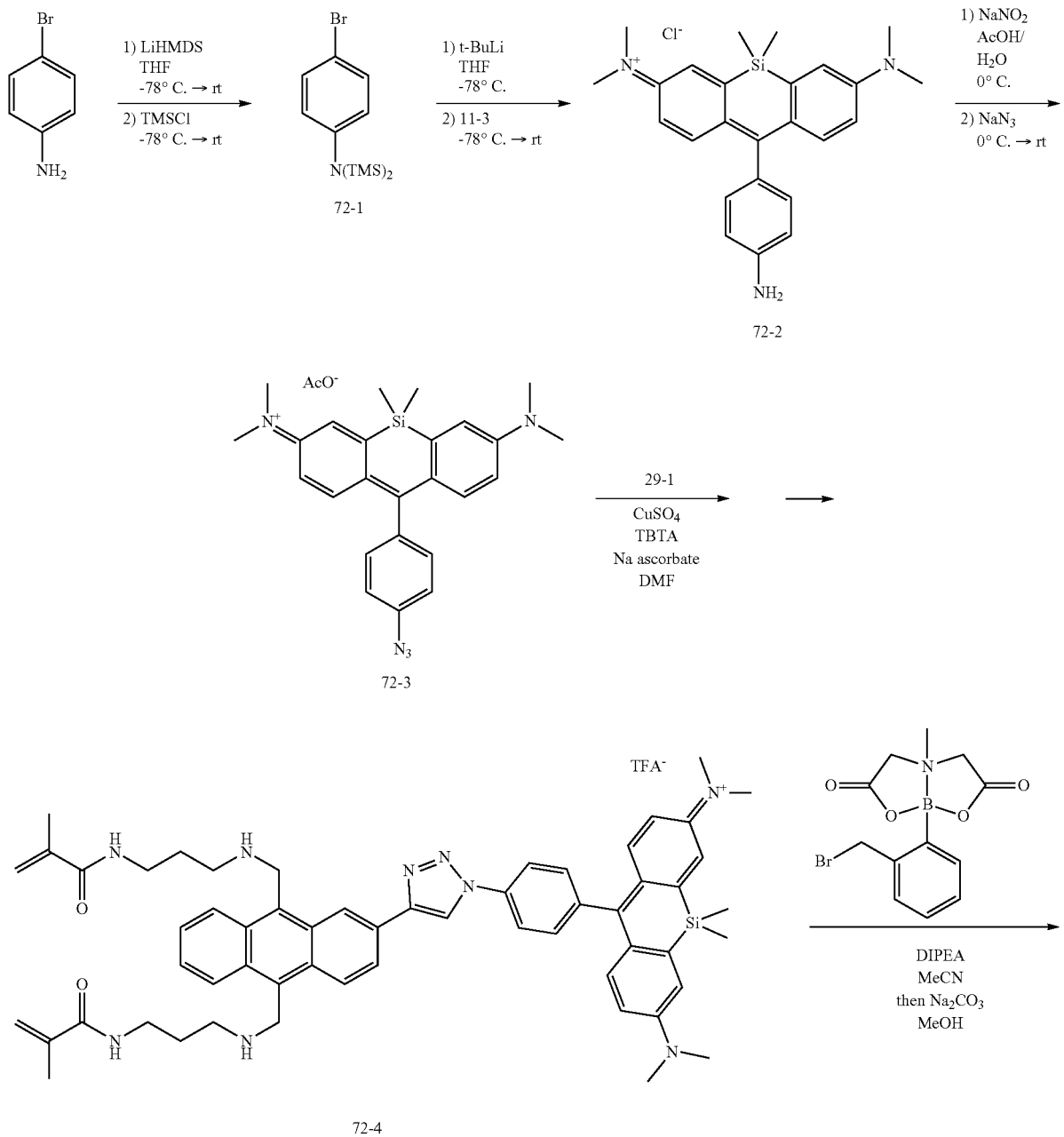

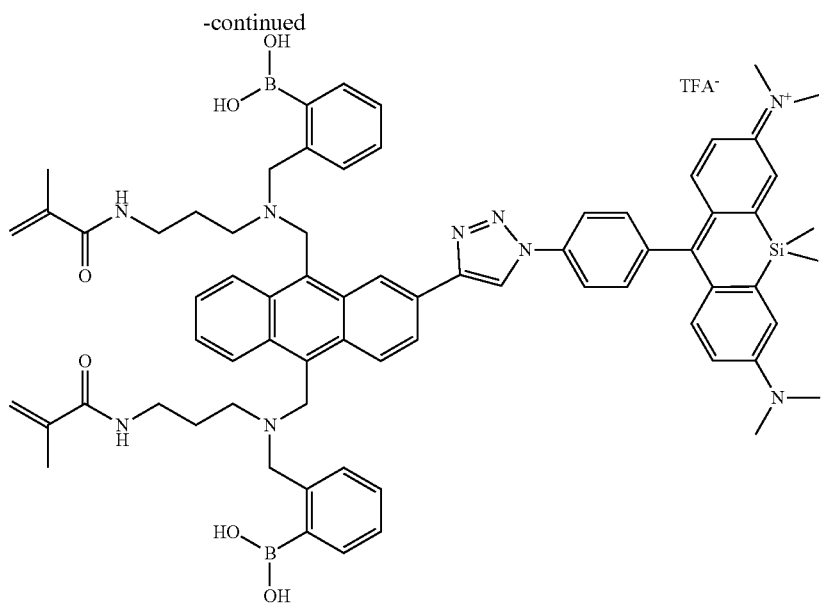
Compound 72
The compound 72 was synthesized via the same steps described for compound 70, starting from 4-bromoaniline and intermediates 11-3 and 29-1 (see the scheme above). HPLC-MS: 1205.5 (calcd. 1204.6 for M$^+$). UV/Vis: $\lambda_{max}$=650 nm.
Preparation of Compound 32
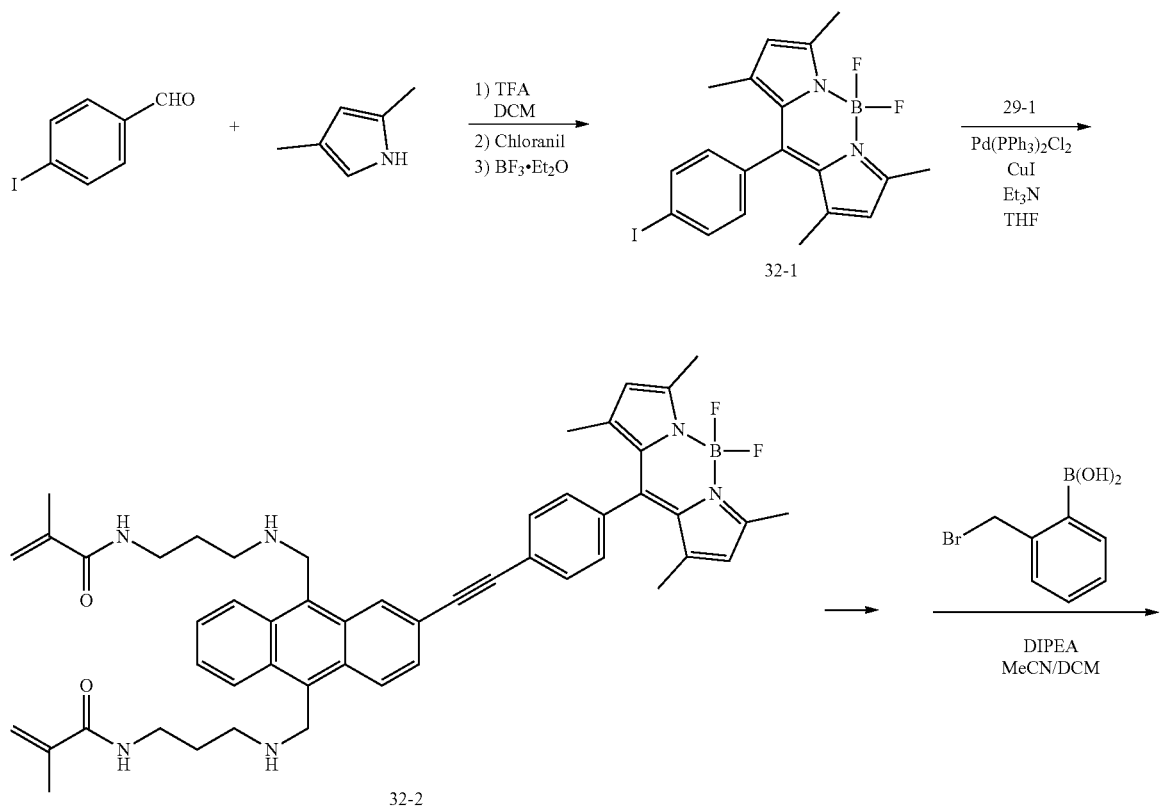

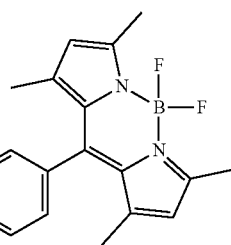
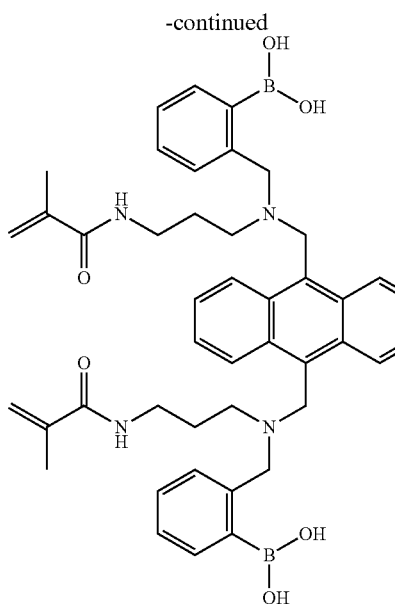

Compound 32

Compound 32 was prepared from 4-iodobenzaldehyde, 2,4-dimethylpyrrole, and intermediate 29-1 following the general procedures VII, XXIV, and V, as outlined in the scheme above. HPLC-MS: m/z 1102.0 (calcd. 1101.6 for M+H$^+$). UV/Vis: $\lambda_{max}$=500 nm. $^1$H NMR (400 MHz, MeOH-d$_4$) δ ppm 8.42 (d, J=8.5 Hz, 2H), 8.28 (d, J=8.8 Hz, 2H), 7.85 (d, J=8.0 Hz, 2H), 7.48-7.63 (m, 4H), 7.44 (d, J=8.0 Hz, 2H), 7.36-7.48 (m, 3H), 7.20-7.36 (m, 4H), 6.09 (s, 2H), 5.37 (s, 1H), 5.35 (s, 1H), 5.20 (quin, J=1.5 Hz, 1H), 5.16 (quin, J=1.5 Hz, 1H), 4.51-4.76 (m, 4H), 4.04 (br. s., 2H), 3.97 (s, 2H), 3.02 (t, J=7.0 Hz, 4H), 2.67 (t, J=7.4 Hz, 2H), 2.56-2.63 (m, 2H), 2.51 (s, 6H), 1.74-1.90 (m, 4H), 1.72 (s, 3H), 1.70 (s, 3H), 1.52 (s, 6H).

Preparation of Compound 34

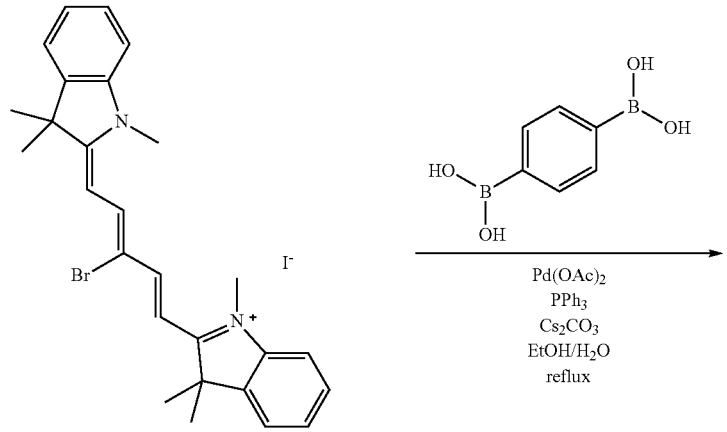

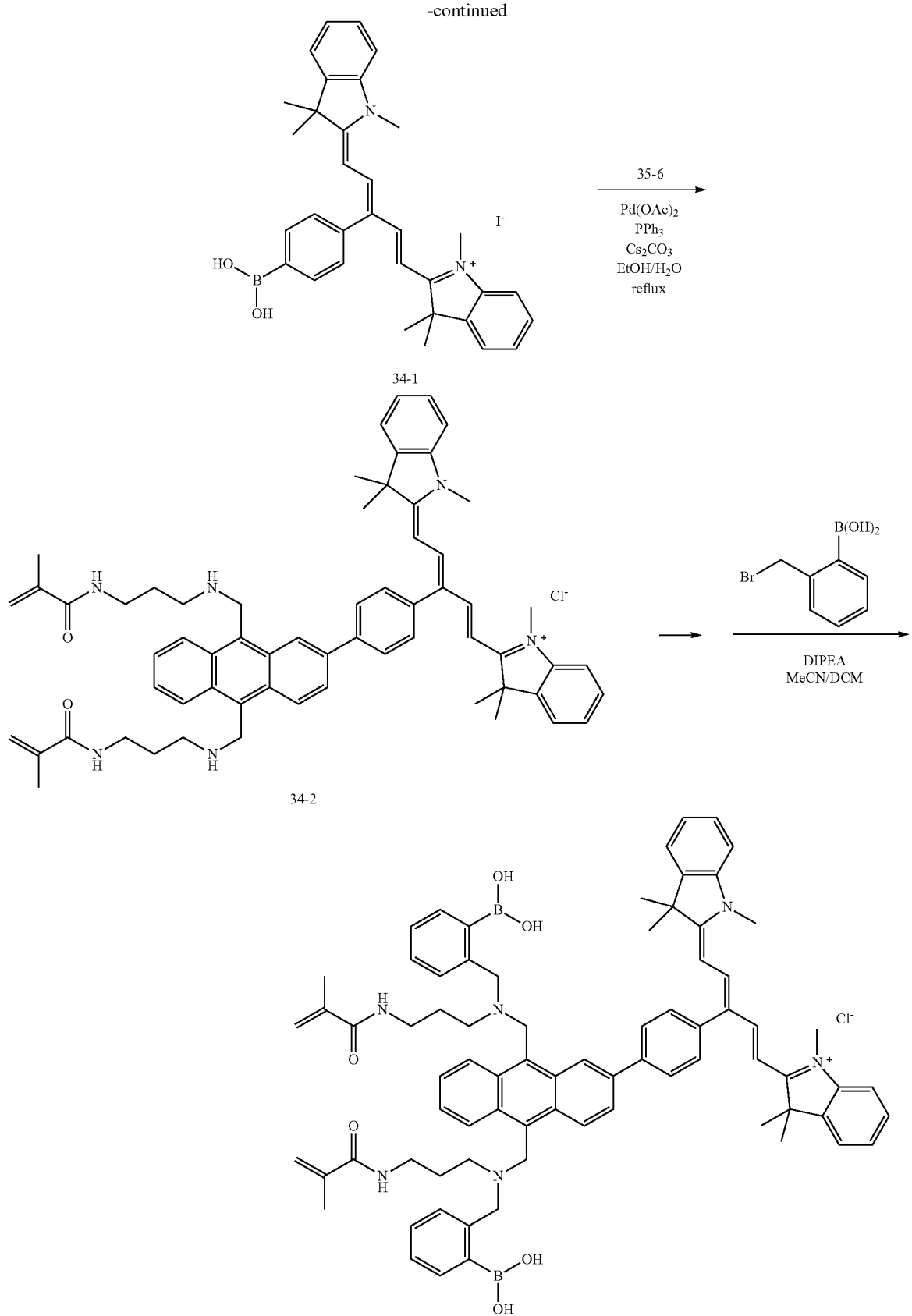
Compound 34

Compound 34 was prepared from benzene-1,4-diboronic acid and intermediates 1-2 and 35-6, following the general procedures III (twice) and V, as outlined in the scheme above. HPLC-MS: m/z 1212.6 (calcd. 1211.7 for M$^+$). UV/Vis: $\lambda_{max}$=635 nm. $^1$H NMR (400 MHz, CDCl$_3$) δ ppm 8.14-8.44 (m, 5H), 8.08 (br. s., 1H), 7.95 (br. s., 1H), 7.83 (t, J=8.3 Hz, 3H), 7.68 (d, J=7.9 Hz, 1H), 7.30-7.51 (m, 15H), 7.07-7.15 (m, 3H), 5.86 (d, J=14.0 Hz, 2H), 5.37 (s, 2H), 5.34 (s, 1H), 5.32 (s, 1H), 5.11 (br. s, 2H), 5.09 (br. s, 2H), 4.54 (s, 2H), 4.51 (s, 2H), 3.94 (br. s, 3H), 3.92 (br. s, 3H), 3.39-3.43 (m, 2H), 2.88-2.93 (m, 2H), 2.46-2.62 (m, 4H), 1.82 (s, 12H), 1.69 (s, 3H), 1.67 (s, 3H), 1.52-1.63 (m, 4H).
Preparation of Compound 30
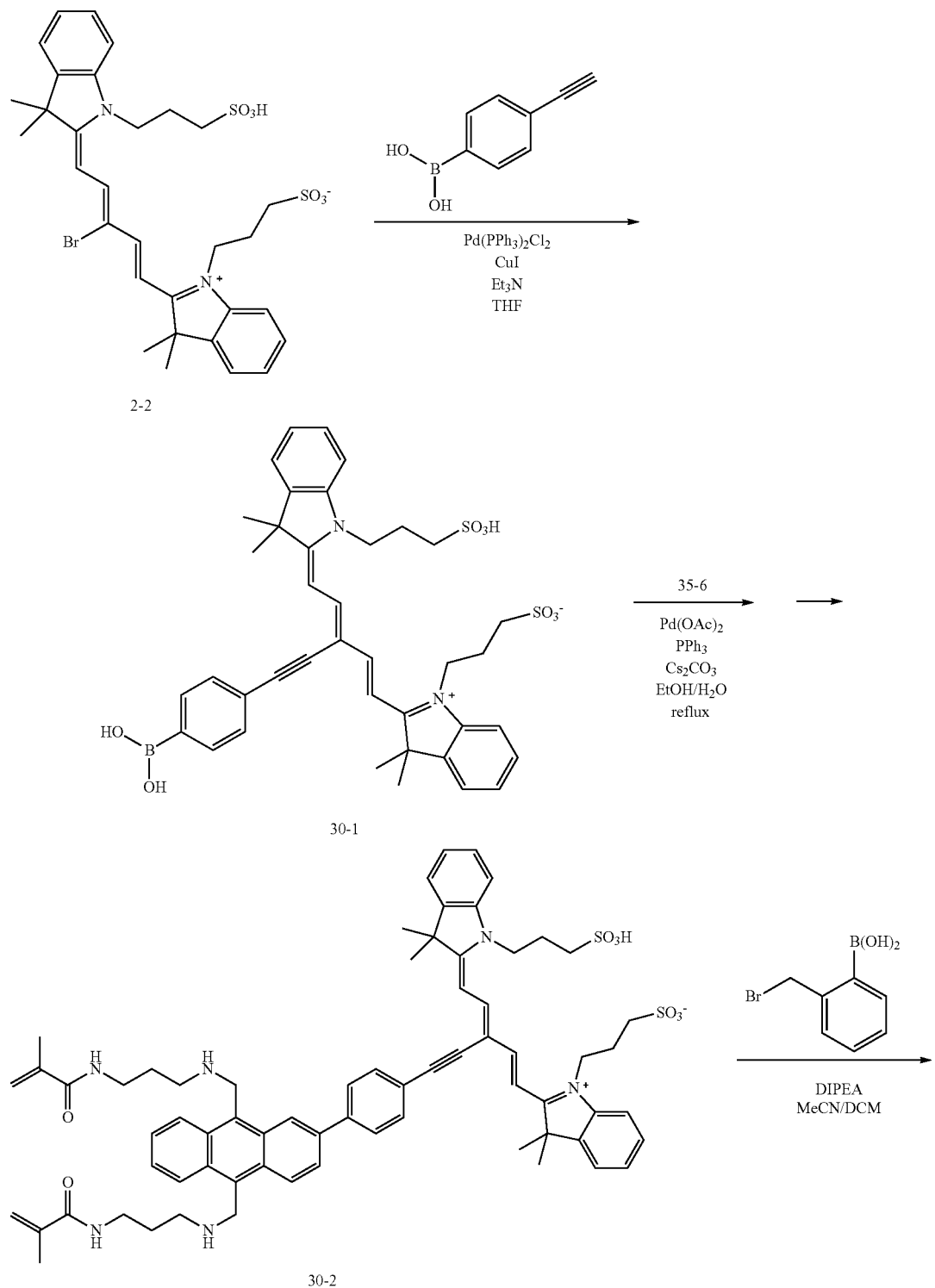

-continued
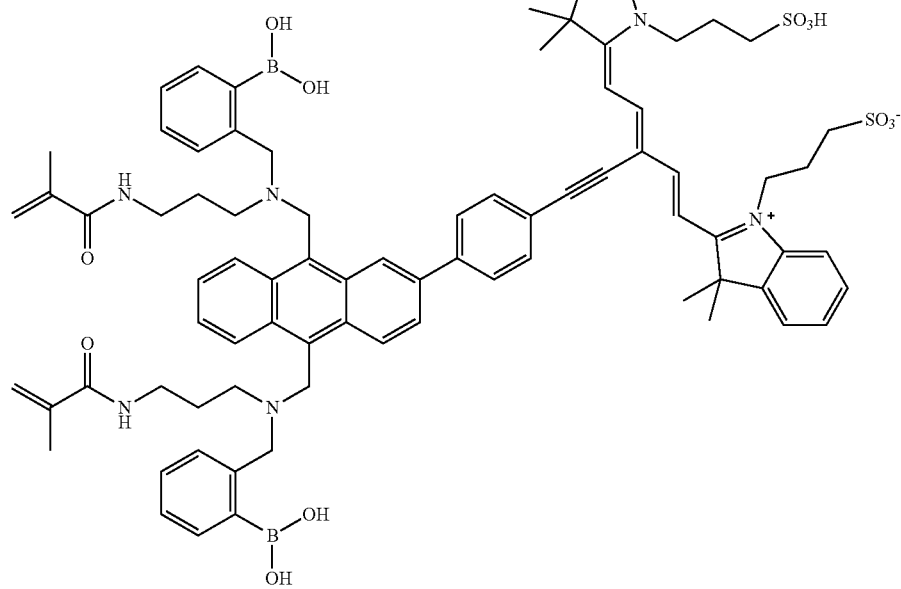
Compound 30
Compound 30 was prepared from 4-ethynylphenylboronic acid and intermediates 2-2 and 35-6 following the general procedures XXIV, III, and V, as outlined in the scheme above. HPLC-MS: m/z 1452.0 (calcd. 1451.7 for M+H$^+$). UV/Vis: $\lambda_{max}$=650 nm. $^1$H NMR (400 MHz, MeOH-d$_4$) δ ppm 8.45 (d, J=14.0 Hz, 2H), 7.90-8.04 (m, 3H), 7.72-7.75 (m, 1H), 7.60-7.70 (m, 3H), 7.37-7.59 (m, 13H), 7.16-7.37 (m, 7H), 6.78 (d, J=14.0 Hz, 2H), 5.38 (s, 1H), 5.37 (s, 1H), 5.17 (br. s, 1H), 5.15 (s, 1H), 4.40-4.53 (m, 4H), 3.09 (t, J=7.2 Hz, 4H), 3.03 (t, J=6.6 Hz, 4H), 2.41 (quin, J=7.7 Hz, 4H), 1.68-1.72 (m, 3H), 1.67 (s, 3H), 1.26-1.33 (m, 16H).
Preparation of Compound 31
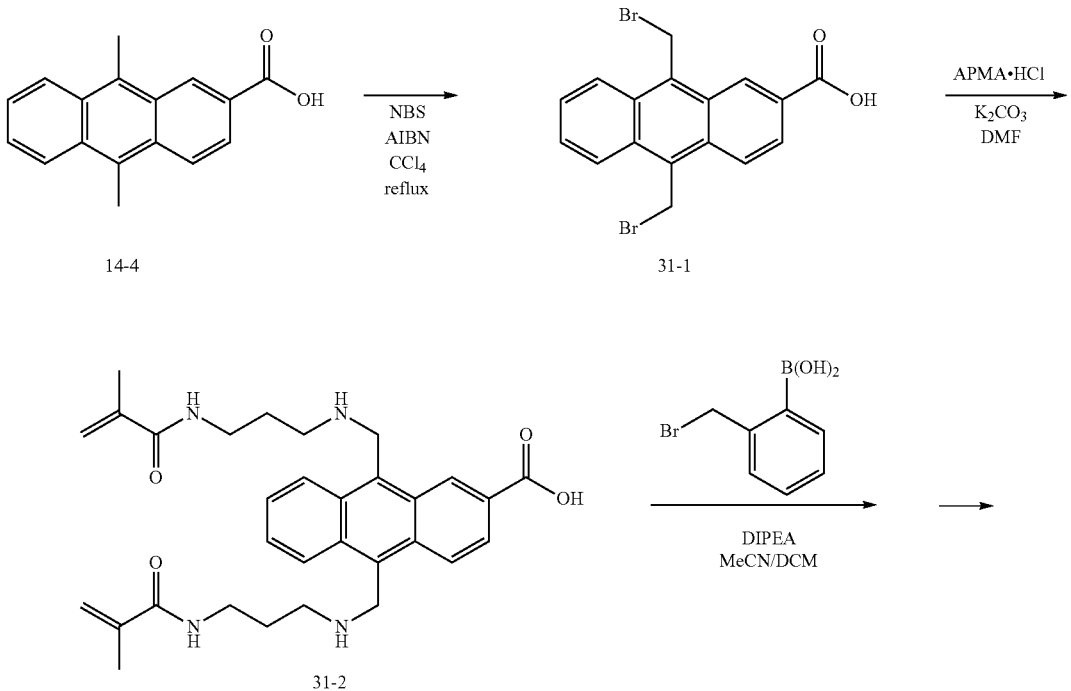

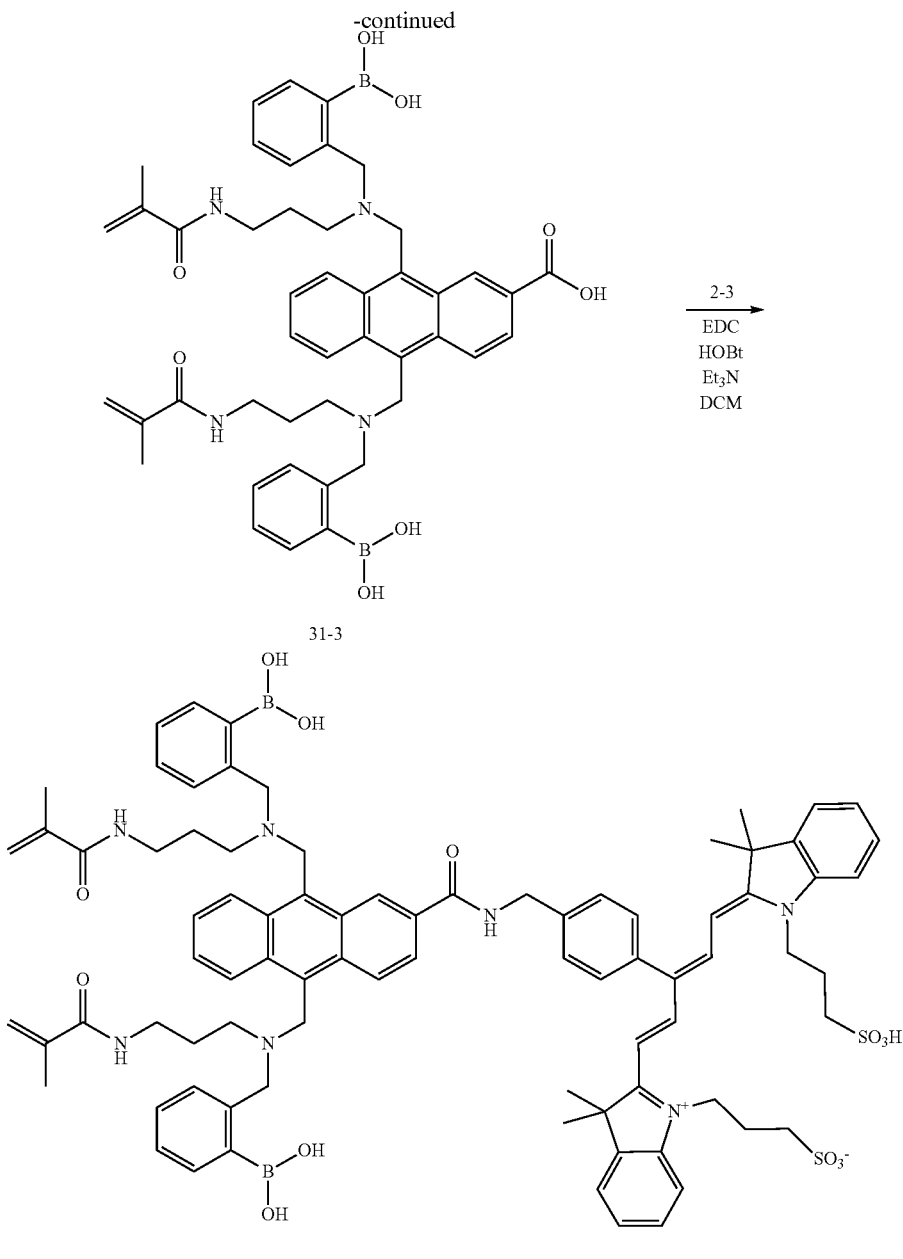

Compound 31

Intermediate 31-1 was prepared from intermediate 14-4 following the general procedure XIX.

Preparation of Compound 31-2

A mixture of bis-bromomethyl anthracene 31-1 (520 mg, 1.33 mmol), APMA.HCl (711 mg, 4.0 mmol), and potassium carbonate (1.57 g, 8.0 mmol) in anhydrous DMF (40 mL) was stirred at room temperature for 5 h. The solvent was then removed under reduced pressure. The residue was resuspended in minimal amount of MeOH and filtered. Filtrate was diluted with 0.1 M HCl and purified by reversed phase flash chromatography (C18 SiO$_2$, gradient of MeOH in water+0.25% HCl). This afforded intermediate 31-2 (118 mg, 17%) as a yellow oil.

Intermediate 31-3 was prepared from 31-2 following the general procedure V.

Preparation of Compound 31

A mixture of carboxylic acid 31-3 (11 mg, 0.014 mmol), Cy5 amine 2-3 (11 mg, 0.015 mmol), HOBt (2 mg, 0.015 mmol), EDC (3 mg, 0.016 mmol), and triethylamine (3 mg, 0.03 mmol) in anhydrous DCM (4 mL) was stirred at room temperature for 24 h. Then the reaction mixture was concentrated and the residue was purified by reversed phase flash chromatography (C18 SiO$_2$, eluted with gradient from 10% to 100% MeOH in water). This afforded compound 31 (15 mg, 70% yield) as dark blue solid. HPLC-MS: m/z 1487.9 (calcd. 1484.7 for M+H$^+$). UV/Vis: $\lambda_{max}$=650 nm.

Preparation of Compound 38
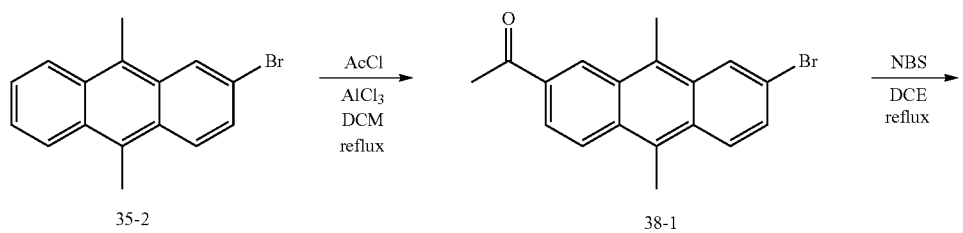
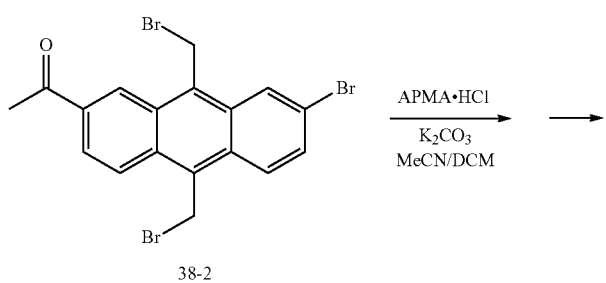
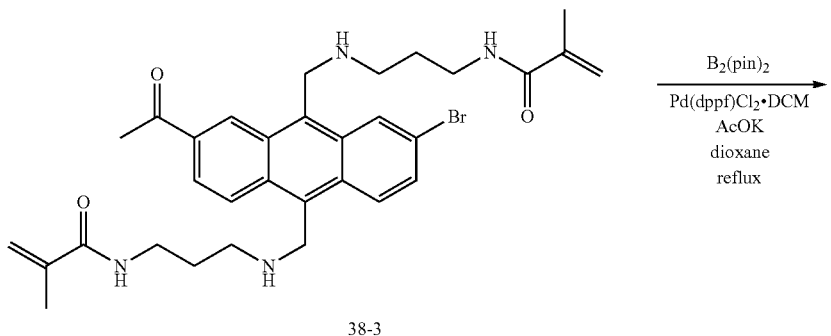
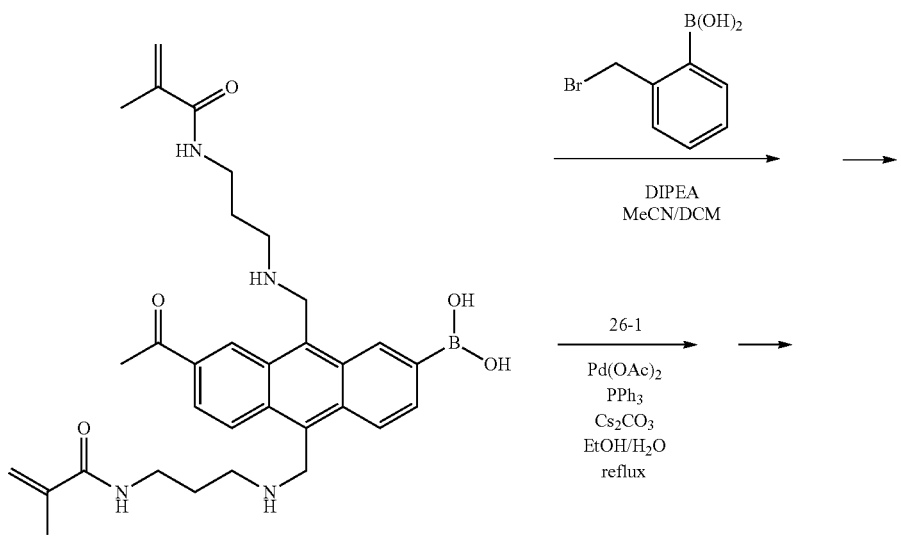

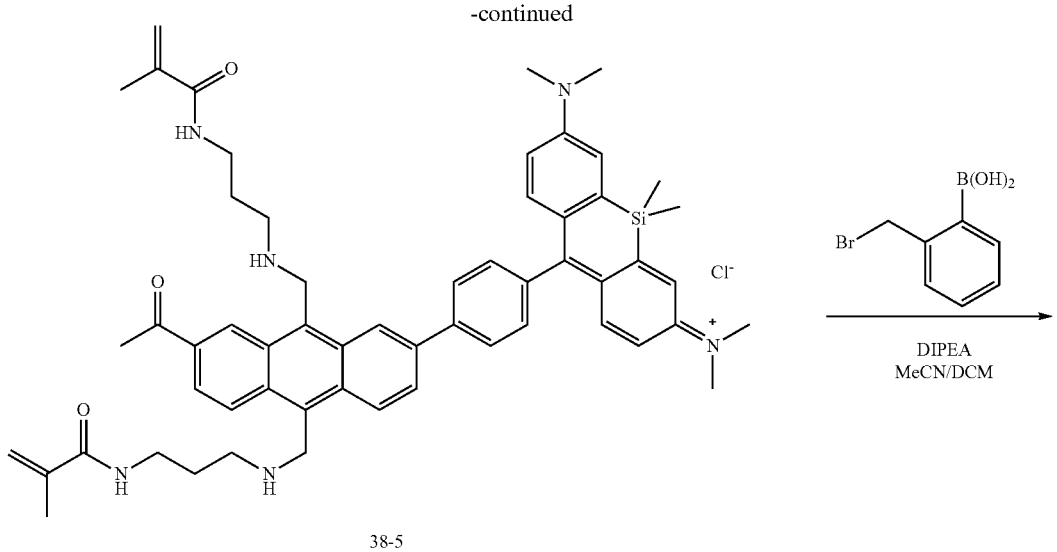

38-5

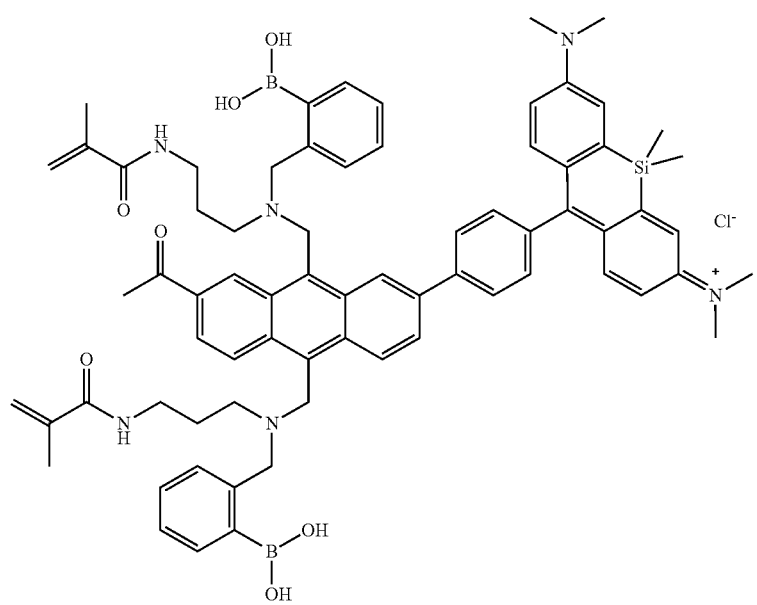

Compound 38

Preparation of Compound 38-1

The mixture of 2-bromo-9,10-dimethylanthracene 35-2 (2.5 g, 8.8 mmol), acetyl chloride (0.89 mL, 13.7 mmol), and anhydrous aluminum chloride (1.68 g, 12.6 mmol) in anhydrous DCM (200 mL) was stirred at ambient temperature for 24 h. Then water (200 mL) was added and layers were separated. Aqueous layer was additionally extracted with DCM (4×100 mL). The combined extracts were dried over anhydrous MgSO$_4$, filtered, and concentrated under reduced pressure. The residue was purified by flash chromatography (SiO$_2$, eluted with gradient from 0 to 100% of DCM in hexanes). The product was obtained as a bright-yellow solid; ~1:5 mixture of 6-acetyl and 7-acetyl regioisomers (2.74 g, 95%).

Preparation of Compound 38-2

The mixture of intermediate 38-1 (2.74 g, 9.6 mmol), N-bromosuccinimide (3.76 g, 21 mmol), and AIBN (5 mg, 0.03 mmol) was refluxed in anhydrous CCl$_4$ (120 mL) for 3 h. Then the reaction mixture was concentrated under reduced pressure. The residue was triturated with MeOH (200 mL). Collected solid was dried under high vacuum to yield the desired product 38-2 (3.27 g, 70%) as a yellow-orange powder.

Preparation of Compound 38-3

To the suspension of APMA.HCl (9.9 g, 56 mmol) and K$_2$CO$_3$ (21 g, 155 mmol) in a mixture of anhydrous DCM and MeCN (1:1 v/v, 200 mL) that was pre-stirred at ambient temperature for 3 h, solid intermediate 38-2 (3.0 g, 6.2 mmol) was added. The reaction mixture was vigorously stirred at ambient temperature for 18 h. Then the reaction mixture was filtered and the filtrate was concentrated under reduced pressure. The residue was purified by reversed-phase flash chromatography (C18 SiO$_2$, eluted with gradient from 0 to 25% of MeOH in 0.1% HCl). Yield: 2.2 g (59%) of free base as a yellow solid; ca. 8:3 mixture of regioisomers.

Compound 38 was prepared from 38-3 and 26-1 according to the general procedures XII, III, and V, as outlined in the scheme above. HPLC-MS: m/z 1180.2 (calcd. 1179.6 for M$^+$). UV/Vis: $\lambda_{max}$=650 nm.

Preparation of Compound 41

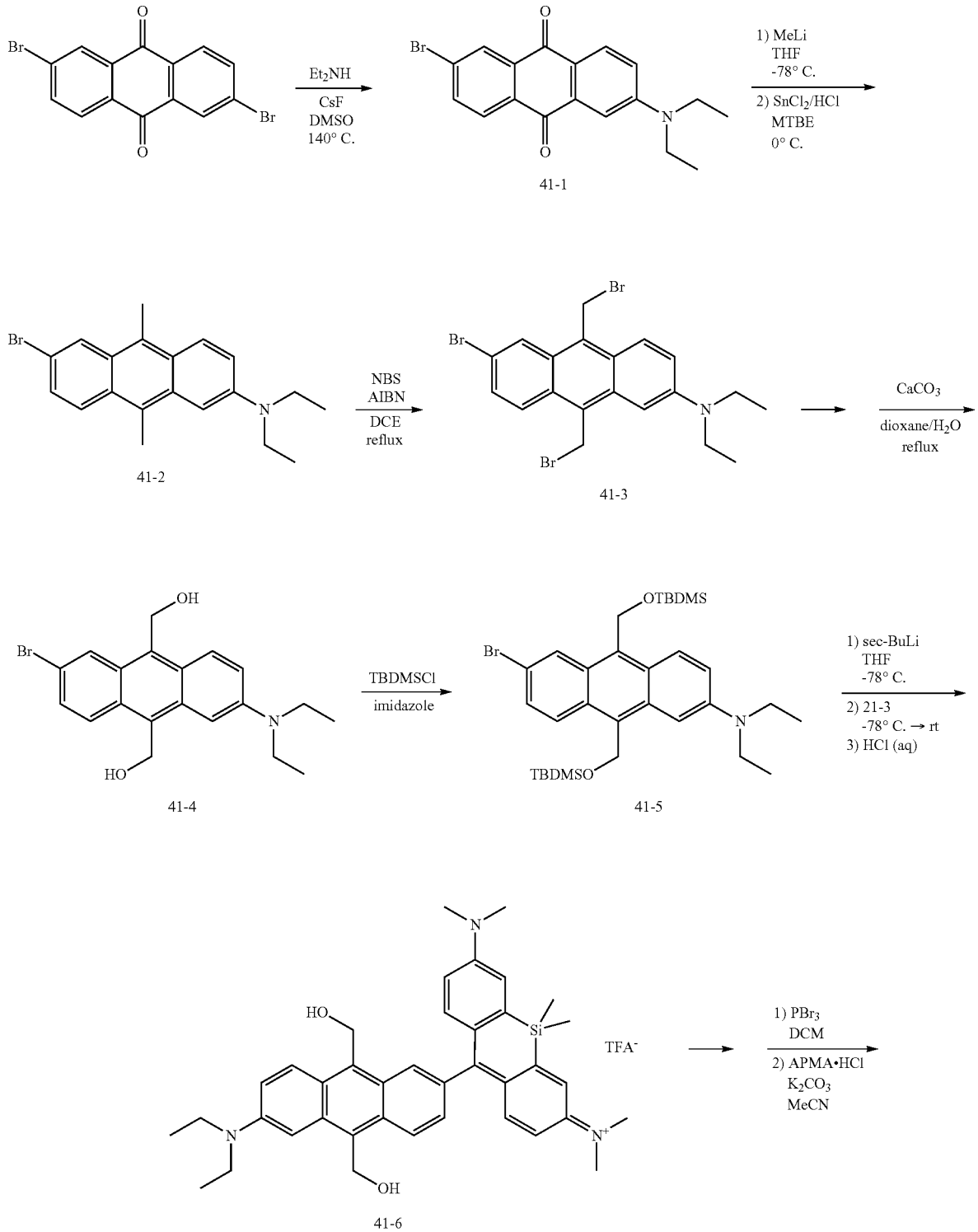

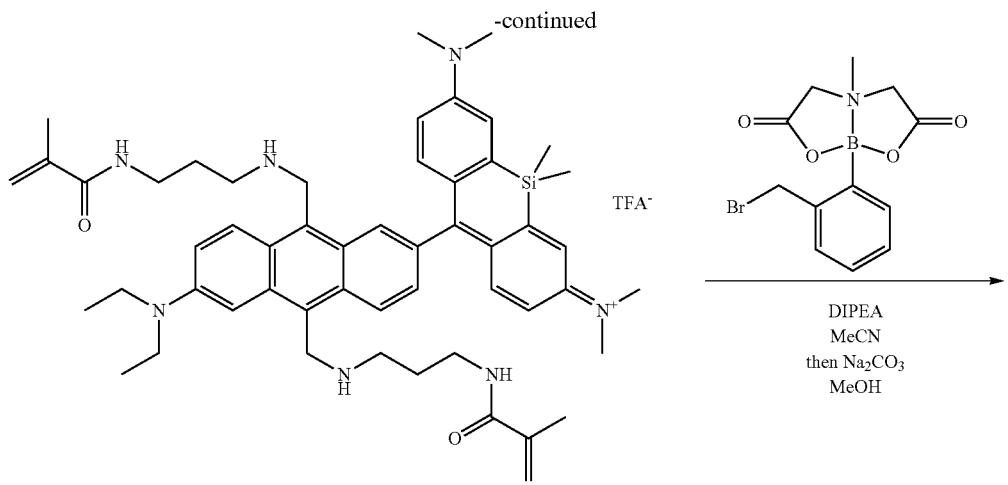

41-7

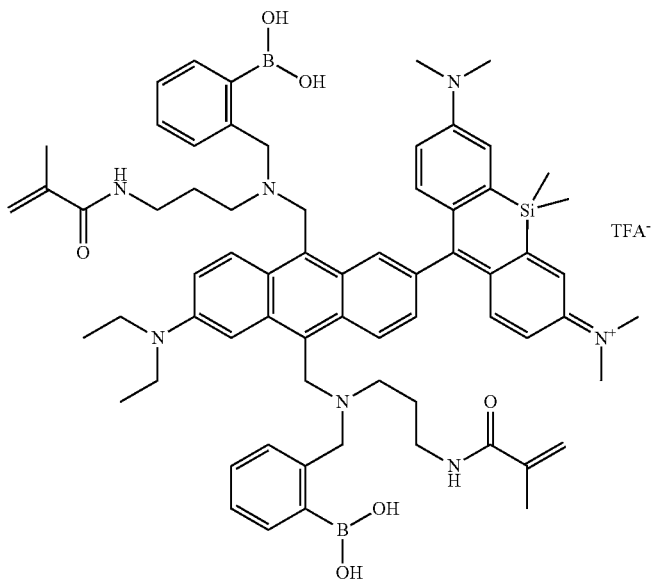

Compound 41

Preparation of Compound 41-1

A mixture of 2,6-dibromoanthraquinone (5.24 g, 14.4 mmol) and CsF (2.40 g, 15.8 mmol) in anhydrous DMSO (300 mL) was heated at 140° C. in a closed vessel under argon atmosphere for 6 h and then the mixture was cooled to ambient temperature. Diethylamine (3.0 mL, 2.1 mmol) and $K_2CO_3$ (3.98 g, 28.8 mmol) were added, and the reaction was continued at 50° C. for 48 h. Then the reaction mixture was diluted with water (1.5 L) and extracted with DCM (5×200 mL). Combined extracts were washed with brine and concentrated under reduced pressure. The residue was purified by flash chromatography ($SiO_2$, eluted with gradient from 0 to 100% of EtOAc in hexanes). The product 41-1 was obtained as a red solid (1.63 g, 32%).

Preparation of Compound 41-2

The solution of anthraquinone 41-1 (1.63 g, 5.68 mmol) in anhydrous THF (100 mL) was cooled to −78° C. under argon atmosphere. MeLi (1.6 M, 7.8 mL, 12.5 mmol) was added dropwise over 10 min, and the reaction was continued for 1 h at −78° C. Then the reaction mixture was allowed to warm up to room temperature, and was quenched with saturated $NH_4Cl$. The slurry was diluted with water and extracted with diethyl ether. The extract was concentrated under reduced pressure and the residue was purified by flash chromatography (SiO$_2$, eluted with gradient from 0 to 25% EtOAc in DCM). The purified intermediate diol was dissolved in THF (30 mL) and added dropwise to the mixture of SnCl$_2$ (9.48 g, 42 mmol) in 1 M HCl (20 mL) and diethyl ether (100 mL) at ambient temperature. The reaction mixture was stirred for 1.5 h and then diluted with water (100 mL), basified with 1 M NaOH to pH ~4. Layers were separated and the aqueous layer was additionally extracted with DCM. Combined ether layer and DCM extracts were concentrated under reduced pressure, and the residue was purified by flash chromatography (SiO$_2$, eluted with gradient from 0% to 20% of MeOH in DCM). Yield: 118 mg (6%) as an orange solid.

Compound 41 was synthesized from intermediate 41-2, following the sequence of general procedures XIX, XI, XIII, X, XIV, and XV, as outlined in the scheme above. HPLC-MS: m/z 1133.4 (calcd. 1132.6 for M$^+$). UV/Vis: $\lambda_{max}$=660 nm.

Preparation of Compounds 87 and 88

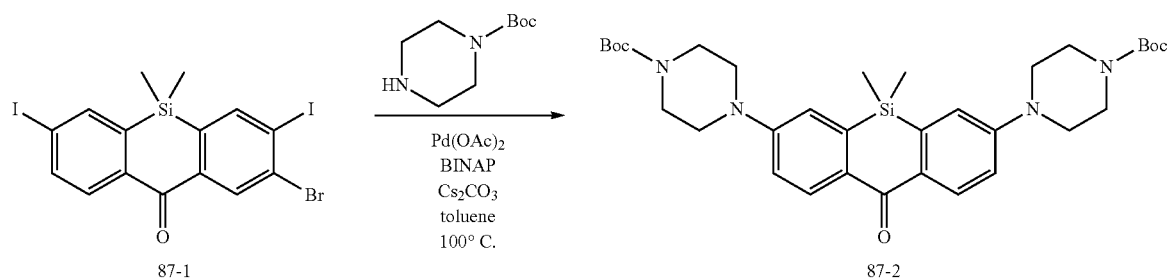

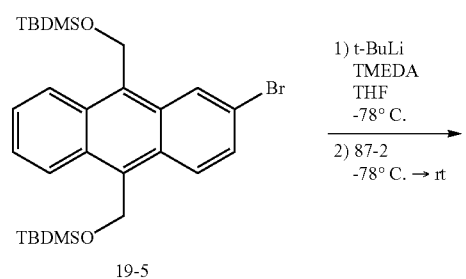

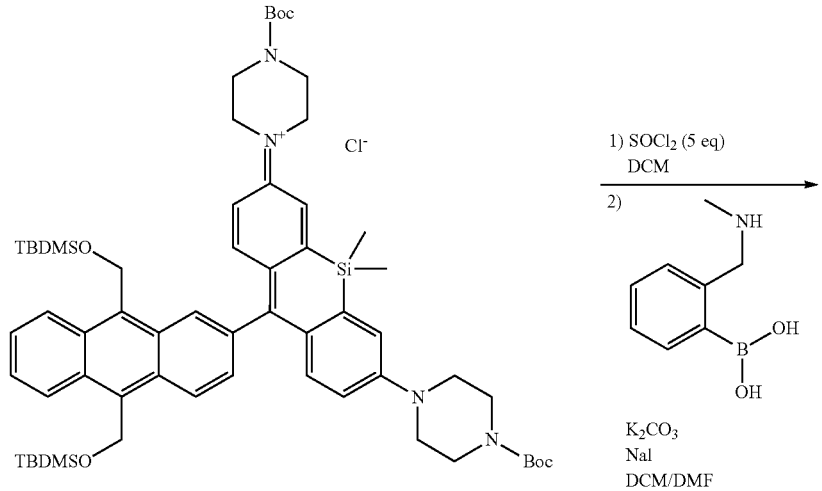

-continued
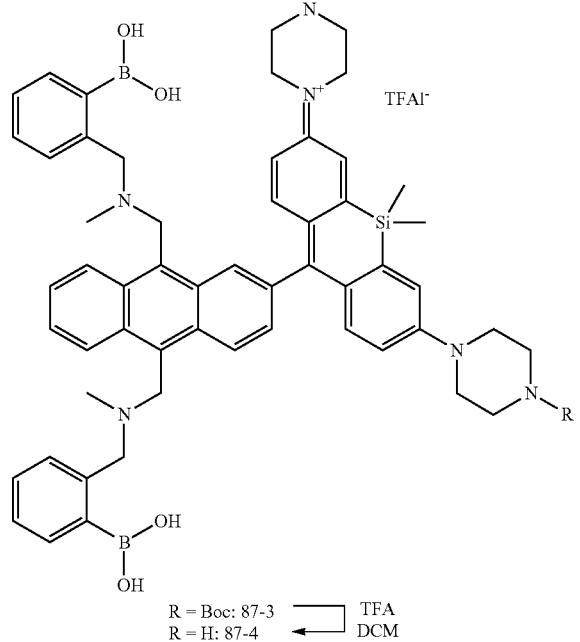
R = Boc: 87-3
R = H: 87-4
TFA / DCM
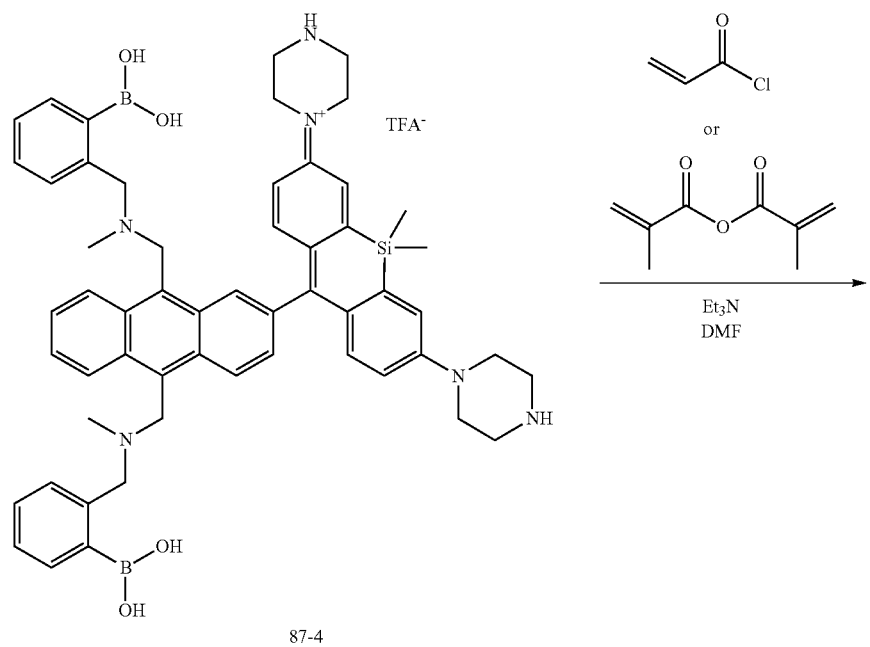
87-4

-continued

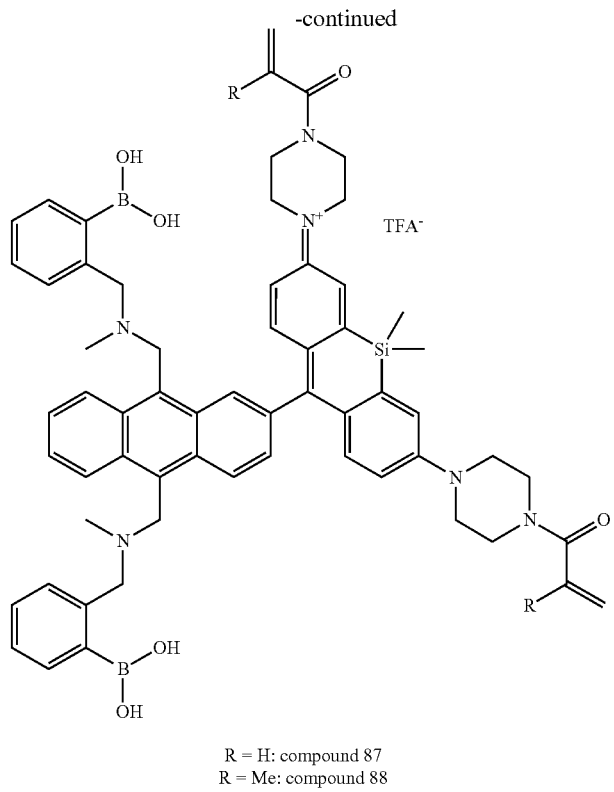

R = H: compound 87
R = Me: compound 88

Silaxanthone 87-2 was synthesized from diiodosilaxanthone 87-1 and 1-Boc-piperazine according to the method described in literature (Myochin, T.; Hanaoka, K.; Iwaki, S.; Ueno, T.; Komatsu, T.; Terai, T.; Nagano, T.; Urano, Y. *J. Am. Chem. Soc.* 2015, 137 (14), 4759-4765).

Intermediate 87-3 was synthesized from bromoanthracene 19-5, silaxanthone 87-2, and 2-(aminomethylamino)phenylboronic acid, following the general procedures XVI and XVIIB, as outlined in the scheme above.

Preparation of Compound 87-4

Solution of bis-Boc-protected intermediate 87-3 (66.4 mg, 0.054 mmol) in DCM (2 mL) was treated with TFA (0.5 mL) at ambient temperature for 1 h. The solvent was then removed under argon stream and the residue was extensively dried under high vacuum. The crude product was used in the next step without further purification.

Preparation of Compound 87

A solution of crude intermediate 87-4 (0.025 mmol) and triethylamine (0.03 mL, 0.22 mmol) in anhydrous DMF (3 mL) was treated with acryloyl chloride (0.01 mL, 0.12 mmol) at ambient temperature under argon atmosphere. After 2 h, the reaction mixture was poured into half-saturated aqueous $NaHCO_3$ and the mixture was extracted with DCM. Combined extracts were dried over anhydrous $Na_2SO_4$, filtered, and concentrated under reduced pressure. The residue was purified by reversed-phase chromatography (C18 $SiO_2$, eluted with gradient from 5% to 100% MeOH in water+0.05% TFA). The title product was obtained (12 mg, 42% yield) as a dark-blue solid. HPLC-MS: m/z 1030.1 (calcd. 1029.5 for M+). UV/Vis: $\lambda_{max}$=660 nm.

Preparation of Compound 88

A solution of crude intermediate 87-4 (0.025 mmol) and triethylamine (0.03 mL, 0.22 mmol) in anhydrous DMF (3 mL) was treated with methacrylic anhydride (0.02 mL, 0.13 mmol) at ambient temperature under argon atmosphere. After 2 h, the reaction mixture was poured into half-saturated aqueous $NaHCO_3$ and the mixture was extracted with DCM. Combined extracts were dried over anhydrous $Na_2SO_4$, filtered, and concentrated under reduced pressure. The residue was purified by reversed-phase chromatography (C18 $SiO_2$, eluted with gradient from 5% to 100% MeOH in water+0.05% TFA). The title product was obtained (8.5 mg, 29% yield) as a dark-blue solid. HPLC-MS: m/z 1058.1 (calcd. 1057.5 for M+). UV/Vis: $\lambda_{max}$=660 nm.

Synthesis of Hydrogel H (DMA/PEGDAAm/AAm)

DMA (N,N-Dimethylacrylamide) (23.6 uL), AAm (acrylamide) (23.6 mg), PEGDAAm (Poly-ethylene glycol diacrylamide) (20.3 mg), 2,2'-Azobis[2-(2-imidazolin-2-yl)propane]dihydrochloride (0.75 mg), Dye (16.7 uL of 90 mM stock solution in DMSO), and water (65.1 uL) were mixed together until a homogenous solution was obtained. In some cases, some water was substituted for DMSO to increase solubility. The monomer mix was purged with argon for 1 minute to remove oxygen. The solution was then injected in between two glass plates separated by a 0.01"-0.02" thick Teflon spacer, and held together with binder clips. The filled plates (hydrogel mold) were then placed in a desiccator and vacuum purged with argon twice (vacuum was purged for 1 min for each cycle). The hydrogel mold was then heated in an argon purged oven at 45° C. for 4 hours. The resulting hydrogel was removed from the mold and washed with pH 7.4 PBS. The wash step consisted of shaking the gel (on an orbital shaker) in ~50 mL of PBS for 2 hours during which the PBS was exchanged 3×. A 5 mm-diameter disc was cut out of the gel slab using a biopsy punch and placed into a 96-well plate containing 150 uL of PBS. Absorbance and emission scans were taken of gel disc using a spectrofluorimeter.

Synthesis of Hydrogel A
(AETACI/CEA/PEGDAAm)

AETACI ([2-(Acryloyloxy)ethyl]trimethylammonium chloride) (28.5 uL of an 80 wt. % solution in $H_2O$), CEA (2-carboxyethyl acrylate) (39 uL), PEGDAAm (Poly-ethylene glycol diacrylamide) (7.5 mg), 2,2'-Azobis[2-(2-imidazolin-2-yl)propane]dihydrochloride (0.75 mg), Dye (16.7 uL of 90 mM stock solution in DMSO), DMSO (15 uL) and water (42.6 uL) were mixed together until a homogenous solution was obtained. The monomer mix was purged with argon for 1 minute to remove oxygen. The solution was then injected in between two glass plates separated by a 0.01"-0.02" thick Teflon spacer, and held together with binder clips. The filled plates (hydrogel mold) were then placed in a desiccator and vacuum purged with argon twice (vacuum was purged for 1 min for each cycle). The hydrogel mold was then heated in an argon purged oven at 45° C. for 4 hours. The resulting hydrogel was removed from the mold and washed with pH 7.4 PBS. The wash step consisted of shaking the gel (on an orbital shaker) in ~50 mL of PBS for 2 hours during which the PBS was exchanged 3×. A 5 mm-diameter disc was cut out of the gel slab using a biopsy punch and placed into a 96-well plate containing 150 uL of PBS. Absorbance and emission scans were taken of gel disc using a spectrofluorimeter.

Synthesis of Hydrogel B
(HEMA/DMA/PEGDAAm)

HEMA (2-Hydroxyethyl methacrylate) (44.1 uL), DMA (N,N-Dimethylacrylamide) (29.4 uL), PEGDAAm (Poly-ethylene glycol diacrylamide) (1.5 mg), 2,2'-Azobis[2-(2-imidazolin-2-yl)propane]dihydrochloride (0.75 mg), Dye (16.7 uL of 90 mM stock solution in DMSO), DMSO (15 uL) and water (42.6 uL) were mixed together until a homogenous solution was obtained. The monomer mix was purged with argon for 1 minute to remove oxygen. The solution was then injected in between two glass plates separated by a 0.01"-0.02" thick Teflon spacer, and held together with binder clips. The filled plates (hydrogel mold) were then placed in a desiccator and vacuum purged with argon twice (vacuum was purged for 1 min for each cycle). The hydrogel mold was then heated in an argon purged oven at 45° C. for 4 hours. The resulting hydrogel was removed from the mold and washed with pH 7.4 PBS. The wash step consisted of shaking the gel (on an orbital shaker) in ~50 mL of PBS for 2 hours during which the PBS was exchanged 3×. A 5 mm-diameter disc was cut out of the gel slab using a biopsy punch and placed into a 96-well plate containing 150 uL of PBS. Absorbance and emission scans were taken of gel disc using a spectrofluorimeter.

Synthesis of Hydrogel C
(DMA/PEGDAAm/AAm/Catalase/Reference Dye)

DMA (N,N-Dimethylacrylamide) (31.5 uL), AAm (acrylamide) (31.5 mg), PEGDAAm (Poly-ethylene glycol diacrylamide) (27 mg), 2,2'-Azobis[2-(2-imidazolin-2-yl)propane]dihydrochloride (1 mg), Dye #21 (16 uL of 50 mM stock solution in DMSO), CF750-SE (14.6 uL of a 13.73 mM solution in DMSO, with 15 mM triethylamine, and 20 mM aminopropylmethacrylamide), catalase (7 mg), and water (70 uL) were mixed together until a homogenous solution was obtained. The monomer mix was purged with argon for 1 minute to remove oxygen. The solution was then injected in between two glass plates separated by a 0.015" thick Teflon spacer, and held together with binder clips. The filled plates (hydrogel mold) were then placed in a desiccator and vacuum purged with argon 5 times (vacuum was purged for 1 min for each cycle). The hydrogel mold was then heated in an argon purged oven at 45° C. for 4 hours. The resulting hydrogel was removed from the mold and washed with pH 7.4 PBS. The wash step consisted of shaking the gel (on an orbital shaker) in ~50 mL of PBS for 2 hours during which the PBS was exchanged 3 times. 5 mm long×0.75 mm wide strips were out of the gel slab using a razor blade.

Measurement of Glucose In Vitro

Glucose sensors were prepared as described above (Sensors, A, B, C, or H). A 5 mm-diameter disc of hydrogel was placed into a well of a clear-bottom 96-well plate. 150 uL of PBS was added to the well, and the plate was inserted into a spectrofluorimeter and warmed to 37° C. At 37 C, the fluorescence emission of the gel was collected (bottom read kinetic mode) every minute. Glucose solution was dispensed into the well via an injector module every 30 minutes to achieve final concentrations of 50, 100, 200, and 400 mg/dL glucose. The fluorescence intensity of the gel's emission in response to each glucose level was measured.

Measurement of Glucose in Tissue

Figure 2:
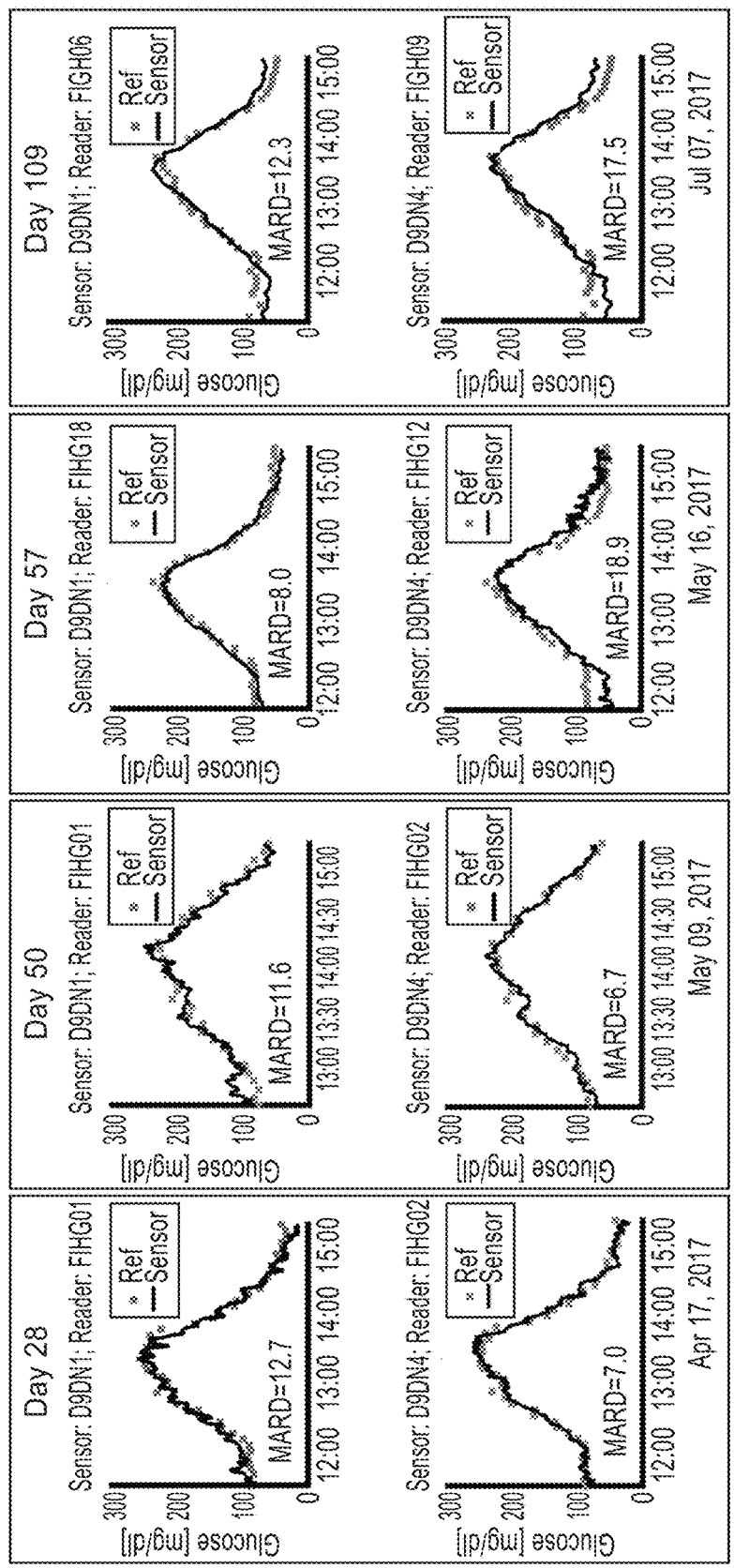
FIG. 2 depicts long-term stability and performance of two glucose sensors prepared by co-polymerization of an exemplary compound (compound 21) implanted in the subcutaneous tissue of a pig.

A glucose sensor was prepared as described above (Sensor C) and cut into a rod measuring approximately 5 mm×0.75 mm×0.65 mm. The sensor rod was inserted with an 18G needle into the subcutaneous tissue of a pig under anesthesia. FIG. 1 shows continuous glucose-sensing performance of the sensor in a live pig 28 days after implantation in the tissue. For comparison, reference blood glucose measurements were taken with a commercial glucometer every 5 minutes. The sensor data shown was collected transcutaneously with a custom optical reader containing an LED excitation source and a fluorescence photodetector. FIG. 2 shows the plots of fluorescence signals of two sensors, both containing compound #21, a representative compound, implanted in the subcutaneous tissue of an anesthetized pig. The sensor signals were read through the pig skin after 28, 50, 57, and 109 days of in vivo implantation time. The mean absolute relative difference (MARD) of the glucose values reported by the sensor compared to that of actual blood glucose reference values was calculated. The data demonstrates that the sensors exhibit long-term stability when implanted into a mammalian subcutaneous tissue.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

TABLE 1
| Compound No | Structure | Glucose Response (50 to 200 mg/dL): (I200 − I50)/I50 = |
|---|---|---|
| 1 | 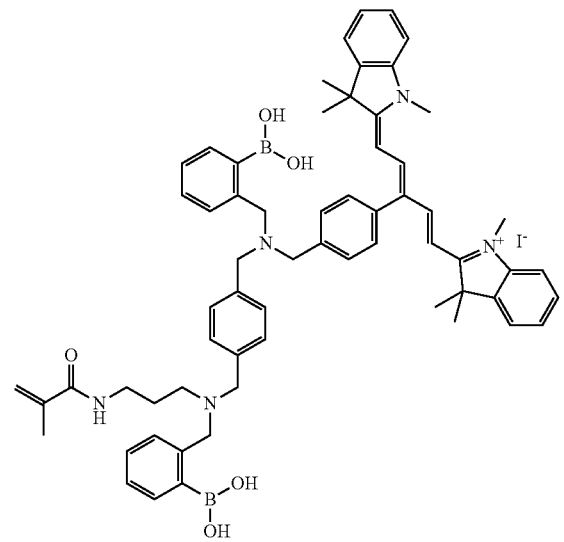 | 7% |
| 2 | 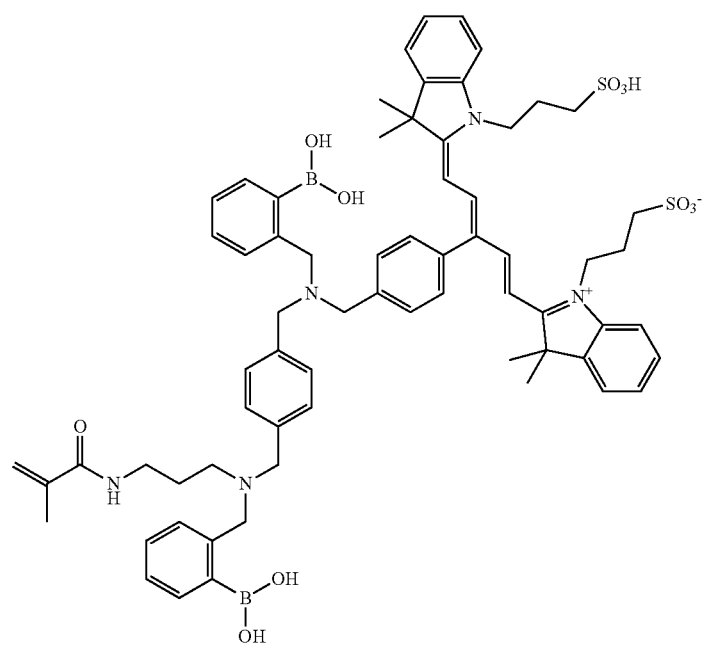 | 9% |

TABLE 1-continued
| 3 | 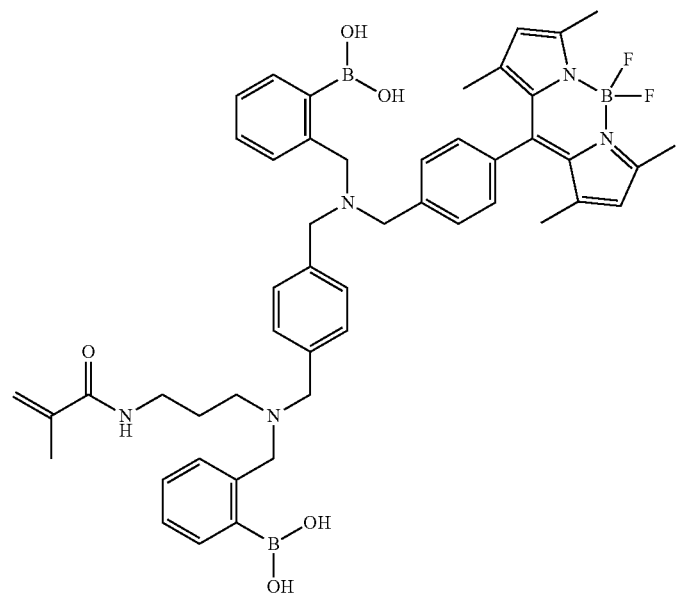 | 0% |
| 4 | 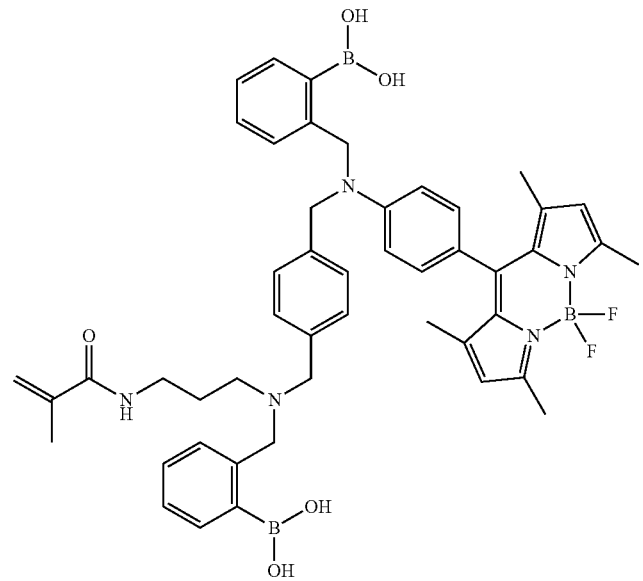 | 10% |

TABLE 1-continued
| 5 | 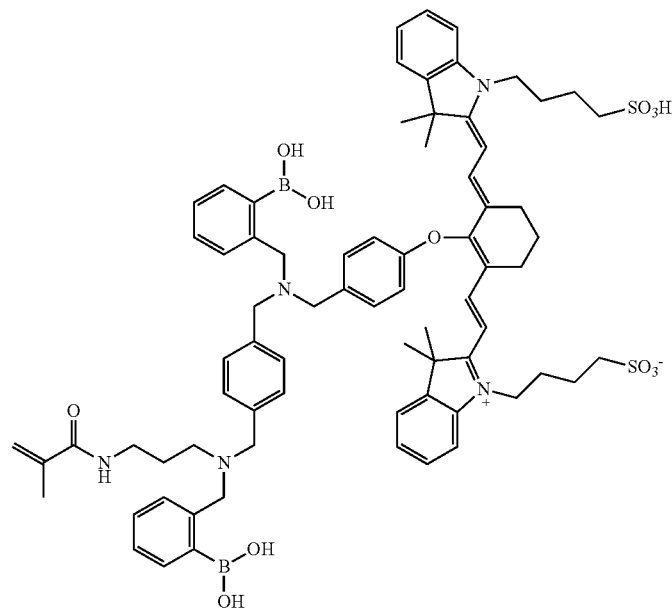 | 5% |
|---|---|---|
| 6 | 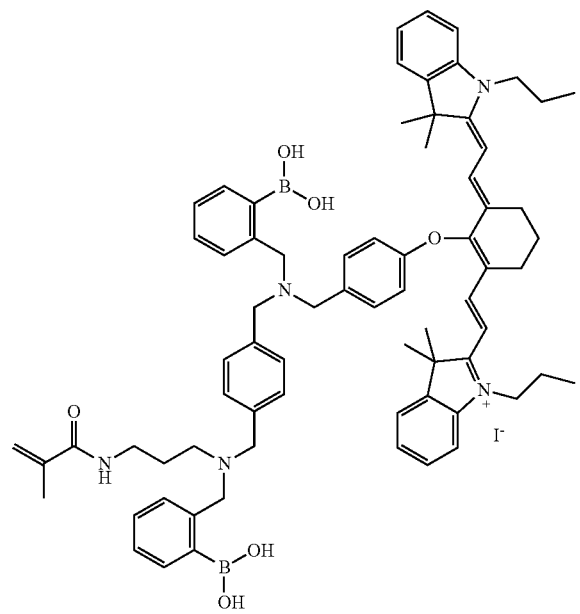 | 10% |

TABLE 1-continued
| 7 | 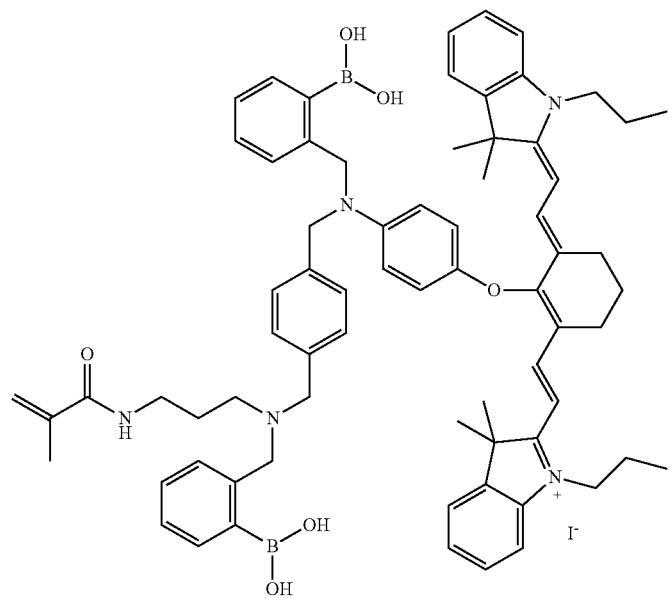 | 5% |
| 8 | 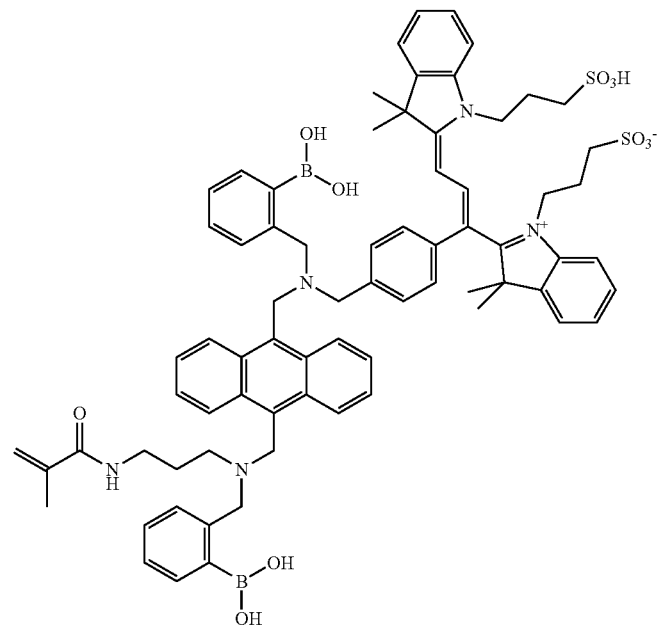 | 30% |

TABLE 1-continued
| 9 | 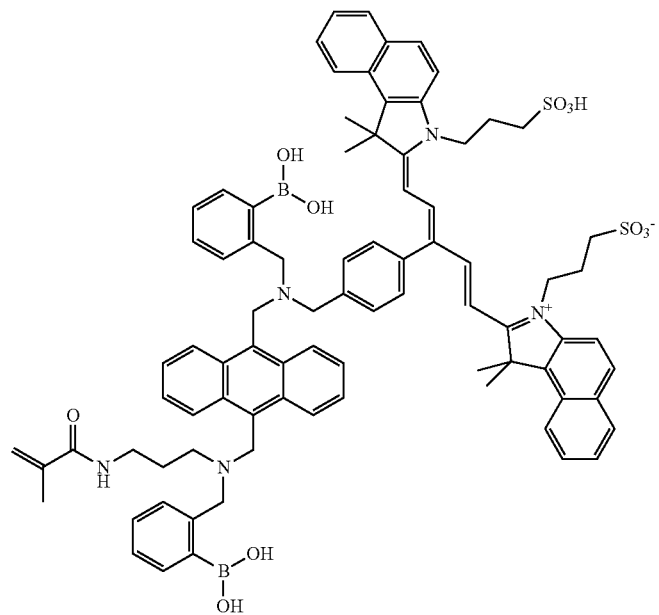 | 25% |
|---|---|---|
| 10 | 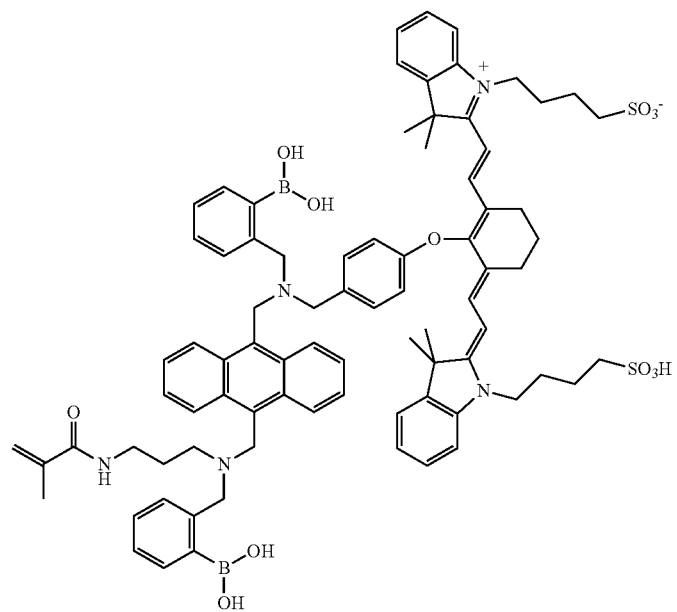 | 35% |

TABLE 1-continued
| 11 | 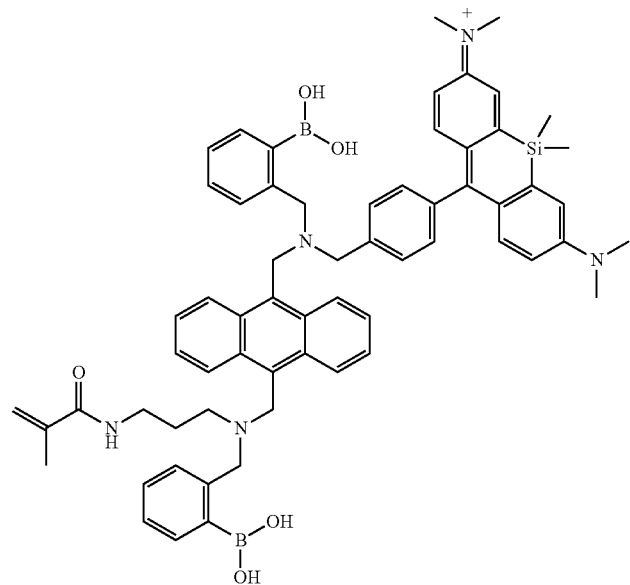 | 20% |
| 12 | 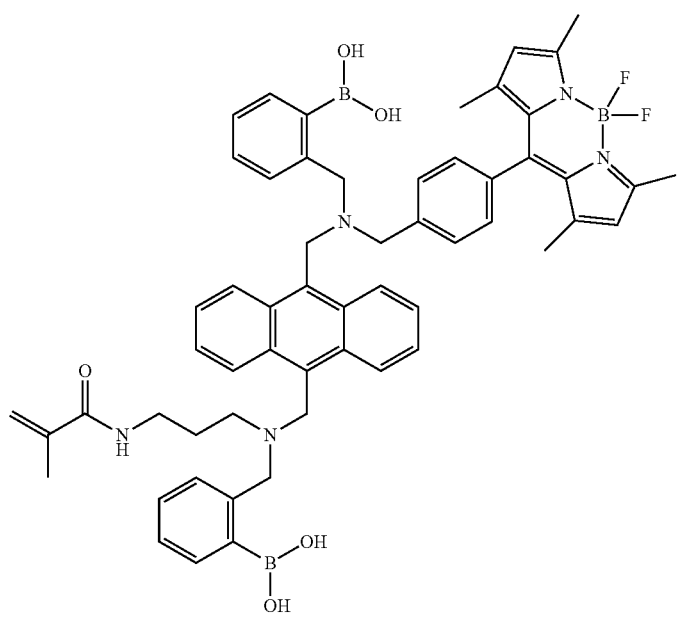 | 15% |

TABLE 1-continued
| 13 | 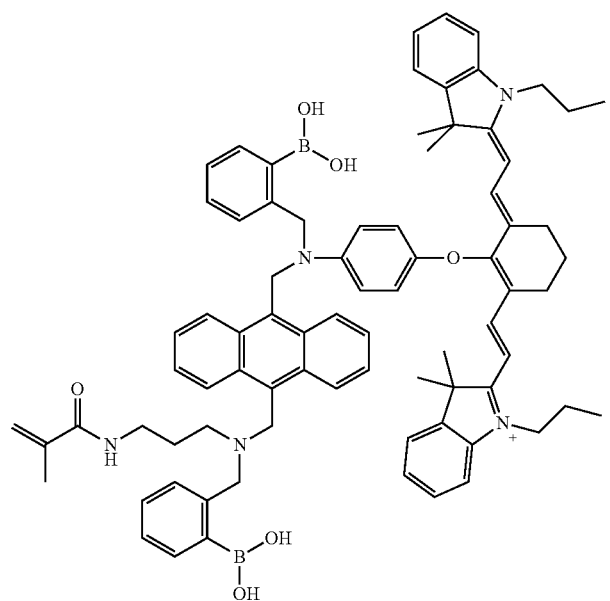 | 8% |
| 14 | 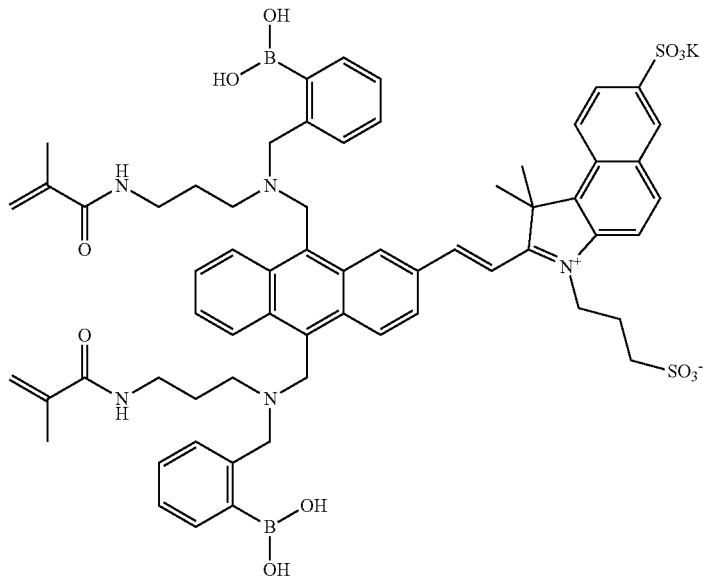 | 0% |

TABLE 1-continued
| 15 | 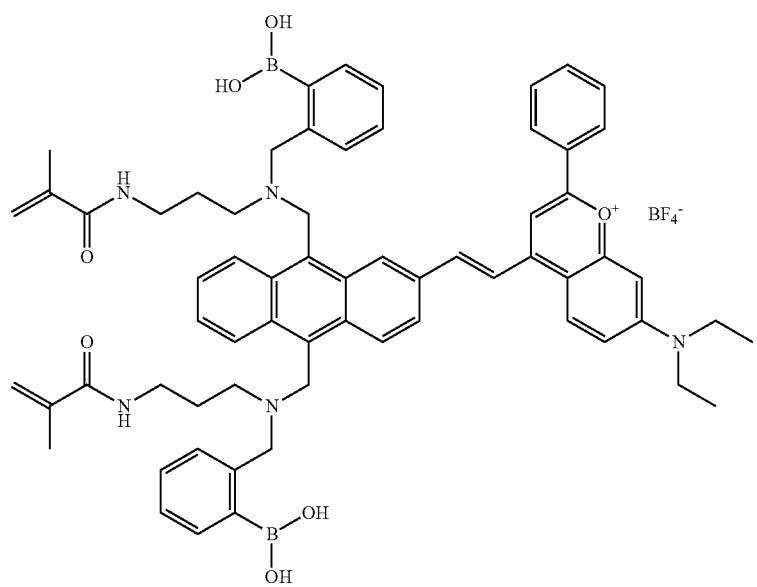 | 1% |
| 17 | 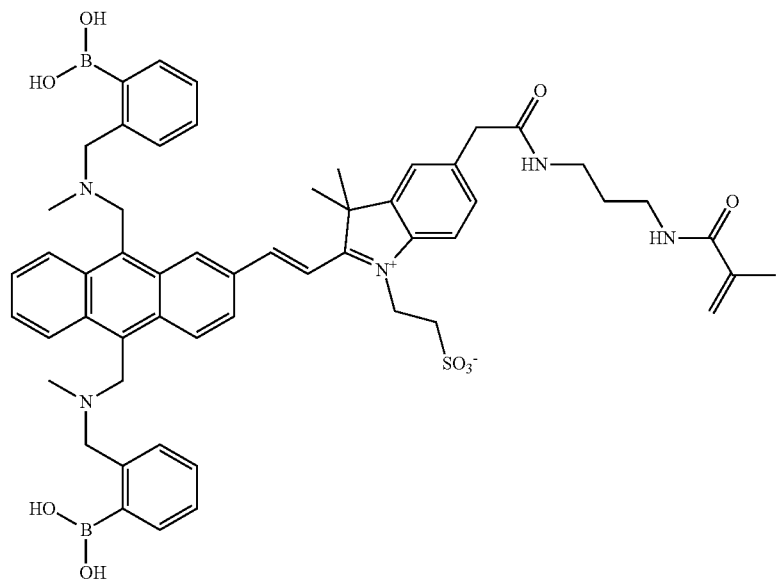 | 15% |

TABLE 1-continued
| 18 | 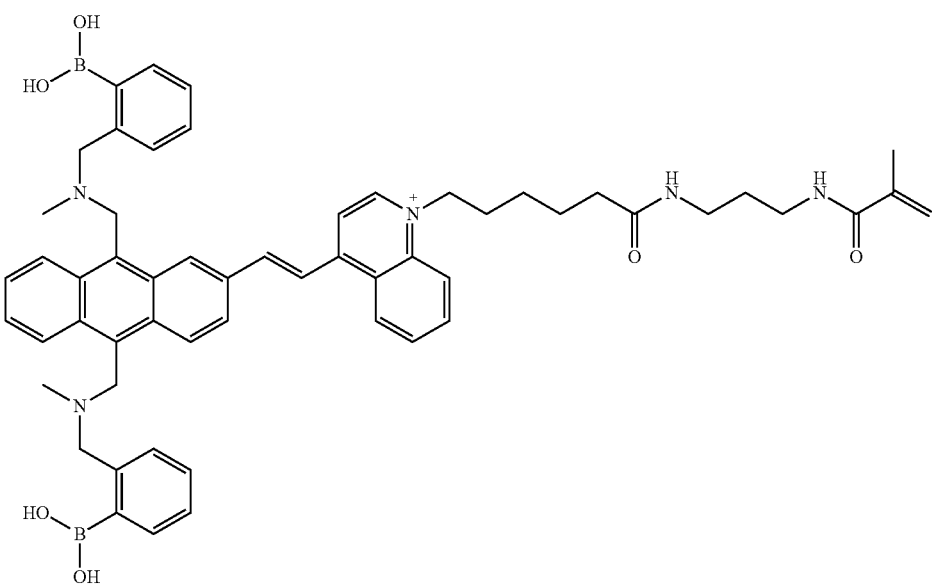 | 19% |
|---|---|---|
| 19 | 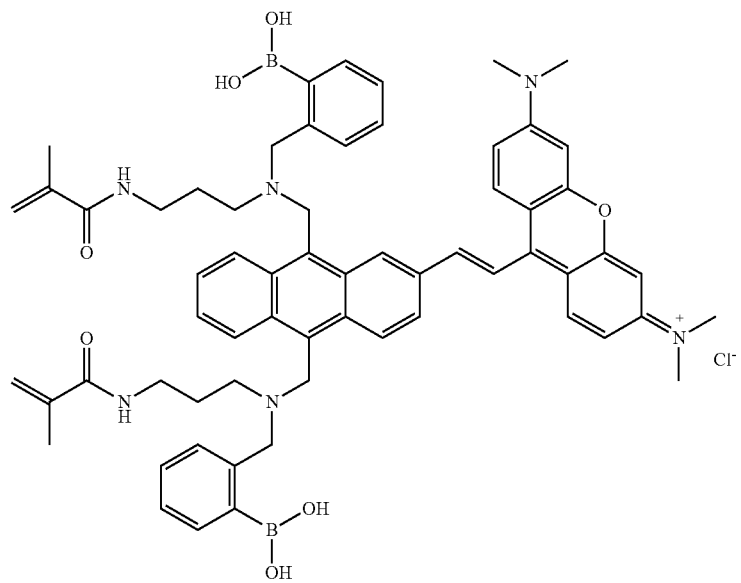 | 10% |

TABLE 1-continued
| 20 | 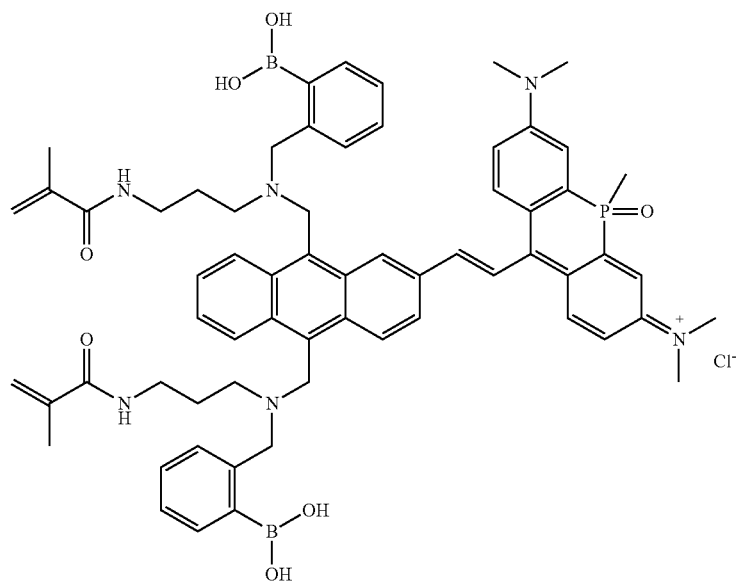 | 55% |
| 21 | 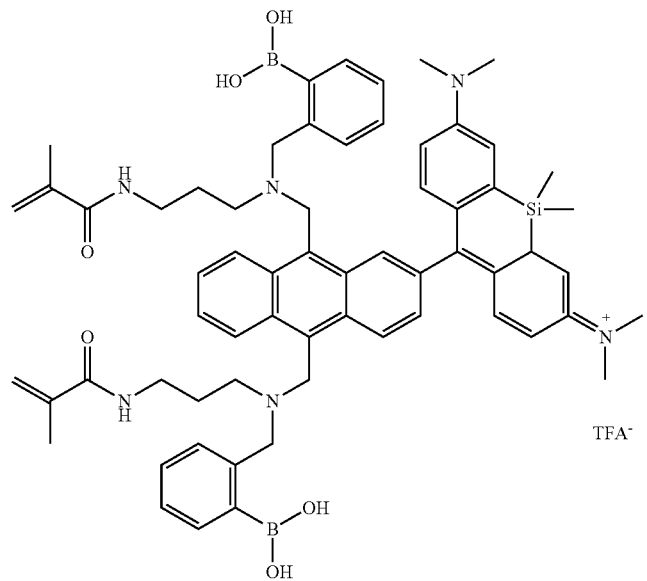 | 27% |

TABLE 1-continued
| 22 | 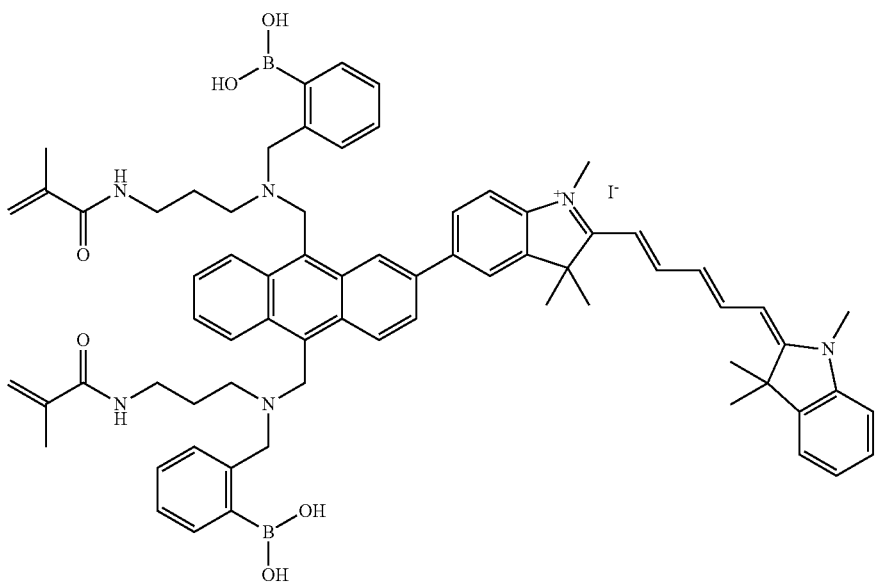 [SMILES: C=C(C)C(=O)NCCCN(Cc1ccccc1B(O)O)Cc1c2ccccc2c(CN(CCCNC(=O)C(=C)C)Cc2ccccc2B(O)O)c2cc(-c3ccc4c(c3)C(C)(C)C(/C=C/C=C/C=C3/N(C)c5ccccc5C3(C)C)=[N+]4C)ccc12 ; [I-]] | 30% |
| 23 | 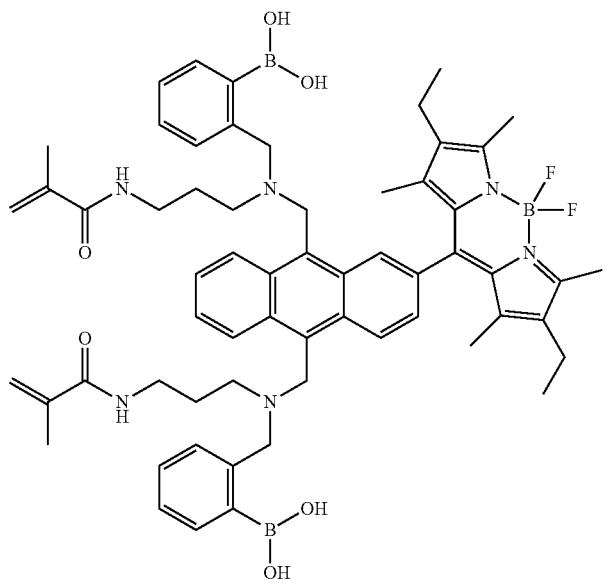 | 0% |

TABLE 1-continued
| 24 | 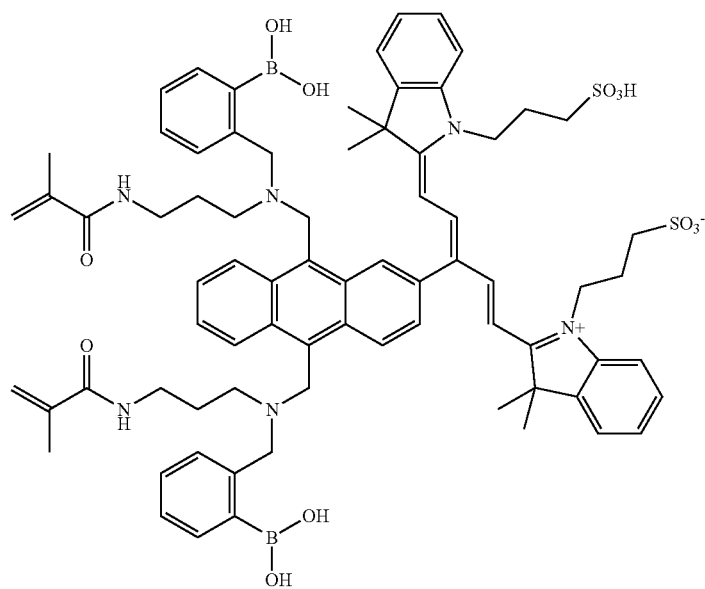 | 0% |
| 25 | 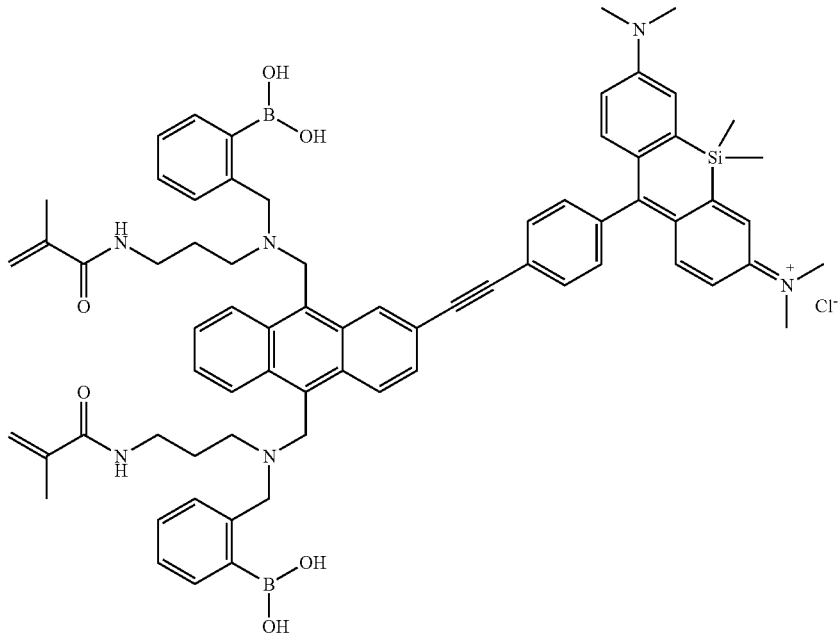 | 6% |

TABLE 1-continued
| 26 | 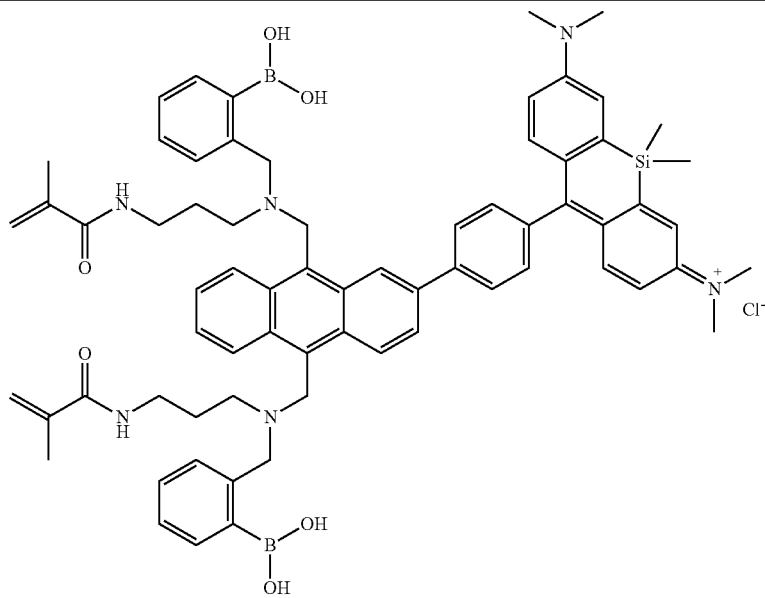 | 24% |
| 27 | 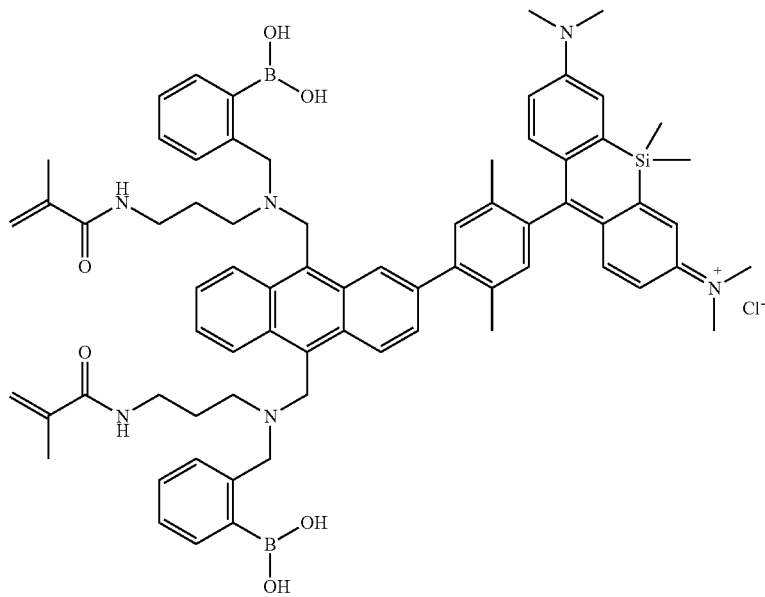 | 15% |

TABLE 1-continued
| 28 | 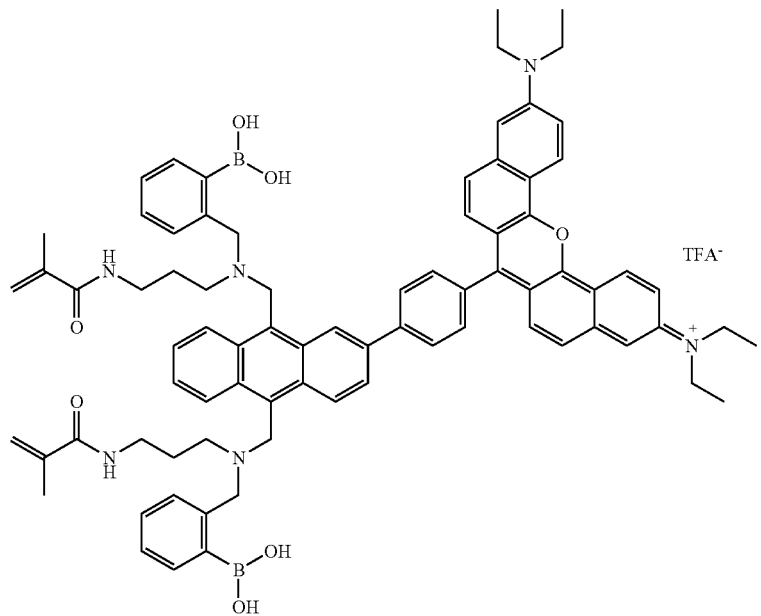 | 0% |
|---|---|---|
| 29 | 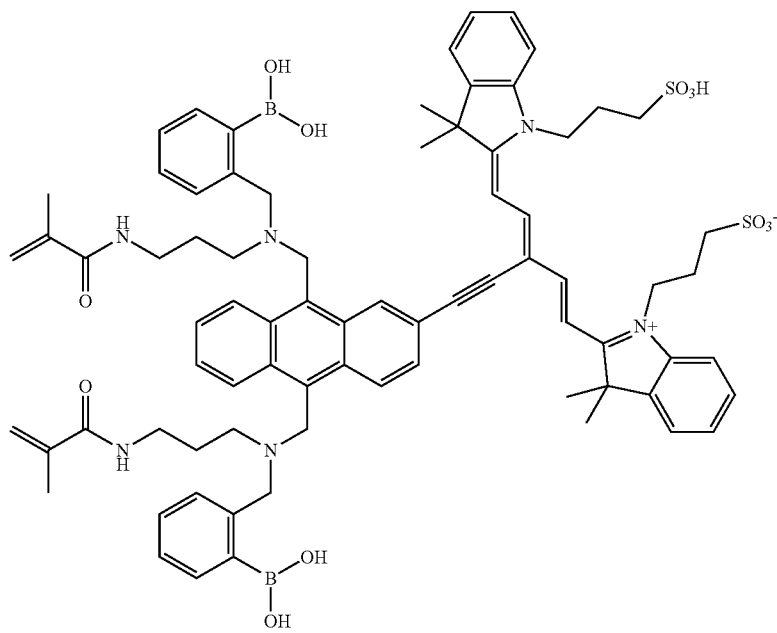 | 7% |

| 30 | 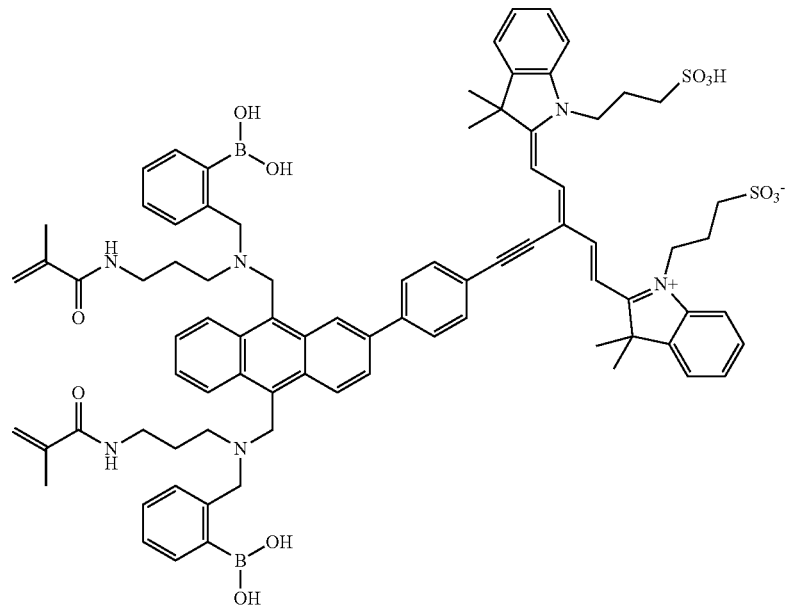 | 17% |
|---|---|---|
| 31 | 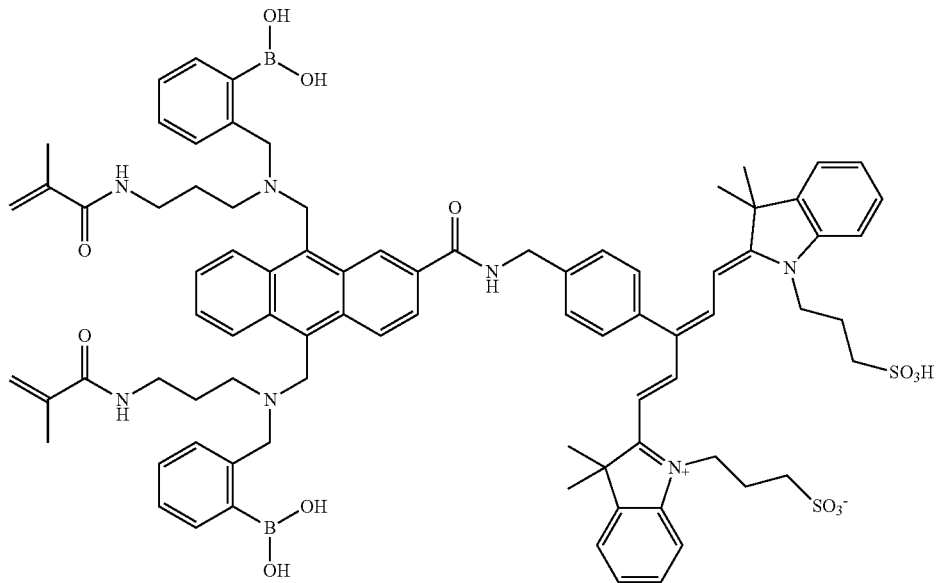 | 1% |
|---|---|---|

TABLE 1-continued
| 32 | 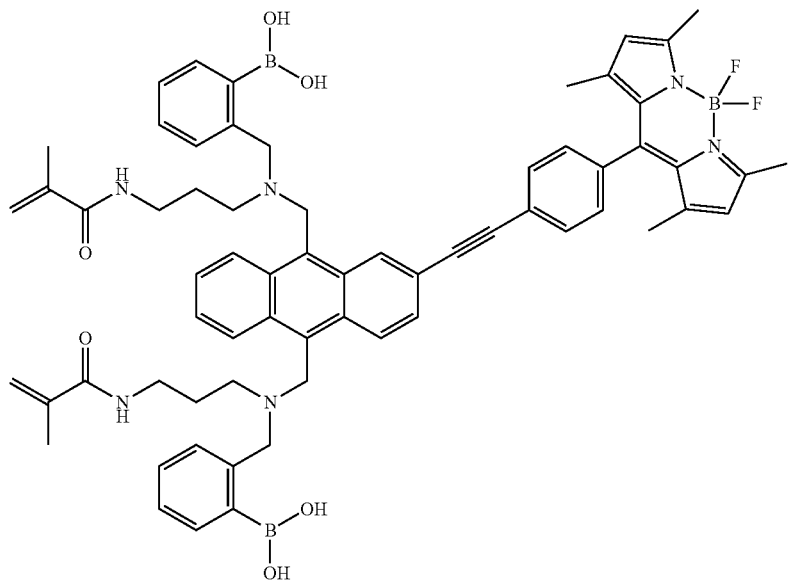 | 4% |
| 33 | 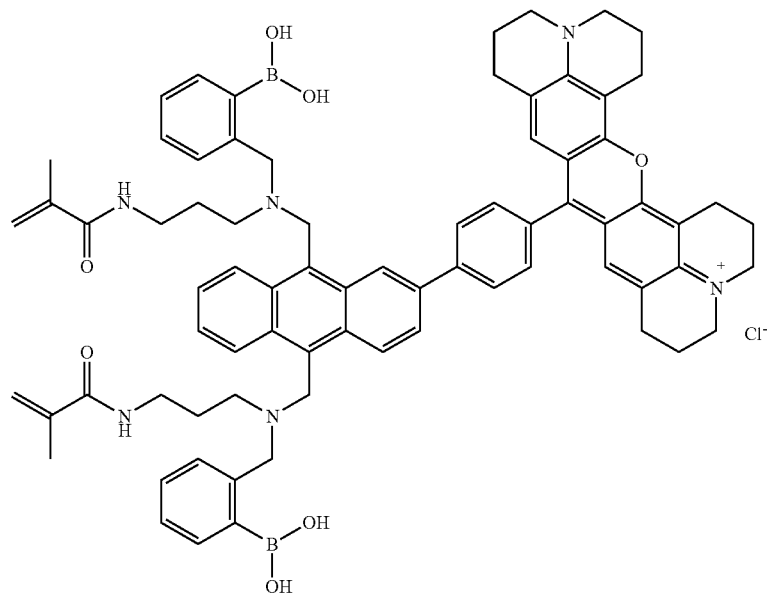 | 11% |

TABLE 1-continued
| 34 | 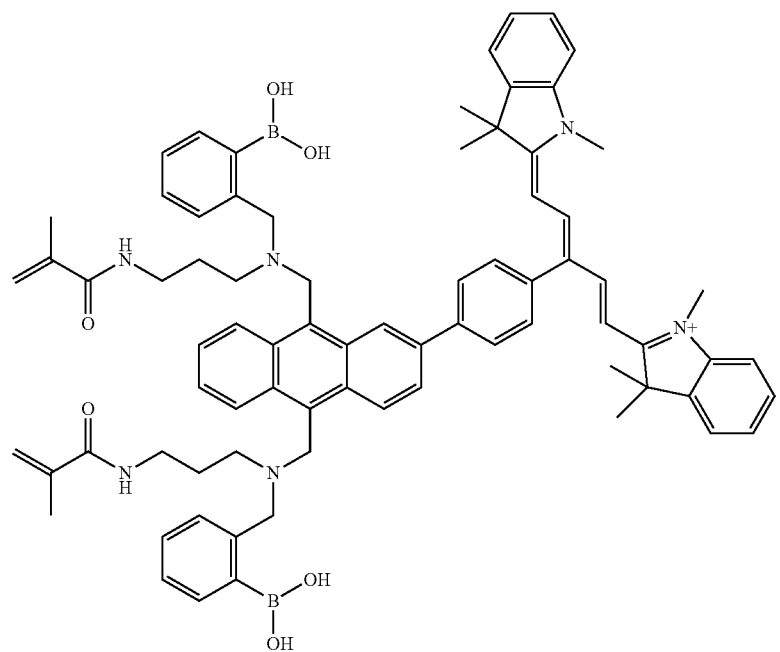 [SMILES: C=C(C)C(=O)NCCCN(Cc1ccccc1B(O)O)Cc1c2ccccc2c(CN(CCCNC(=O)C(=C)C)Cc2ccccc2B(O)O)c2cc(-c3ccc(C(=C\C=C4/N(C)c5ccccc5C4(C)C)/C=C/C4=[N+](C)c5ccccc5C4(C)C)cc3)ccc12] | 17% |
| 35 | 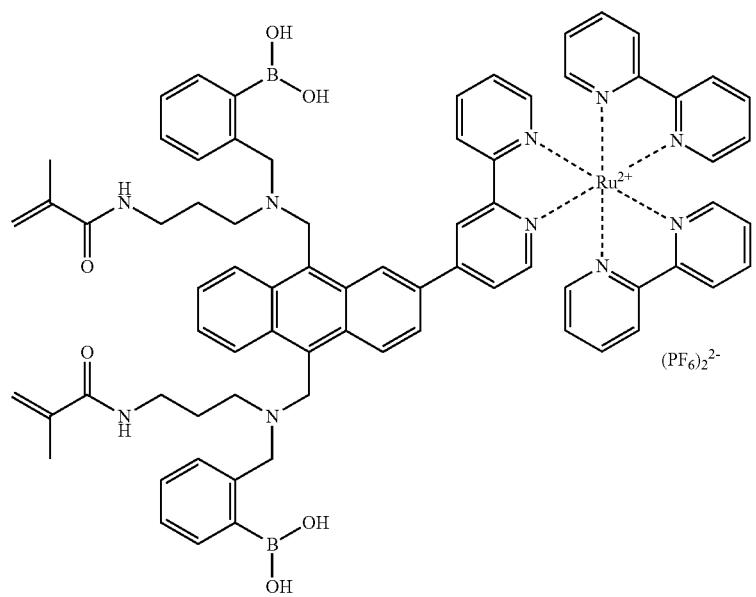 | 0% |

| 36 | 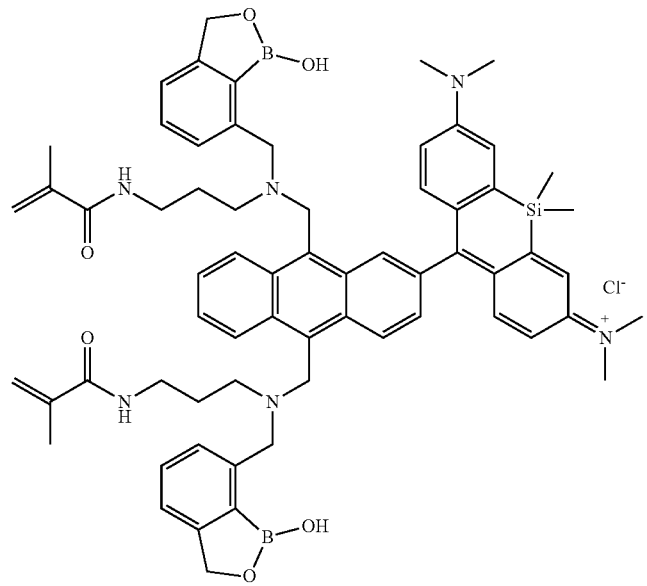 | 15% |
|---|---|---|
| 37 | 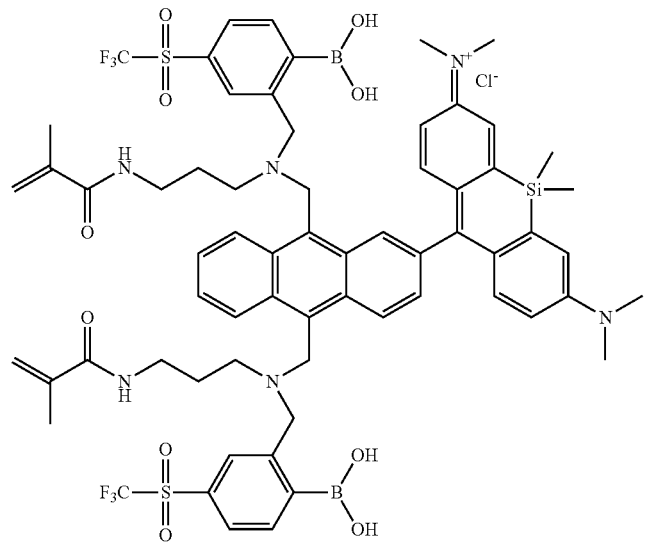 [SMILES: C=C(C)C(=O)NCCCN(Cc1cc(S(=O)(=O)C(F)(F)F)ccc1B(O)O)Cc1c2ccccc2c(CN(CCCNC(=O)C(=C)C)Cc2cc(S(=O)(=O)C(F)(F)F)ccc2B(O)O)c2cc(C3=C4C=CC(=[N+](C)C)C=C4[Si](C)(C)c4cc(N(C)C)ccc43)ccc12 ; [Cl-]] | 15% |

TABLE 1-continued
| 38 | 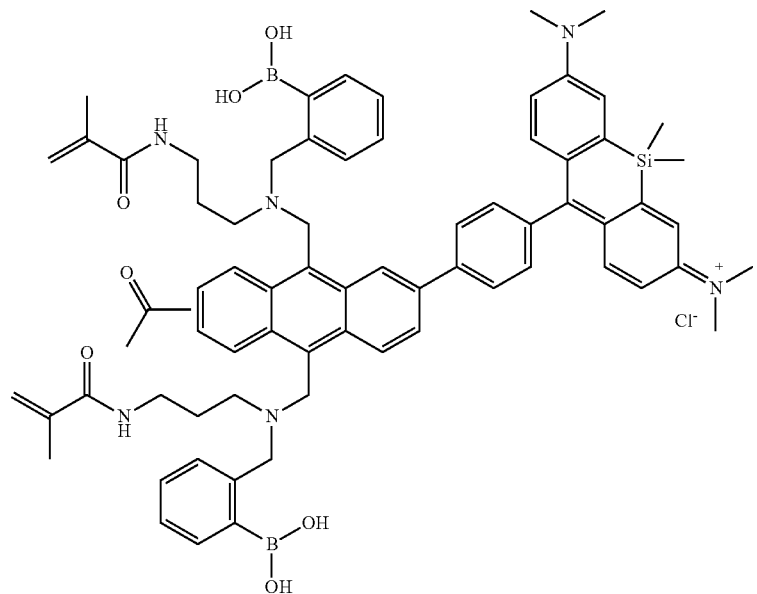 Compound 38 | 2% |
| 39 | 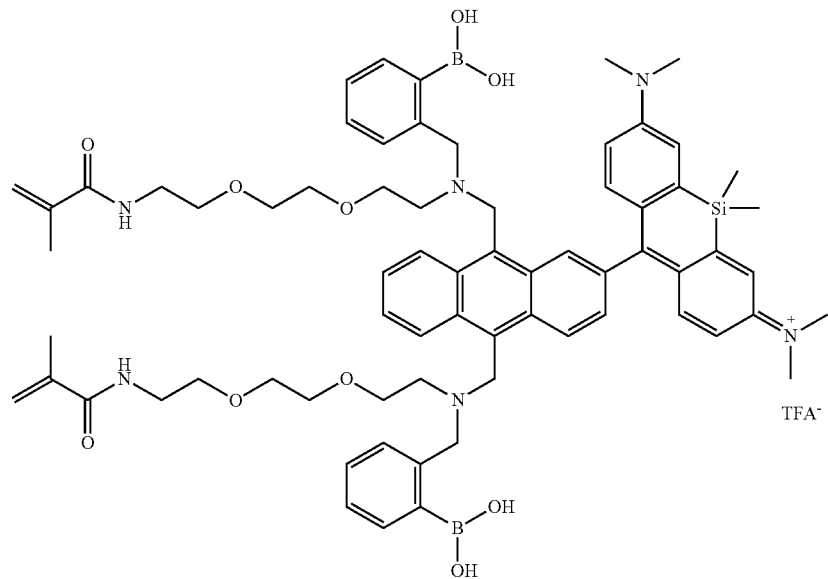 | 25% |

TABLE 1-continued
| 40 | 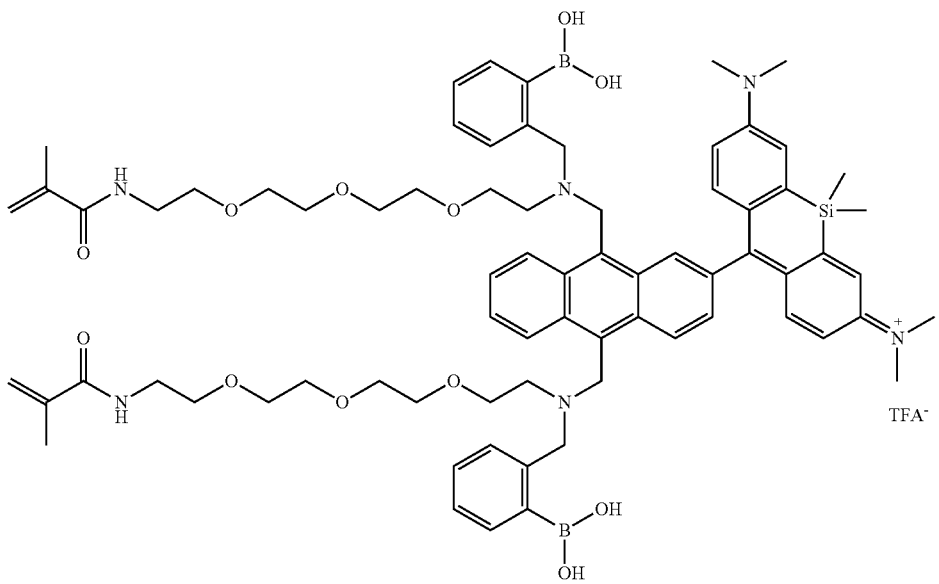 | 27% |
| 41 | 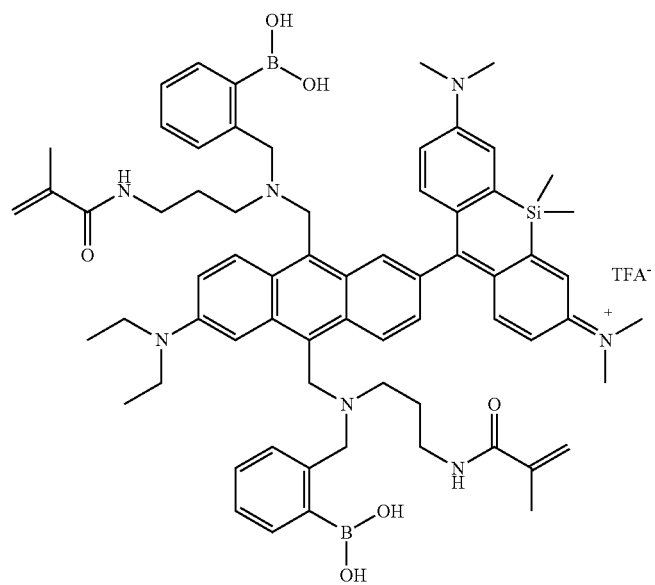 | 2% |
| 42 | 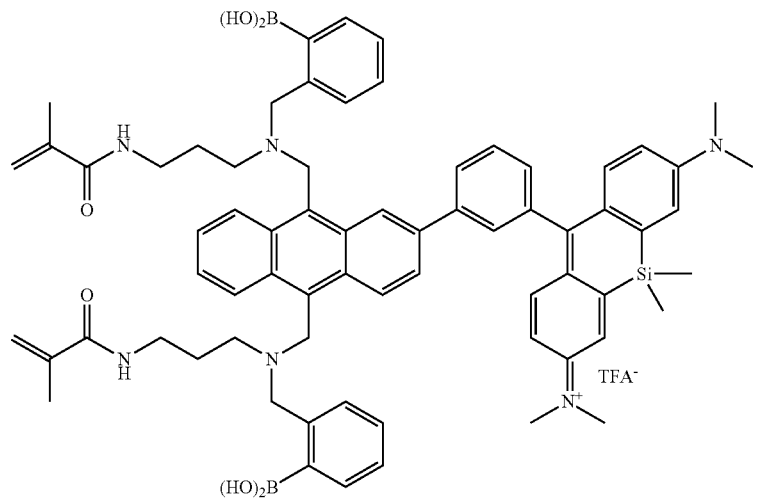 | 36% |

TABLE 1-continued
43 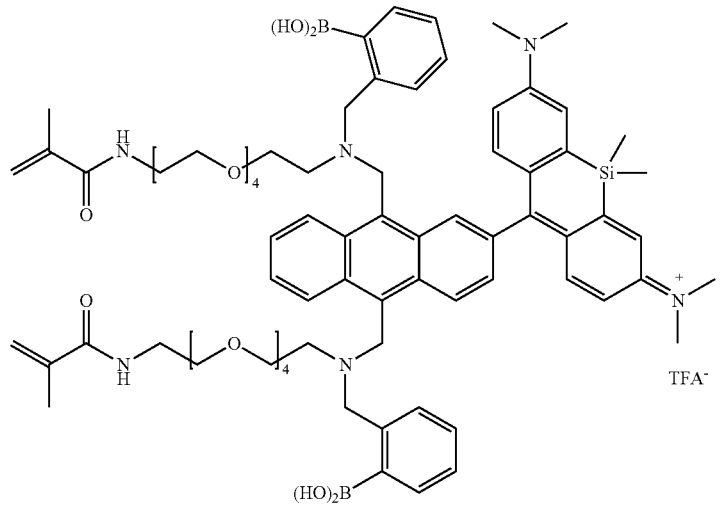 38%
44 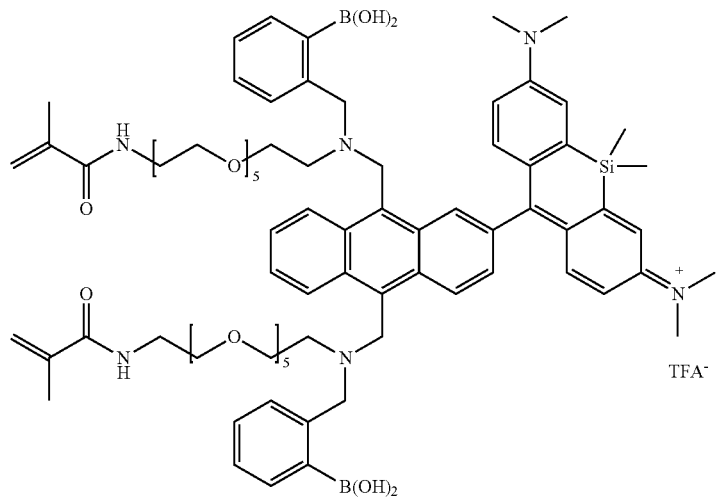 31%
45 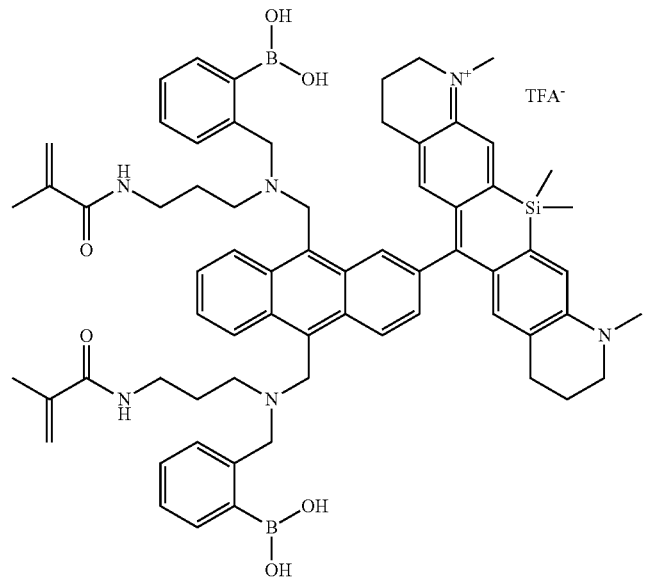 9%

TABLE 1-continued
| 46 | 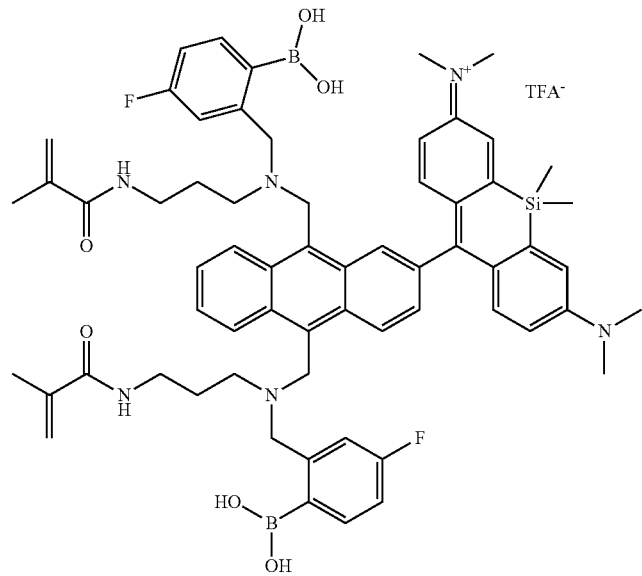 | 8% |
| 47 | 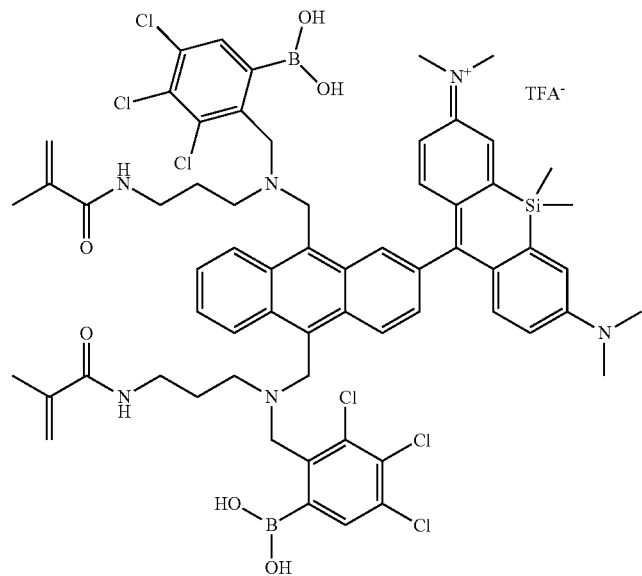 | 10% |

TABLE 1-continued
| 48 | 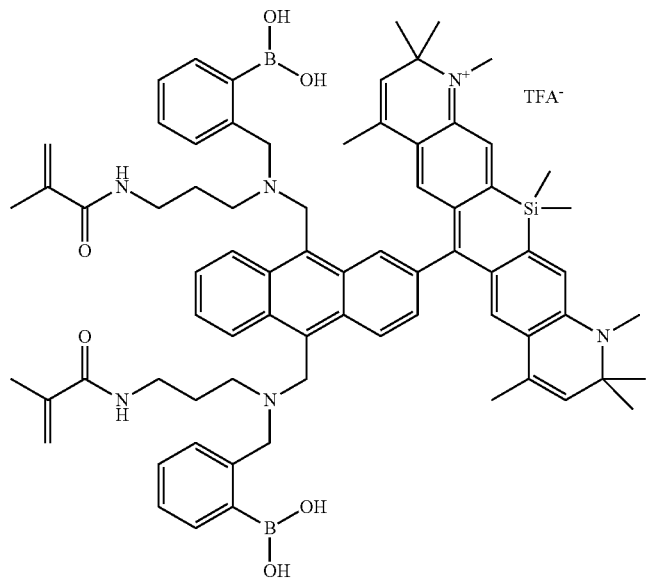 | 27% |
| 49 | 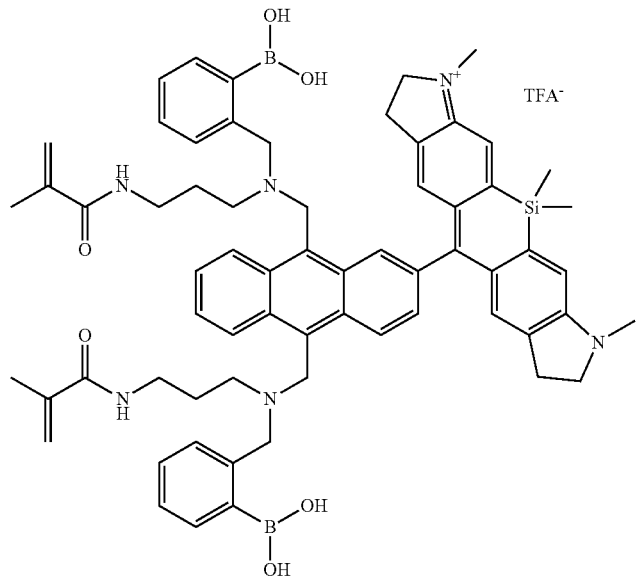 [SMILES: C=C(C)C(=O)NCCCN(Cc1ccccc1B(O)O)Cc1c2ccccc2c(CN(CCCNC(=O)C(=C)C)Cc2ccccc2B(O)O)c2cc(C3=c4cc5c(cc4[Si](C)(C)c4cc6c(cc43)CCN6C)=[N+](C)CC5)ccc12 ; "TFA-"] | 10% |

| 50 | 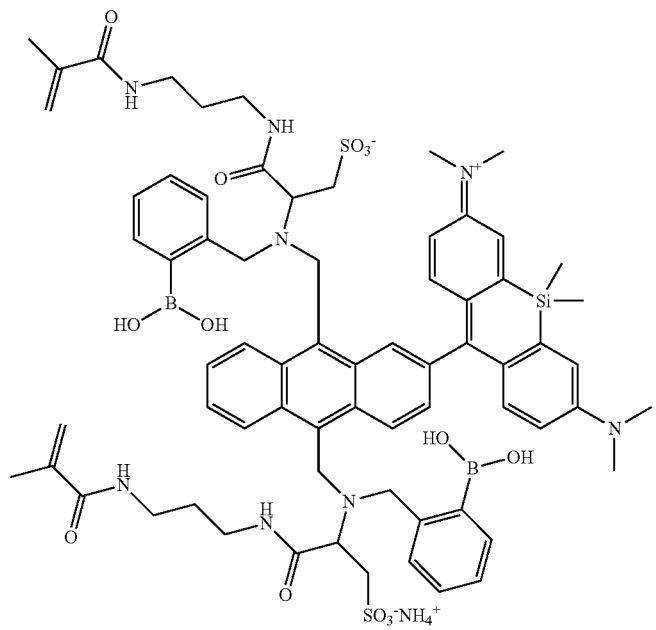 | 2% |
|---|---|---|
| 51 | 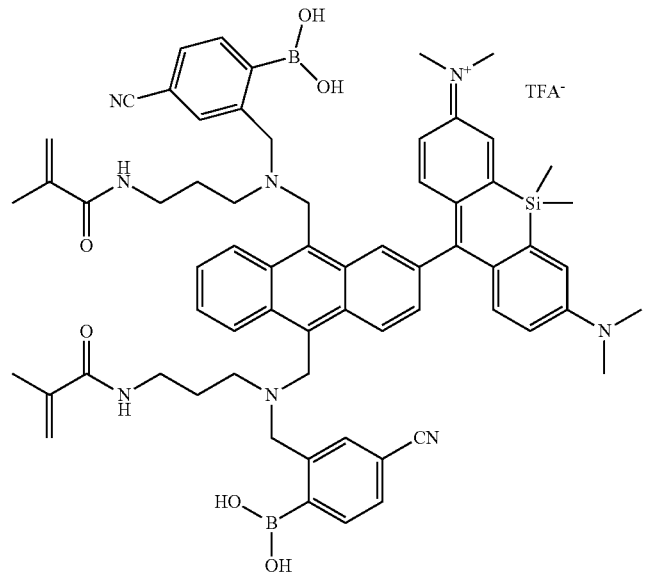 | 25% |

| 52 | 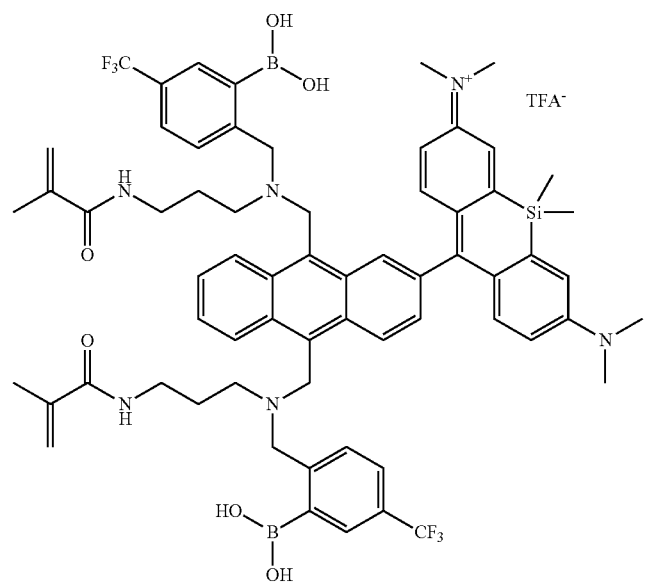 | 26% |
|---|---|---|
| 53 | 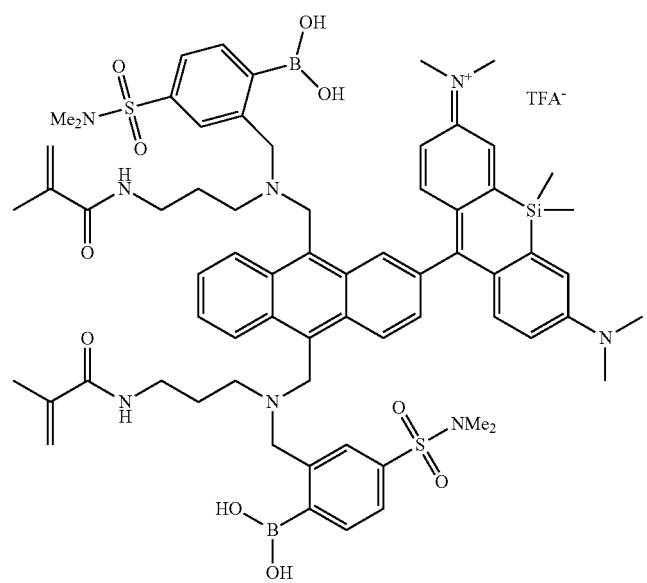 | 27% |

| | |
|---|---|
| 54 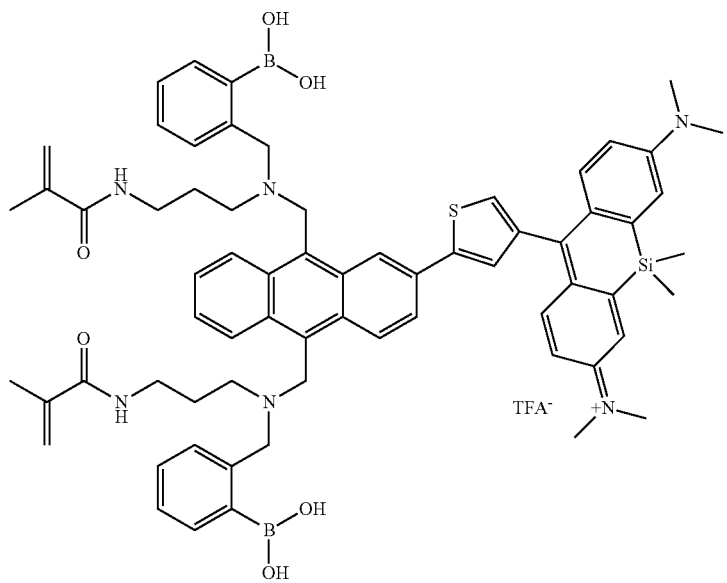 [SMILES: C=C(C)C(=O)NCCCN(Cc1ccccc1B(O)O)Cc1c2ccccc2c(CN(CCCNC(=O)C(=C)C)Cc2ccccc2B(O)O)c2cc(-c3cc(C4=C5C=CC(=[N+](C)C)C=C5[Si](C)(C)c5cc(N(C)C)ccc54)cs3)ccc12 ; "TFA-"] | 55% |
| 55 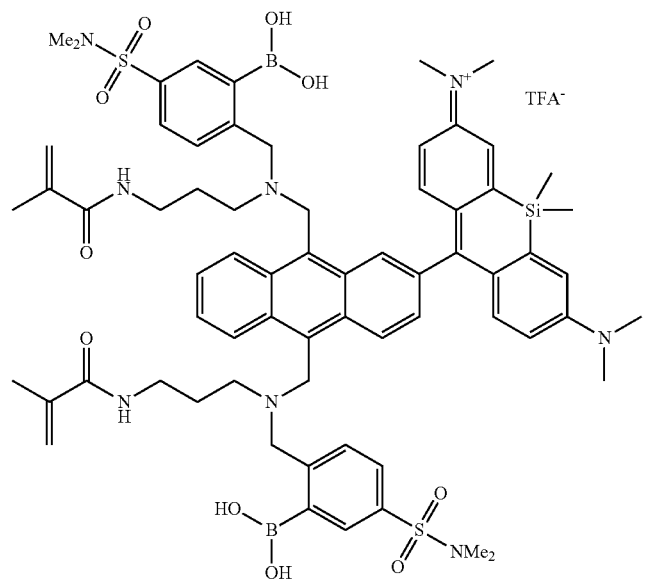 | 25% |

TABLE 1-continued
| 56 | 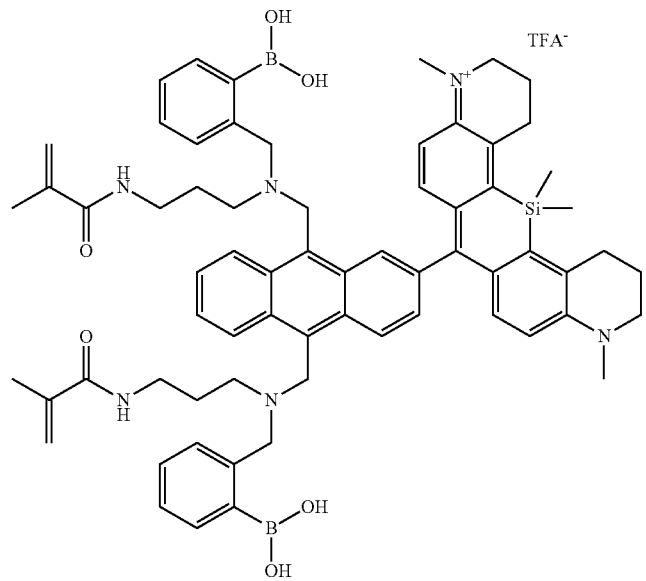 | 10% |
|---|---|---|
| 57 | 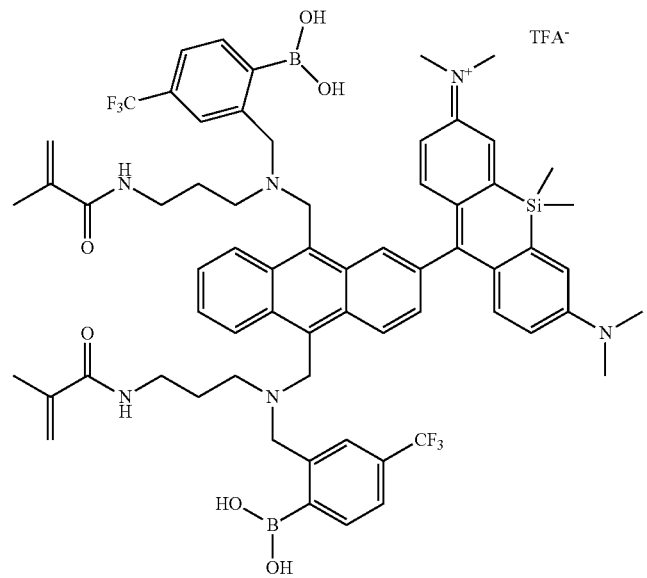 | 23% |

TABLE 1-continued
| 58 | 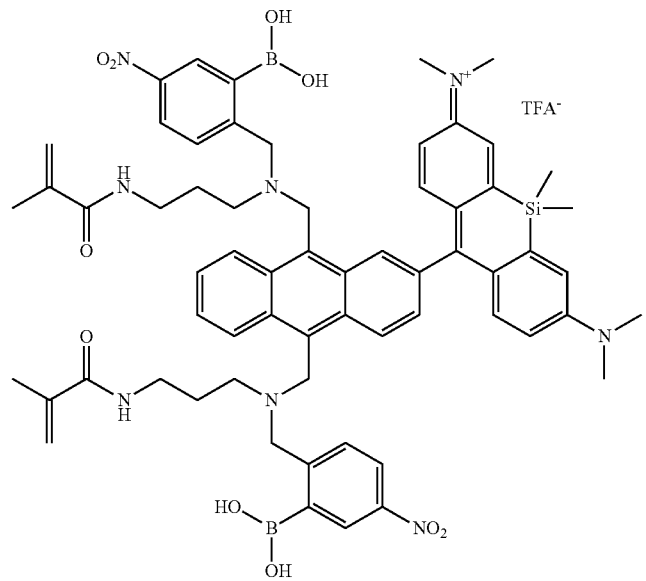 | 45% |
| 59 | 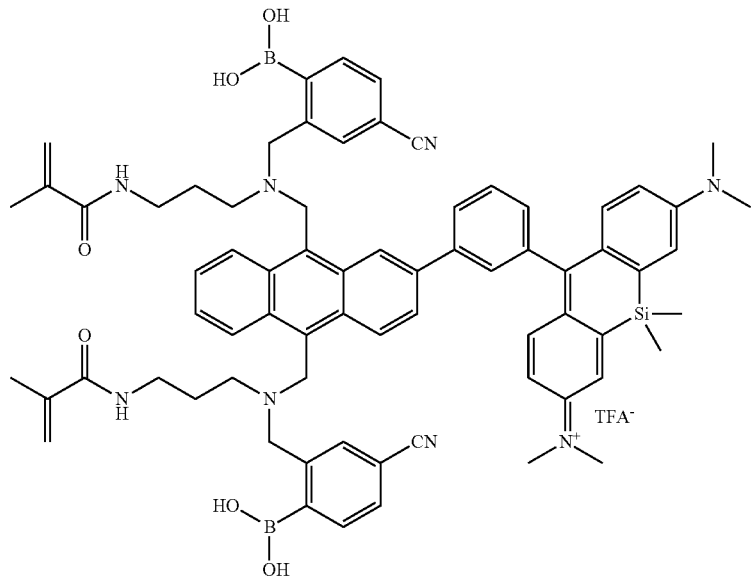 | 40% |

TABLE 1-continued
| 60 | 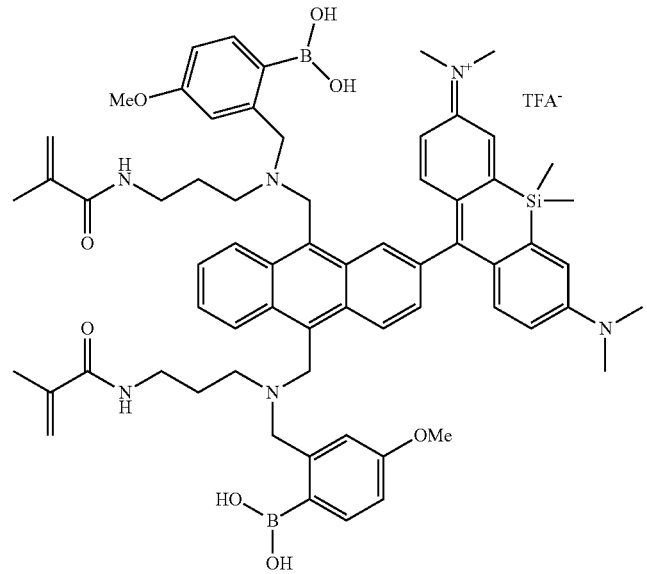 | 3% |
| 61 | 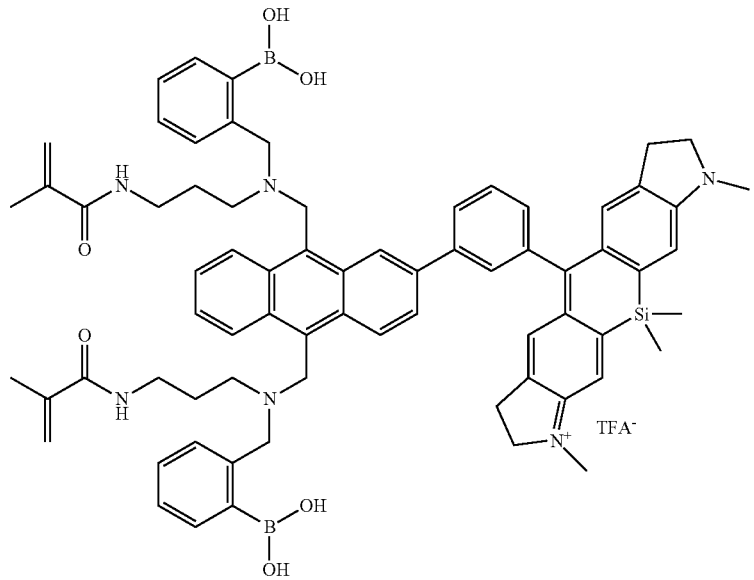 | 8% |

| 62 | 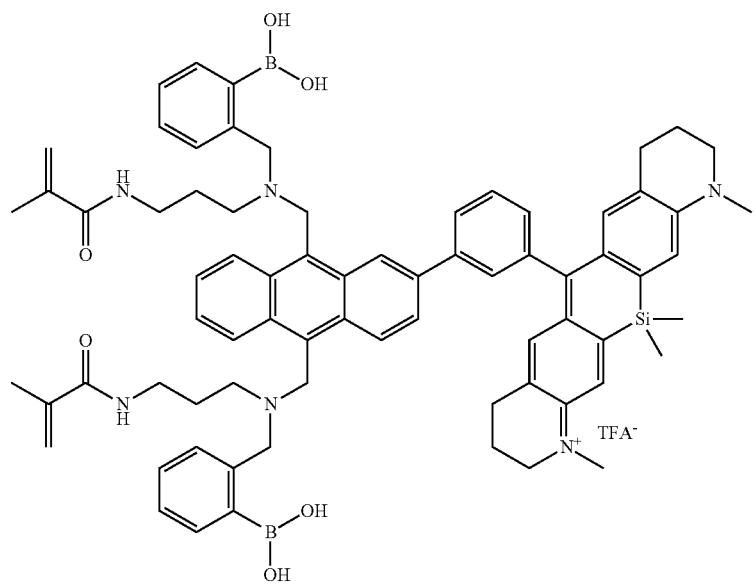 | 14% |
|---|---|---|
| 63 | 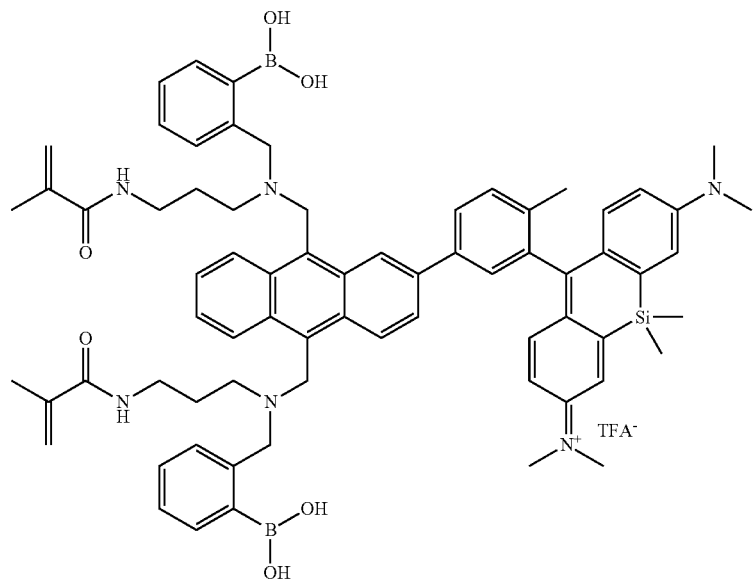 | 57% |

| | | |
|---|---|---|
| 64 | 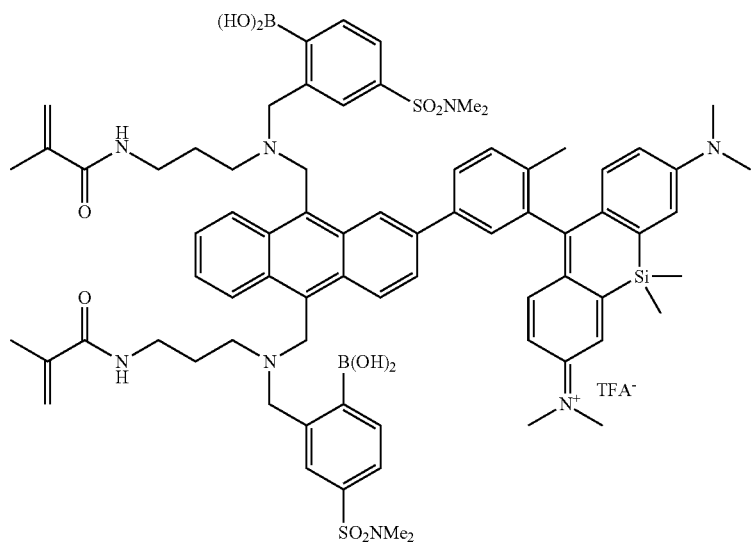 | 44% |
| 65 | 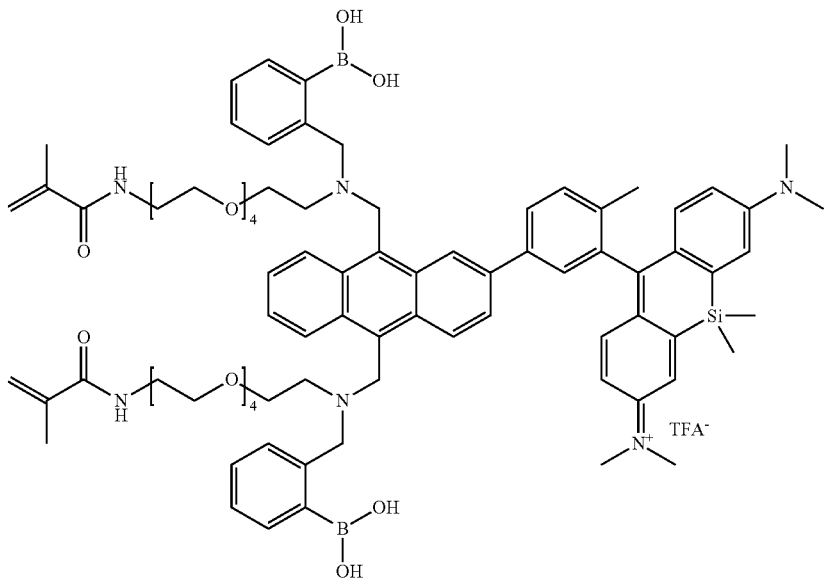 | 56% |

| | | |
|---|---|---|
| 66 | 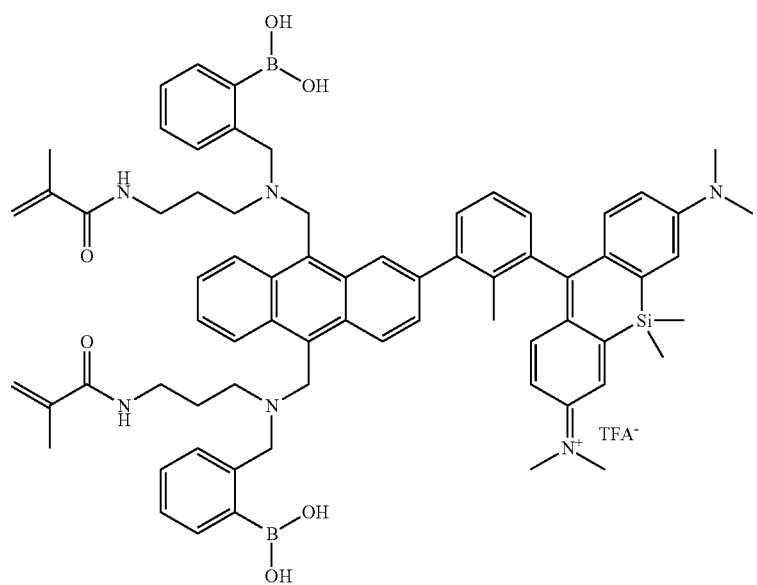 | 28% |
| 67 | 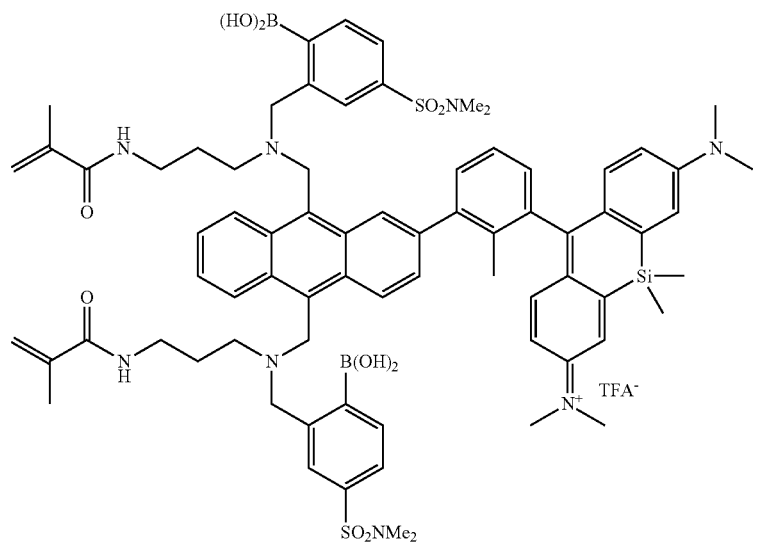 | 37% |

TABLE 1-continued
| 68 | 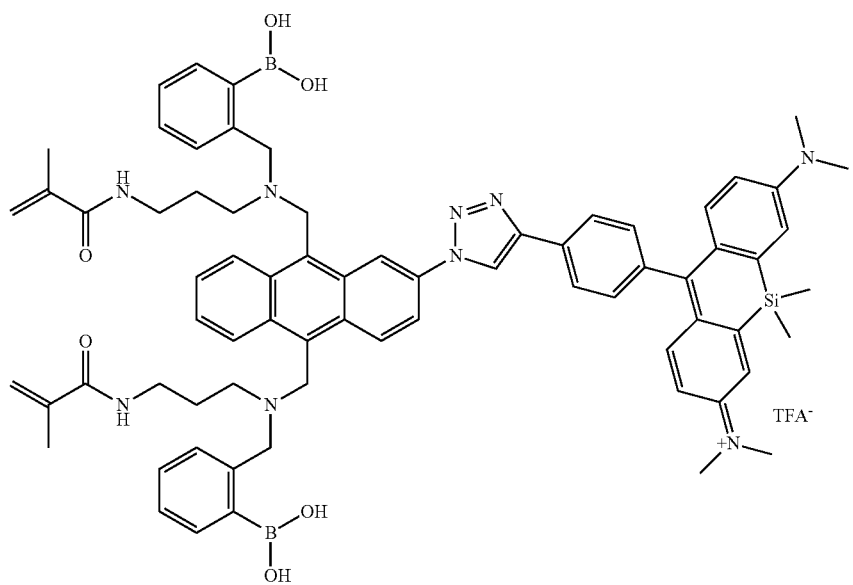 | 6% |
| 69 | 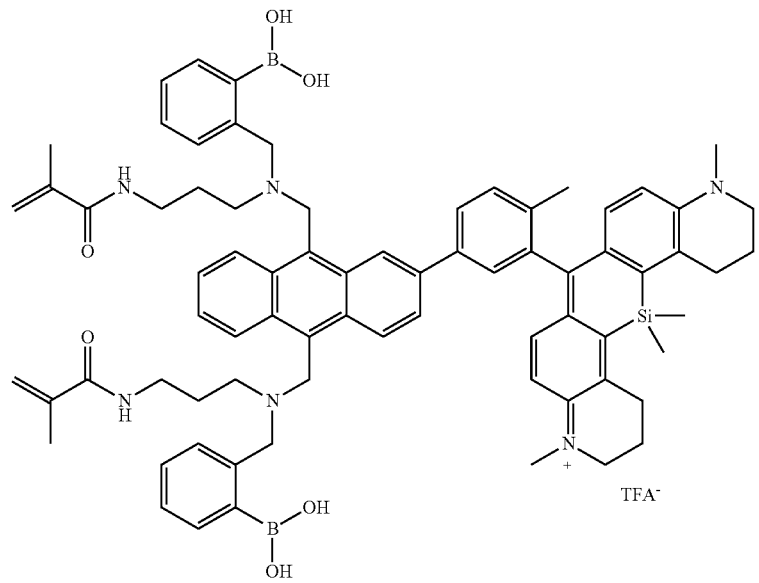 | 27% |

| | | |
|---|---|---|
| 70 | 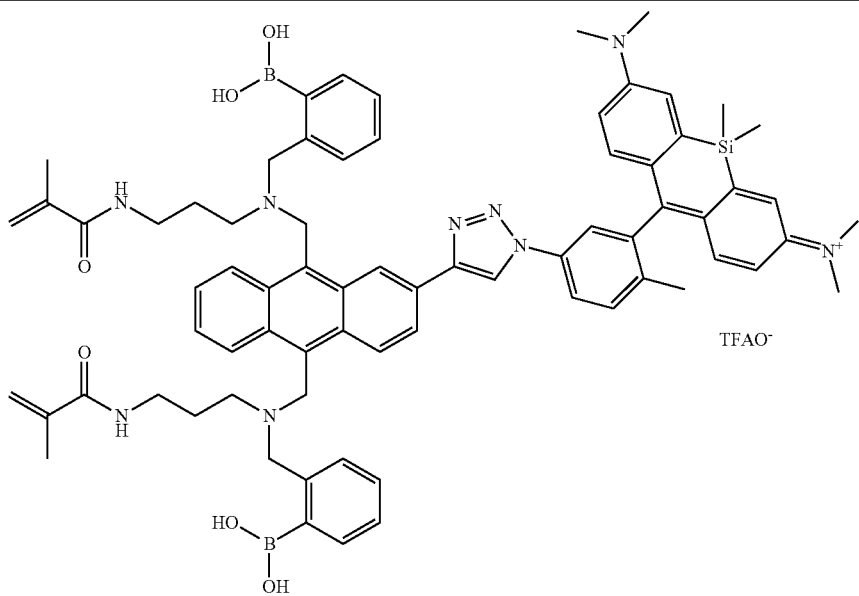 | 9% |
| 71 | 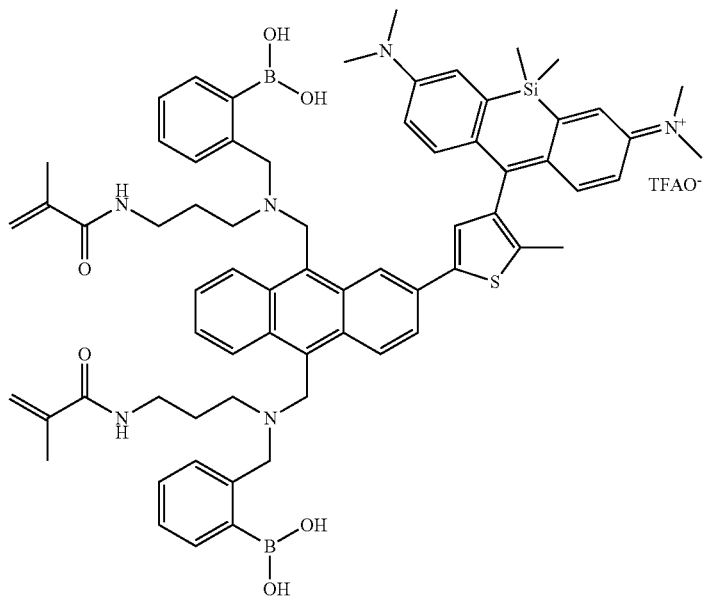 | 64% |

TABLE 1-continued
72 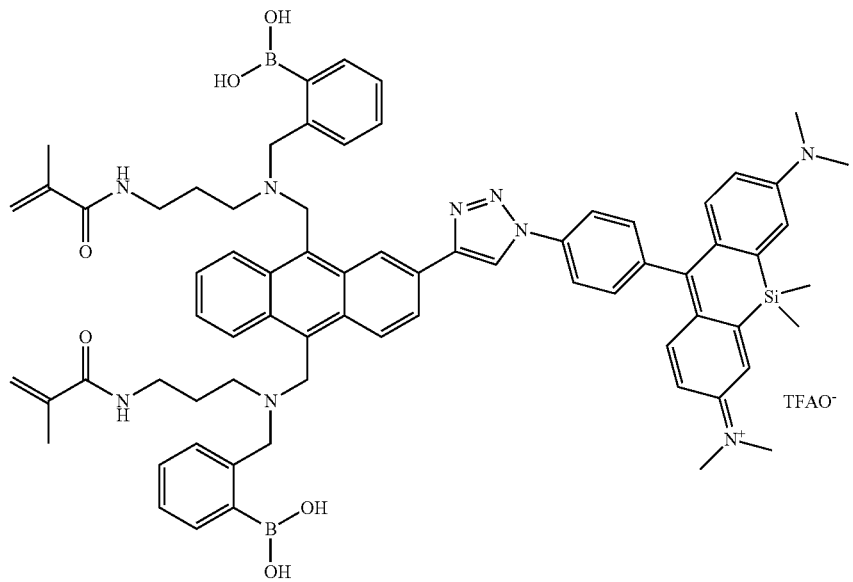 5%
73 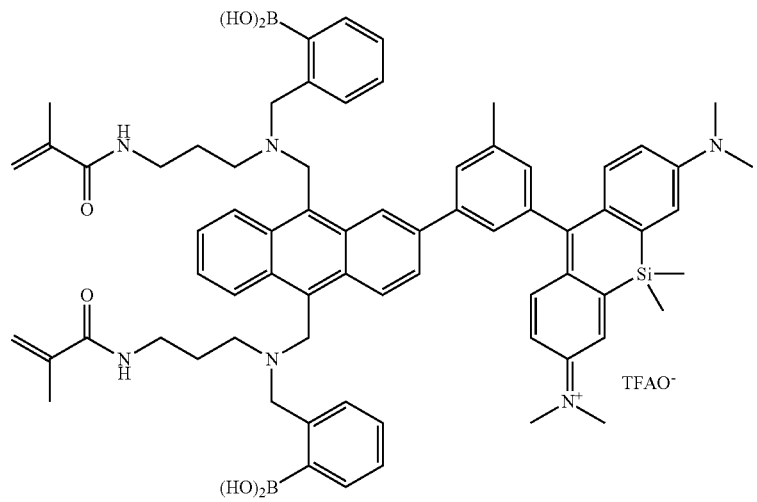 42%

| | | |
|---|---|---|
| 74 | 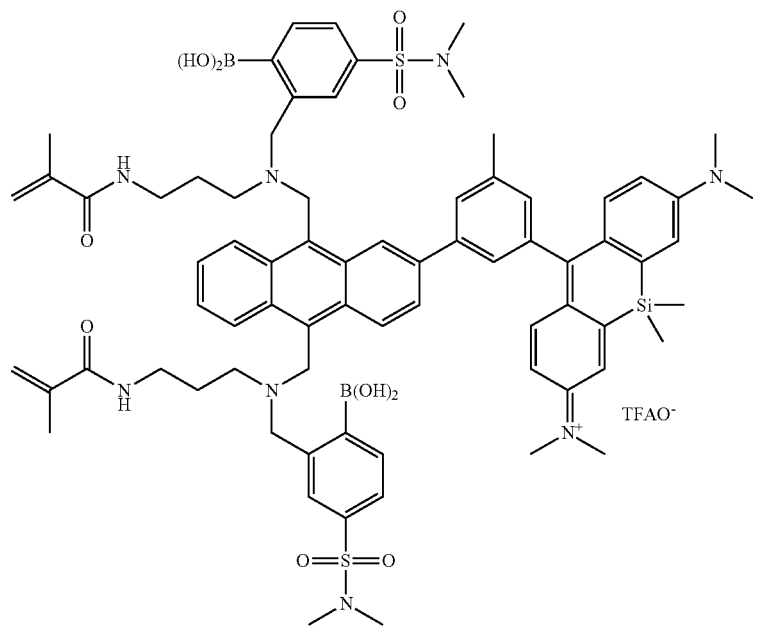 | 33% |
| 75 | 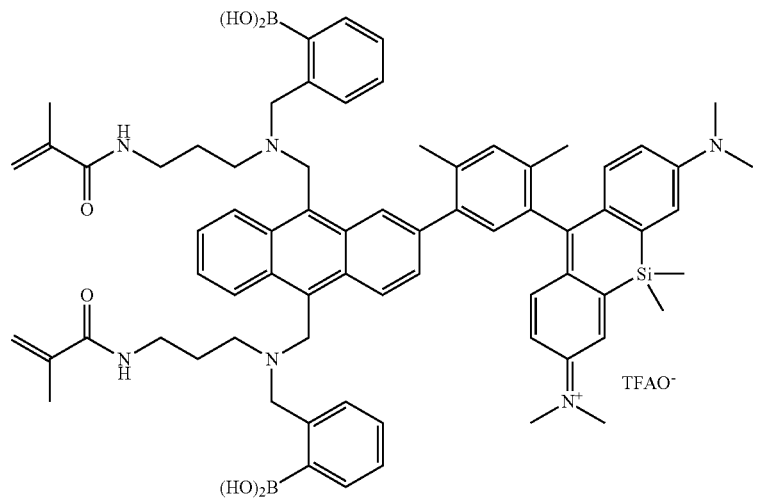 | 36% |

| | | |
|---|---|---|
| 76 | 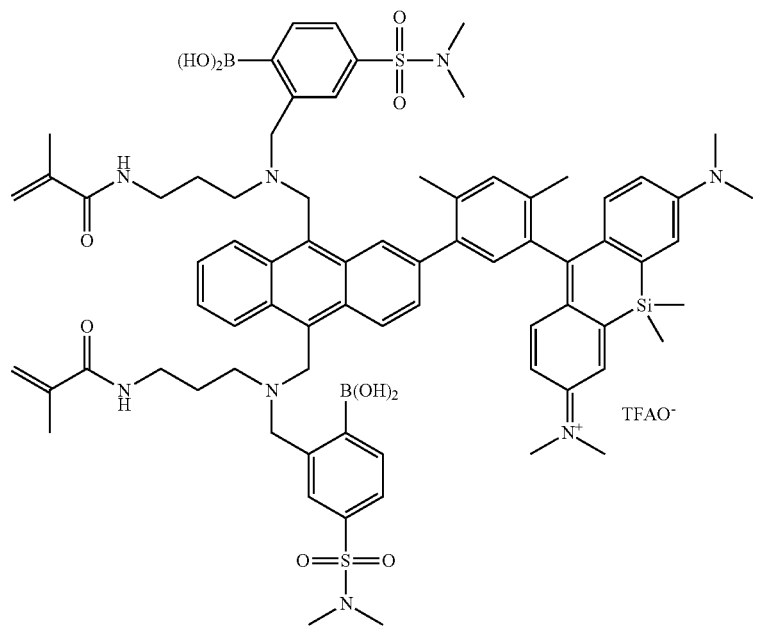 | 35% |
| 77 | 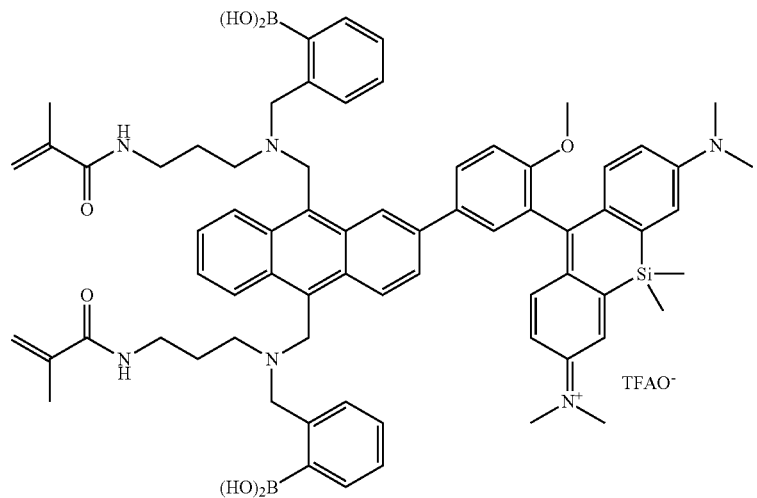 | 61% |

| | | |
|---|---|---|
| 78 | 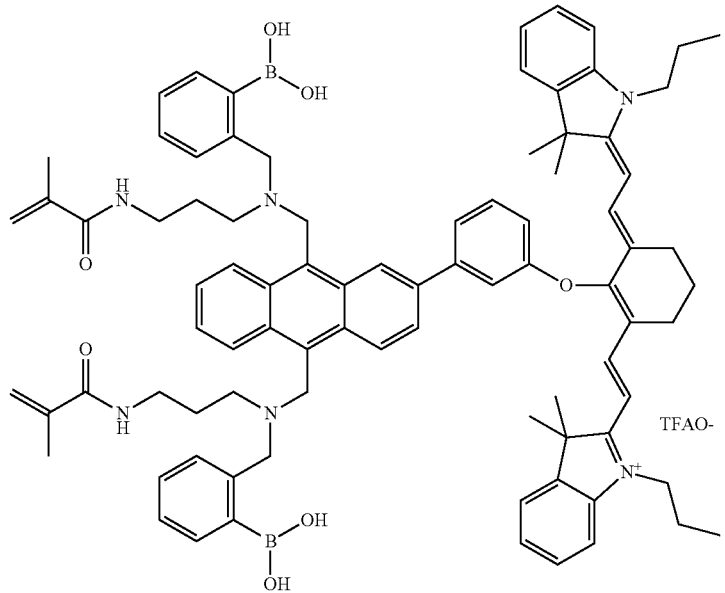 | 5% |
| 79 | 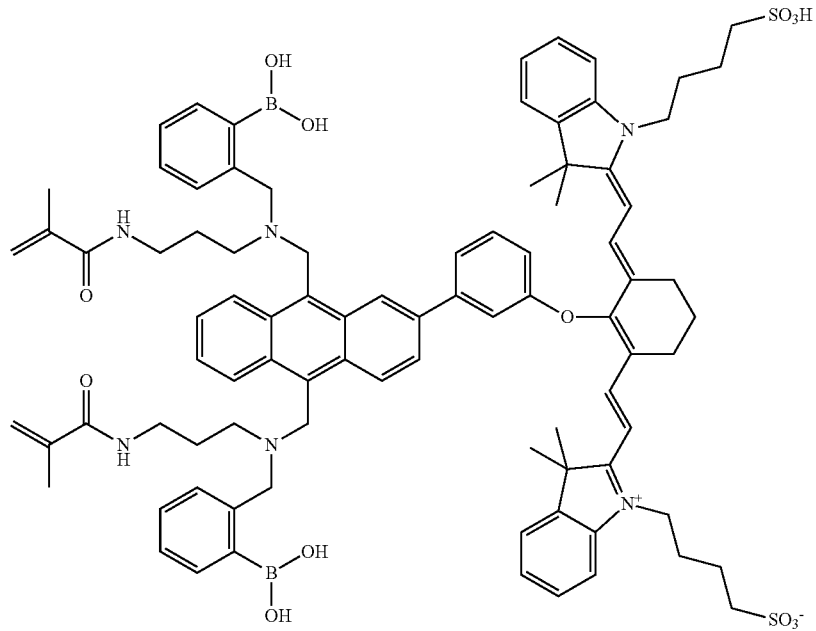 | 16% |

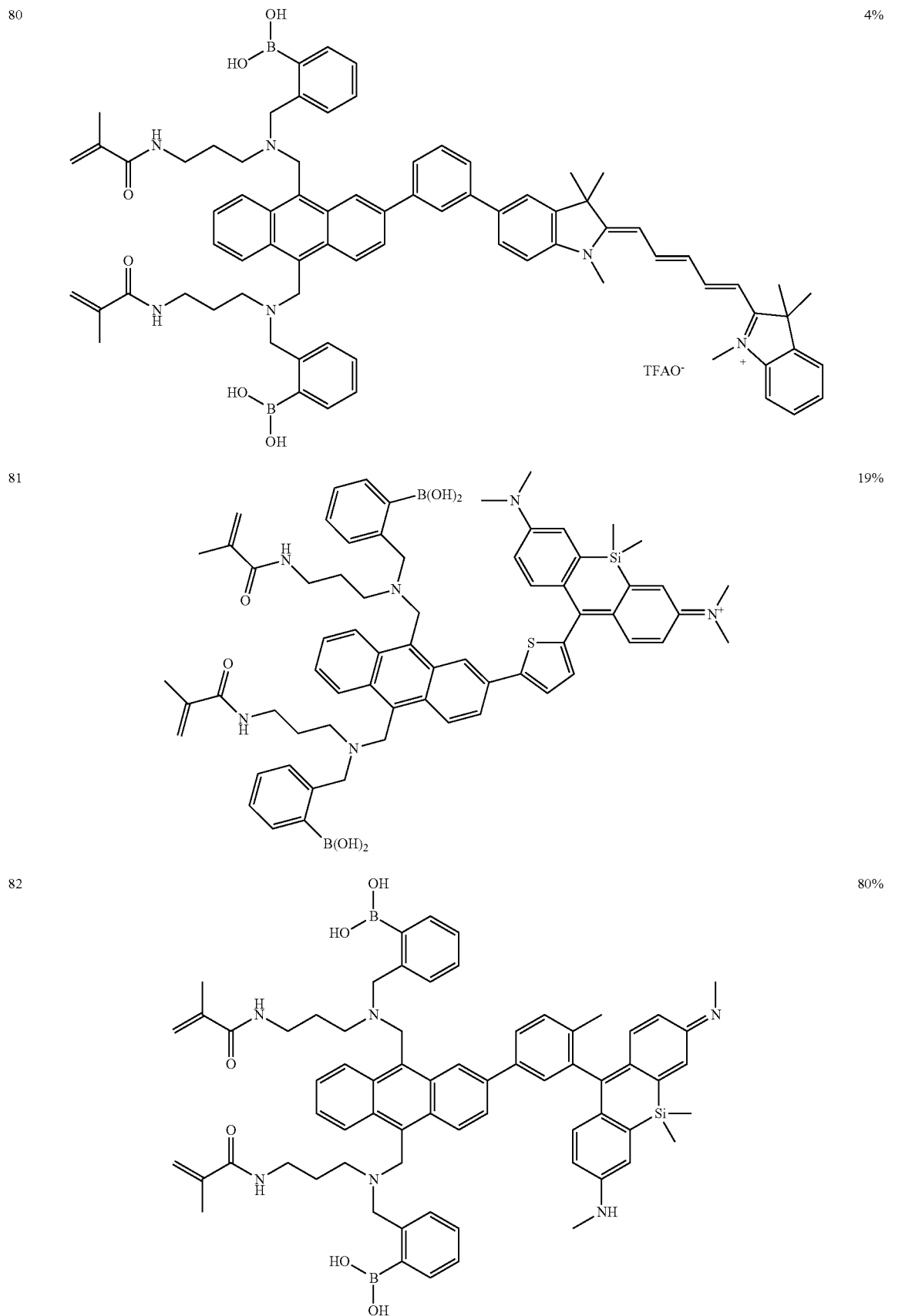

TABLE 1-continued
| 83 | 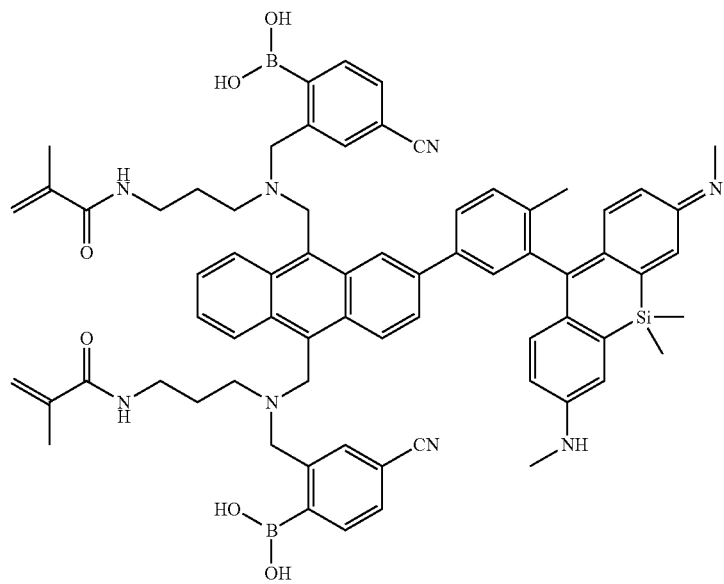 [SMILES: C=C(C)C(=O)NCCCN(Cc1cc(C#N)ccc1B(O)O)Cc1c2ccccc2c(CN(CCCNC(=O)C(=C)C)Cc2cc(C#N)ccc2B(O)O)c2cc(-c3ccc(C)c(C4=C5C=C/C(=N\C)C=C5[Si](C)(C)c5cc(NC)ccc54)c3)ccc12] | 48% |
| 84 | 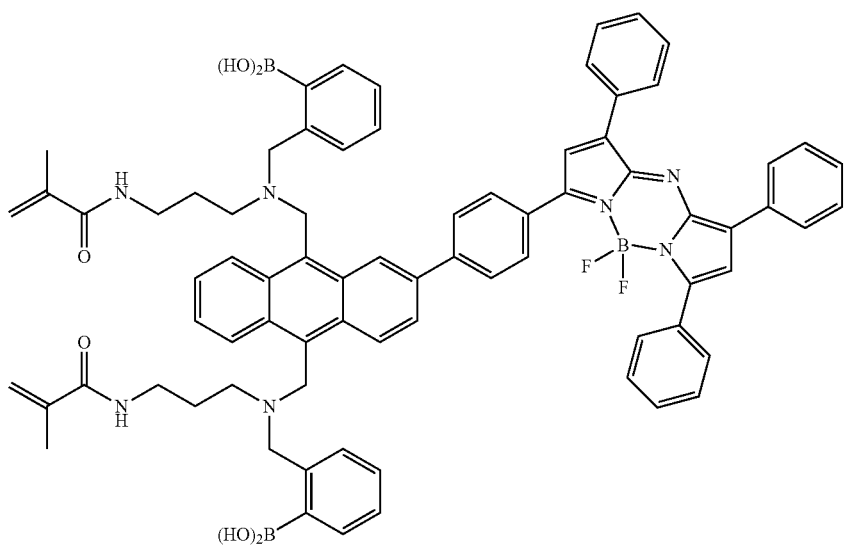 | 0% |
| 85 | 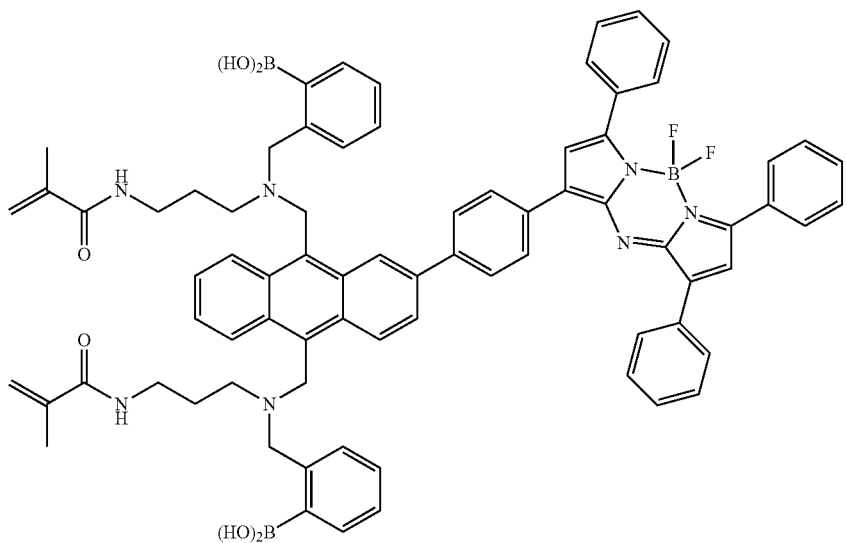 | 0% |

TABLE 1-continued
86 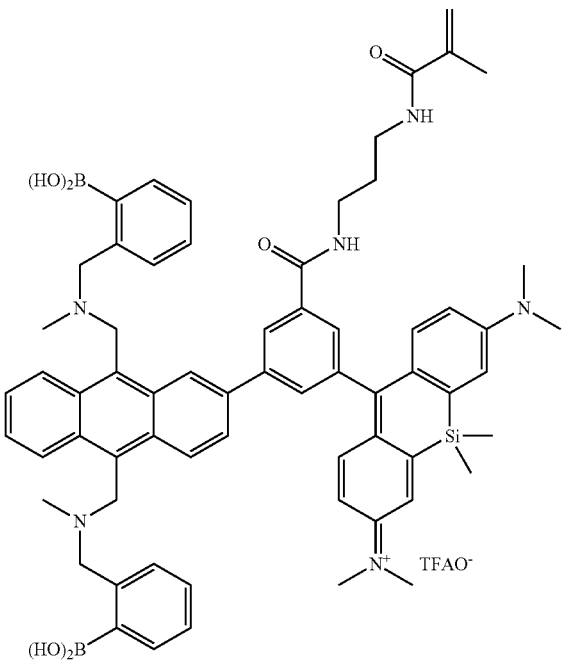 28%
87 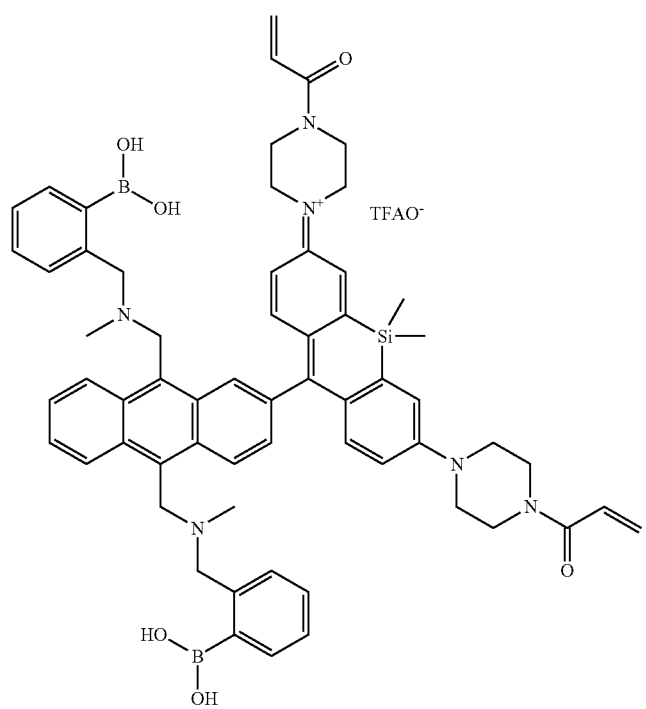 0%

TABLE 1-continued

| 88 | 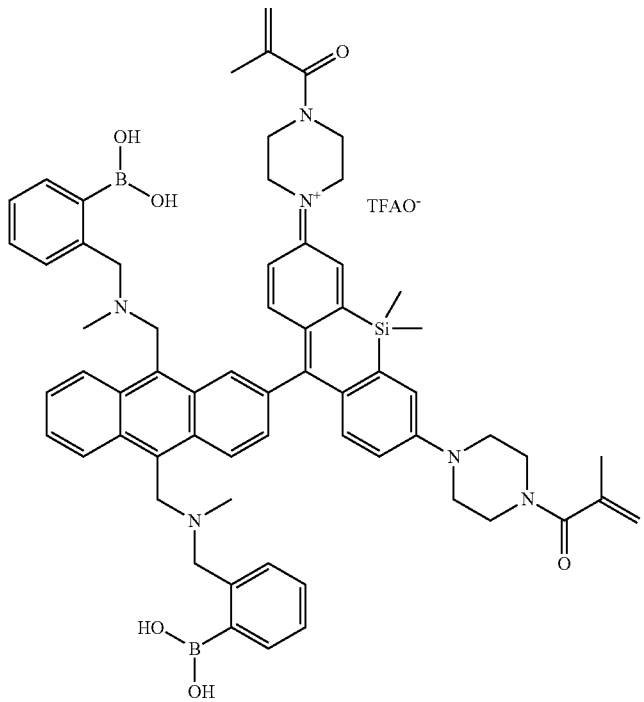 | 0% |

What is claimed is:

1. A compound of Formula III:

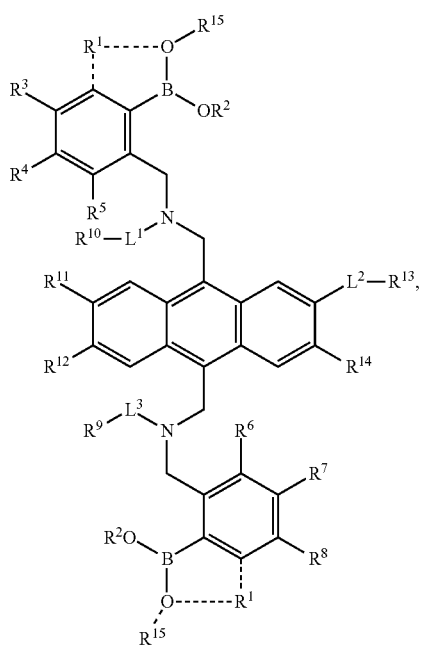

(III)

or a tautomer or a salt thereof, wherein the dotted lines at each occurrence independently denote a bond or absence of a bond; and when the dotted line connecting $R^1$ and O is a bond, $R^1$ is $CX^1X^2$ and $R^{15}$ is absent; and when the dotted line connecting $R^1$ and O is absence of a bond, $R^{15}$ is H or $C_1$-$C_6$ alkyl, and $R^1$, at each occurrence, is H, optionally substituted $C_1$-$C_6$ alkyl, optionally substituted $C_2$-$C_6$ alkenyl, optionally substituted $C_2$-$C_6$ alkynyl, optionally substituted $C_2$-$C_{10}$ heteroalkyl, a polymerizable moiety, an NIR dye moiety, an electron-withdrawing group, or an electron-donating group;

$X^1$ and $X^2$ are independently H or $C_1$-$C_6$ alkyl;

$R^2$ is H or $C_1$-$C_6$ alkyl;

$R^3$, $R^4$, $R^5$, $R^6$, $R^7$, $R^8$, $R^{11}$, $R^{12}$, and $R^{14}$ are independently H, $C_1$-$C_6$ alkyl, polymerizable moiety, electron-withdrawing group, or electron-donating group;

$R^9$ and $R^{10}$ are independently H, $C_1$-$C_6$ alkyl, polymerizable moiety, or NIR dye;

$L^1$ and $L^3$ are independently a bond, optionally substituted $C_1$-$C_{10}$ alkyl, optionally substituted $C_2$-$C_{10}$ alkenyl, optionally substituted $C_2$-$C_{10}$ alkynyl, optionally substituted $C_2$-$C_{20}$ heteroalkyl, or $(CH_2CH_2O)pCH_2CH_2$, wherein p is 2, 3, 4, or 5 or;

$L^2$ is a bond, optionally substituted $C_1$-$C_{10}$ alkyl, optionally substituted $C_2$-$C_{10}$ alkenyl, optionally substituted $C_2$-$C_{10}$ alkynyl, optionally substituted $C_2$-$C_{20}$ heteroalkyl, —O—, optionally substituted —$CH_2C_6H_4O$—, amido, amino, or optionally substituted $C_6$-$C_{10}$ arylene, or optionally substituted $C_2$-$C_{10}$ heteroarylene;

$R^{13}$ is

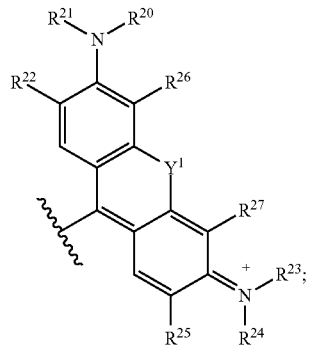

Y¹ is selected from —O—, —P(O)R', —SiR'R", and —NR', wherein R' and R" are independently H or $C_1$-$C_6$ alkyl;

$R^{20}$ and $R^{21}$ are independently —H, $C_1$-$C_6$ alkyl or $R^{21}$ and $R^{20}$, together with the nitrogen atom to which they are attached, form a form a 6- or 5-membered ring optionally substituted with a polymerizable moiety;

$R^{23}$ and $R^{24}$ are independently —H, $C_1$-$C_6$ alkyl, or $R^{23}$ and $R^{24}$, together with the nitrogen atom to which they are attached, form a form a 6- or 5-membered ring optionally substituted with a polymerizable moiety;

$R^{22}$ and $R^{25}$ are independently —H, $C_1$-$C_6$ alkyl, or $R^{21}$ and $R^{22}$, together with the atoms to which they are attached, form a 6- or 5-membered ring, or $R^{24}$ and $R^{25}$, together with the atoms to which they are attached, form a 6- or 5-membered ring;

$R^{26}$ and $R^{27}$ are independently —H, $C_1$-$C_6$ alkyl, or $R^{26}$ and $R^{20}$, together with the atoms to which they are attached, form a 6- or 5-membered ring, or $R^{27}$ and $R^{23}$, together with the atoms to which they are attached, form a 6- or 5-membered ring; and the compound comprises one or more polymerizable moieties.

2. The compound of claim 1, wherein $L^2$ is a bond, or an optionally substituted group selected from phenylene, pyridyl, pyrimidyl, pyrazinyl, thienyl, furanyl, pyrrolyl, pyrazolyl, thiazolyl, oxazolyl, imidazolyl, indolyl, benzimidazolyl, indazolyl, benzotriazolyl, isoquinolyl, quinolyl, benzothiazolyl, benzofuranyl, pyrazolopyridyl, quinazolinyl, quinoxalinyl, and cinnolinyl.

3. The compound of claim 1, wherein $L^2$ is an optionally substituted group selected from phenylene, thiazolyl,

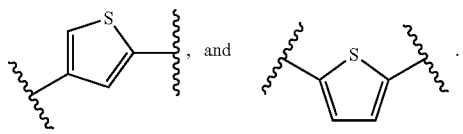 [SMILES: *c1csc(*)c1 ; *c1ccc(*)s1]

4. The compound of claim 1, wherein Y¹ is $SiMe_2$.

5. The compound of claim 1, wherein $R^9$ or $R^{10}$ is —NHC(O)C($CH_3$)$CH_2$, or both $R^9$ and $R^{10}$ are —NHC(O)C($CH_3$)$CH_2$.

6. The compound of claim 1, wherein $R^{20}$, $R^{21}$, $R^{23}$, and $R^{24}$ are —$CH_3$ or —H.

7. The compound of claim 1, wherein $L^1$ is optionally substituted $C_1$-$C_{10}$ alkyl, optionally substituted $C_2$-$C_{20}$ heteroalkyl, or ($CH_2CH_2O$)p$CH_2CH_2$, wherein p is 2, 3, 4, or 5.

8. The compound of claim 1, wherein $L^3$ is optionally substituted $C_1$-$C_{10}$ alkyl, optionally substituted $C_2$-$C_{20}$ heteroalkyl, or ($CH_2CH_2O$)p$CH_2CH_2$, wherein p is 2, 3, 4, or 5.

9. The compound of claim 1, wherein $R^{11}$, $R^{14}$, and $R^{12}$ are H.

10. The compound of claim 1, wherein $R^{22}$, $R^{25}$, $R^{26}$, and $R^{27}$ are H.

11. The compound of claim 1, wherein both $R^{15}$ are H, and $R^1$ at each occurrence is independently selected from the group consisting of H; an electron-withdrawing group selected from the group consisting of halogen, C(O)R', COOR', C(O)$NH_2$, C(O)NR'R", $CF_3$, CN, $SO_3H$, $SO_2CF_3$, $SO_2R'$, $SO_2NR'R"$, ammonium, alkyl ammonium, and $NO_2$, wherein R' and R" are independently H or $C_1$-$C_6$ alkyl; and electron-donating group selected from the group consisting of $NR^{N1}R^{N2}$, OR', NHC(O)R', OC(O)R', phenyl, and vinyl, wherein $R^{N1}$, $R^{N2}$, and R' are independently H or $C_1$-$C_6$ alkyl.

12. The compound of claim 1, wherein the electron-withdrawing group is selected from the group consisting of halogen, C(O)R', COOR', C(O)$NH_2$, C(O)NR'R", $CF_3$, CN, $SO_3H$, $SO_2CF_3$, $SO_2R'$, $SO_2NR'R"$, ammonium, alkyl ammonium, and $NO_2$, wherein R' and R" are independently H or $C_1$-$C_6$ alkyl or the electron-donating group is selected from the group consisting of $NR^{N1}R^{N2}$, OR', NHC(O)R', OC(O)R', phenyl, and vinyl, wherein $R^{N1}$, $R^{N2}$, and R' are independently H or $C_1$-$C_6$ alkyl.

13. The compound of claim 1, wherein $R^9$ and $R^{10}$ are, independently, polymerizable moieties.

14. The compound of claim 13, wherein the polymerizable moiety is selected from —NH(CO)C(R)$CH_2$, —O(CO)C(R)$CH_2$, and —CH$CH_2$, wherein R is H or $C_1$-$C_3$ alkyl.

15. The compound of claim 1, wherein both $R^{15}$ are H.

16. The compound of claim 1, wherein the compound is:

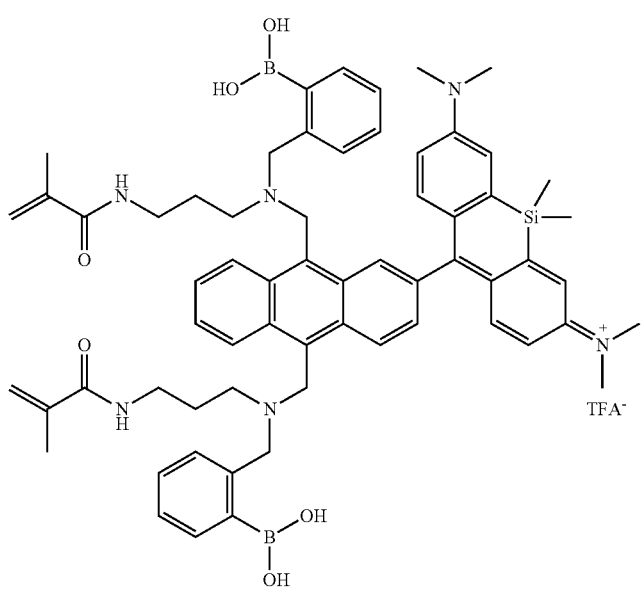

-continued
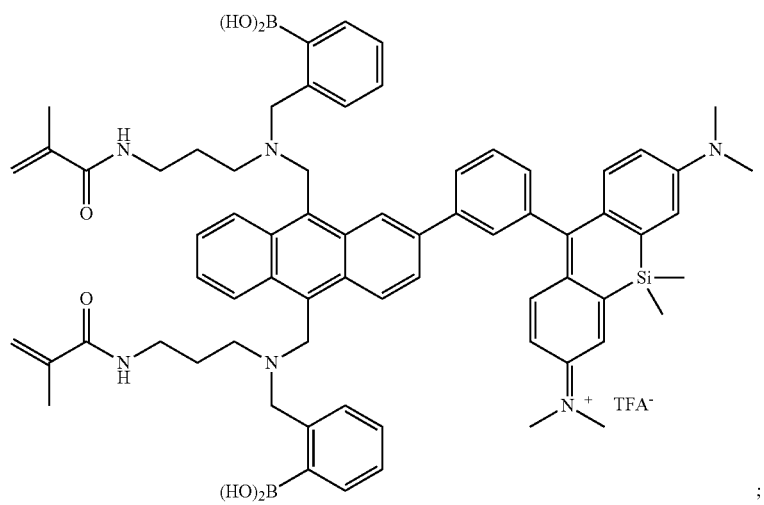
42;
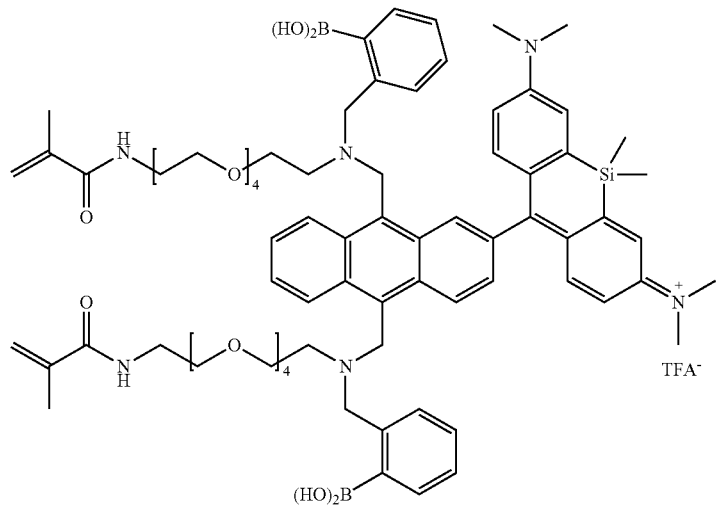
43;
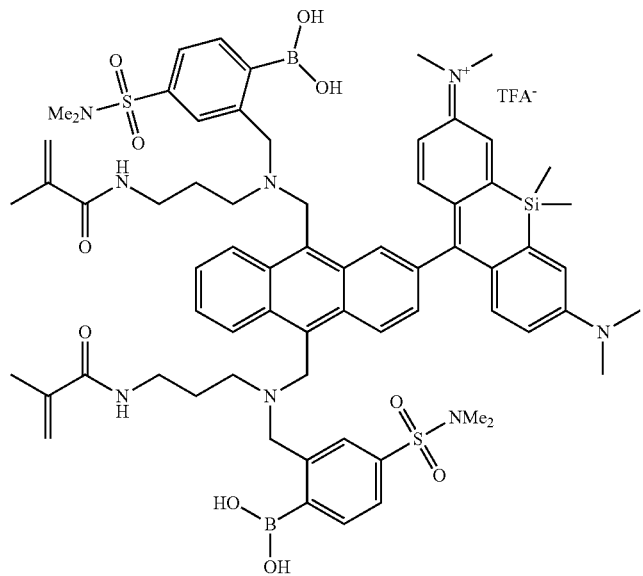
53;

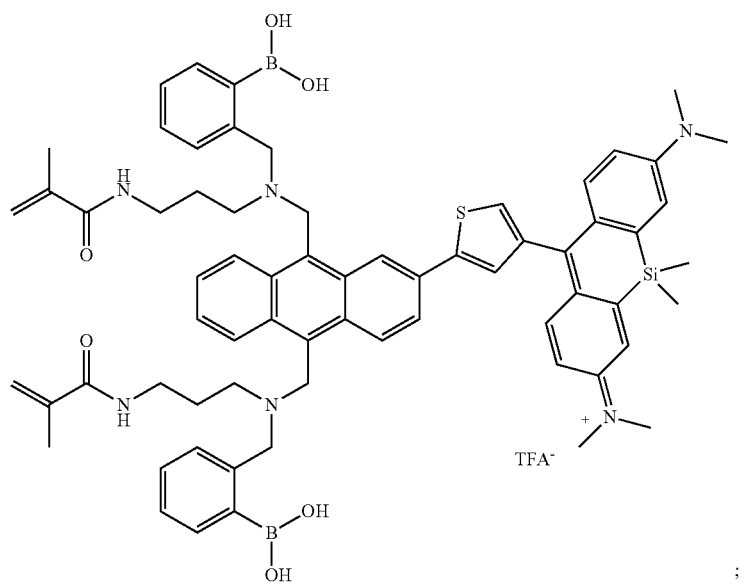
54
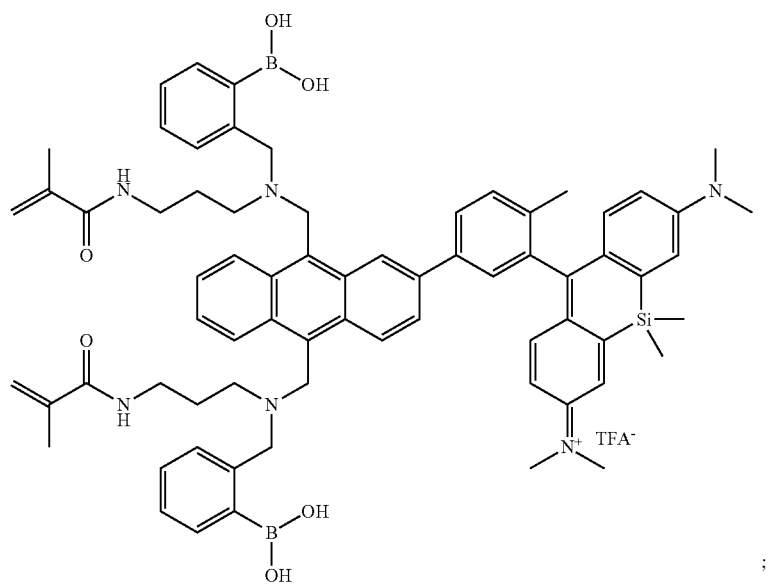
63

64
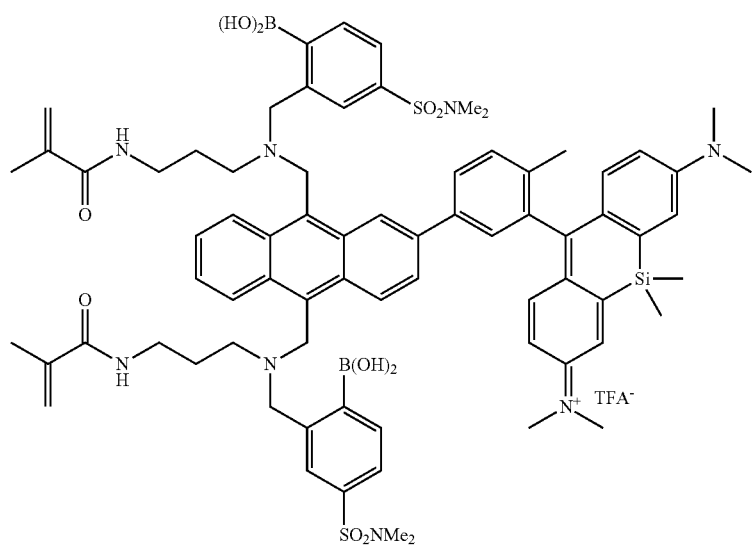
;
65
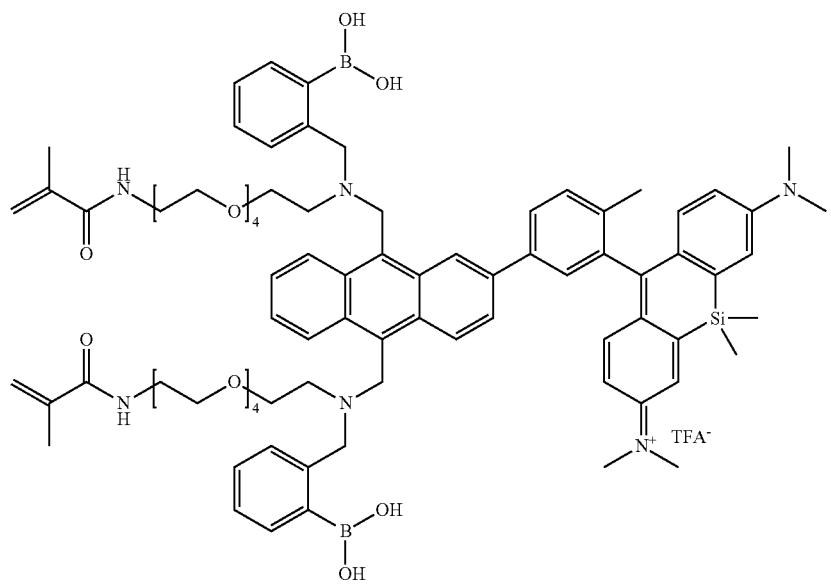
;

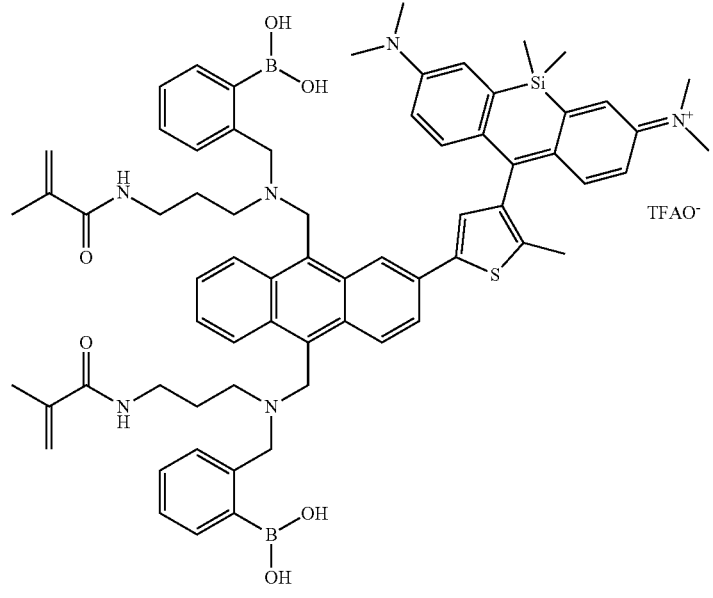
71
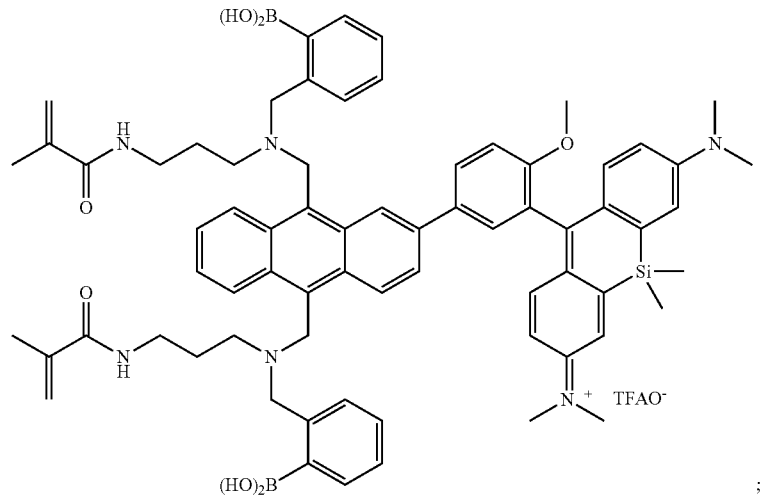
77
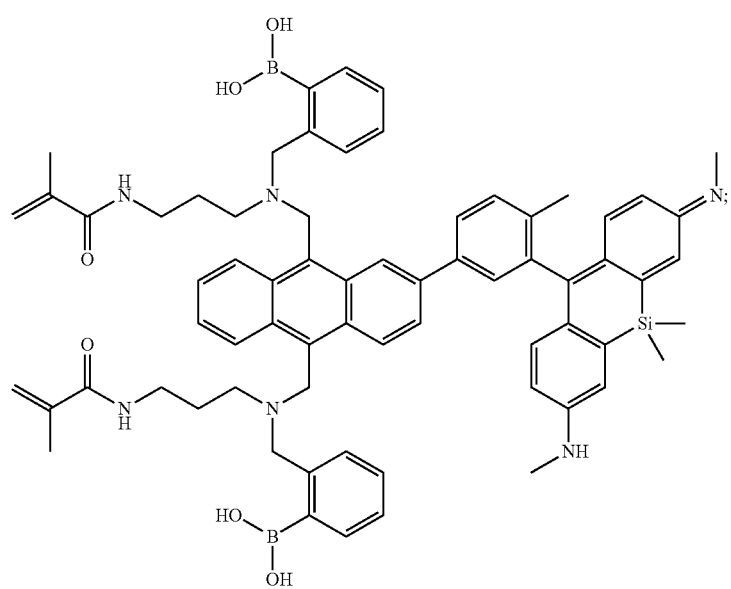
82

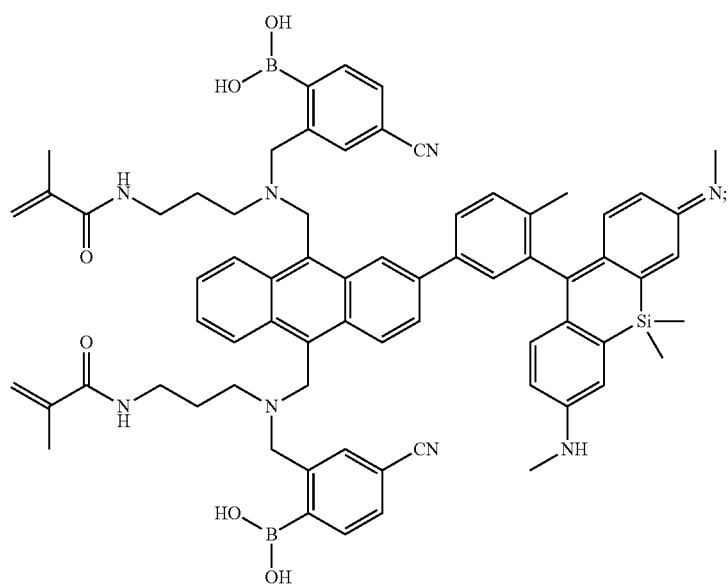

or a tautomer or salt thereof.

17. The compound of claim 1, wherein the compound has an absorption maximum greater than 500 nm.

18. The compound of claim 1, wherein the compound has an emission maximum greater than 550 nm.

19. A sensor for detecting an analyte comprising a polymer, wherein the polymer comprises one or more residues of the compound of claim 1.

20. The sensor of claim 19, wherein the polymer is a hydrogel.

21. The sensor of claim 19, wherein the compound has excitation and emission spectra in the NIR optical window of mammalian skin.

22. The sensor of claim 19, wherein the compound has an absorbtion maximum between about 500 nm and about 900 nm and an emission maximum between about 600 nm and about 1000 nm.

23. The sensor of claim 19, wherein the residue of the compound is present at a concentration from about 0.01 mM to about 20 mM, about 0.1 mM to about 20 mM, about 0.5 mM to about 10 mM, about 1 mM to about 20 mM, about 5 mM to about 20 mM, or about 5 mM to about 10 mM.

24. The sensor of claim 19, wherein the polymer further comprises the residues of HEMA, N,N-dimethylacrylamide, poly-ethylene glycol diacrylamide, or mixtures thereof.

25. The sensor of claim 19, wherein the polymer further comprises the residues of 2-(acryloyloxy)ethyl]trimethylammonium chloride, 2-carboxyethyl acrylate, poly-ethylene glycol diacrylamide, or mixtures thereof.

26. The sensor of claim 19, wherein the polymer further comprises the residues N,N-dimethylacrylamide, acrylamide, poly-ethylene glycol diacrylamide, or mixtures thereof.

27. The sensor of claim 19, wherein the analyte is glucose.

28. The sensor of claim 19, further comprising a catalase.

29. A method of measuring blood glucose concentration in a mammalian subject, comprising:
   a) implanting a sensor of claim 19 into subcutaneous tissue of a mammalian subject;
   b) measuring at least one wavelength of light in the glucose-concentration-dependent luminescent signal from the sensor with a detector to produce a detected luminescent signal; and
   c) processing the detected luminescent signal to produce a glucose concentration.

30. The sensor of claim 19, wherein the polymer comprises one or more residues of a compound having the structure:

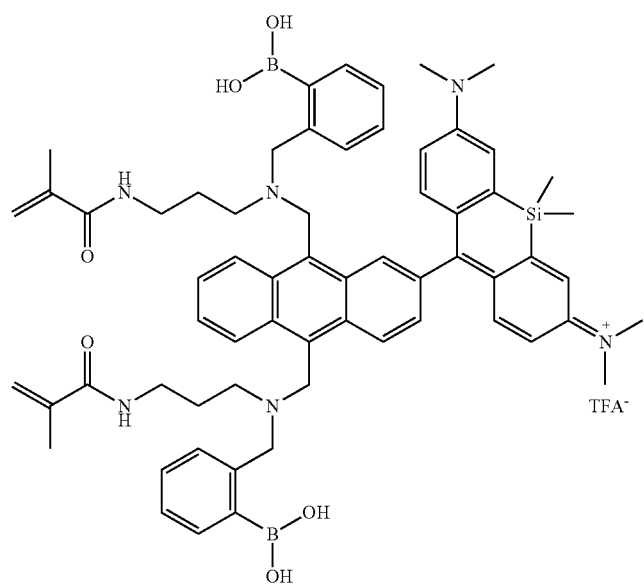
21
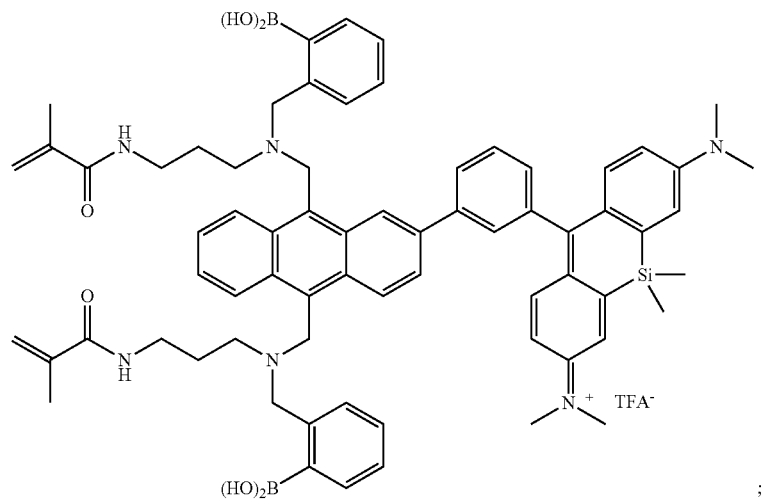
42
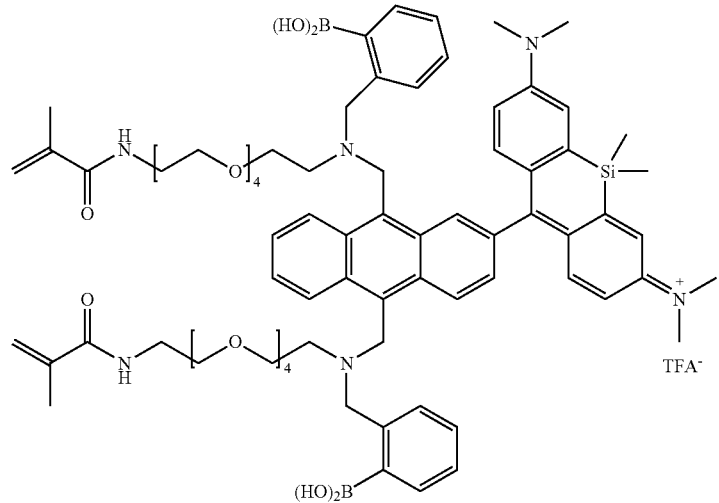
43

-continued
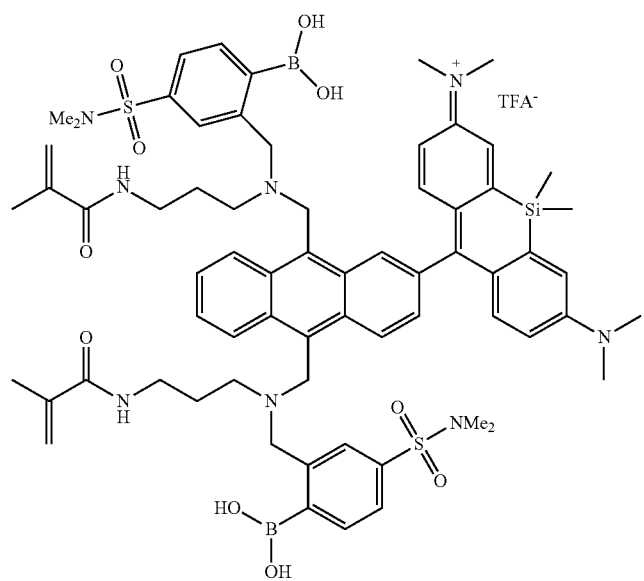
53
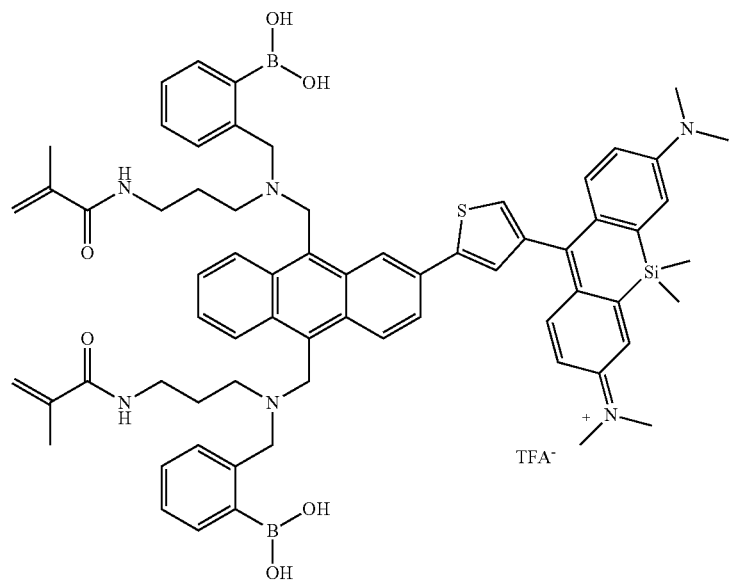
54

63
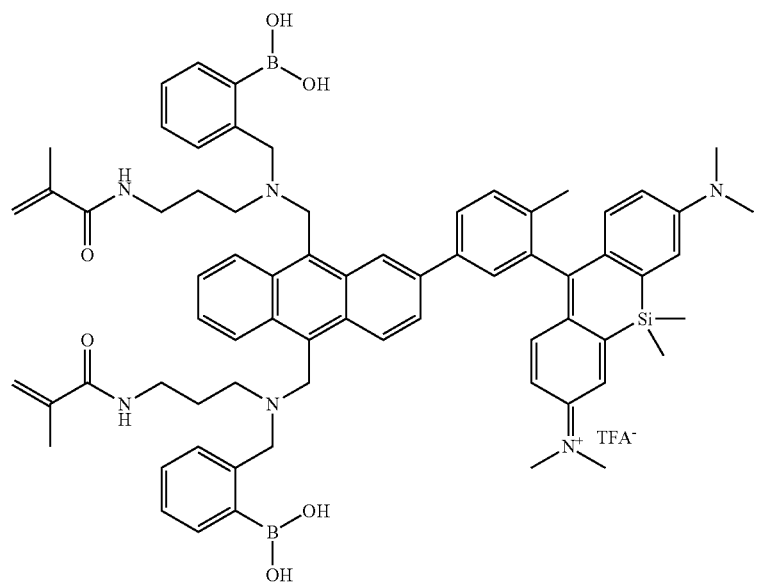
64
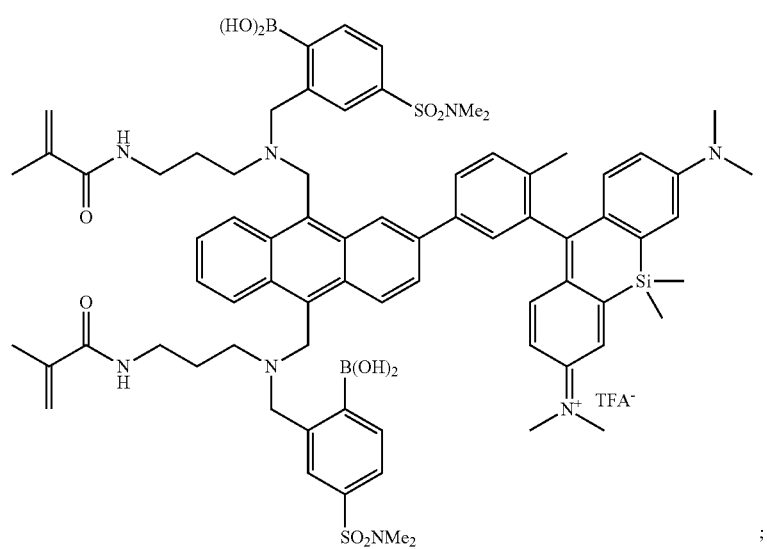

65
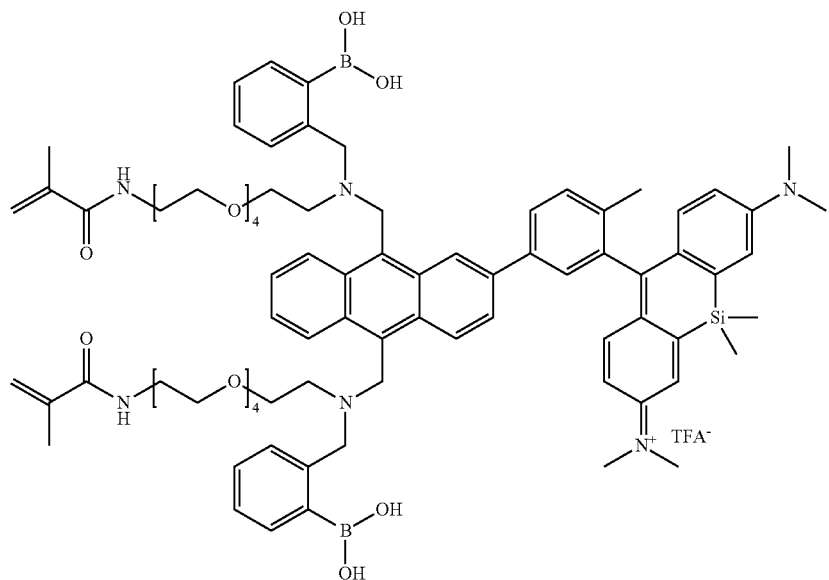
;
71
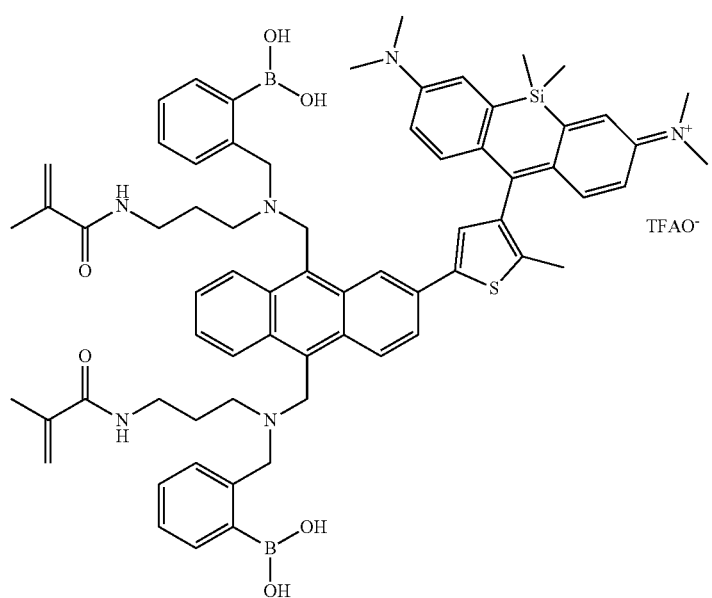
;
77
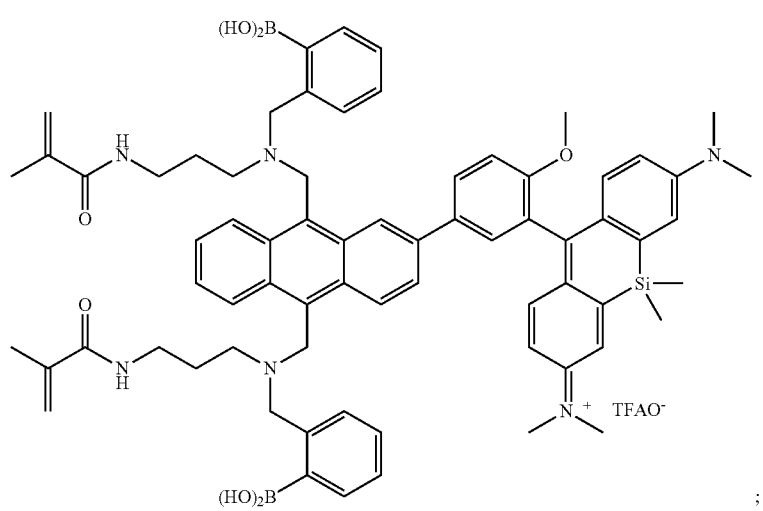
;

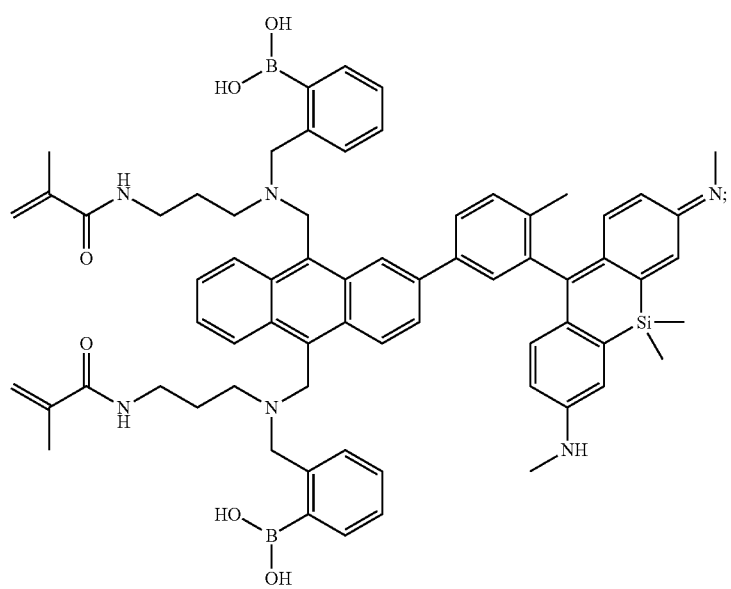
82
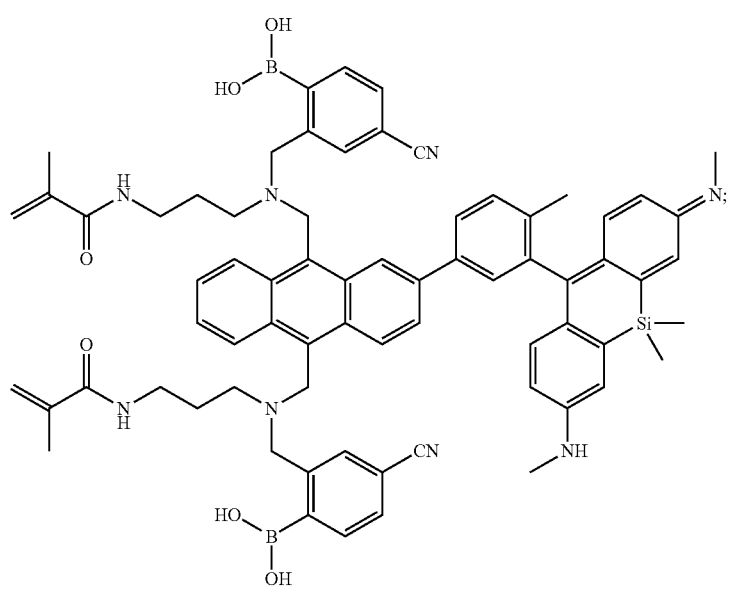
83
or a tautomer or salt thereof.
* * * * *